(12) United States Patent
Ito et al.

(10) Patent No.: US 12,338,234 B2
(45) Date of Patent: *Jun. 24, 2025

(54) COMPOUND, MATERIAL FOR ORGANIC ELECTROLUMINESCENCE DEVICE, ORGANIC ELECTROLUMINESCENCE DEVICE, AND ELECTRONIC DEVICE

(71) Applicant: IDEMITSU KOSAN CO., LTD., Tokyo (JP)

(72) Inventors: Hirokatsu Ito, Sodegaura (JP); Tasuku Haketa, Sodegaura (JP); Yu Kudo, Sodegaura (JP); Yusuke Takahashi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,301

(22) Filed: Jul. 11, 2022

(65) Prior Publication Data

US 2022/0396570 A1   Dec. 15, 2022

Related U.S. Application Data

(63) Continuation of application No. 16/881,656, filed on May 22, 2020, now Pat. No. 11,548,877, which is a
(Continued)

(30) Foreign Application Priority Data

Nov. 30, 2018  (JP) .................................. 2018-225423
Mar. 29, 2019  (JP) .................................. 2019-069354

(51) Int. Cl.
  *C07D 407/12*  (2006.01)
  *H10K 50/15*  (2023.01)
  *H10K 85/60*  (2023.01)

(52) U.S. Cl.
  CPC ......... *C07D 407/12* (2013.01); *H10K 85/631* (2023.02); *H10K 85/6574* (2023.02); *H10K 50/15* (2023.02)

(58) Field of Classification Search
  CPC .................... H10K 85/631; H10K 85/6574
  See application file for complete search history.

(56) References Cited

U.S. PATENT DOCUMENTS 10,249,832 B1   4/2019   Takahashi et al.
10,424,740 B2   9/2019   Haketa et al.
(Continued)

FOREIGN PATENT DOCUMENTS

CN   106463629 A   2/2017
CN   108821934 A   11/2018
(Continued)

OTHER PUBLICATIONS

Extended European Search Report issued Aug. 1, 2022, in corresponding European Patent Application No. 19888913.1, 7 pages.
(Continued)

*Primary Examiner* — Sean M DeGuire
(74) *Attorney, Agent, or Firm* — Oblon, McClelland, Maier & Neustadt, L.L.P.

(57) ABSTRACT

An organic electroluminescence device having an improved performance and a compound represented by formula (1), which is a novel material that enables the organic electroluminescence device:
(Continued)

(1)

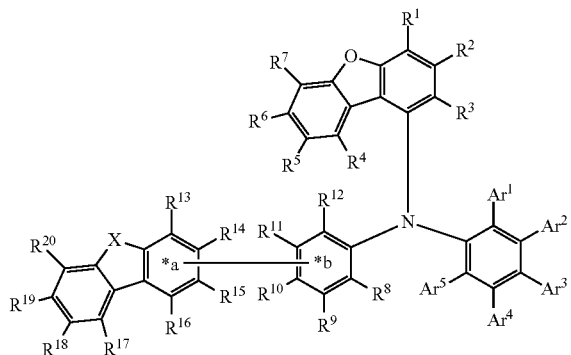

wherein, X, Ar¹ to Ar⁵, R¹ to R²⁰, *a, and *b are the same as those defined in the specification.

21 Claims, 1 Drawing Sheet

Related U.S. Application Data continuation of application No. PCT/JP2019/046861, filed on Nov. 29, 2019.

(56) References Cited

U.S. PATENT DOCUMENTS

| | | | |
|---|---|---|---|
| 10,593,889 B1 | 3/2020 | Takahashi et al. | |
| 10,658,594 B2 | 5/2020 | Takahashi et al. | |
| 10,658,595 B2 | 5/2020 | Yoon et al. | |
| 10,665,809 B2 | 5/2020 | Kim et al. | |
| 10,672,989 B2 | 6/2020 | Takahashi et al. | |
| 10,680,181 B2 | 6/2020 | Takahashi et al. | |
| 11,548,877 B2 * | 1/2023 | Ito | C07D 307/91 |
| 2012/0248426 A1 | 10/2012 | Kato | |
| 2016/0126469 A1 * | 5/2016 | Nakano | C07D 307/91 257/40 |
| 2016/0343514 A1 | 11/2016 | Uchida et al. | |
| 2017/0288147 A1 | 10/2017 | Fujita et al. | |
| 2018/0248123 A1 | 8/2018 | Ishisone et al. | |
| 2019/0044085 A1 | 2/2019 | Jeong et al. | |
| 2019/0181344 A1 | 6/2019 | Herron et al. | |
| 2019/0185460 A1 | 6/2019 | Kim et al. | |
| 2019/0214579 A1 | 7/2019 | Seda et al. | |
| 2019/0273220 A1 | 9/2019 | Kim et al. | |
| 2019/0288220 A1 | 9/2019 | Kim et al. | |
| 2019/0326516 A1 | 10/2019 | Kim et al. | |
| 2019/0326519 A1 | 10/2019 | Shin et al. | |
| 2019/0378981 A1 | 12/2019 | Yoo et al. | |
| 2019/0393429 A1 | 12/2019 | Takahashi et al. | |
| 2020/0048207 A1 | 2/2020 | Parham et al. | |
| 2020/0048273 A1 | 2/2020 | Park et al. | |
| 2020/0052212 A1 | 2/2020 | Tasaki et al. | |
| 2020/0091435 A1 | 3/2020 | Masuda et al. | |
| 2020/0111962 A1 | 4/2020 | Nakano et al. | |
| 2020/0111965 A1 | 4/2020 | Nakano et al. | |
| 2020/0111975 A1 | 4/2020 | Ogata et al. | |
| 2020/0111986 A1 | 4/2020 | Kim et al. | |
| 2020/0144504 A1 | 5/2020 | Ishisone et al. | |
| 2020/0144510 A1 | 5/2020 | Kim et al. | |
| 2020/0259086 A1 | 8/2020 | Kim et al. | |
| 2020/0287140 A1 | 9/2020 | Chae et al. | |
| 2020/0287152 A1 | 9/2020 | Kim et al. | |
| 2020/0290985 A1 | 9/2020 | Kudo et al. | |
| 2020/0317653 A1 | 10/2020 | Ito et al. | |
| 2021/0005825 A1 | 1/2021 | Tasaki et al. | |
| 2021/0005826 A1 | 1/2021 | Tasaki et al. | |
| 2021/0013439 A1 | 1/2021 | Sado et al. | |
| 2021/0028365 A1 | 1/2021 | Tasaki et al. | |

FOREIGN PATENT DOCUMENTS

| | | | |
|---|---|---|---|
| CN | 110615782 A | 12/2019 | |
| EP | 3747876 A1 | 12/2020 | |
| EP | 3763750 A1 | 1/2021 | |
| JP | 2016-066723 A | 4/2016 | |
| JP | 2016-086142 A | 5/2016 | |
| JP | 2016-219797 A | 12/2016 | |
| JP | 2017-522713 A | 8/2017 | |
| JP | 2017-183727 A | 10/2017 | |
| JP | 2019-016675 A | 1/2019 | |
| JP | 2019-119680 A | 7/2019 | |
| KR | 10-2017-0094665 A | 8/2017 | |
| KR | 2017094665 A * | 8/2017 | ........... C07C 211/54 |
| KR | 2018-0041607 A | 4/2018 | |
| KR | 10-2018-0061077 A | 6/2018 | |
| KR | 2018-0061077 A | 6/2018 | |
| KR | 10-2018-0112962 A | 10/2018 | |
| KR | 10-2018-0137315 A | 12/2018 | |
| KR | 10-2019-0005522 A | 1/2019 | |
| KR | 10-2019-0053809 A | 5/2019 | |
| KR | 10-2019-0057229 A | 5/2019 | |
| KR | 10-2019-0079181 A | 7/2019 | |
| KR | 10-2019-118137 A | 10/2019 | |
| KR | 10-2019-140659 A | 12/2019 | |
| WO | WO 2010/061824 A1 | 6/2010 | |
| WO | WO 2011/059099 A1 | 5/2011 | |
| WO | WO 2016/178544 A2 | 11/2016 | |
| WO | WO 2017/012687 A | 1/2017 | |
| WO | WO 2017/148564 A | 9/2017 | |
| WO | WO 2018/164239 A1 | 9/2018 | |
| WO | WO 2018/164265 A1 | 9/2018 | |
| WO | WO 2018/186374 A1 | 10/2018 | |
| WO | WO 2018/186396 A1 | 10/2018 | |
| WO | WO 2019/088231 A1 | 5/2019 | |
| WO | WO 2019/117137 A1 | 6/2019 | |
| WO | WO 2019/124902 A1 | 6/2019 | |
| WO | WO 2019/132028 A1 | 7/2019 | |
| WO | WO 2019/132040 A1 | 7/2019 | |
| WO | WO 2019/146781 A1 | 8/2019 | |
| WO | WO 2019/155363 A1 | 8/2019 | |
| WO | WO 2019/189033 A1 | 10/2019 | |
| WO | WO 2019/194298 A1 | 10/2019 | |
| WO | WO 2019/206291 A1 | 10/2019 | |
| WO | WO 2019/206292 A1 | 10/2019 | |
| WO | WO 2019/216411 A1 | 11/2019 | |
| WO | WO 2020/036459 A1 | 2/2020 | |
| WO | WO 2020/036463 A1 | 2/2020 | |
| WO | WO 2020/064666 A1 | 4/2020 | |
| WO | WO 2020/065471 A1 | 4/2020 | |
| WO | WO 2020/071479 A1 | 4/2020 | |
| WO | WO 2020/075758 A1 | 4/2020 | |
| WO | WO 2020/075759 A1 | 4/2020 | |
| WO | WO 2020/075760 A1 | 4/2020 | |
| WO | WO 2020/080416 A1 | 4/2020 | |
| WO | WO 2020/080417 A1 | 4/2020 | |
| WO | WO 2020/095998 A1 | 5/2020 | |
| WO | WO 2020/096012 A1 | 5/2020 | |
| WO | WO 2020/096021 A1 | 5/2020 | |
| WO | WO 2020/096357 A1 | 5/2020 | |
| WO | WO 2020/096358 A1 | 5/2020 | |
| WO | WO 2020/111251 A1 | 6/2020 | |
| WO | WO 2020/111253 A1 | 6/2020 | |
| WO | WO 2020/115933 A1 | 6/2020 | |
| WO | WO 2020/116561 A1 | 6/2020 | |
| WO | WO 2020/116562 A1 | 6/2020 | |

OTHER PUBLICATIONS

International Search Report mailed Mar. 3, 2020, in PCT/JP2019/046861, filed Nov. 29, 2019.
Combined Chinese Office Action issued on Dec. 23, 2023 in Chinese Patent Application No. 201980078775.1 (with English translation of Office Action), 13 pages.

(56) References Cited

OTHER PUBLICATIONS

Japanese Office Action issued on Dec. 5, 2023 in Japanese Patent Application No. 2020-557867 (with unedited computer-generated English translation), 3 pages.
Official communication issued in CN application 201980078775.1 on Jun. 25, 2024 (with English machine translation).

* cited by examiner

[Fig. 1]
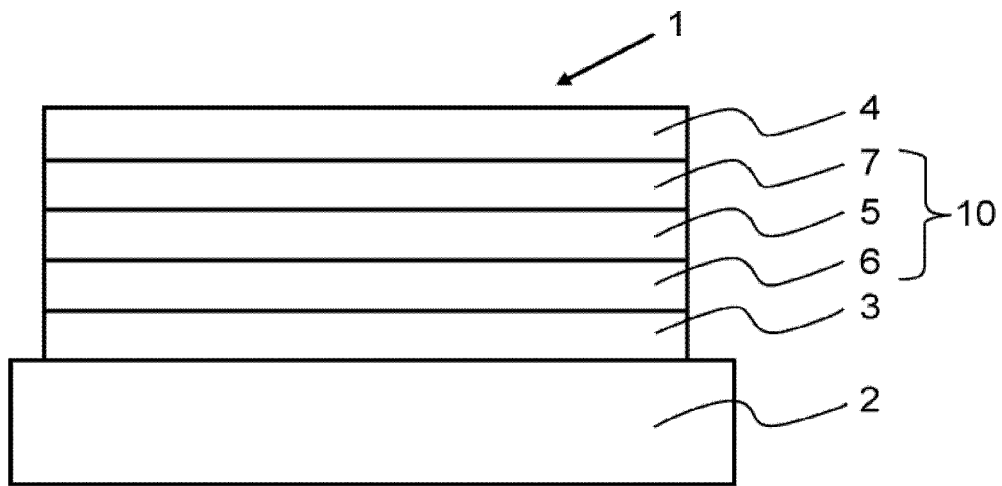
[Fig. 2]
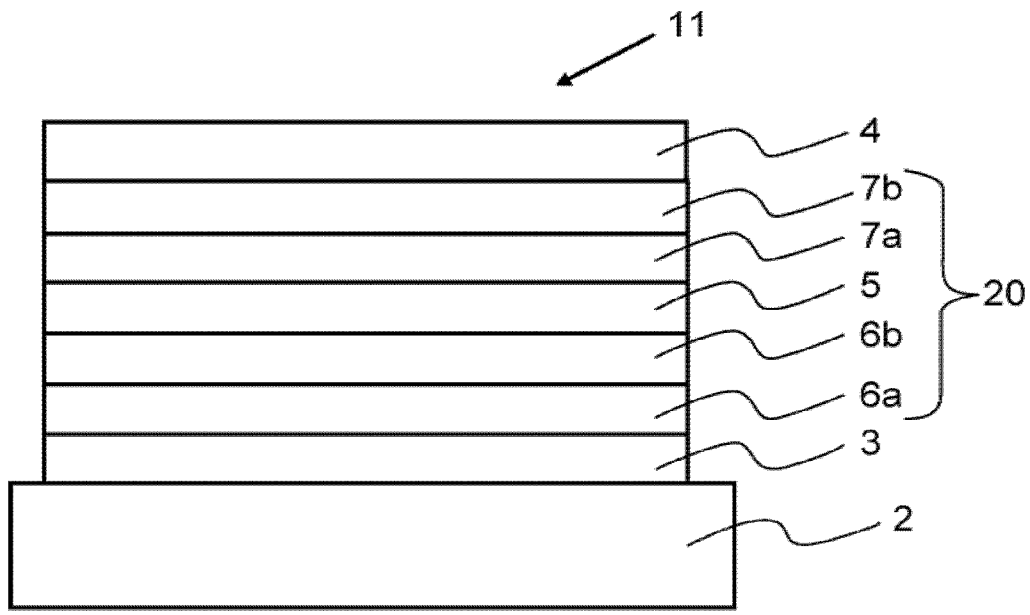

COMPOUND, MATERIAL FOR ORGANIC ELECTROLUMINESCENCE DEVICE, ORGANIC ELECTROLUMINESCENCE DEVICE, AND ELECTRONIC DEVICE

CROSS-REFERENCE TO RELATED APPLICATIONS

The present application is a continuation of U.S. patent application Ser. No. 16/881,656, filed May 22, 2020, which is a continuation application of International Application No. PCT/JP2019/046861, filed Nov. 29, 2019, which claims priority to Japanese Patent Applications No. 2018-225423, filed Nov. 30, 2018 and No. 2019-069354, filed Mar. 29, 2019. The contents of these applications are incorporated herein by reference in their entirety.

TECHNICAL FIELD

The present invention relates to a compound, and a material for an organic electroluminescence device, an organic electroluminescence device, and an electronic device, each containing the compound.

BACKGROUND ART

In general, an organic electroluminescence device (organic EL device) includes an anode, a cathode, and organic layers interposed between the anode and the cathode. When a voltage is applied between both electrodes, electrons from the cathode side and holes from the anode side are injected into a light emitting area, and the injected electrons and holes are recombined in the light emitting area to generate an excited state. Then, when the excited state returns to a ground state, light is emitted. Accordingly, development of a compound by which electrons or holes are efficiently transported to a light emitting area and recombination of the electrons with the holes is promoted is important in obtaining a high-performance organic EL device. Also, in recent years, with the further spread of smart phones, organic EL TVs, and organic EL lightings using organic EL devices, there is a demand for a compound that satisfies both a high efficiency and a sufficient device life.

For example, Patent Literatures 1 to 6 discloses an aromatic amine compound used in an organic EL device.

CITATION LIST

Patent Literature

Patent Literature 1: JP 2016-066723 A
Patent Literature 2: JP 2016-086142 A
Patent Literature 3: KR 10-2017-0094665 A
Patent Literature 4: WO 2010/061824 A
Patent Literature 5: WO 2017/012687 A
Patent Literature 6: WO 2017/148564 A

SUMMARY OF INVENTION

Technical Problem

Many compounds have conventionally been reported as a material for preparing organic EL devices, but there is still a demand for a compound that further improves characteristics of an organic EL device. As for an aromatic amine compound used in the organic EL device as well, there is still a demand for a compound that further improves characteristics of the organic EL device, particularly, a compound that allows compatibility of a prolonged life and a high efficiency with high-performance at a higher level.

The present invention has been made in order to solve the above problems, and an object thereof is to provide an organic EL device having an improved performance, more specifically, an organic EL device that has a prolonged life and a high efficiency, and a novel compound that enables such an organic EL device.

Solution to Problem

The present inventors conducted repetitive intensive studies in order to solve the above problem, and as a result, found that the compound represented by the following formula (1) enables an organic EL device having an improved performance, more specifically an organic EL device that has a prolonged life, and a high efficiency, and then have completed the present invention.

In one embodiment, the present invention provides a compound represented by the formula (1) (hereinafter, also referred to as compound (1)).

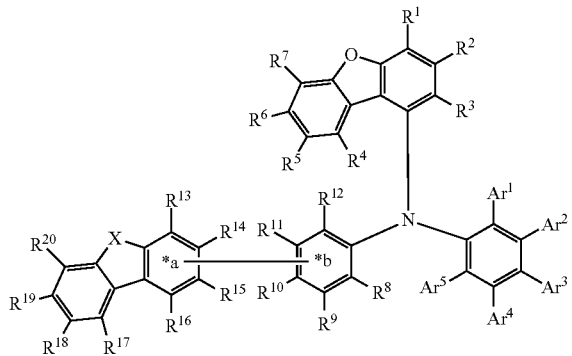

(1)

In the formula (1),

X represents an oxygen atom or a sulfur atom, $Ar^1$ to $Ar^5$ each independently represents a hydrogen atom; or a substituted or unsubstituted aryl group having 6 to 30 ring carbon atoms, provided that $Ar^1$ to $Ar^5$ each is not bonded to the other group to form a ring, $R^1$ to $R^{20}$ each is independently selected from a hydrogen atom; a cyano group; a nitro group; a halogen atom; a substituted or unsubstituted alkyl group having 1 to 30 carbon atoms; a substituted or unsubstituted cycloalkyl group having 3 to 30 ring carbon atoms; a substituted or unsubstituted aralkyl group having 7 to 36 carbon atoms; a substituted or unsubstituted alkoxy group having 1 to 30 carbon atoms; a substituted or unsubstituted aryloxy group having 6 to 30 ring carbon atoms; a mono-, di- or tri-substituted silyl group having a substituent selected from a substituted or unsubstituted alkyl group having 1 to 30 carbon atoms and a substituted or unsubstituted aryl group having 6 to 30 ring carbon atoms; a substituted or unsubstituted haloalkyl group having 1 to 30 carbon atoms; and a substituted or unsubstituted aryl group having 6 to 30 ring carbon atoms, provided that $R^1$ to $R^{20}$ each is not bonded to the other group to form a ring, and

*a and *b each represents a bonding position on a benzene ring, provided that one of $R^{13}$ to $R^{16}$ represents a single bond bonded to *a and one of $R^8$ to $R^{12}$ represents a single bond bonded to *b.

In another embodiment, the present invention provides a material for an organic electroluminescence device, containing the compound (1).

In a further embodiment, the present invention provides an organic electroluminescence device including a cathode, an anode, and organic layers disposed between the cathode and the anode, wherein one of the organic layers is a light emitting layer, and at least one layer of the organic layers contains the compound (1).

In a still another embodiment, the present invention provides an electronic device including the above organic electroluminescence device.

Advantageous Effects of Invention

The compound (1) realizes an organic EL device having an improved performance, and more specifically, realizes the organic EL device capable of realizing a prolonged life and a high efficiency.

BRIEF DESCRIPTION OF DRAWINGS

FIG. 1 is a schematic view illustrating an example of a layer configuration of an organic EL device according to an embodiment of the present invention.
FIG. 2 is a schematic view illustrating another example of a layer configuration of the organic EL device according to the embodiment of the present invention.

DESCRIPTION OF EMBODIMENTS

In the present specification, the word "XX to YY carbon atoms" in the expression "a substituted or unsubstituted ZZ group having XX to YY carbon atoms" indicates the number of carbon atoms when the ZZ group is unsubstituted, and do not include the number of carbon atoms of a substituent in the case of being substituted.

In the present specification, the word "XX to YY atoms" in the expression "a substituted or unsubstituted ZZ group having XX to YY atoms" indicates the number of atoms when the ZZ group is unsubstituted, and do not include the number of atoms of a substituent in the case of being substituted.

In the present specification, the word "unsubstituted ZZ group" in the case of the "substituted or unsubstituted ZZ group" indicates that a hydrogen atom in the ZZ group is not substituted with a substituent.

In the present specification, the "hydrogen atom" includes isotopes having different numbers of neutrons, that is, protium, deuterium, and tritium.

In the present specification, the number of "ring carbon atoms" indicate the number of carbon atoms among atoms constituting the ring itself in a compound with a structure in which the atoms are cyclically bonded (for example, a monocyclic compound, a condensed ring compound, a cross-linked compound, a carbocyclic compound, or a heterocyclic compound). When the ring is substituted with a substituent, carbon included in the substituent is not included in the ring carbon atoms. This is the same for "ring carbon atoms" to be described below unless otherwise specified. For example, a benzene ring has 6 ring carbon atoms, a naphthalene ring has 10 ring carbon atoms, a pyridine ring has 5 ring carbon atoms, and a furan ring has 4 ring carbon atoms. Also, when the benzene ring or the naphthalene ring is substituted with, for example, an alkyl group as a substituent, the number of carbon atoms in the alkyl group is not included in the number of ring carbon atoms. Also, when a fluorene ring is bonded to, for example, a fluorene ring as a substituent (including a spirofluorene ring), the number of carbon atoms of the fluorene ring as the substituent is not included in the number of ring carbon atoms.

In the present specification, the number of "ring atoms" indicate the number of atoms constituting the ring itself (for example, a single ring, a condensed ring, or a ring set) in a compound with a structure in which the atoms are cyclically bonded (for example, a monocyclic compound, a condensed ring compound, a cross-linked compound, a carbocyclic compound, or a heterocyclic compound). An atom not constituting a ring (for example, a hydrogen atom that terminates a bond of atoms constituting the ring) or an atom included in a substituent in the case where the ring is substituted with the substituent is not included in the number of ring atoms. This is the same for "ring atoms" to be described below unless otherwise specified. For example, a pyridine ring has 6 ring atoms, a quinazoline ring has 10 ring atoms, and a furan ring has 5 ring atoms. A hydrogen atom bonded to each ring carbon atom in the pyridine ring or the quinazoline ring or an atom constituting a substituent is not included in the number of ring atoms. Also, when a fluorene ring is bonded to, for example, a fluorene ring as a substituent (including a spirobifluorene ring), the number of atoms of the fluorene ring as the substituent is not included in the number of ring atoms.

In the present specification, the "aryl group" indicates a residue generated by removing one hydrogen atom bonded to an aromatic hydrocarbon ring, and does not include a cyclic aromatic group (a heteroaryl group) having one or more atoms other than carbon in the ring.

In the present specification, it can be said that a preferred embodiment (for example, compounds, various groups, and numerical ranges) may be arbitrarily combined with any other embodiment (for example, compounds, various groups, and numerical ranges), and also, a combination of preferred embodiments (including a more preferable embodiment, a further preferable embodiment, and a particularly preferable embodiment) is more preferred.

A compound (1) according to one embodiment of the present invention is represented by the formula (1).

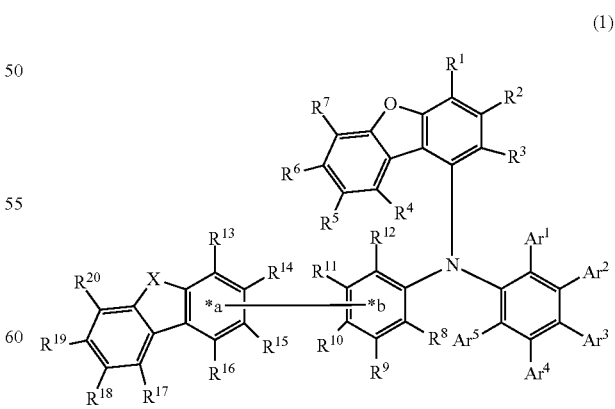

(1)

In one embodiment of the present invention, the compound (1) is preferably represented by the following formula (1-1).

(1-1)

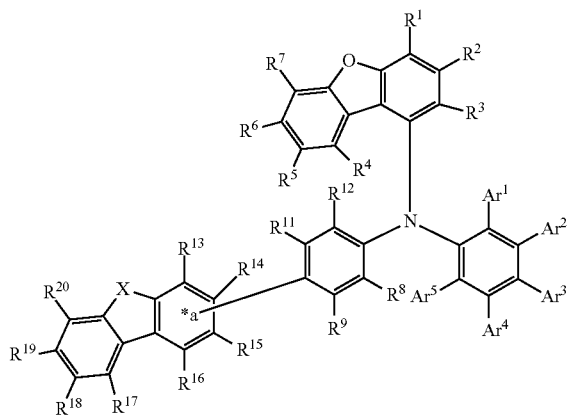

In one embodiment of the present invention, the compound (1) is more preferably represented by the following formula (1-2a) or the following formula (1-2b).

(1-2a)

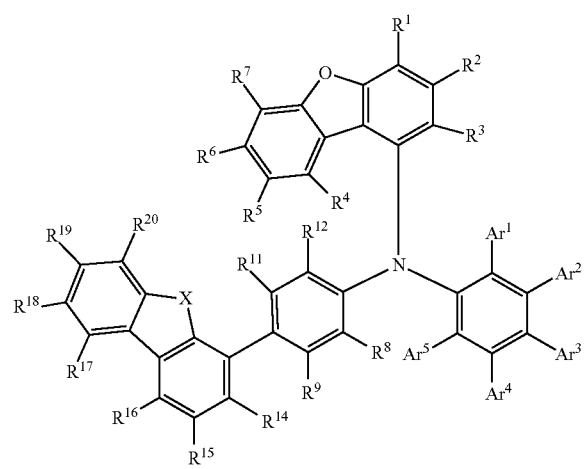

(1-2b)

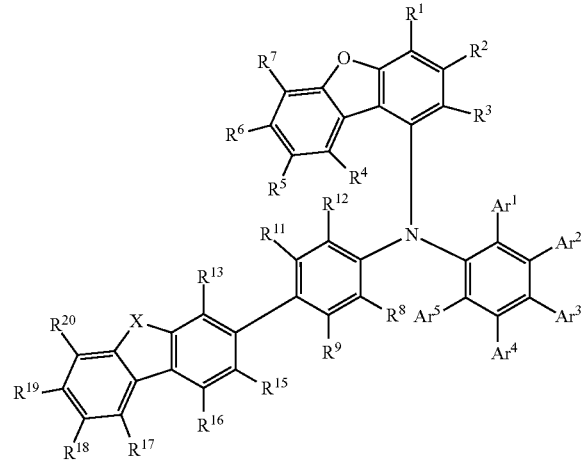

Next, descriptions will be made on each symbol in the formula (1), the formula (1-1), the formula (1-2a), and the formula (1-2b) (hereinafter, referred to as the formula (1) to the formula (1-2b)).

X represents an oxygen atom or a sulfur atom.

$Ar^1$ to $Ar^5$ each independently represents a hydrogen atom; or a substituted or unsubstituted aryl group having 6 to 30 ring carbon atoms. $Ar^1$ to $Ar^5$ are not bonded to each other to form a ring. Also, $Ar^1$ to $Ar^5$ and $R^1$ to $R^{20}$ described below are not bonded to each other to form a ring.

$R^1$ to $R^{20}$ each is independently selected from a hydrogen atom; a cyano group; a nitro group; a halogen atom; a substituted or unsubstituted alkyl group having 1 to 30 carbon atoms; a substituted or unsubstituted cycloalkyl group having 3 to 30 ring carbon atoms; a substituted or unsubstituted aralkyl group having 7 to 36 carbon atoms; a substituted or unsubstituted alkoxy group having 1 to 30 carbon atoms; a substituted or unsubstituted aryloxy group having 6 to 30 ring carbon atoms; a mono-, di- or tri-substituted silyl group having a substituent selected from a substituted or unsubstituted alkyl group having 1 to 30 carbon atoms and a substituted or unsubstituted aryl group having 6 to 30 ring carbon atoms; a substituted or unsubstituted haloalkyl group having 1 to 30 carbon atoms; and a substituted or unsubstituted aryl group having 6 to 30 ring carbon atoms. $R^1$ to $R^{20}$ are not bonded to each other to form a ring.

*a and *b each represents a bonding position on a benzene ring. One of $R^{13}$ to $R^{16}$ represents a single bond bonded to *a. One of $R^8$ to $R^{12}$ represents a single bond bonded to *b.

In one embodiment of the present invention, in the formula (1-1), $R^{13}$ to $R^{16}$ which are not bonded to *a each represents a hydrogen atom.

Also, in one embodiment of the present invention, in the formula (1-2a), $R^{14}$ to $R^{20}$ each represents a hydrogen atom.

Also, in one embodiment of the present invention, in the formula (1-2b), $R^{13}$ and $R^{15}$ to $R^{20}$ each represents a hydrogen atom.

In one embodiment of the present invention, in the formula (1), $R^8$ to $R^{12}$ which are not bonded to *b each represents a hydrogen atom.

Also, in one embodiment of the present invention, in the formula (1) to the formula (1-2b), $R^8$, $R^9$, $R^{11}$, and $R^{12}$ each represents a hydrogen atom.

In one embodiment of the present invention, in the formula (1) to the formula (1-2b), $R^1$ to $R^7$ each represents a hydrogen atom.

In the substituted or unsubstituted aryl group having 6 to 30 ring atoms represented by $Ar^1$ to $Ar^5$, the aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

A phenyl group, a biphenylyl group, a terphenylyl group, a naphthyl group, a phenanthryl group, a benzophenanthryl group, a triphenylenyl group, a pyrenyl group, or a benzotriphenylenyl group is preferred, and a phenyl group, a biphenylyl group, a terphenylyl group, a naphthyl group, or a phenanthryl group is more preferred.

The terphenylyl group is 1,1':4',1"-terphenyl group, 1,1':3',1"-terphenyl group, or 1,1':2',1"-terphenyl group. Then, 1,1':4',1"-terphenyl-2-yl group, 1,1':4',1"-terphenyl-3-yl group, 1,1':4',1"-terphenyl-4-yl group, 1,1':3',1"-terphenyl- 2-yl group, 1,1':3',1"-terphenyl-3-yl group, 1,1':3',1"-terphenyl-4-yl group, 1,1':2',1"-terphenyl-2-yl group, 1,1':2',1"-terphenyl-3-yl group, 1,1':2',1"-terphenyl-4-yl group, or 1,1':3',1"-terphenyl-5'-yl group is preferred, and 1,1':4',1"-terphenyl-2-yl group, 1,1':4',1"-terphenyl-3-yl group, 1,1':4',1"-terphenyl-4-yl group, or 1,1':3',1"-terphenyl-5'-yl group is more preferred.

The naphthyl group includes a 1-naphthyl group or a 2-naphthyl group.

The phenanthryl group is a 1-, 2-, 3-, 4-, or 9-phenanthryl group, preferably a 2- or 9-phenanthryl group.

The triphenylenyl group is preferably a 2-triphenylenyl group.

The above substituted or unsubstituted aryl group having 6 to 30 ring carbon atoms may include an isomer group thereof if present.

It is preferable that at least one of $Ar^1$ to $Ar^5$ represents a substituted or unsubstituted aryl group having 6 to 30 ring carbon atoms. It is more preferable that one or two of $Ar^1$ to $Ar^5$ represent(s) a substituted or unsubstituted aryl group(s) having 6 to 30 ring carbon atoms, and the others represent hydrogen atoms, and it is further preferable that one of $Ar^1$ to $Ar^5$ represents a substituted or unsubstituted aryl group having 6 to 30 ring carbon atoms, and the others represent hydrogen atoms.

In one embodiment of the present invention, a benzene ring portion including $Ar^1$ to $Ar^5$ in the compound (1) is represented by the following formula (2a), (2b), (2c), (2d), (2e), (2f), (2g), (2h), or (2i).

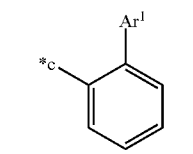
(2a)

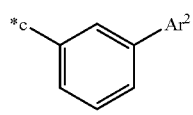
(2b)

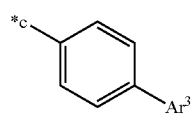
(2c)

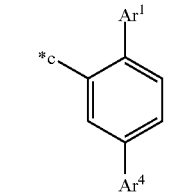
(2d)

(2e)

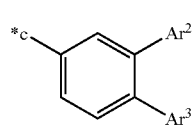
(2f)

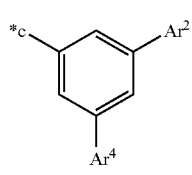
(2g)

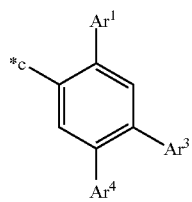
(2h)

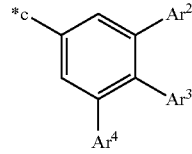
(2i)

In the formulas (2a) to (2i), each of $Ar^1$ to $Ar^4$ independently represents a substituted or unsubstituted aryl group having 6 to 30 ring carbon atoms.

*c represents a single bond bonded to a nitrogen atom.

In one preferred embodiment of the present invention, the benzene ring portion including $Ar^1$ to $Ar^5$ in the compound (1) has a structure of any one of the above formulas (2a) to (2g).

When the compound (1) has a structure of any one of the above formulas (2a) to (2c), in one embodiment, each of $Ar^1$, $Ar^2$, and $Ar^3$ is preferably an aryl group having 10 to 30 ring carbon atoms, and is more preferably selected from a phenyl group, a biphenylyl group, a terphenylyl group, a naphthyl group, and a phenanthryl group.

Also, when the compound (1) has a structure of any one of the above formulas (2a) to (2c), in one preferred embodiment, each of $Ar^1$, $Ar^2$, and $Ar^3$ is an aryl group having 6 to 30 ring carbon atoms, which has a substituent, more preferably, an aryl group having 6 to 30 ring carbon atoms, which has, as a substituent, an alkyl group having 1 to 18 carbon atoms or an aryl group having 6 to 18 ring carbon atoms.

When the compound (1) has a structure of the above formulas (2d) to (2g), in one embodiment, two of $Ar^1$ to $Ar^4$ are aryl groups having 6 to 30 ring carbon atoms, and preferably two of $Ar^1$ to $Ar^4$ are the same.

In the formula (1) to the formula (1-2b), and the formula (2d) to the formula (2i), when two or more of $Ar^1$ to $Ar^5$ are substituted or unsubstituted aryl groups having 6 to 30 ring carbon atoms, they may have the same structure or different structures.

Examples of the halogen atom that may be $R^1$ to $R^{20}$ include a fluorine atom, a chlorine atom, a bromine atom, and an iodine atom.

The alkyl group having 1 to 30 carbon atoms which may be $R^1$ to $R^{20}$ is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group, preferably, a methyl group, an ethyl group, an n-propyl group, an isopropyl group, an n-butyl group, an isobutyl group, an s-butyl group, a t-butyl group, or a pentyl group, more preferably, a methyl group, an ethyl group, an n-propyl group, an isopropyl group, an n-butyl group, an isobutyl group, an s-butyl group, or a t-butyl group, and further preferably, a methyl group or a t-butyl group.

The above alkyl group having 1 to 30 carbon atoms may include an isomer group thereof if present.

The cycloalkyl group having 3 to 30 ring carbon atoms which may be $R^1$ to $R^{20}$ is, for example, a cyclopropyl group, a cyclobutyl group, a cyclopentyl group, a cyclohexyl group, or a cycloheptyl group, preferably, a cyclopentyl group or a cyclohexyl group.

The above cycloalkyl group having 3 to 30 ring carbon atoms may include an isomer group thereof if present.

In the aralkyl group having 7 to 36 carbon atoms which may be $R^1$ to $R^{20}$, the aryl moiety of the aralkyl group having 7 to 36 carbon atoms is selected from aryl groups having 6 to 30 (preferably 6 to 25, more preferably 6 to 18) ring carbon atoms, and the alkyl moiety is selected from alkyl groups having 1 to 30 (preferably 1 to 18, more preferably 1 to 8) carbon atoms. The aralkyl group having 7 to 36 carbon atoms is, for example, a benzyl group, a phenethyl group, or a phenylpropyl group, and a benzyl group is preferred.

The above aralkyl group having 7 to 36 carbon atoms may include an isomer group thereof if present.

In the alkoxy group having 1 to 30 carbon atoms which may be $R^1$ to $R^{20}$, the alkyl moiety of the alkoxy group having 1 to 30 carbon atoms is selected from the above substituted or unsubstituted alkyl groups having 1 to 30 (preferably 1 to 18, more preferably 1 to 8) carbon atoms. The alkoxy group having 1 to 30 carbon atoms is, for example, a t-butoxy group, a propoxy group, an ethoxy group, or a methoxy group, preferably, an ethoxy group or a methoxy group, and more preferably, a methoxy group.

The above alkoxy group having 1 to 30 carbon atoms may include an isomer group thereof if present.

In the aryloxy group having 6 to 30 ring carbon atoms which may be $R^1$ to $R^{20}$, the aryl moiety of the aryloxy group having 6 to 30 ring carbon atoms is selected from aryl groups having 6 to 30 (preferably 6 to 25, more preferably 6 to 18) ring carbon atoms. The aryloxy group having 6 to 30 ring carbon atoms is, for example, a terphenyloxy group, a biphenyloxy group, or a phenoxy group, preferably, a biphenyloxy group or a phenoxy group, and more preferably, a phenoxy group.

The above aryloxy group having 6 to 30 ring carbon atoms may include an isomer group thereof if present.

The substituent included in the mono-, di- or tri-substituted silyl group that may be $R^1$ to $R^{20}$ is selected from alkyl groups having 1 to 30 (preferably 1 to 18, more preferably 1 to 8) carbon atoms, and the above aryl groups having 6 to 30 (preferably 6 to 25, more preferably 6 to 18) ring carbon atoms. A tri-substituted silyl group is preferred, and for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group is more preferred.

The above mono-, di- or tri-substituted silyl group may include an isomer group thereof if present.

The haloalkyl group having 1 to 30 carbon atoms which may be $R^1$ to $R^{20}$ is a group obtained when at least one hydrogen atom (preferably 1 to 7 hydrogen atoms, or all hydrogen atoms) of the alkyl group having 1 to 30 (preferably 1 to 18, more preferably 1 to 8) carbon atoms is substituted with an halogen atom(s). The halogen atom is selected from a fluorine atom, a chlorine atom, a bromine atom, and an iodine atom, and is preferably a fluorine atom. As for the haloalkyl group, a fluoroalkyl group having 1 to 30 (preferably 1 to 18, more preferably 1 to 8) carbon atoms is preferred, a heptafluoropropyl group, a pentafluoroethyl group, a 2,2,2-trifluoroethyl group, or a trifluoromethyl group is more preferred, a pentafluoroethyl group, a 2,2,2-trifluoroethyl group, or a trifluoromethyl group is further preferred, and a trifluoromethyl group is particularly preferred.

The above haloalkyl group having 1 to 30 carbon atoms may include an isomer group thereof if present.

The aryl group having 6 to 30 ring carbon atoms which may be $R^1$ to $R^{20}$ is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

A phenyl group, a biphenylyl group, a terphenylyl group, or a naphthyl group is preferred, and a phenyl group, or a naphthyl group is more preferred.

In the definition of $Ar^1$ to $Ar^5$ and $R^1$ to $R^{20}$, in the case of "substituted or unsubstituted," an arbitrary substituent is at least one substituent A selected from the group consisting of: a cyano group; a halogen atom; an alkyl group having 1 to 30, preferably 1 to 18, more preferably 1 to 6, and particularly preferably 1 to 3 carbon atoms; a cycloalkyl group having 3 to 30, preferably 3 to 10, more preferably 3 to 8, and further preferably 5 or 6 ring carbon atoms; an aralkyl group having 7 to 36, preferably 7 to 26, and more preferably 7 to 20 carbon atoms; an alkoxy group having 1 to 30, preferably 1 to 18, more preferably 1 to 6, and particularly preferably 1 to 3 carbon atoms; an aryloxy group having 6 to 30, preferably 6 to 25, more preferably 6 to 18, and particularly preferably 6 to 10 ring carbon atoms; a mono-, di- or tri-substituted silyl group having a substituent selected from an alkyl group having 1 to 30, preferably 1 to 18, more preferably 1 to 6, and particularly preferably 1 to 3 carbon atoms, and an aryl group having 6 to 30, preferably 6 to 25, more preferably 6 to 18, and particularly preferably 6 to 10 ring carbon atoms; a haloalkyl group having 1 to 30, preferably 1 to 18, more preferably 1 to 8, and particularly preferably 1 to 3 carbon atoms; an aryl group having 6 to 30, preferably 6 to 25, more preferably 6 to 18, and particularly preferably 6 to 10 ring carbon atoms; a boryl group substituted with an aryl group having 6 to 30, preferably 6 to 25, more preferably 6 to 18, and particularly preferably 6 to 10 ring carbon atoms; an alkylthio group having 1 to 30, preferably 1 to 18, more preferably 1 to 6, and particularly preferably 1 to 3 carbon atoms; and an arylthio group having 6 to 30, preferably 6 to 25, more preferably 6 to 18, and particularly preferably 6 to 10 ring carbon atoms. The above substituent A may be further substituted with an arbitrary substituent such as a substituent A.

The same groups as those described for $R^1$ to $R^{20}$ may be exemplified as the alkyl group having 1 to 30 carbon atoms, the cycloalkyl group having 3 to 30 ring carbon atoms, the aralkyl group having 7 to 36 carbon atoms, the alkoxy group having 1 to 30 carbon atoms, the aryloxy group having 6 to 30 ring carbon atoms, the mono-, di- or tri-substituted silyl group having a substituent selected from aryl groups having 1 to 30 carbon atoms, the haloalkyl group having 1 to 30 carbon atoms, and the aryl group having 6 to 30 ring carbon atoms which may be the substituent A.

The substituent included in the boryl group which may be the above substituent A is selected from aryl groups having 6 to 30, preferably 6 to 25, and more preferably 6 to 18 ring carbon atoms. The boryl group substituted with the aryl group having 6 to 30 ring carbon atoms is, for example, a diphenylboryl group.

In the alkylthio group having 1 to 30 carbon atoms which may be the above substituent A, the alkyl group moiety of the alkylthio group having 1 to 30 carbon atoms is selected from alkyl groups having 1 to 30, preferably 1 to 18, and more preferably 1 to 8 carbon atoms. The alkylthio group is, for example, a methylthio group, an ethylthio group, a propylthio group, or a butylthio group.

In the arylthio group having 6 to 30 ring carbon atoms which may be the above substituent A, the aryl moiety of the arylthio group having 6 to 30 ring carbon atoms is selected from aryl groups having 6 to 30, preferably 6 to 25, and more preferably 6 to 18 ring carbon atoms. The arylthio group is, for example, a phenylthio group, or a tolylthio group.

It is presumed that the compound represented by each of the above described formulas becomes a compound that is very stable to electrons or excitons and has a high barrier ability in confining the excitons in a light emitting layer because one dibenzofuranyl skeleton and a phenyl group are directly connected to an amine skeleton in a form having steric hindrance, and another dibenzofuranyl skeleton or dibenzothienyl skeleton is connected to the amine skeleton via a phenylene group.

In one preferred embodiment of the present invention, none of $Ar^1$ to $Ar^5$, $R^1$ to $R^7$, $R^8$ to $R^{12}$ except for one which represents the single bond bonded to *b, $R^{13}$ to $R^{16}$ except for one which represents the single bond bonded to *a, and $R^{17}$ to $R^{20}$ have any substituent.

Also, in one preferred embodiment of the present invention, all of $R^1$ to $R^7$, $R^8$ to $R^{12}$ except for one which represents the single bond bonded to *b, $R^{13}$ to $R^{16}$ except for one which represents the single bond bonded to *a, and $R^{17}$ to $R^{20}$, each is a hydrogen atom.

As described above, the "hydrogen atom" used in the present specification includes a protium atom, a deuterium atom, and a tritium atom. Accordingly, the compound (1) may contain a naturally occurring deuterium atom.

Also, by using a deuterated compound for a part or all of raw material compounds, a deuterium atom may be intentionally introduced into the compound (1). Accordingly, in one embodiment of the present invention, the compound (1) contains at least one deuterium atom. That is, the compound (1) may be a compound which is represented by the formula (1) or a formula of a preferred embodiment thereof, and in which at least one of hydrogen atoms included in the compound is a deuterium atom.

Also, in one embodiment of the present invention, in the formula (1), at least one hydrogen atom selected from (i) hydrogen atoms represented by $R^1$ to $R^7$, $R^8$ to $R^{12}$ except for one which represents the single bond bonded to *b, $R^{13}$ to $R^{16}$ except for one which represents the single bond bonded to *a, and $R^{17}$ to $R^{20}$, (ii) hydrogen atoms included in the alkyl group, the cycloalkyl group, the aralkyl group, the alkoxy group, the aryloxy group, the di- or tri-substituted silyl group, the haloalkyl group, and the aryl group which are represented by $R^1$ to $R^7$, $R^8$ to $R^{12}$ except for one which represents the single bond bonded to *b, $R^{13}$ to $R^{16}$ except for one which represents the single bond bonded to *a, and $R^{17}$ to $R^{20}$, (iii) hydrogen atoms represented by $Ar^1$ to $Ar^5$ and (iv) hydrogen atoms included in the aryl group represented by $Ar^1$ to $Ar^5$, is a deuterium atom.

In one embodiment of the present invention, the compound (1) contains deuterium. In this case, the deuteration ratio (the ratio of the number of deuterium atoms to the total number of hydrogen atoms in the compound (1)) depends on the deuteration ratio of used raw material compounds. Since it is usually difficult to make the deuteration ratio of all the used raw material compounds 100%, the deuteration ratio of the compound (1) is less than 100%, preferably 95% or less, more preferably 90% or less, and further preferably 80% or less.

In the case where the compound (1) contains deuterium, the deuteration ratio (the ratio of the number of deuterium atoms to the total number of hydrogen atoms in the compound (1)) is 1% or more, preferably 3% or more, more preferably 5% or more, and further preferably 10% or more.

The compound (1) may be a mixture containing a deuterated compound and a non-deuterated compound, or a mixture of two or more compounds having different deuteration ratios. The deuteration ratio of such a mixture (the ratio of the number of deuterium atoms to the total number of hydrogen atoms in the compound (1) included in the mixture) is 1% or more, preferably 3% or more, more preferably 5% or more, and further preferably 10% or more, and also, is less than 100%, preferably 95% or less, and more preferably 90% or less.

In one embodiment of the present invention, the compound (1) contains deuterium, in which at least one hydrogen atom selected from hydrogen atoms of the hydrogen atoms represented by $R^1$ to $R^7$, and hydrogen atoms included in the alkyl group, the cycloalkyl group, the aralkyl group, the alkoxy group, the aryloxy group, the di- or tri-substituted silyl group, the haloalkyl group, and the aryl group which are represented by $R^1$ to $R^7$ is a deuterium atom. The deuteration ratio (the ratio of the number of deuterium atoms to the number of all hydrogen atoms represented by $R^1$ to $R^7$, or all hydrogen atoms included in the alkyl group, the cycloalkyl group, the aralkyl group, the alkoxy group, the aryloxy group, the di- or tri-substituted silyl group, the haloalkyl group, and the aryl group which are represented by $R^1$ to $R^7$) is 1% or more, preferably 3% or more, more preferably 5% or more, and further preferably 10% or more, and also, less than 100%, preferably 95% or less, and more preferably 90% or less.

In one embodiment of the present invention, the compound (1) contains deuterium, in which at least one hydrogen atom selected from hydrogen atoms represented by $R^8$ to $R^{12}$ except for one which represents the single bond bonded to *b, and hydrogen atoms included in the alkyl group, the cycloalkyl group, the aralkyl group, the alkoxy group, the aryloxy group, the di- or tri-substituted silyl group, the haloalkyl group, and the aryl group which are represented by $R^8$ to $R^{12}$ except for one which represents the single bond bonded to *b is a deuterium atom. The deuteration ratio (the ratio of the number of deuterium atoms to the number of all hydrogen atoms represented by $R^8$ to $R^{12}$ except for one which represents the single bond bonded to *b or all hydrogen atoms included in the alkyl group, the cycloalkyl group, the aralkyl group, the alkoxy group, the aryloxy group, the di- or tri-substituted silyl group, the haloalkyl group, and the aryl group which are represented by $R^8$ to $R^{12}$ except for one which represents the single bond bonded to *b) is 1% or more, preferably 3% or more, more preferably 5% or more, and further preferably 10% or more, and also, less than 100%, preferably 95% or less, and more preferably 90% or less.

In one embodiment of the present invention, the compound (1) contains deuterium, in which at least one hydrogen atom selected from hydrogen atoms represented by $R^{13}$ to $R^{16}$ except for one which represents the single bond bonded to *a, and $R^{17}$ to $R^{20}$, and hydrogen atoms included in the alkyl group, the cycloalkyl group, the aralkyl group, the alkoxy group, the aryloxy group, the di- or tri-substituted silyl group, the haloalkyl group, and the aryl group which are represented by $R^{13}$ to $R^{16}$ except for one which represents the single bond bonded to *a, and $R^{17}$ to $R^{20}$ is a deuterium atom. The deuteration ratio (the ratio of the number of deuterium atoms to the number of all hydrogen atoms represented by $R^{13}$ to $R^{16}$ except for one which represents the single bond bonded to *a, and $R^{17}$ to $R^{20}$, or all hydrogen atoms included in the alkyl group, the cycloalkyl group, the aralkyl group, the alkoxy group, the aryloxy group, the di- or tri-substituted silyl group, the haloalkyl group, and the aryl group which are represented by $R^{13}$ to $R^{16}$ except for one which represents the single bond bonded to *a, and $R^{17}$ to $R^{20}$) is 1% or more, preferably 3% or more, more preferably 5% or more, and further preferably 10% or more, and also, less than 100%, preferably 95% or less, and more preferably 90% or less.

In one embodiment of the present invention, the compound (1) contains deuterium, in which at least one hydrogen atom selected from hydrogen atoms represented by $Ar^1$ to $Ar^5$, and hydrogen atoms included in the aryl group represented by $Ar^1$ to $Ar^5$ is a deuterium atom. The deuteration ratio (the ratio of the number of deuterium atoms to the number of all hydrogen atoms represented by $Ar^1$ to $Ar^5$, or all hydrogen atoms included in the aryl group represented by $Ar^1$ to $Ar^5$) is 1% or more, preferably 3% or more, more preferably 5% or more, and further preferably 10% or more, and also, less than 100%, preferably 95% or less, and more preferably 90% or less.

In a particularly preferred embodiment of the present invention, the compound (1) is selected from the following compound group.

Compound 1

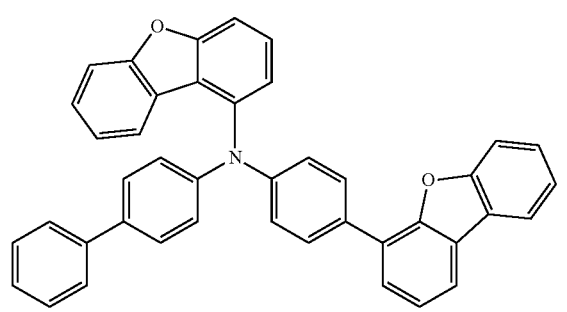

Compound 2

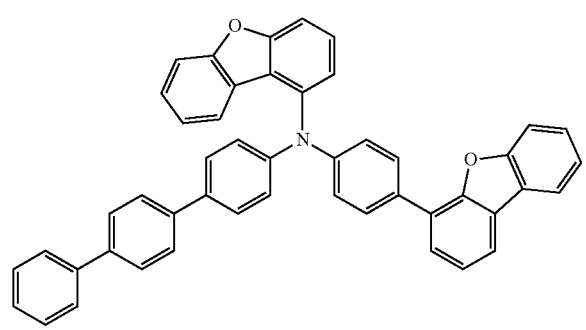

Compound 3

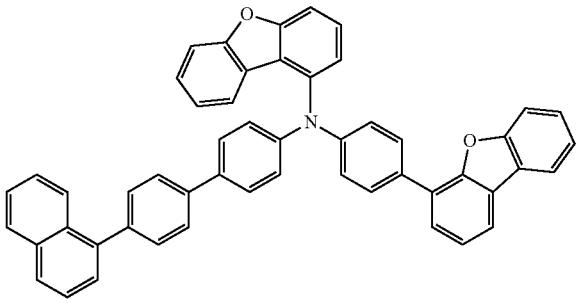

Compound 4

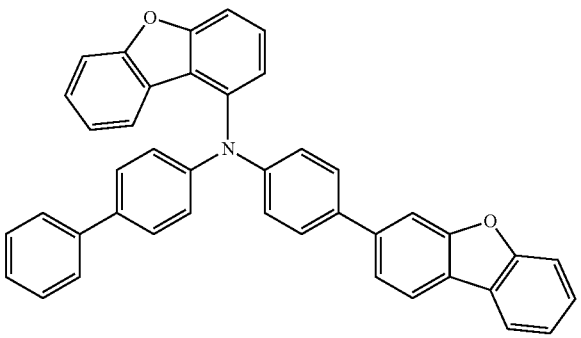

Compound 5

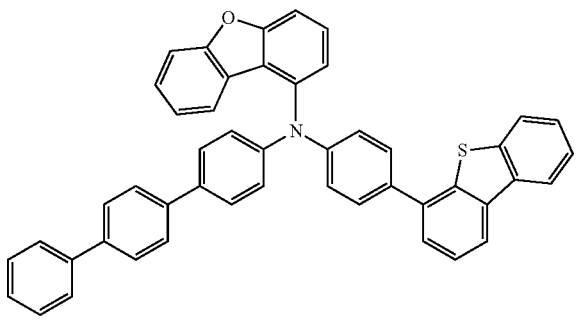

Compound 6

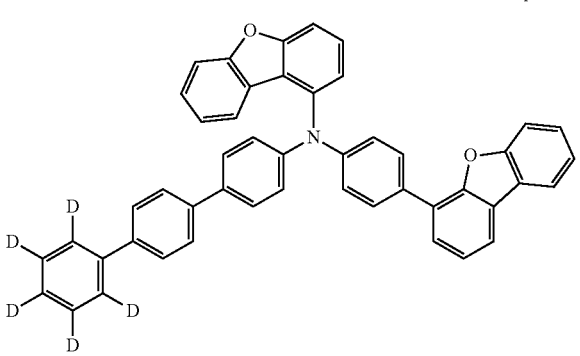

Specific examples of the compound according to the present invention are as follows, but are not particularly limited thereto.

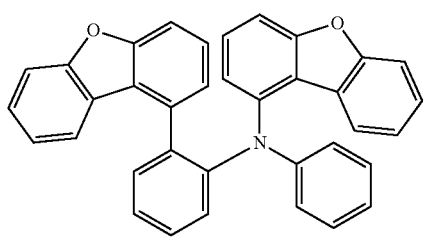
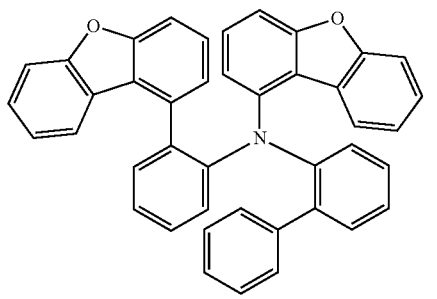
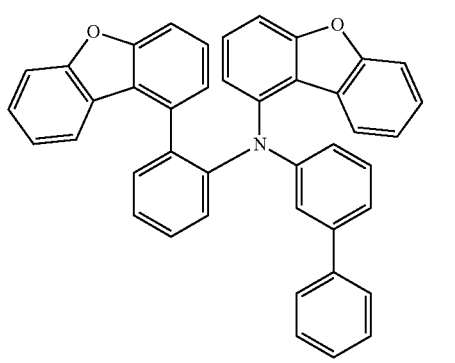
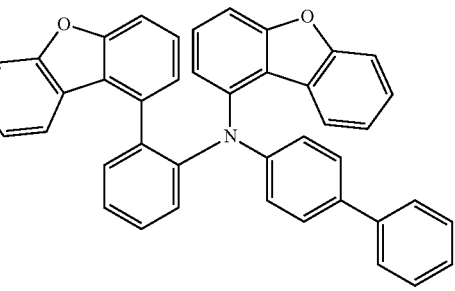
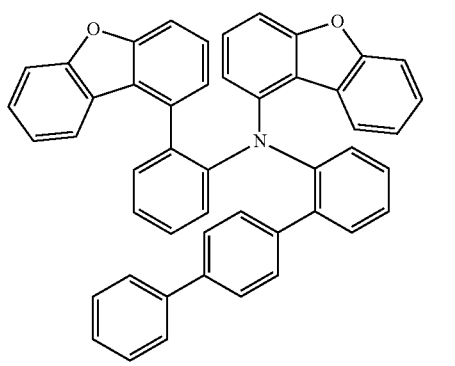
-continued
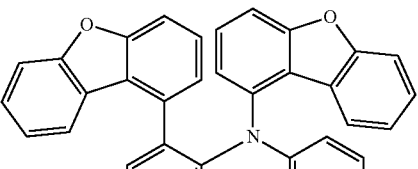
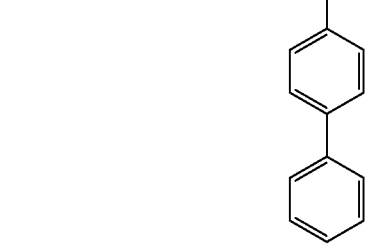
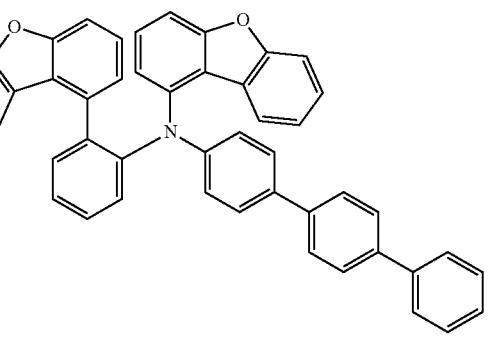
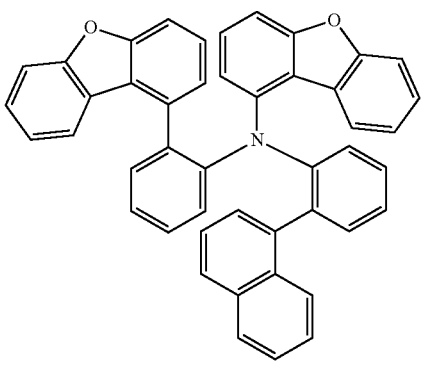
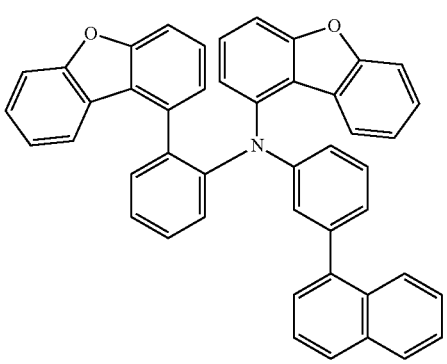

-continued
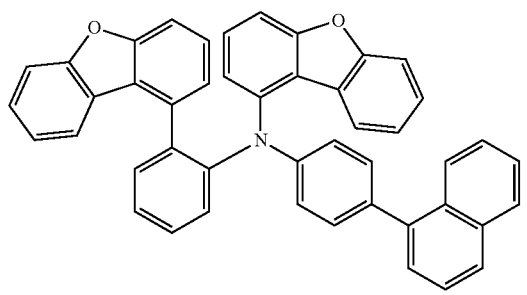
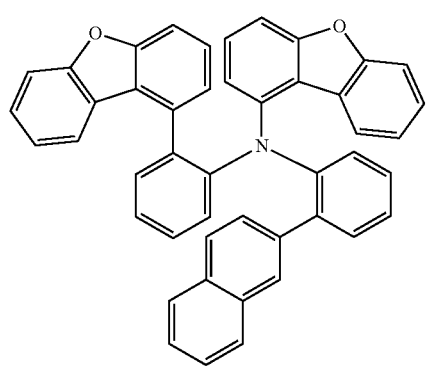
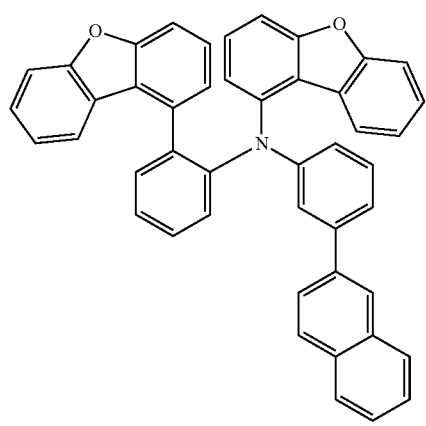
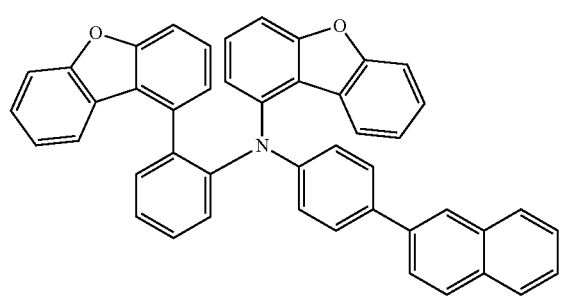
-continued
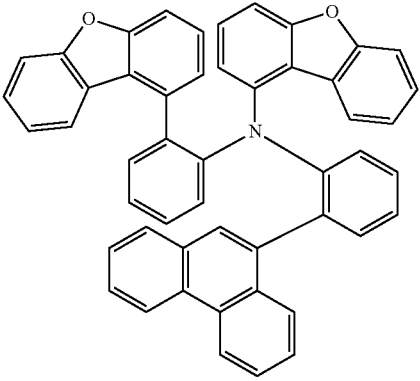
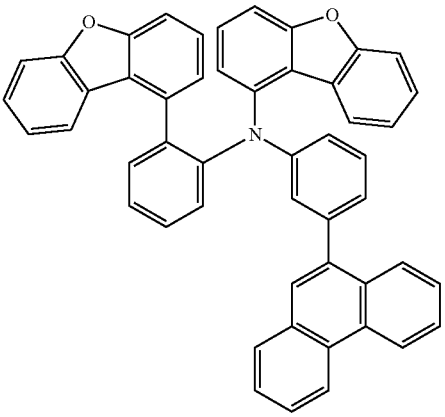
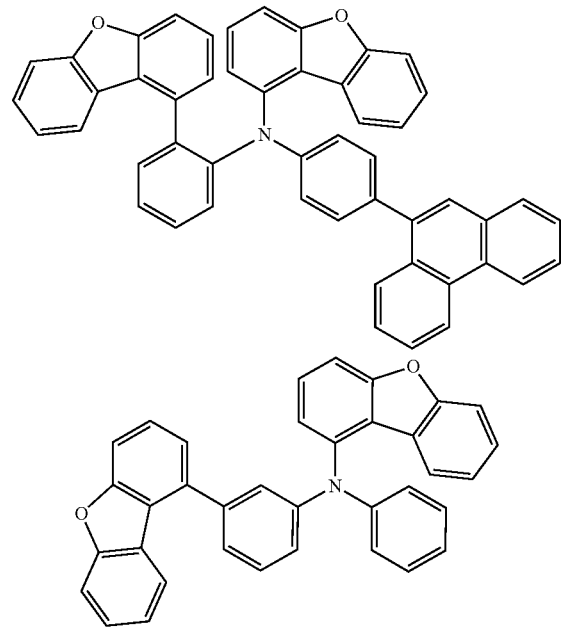
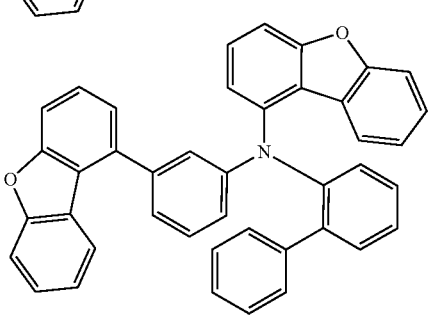

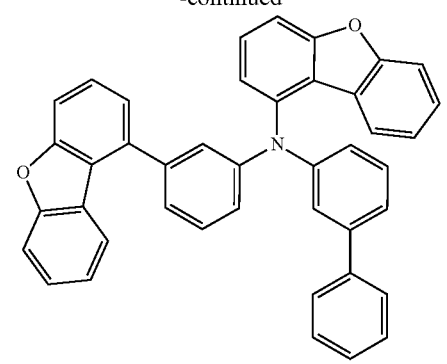
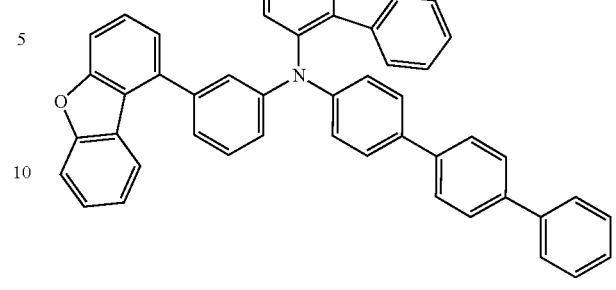
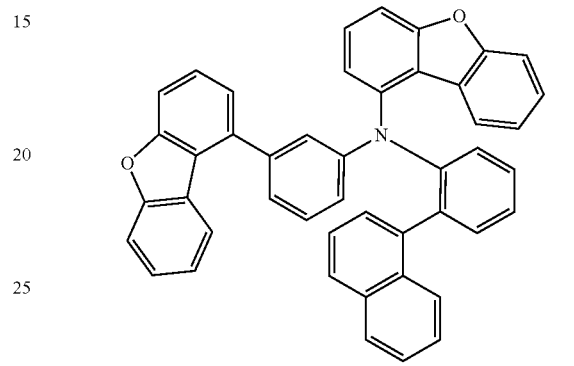
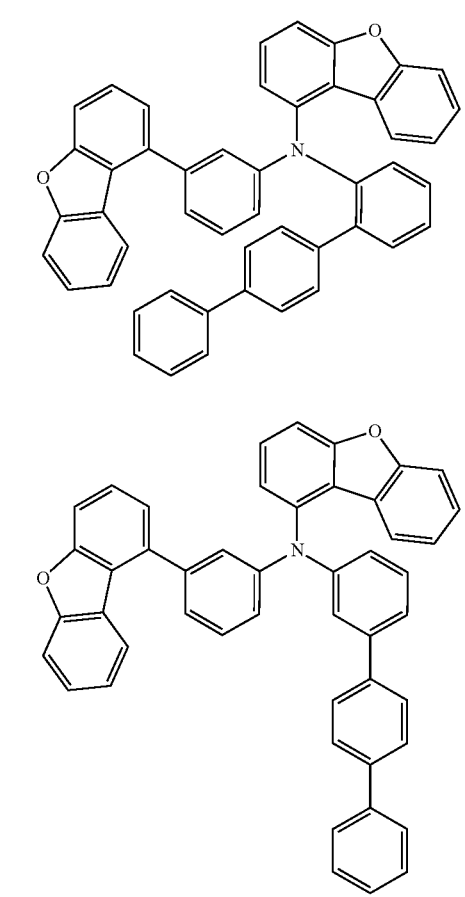
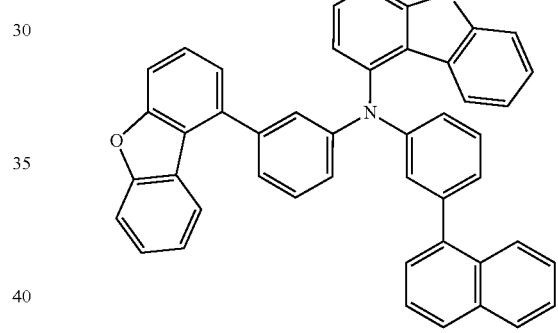
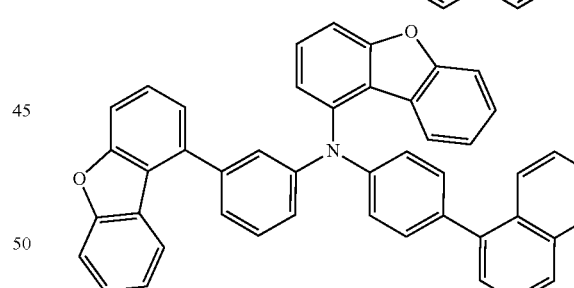
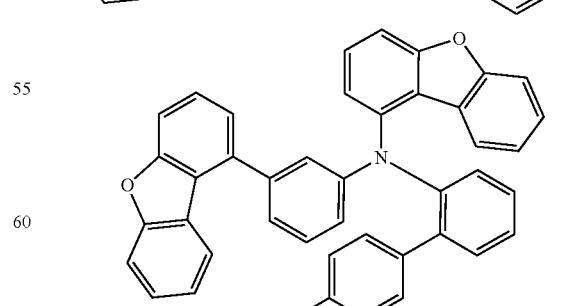
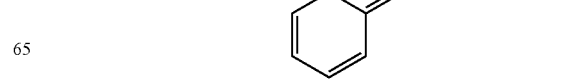

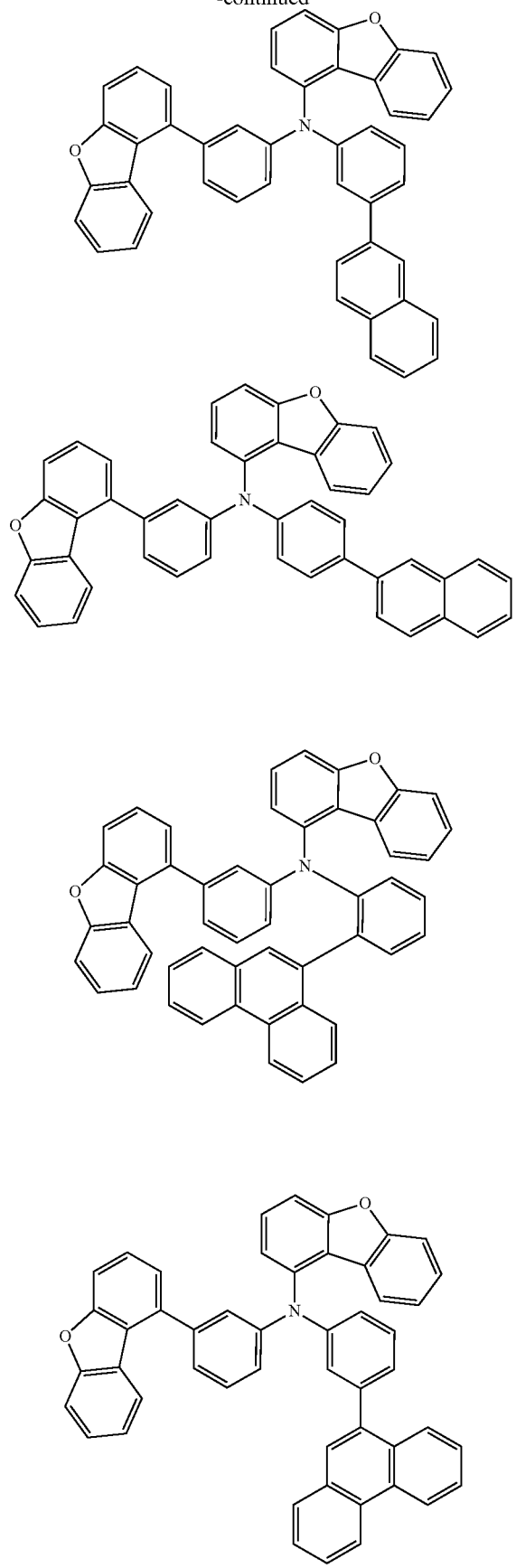
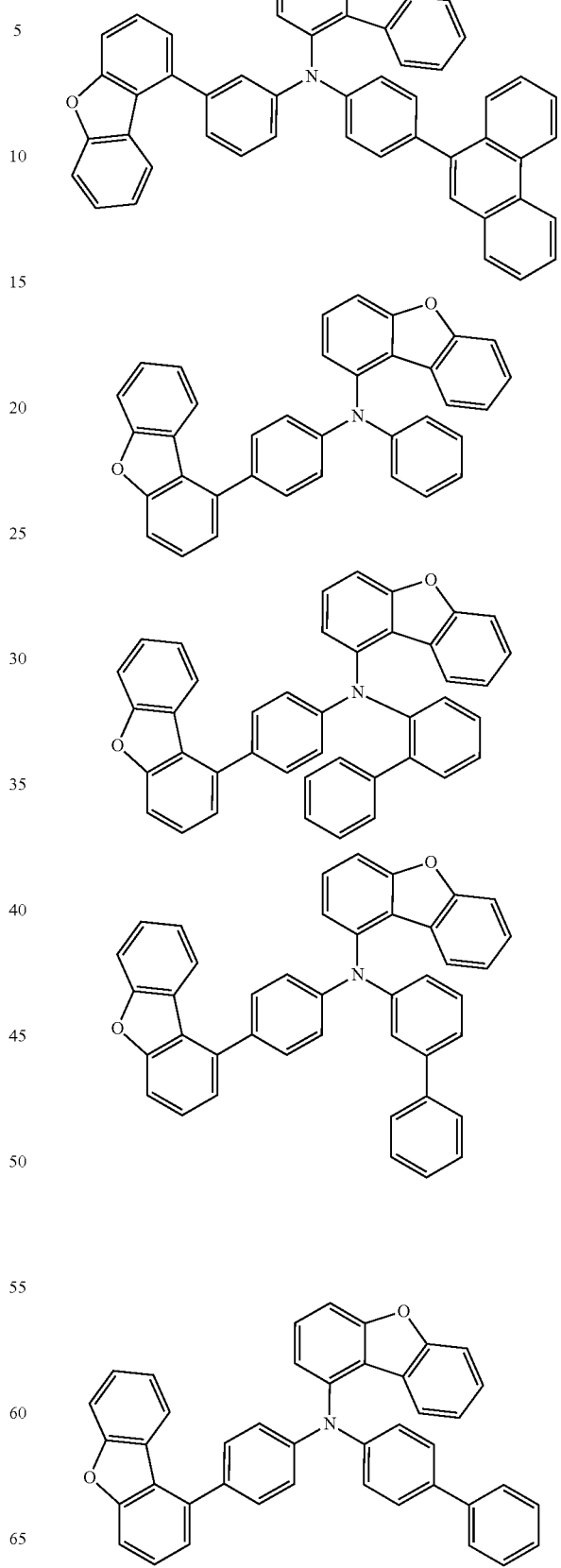

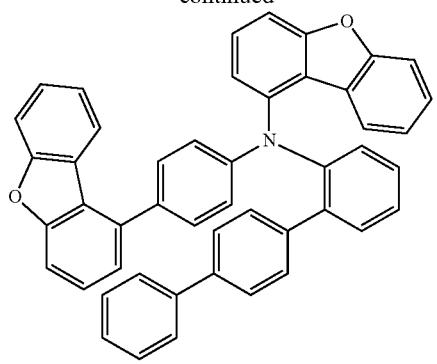
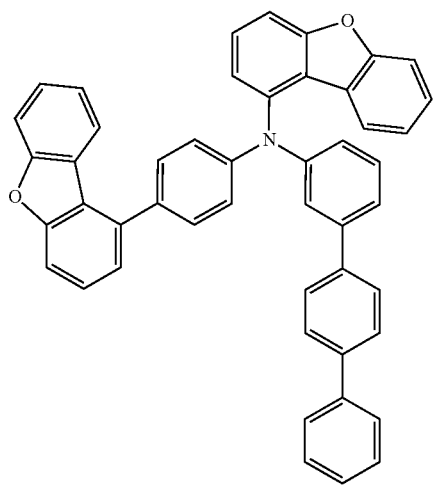
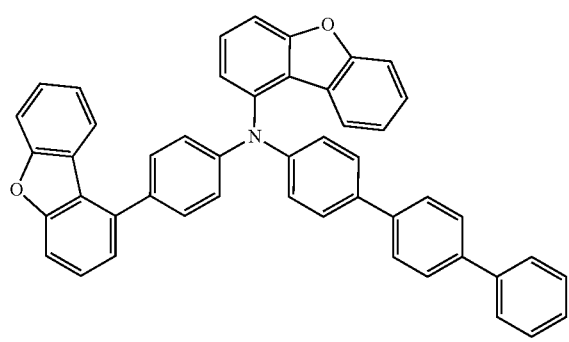
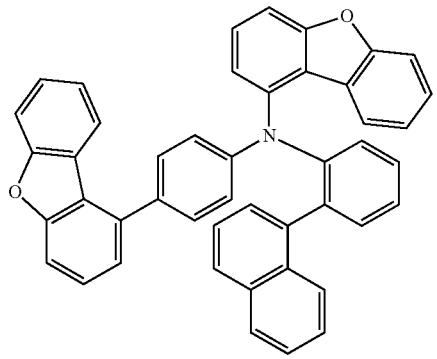
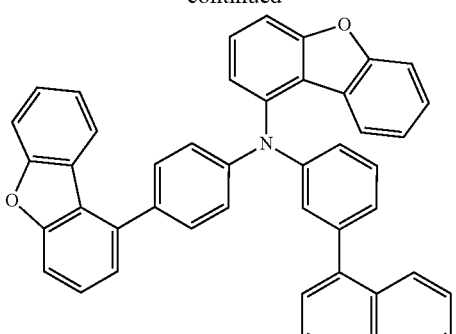
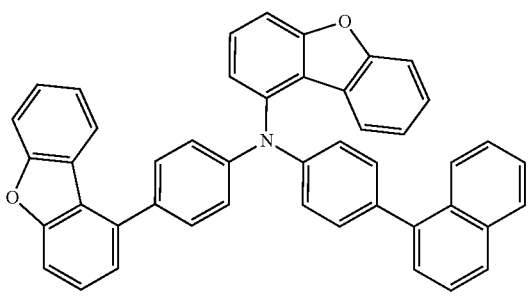
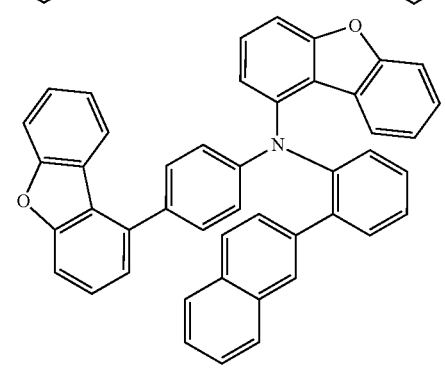
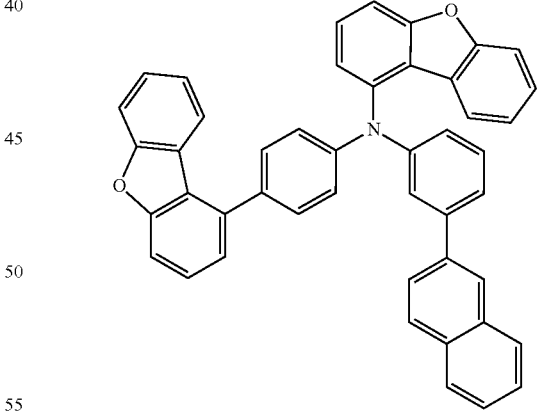
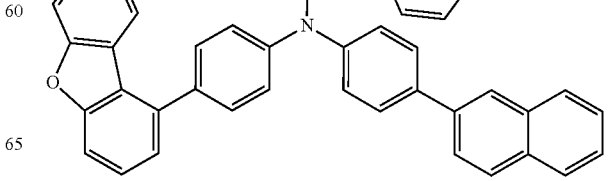

25
-continued
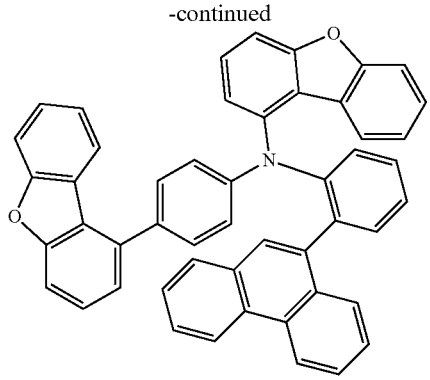
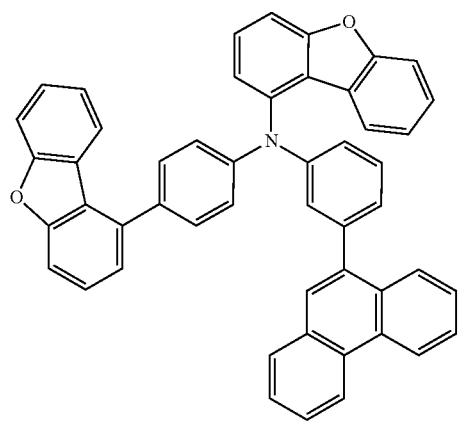
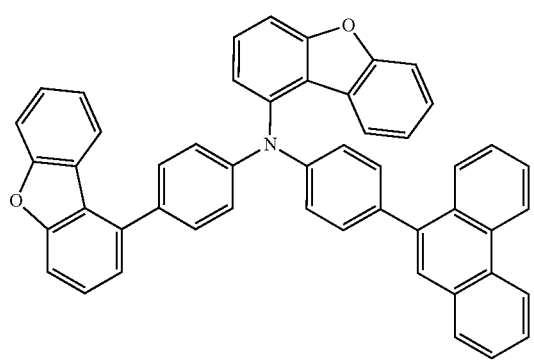
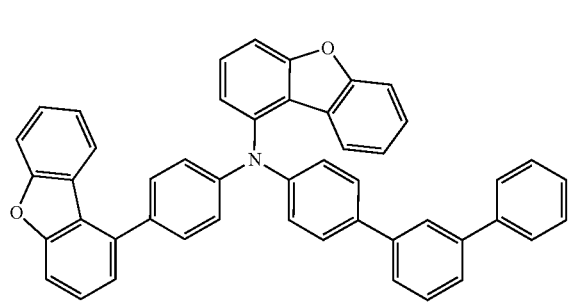
26
-continued
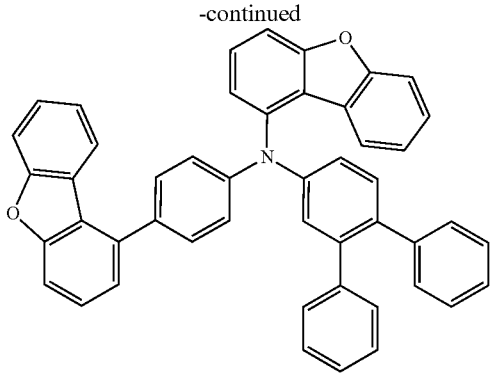
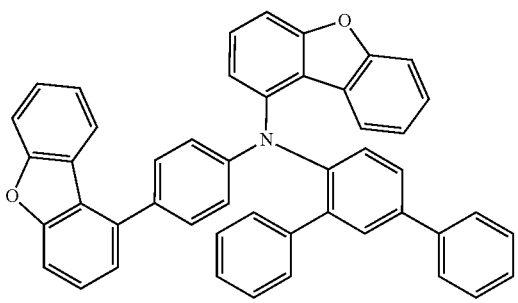
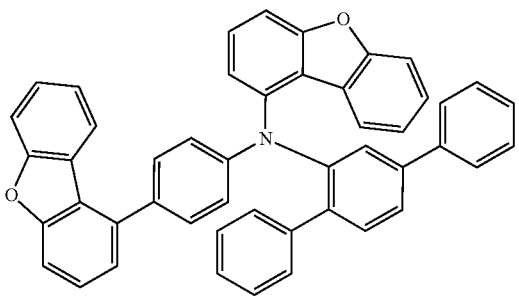
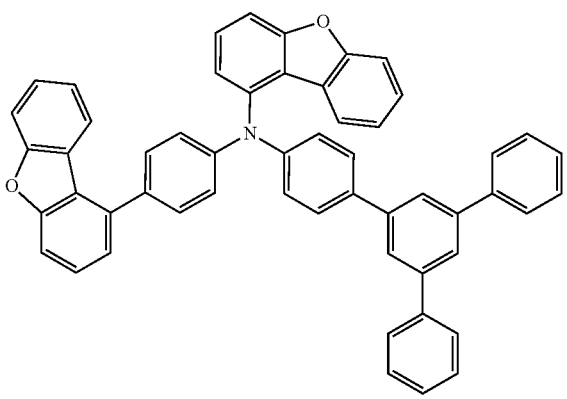

-continued
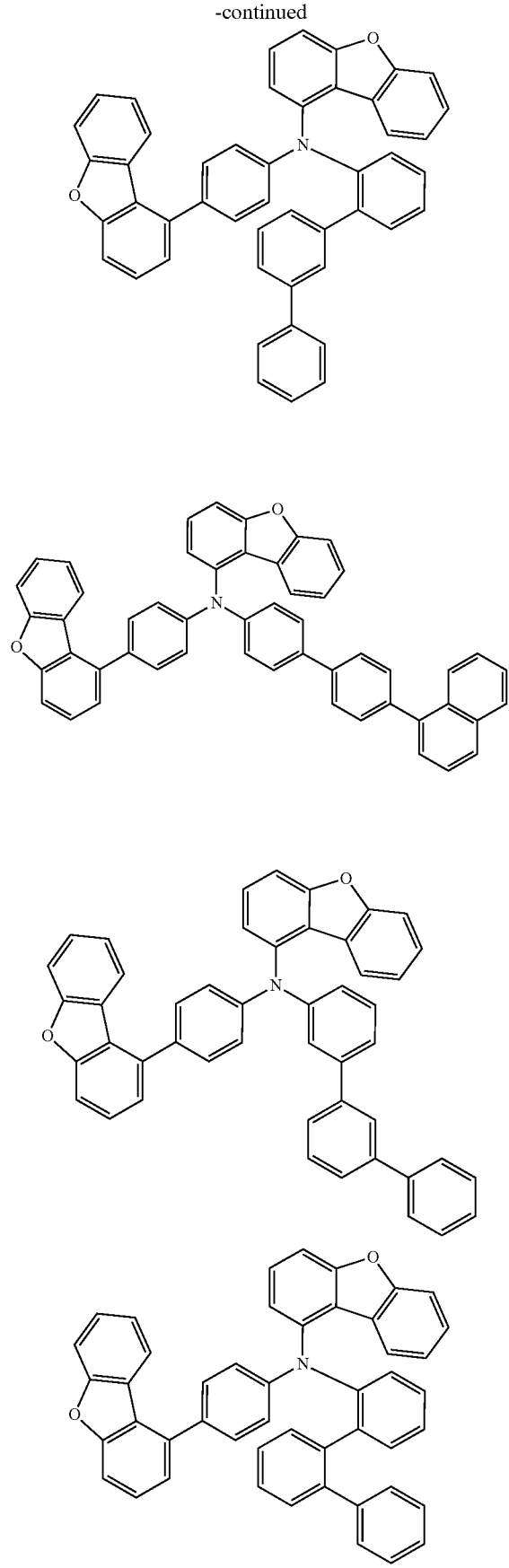
-continued
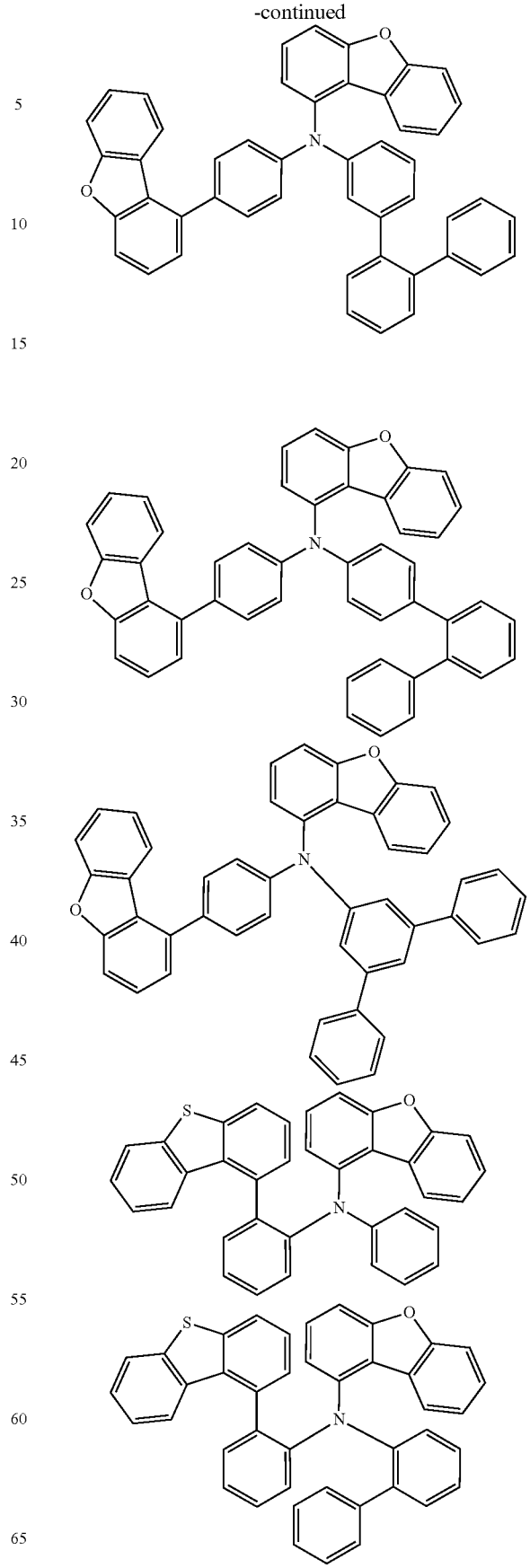

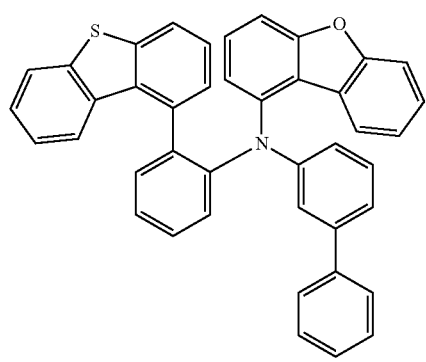
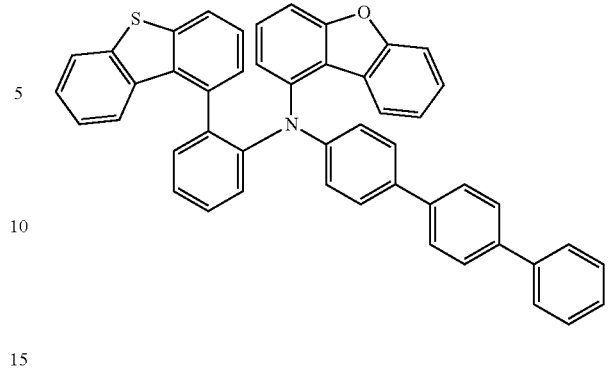
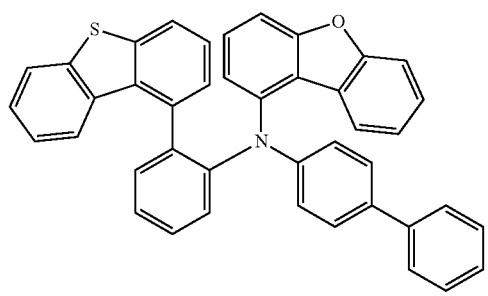
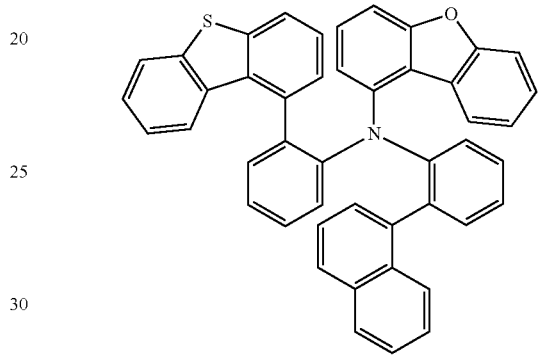
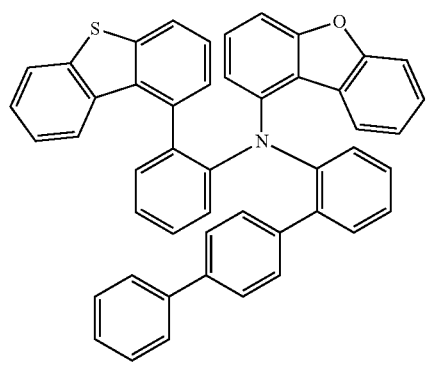
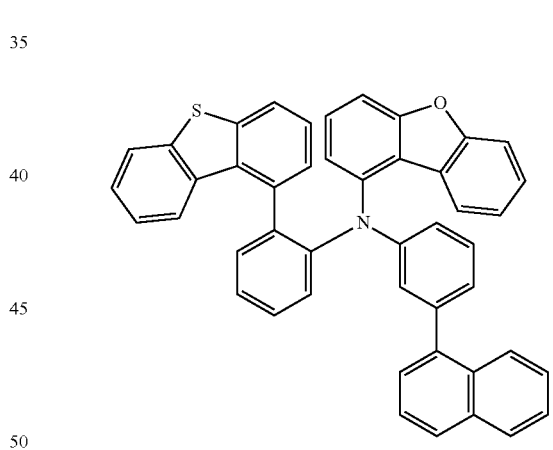
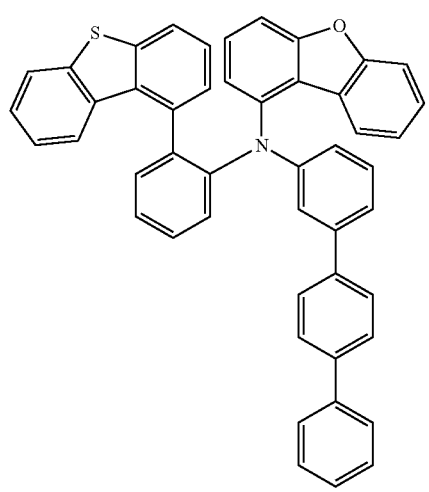
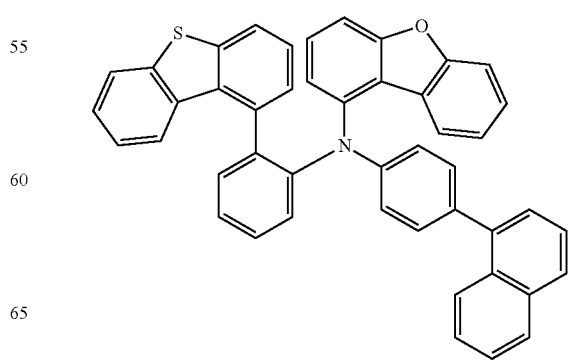

31
-continued
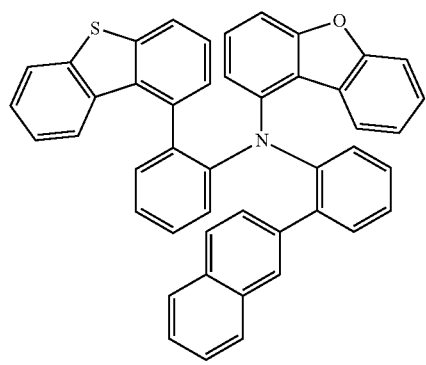
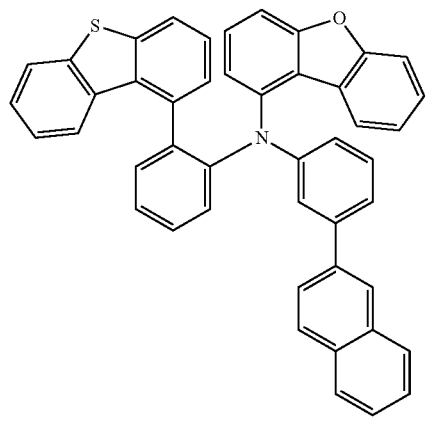
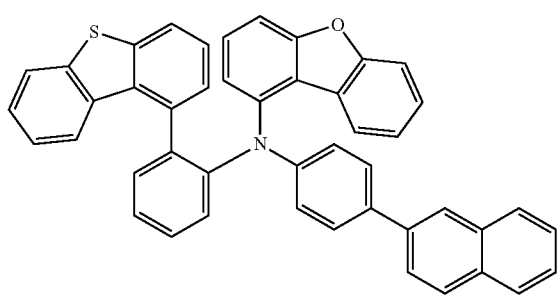
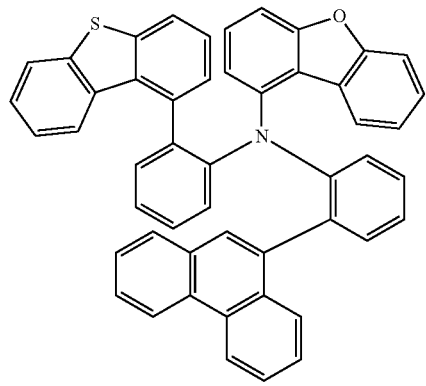
32
-continued
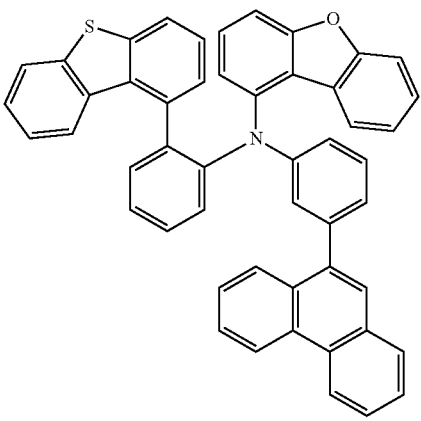
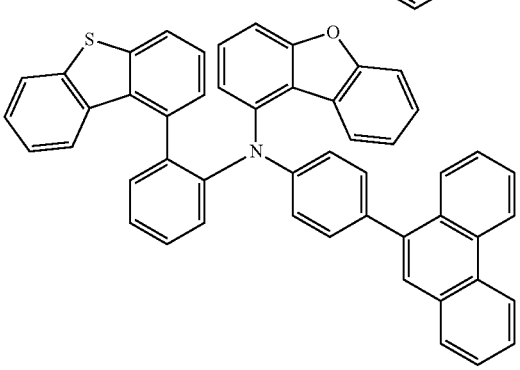
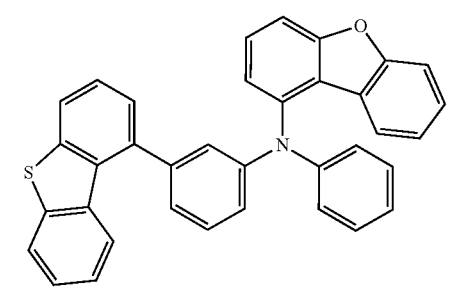
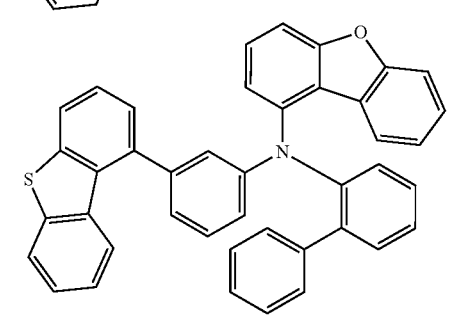
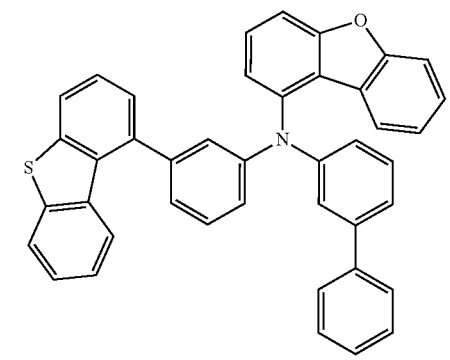

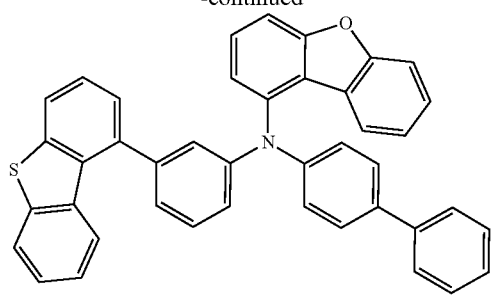
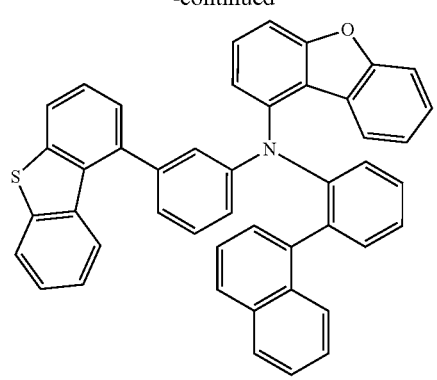
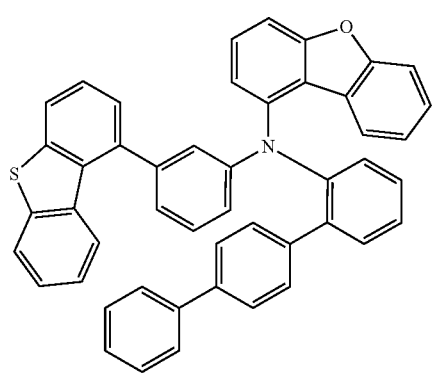
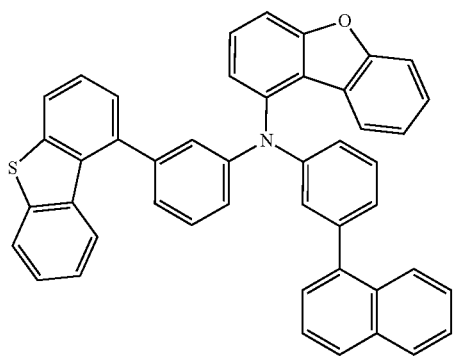
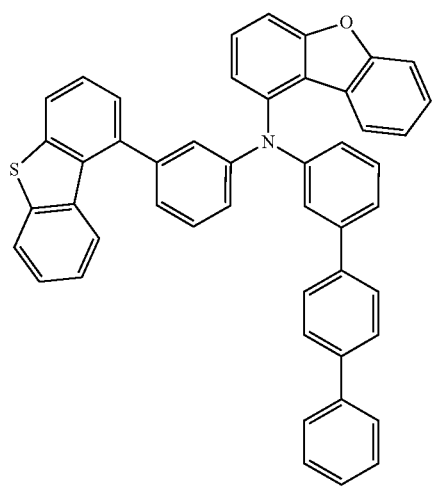
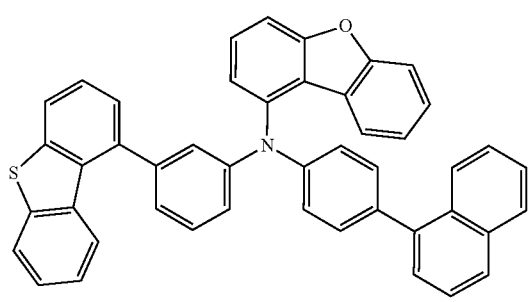
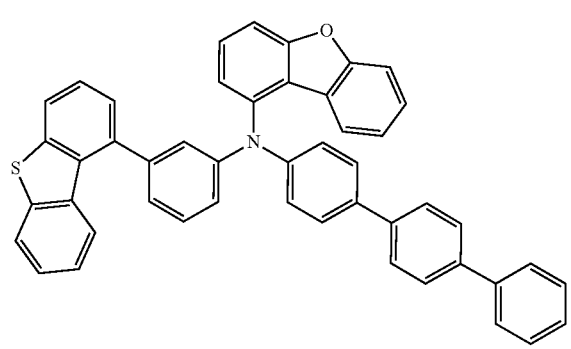
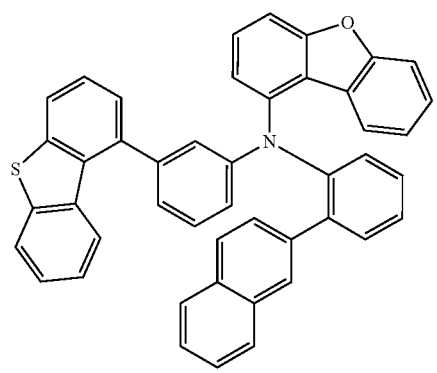

35
-continued
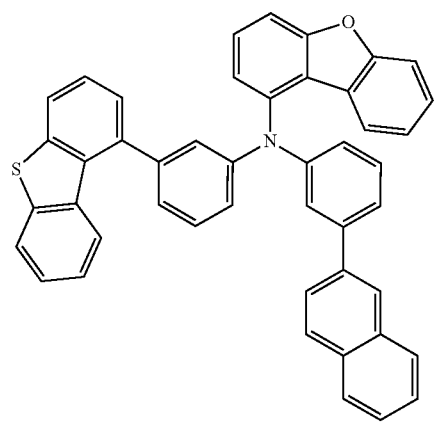
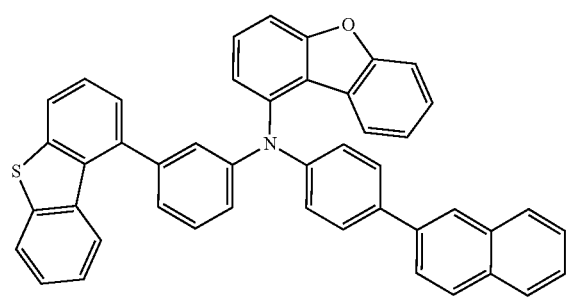
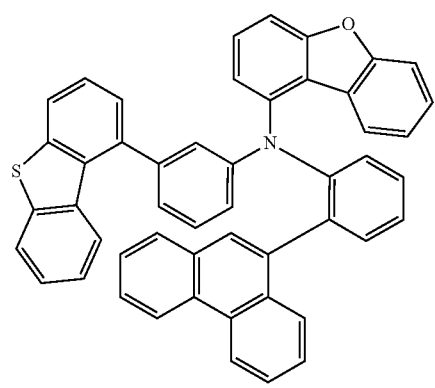
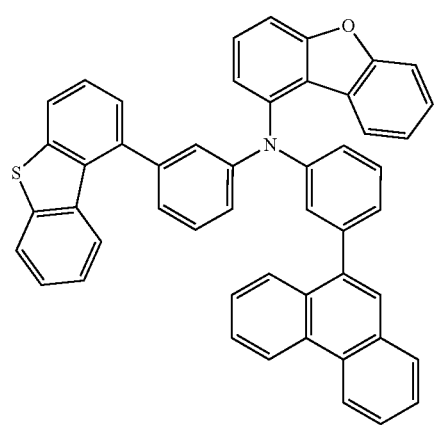
36
-continued
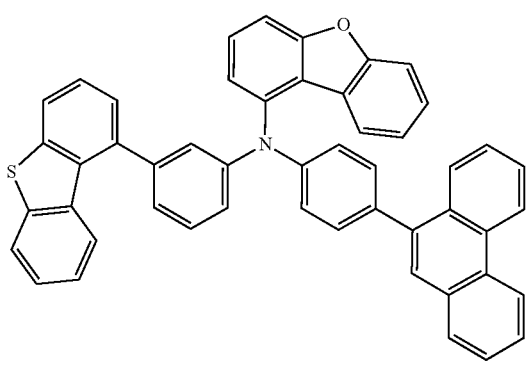
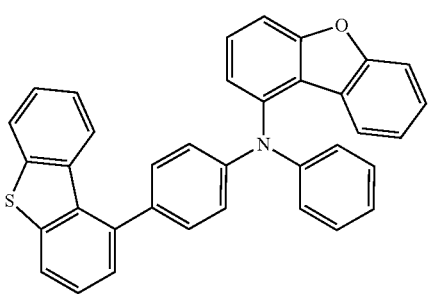
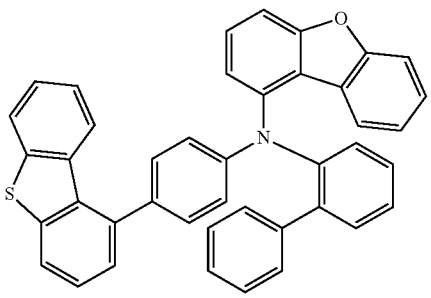
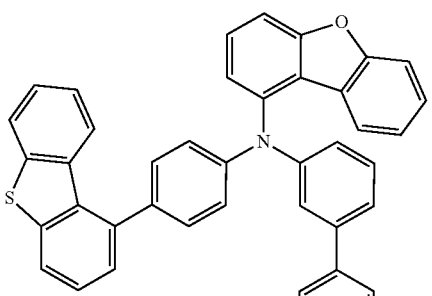
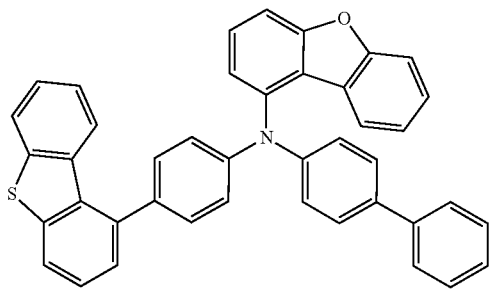

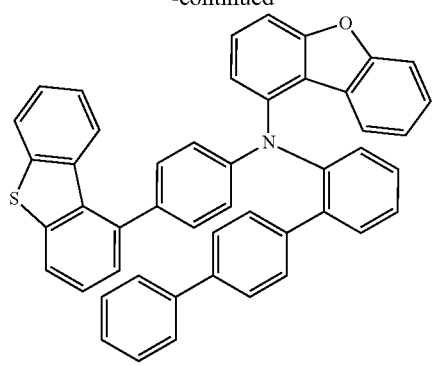
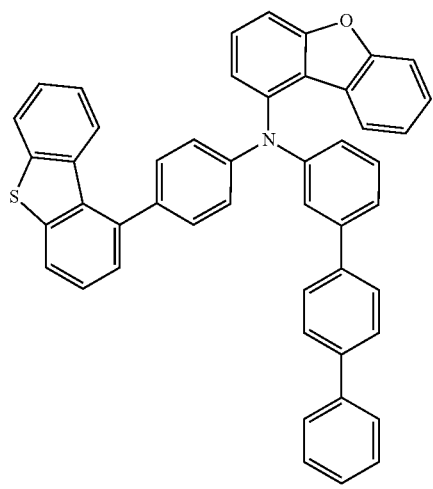
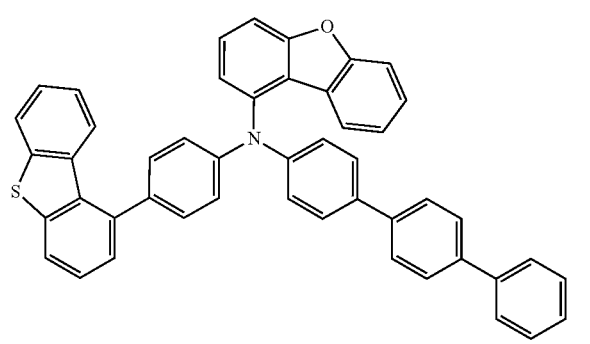
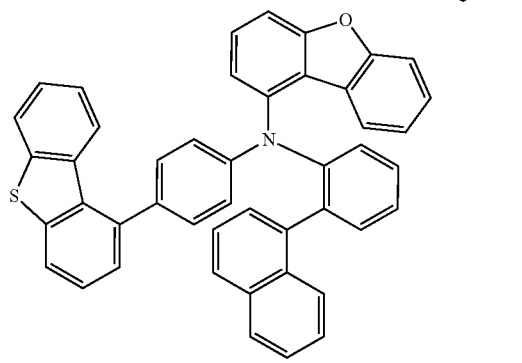
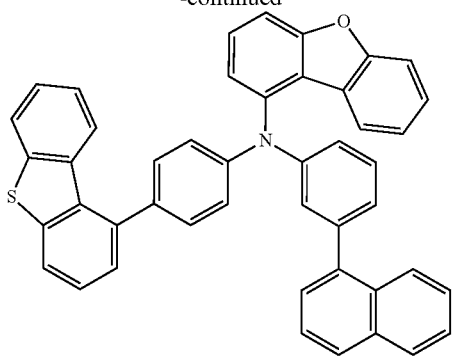
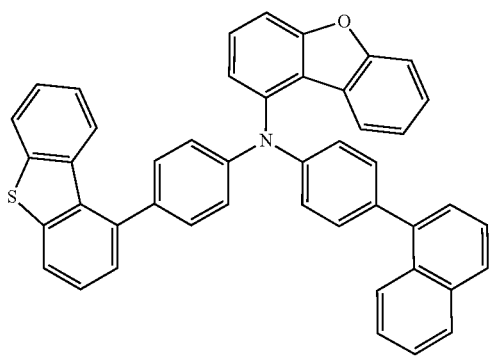
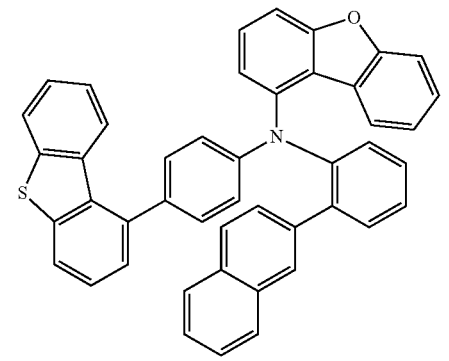
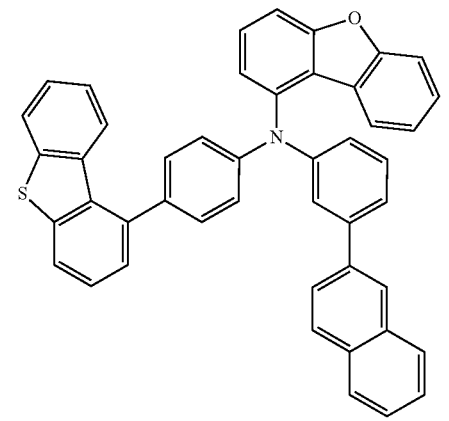

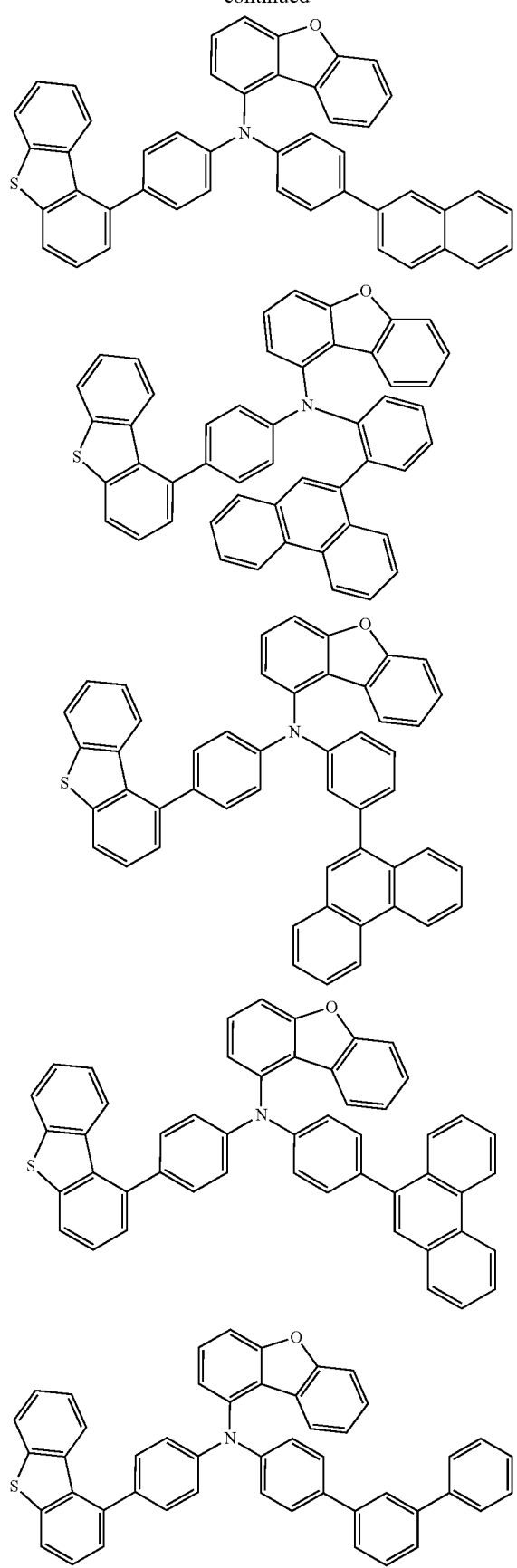
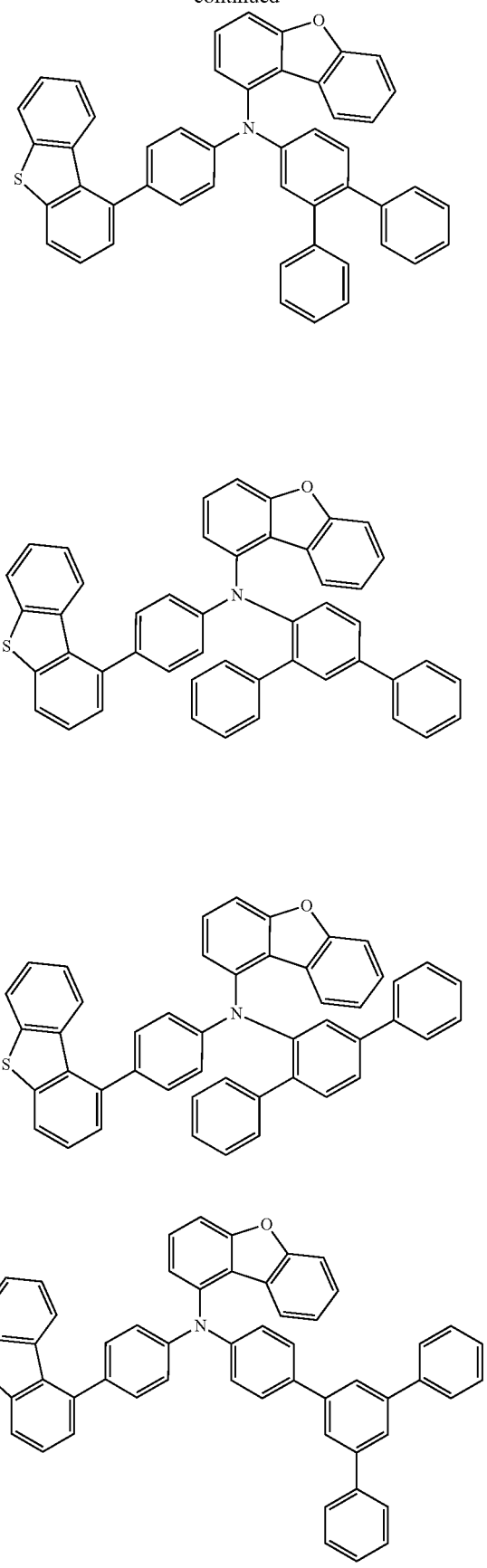

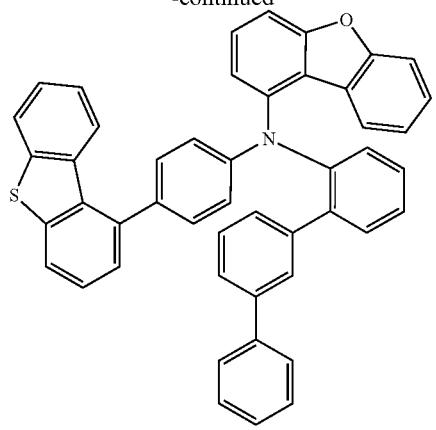
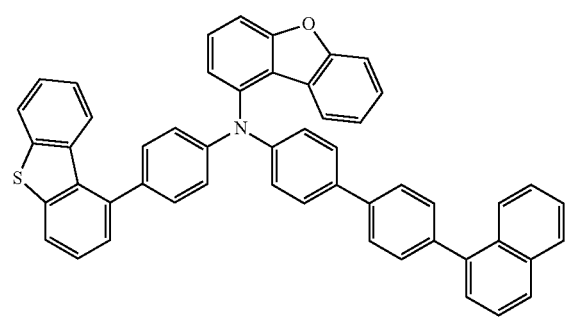
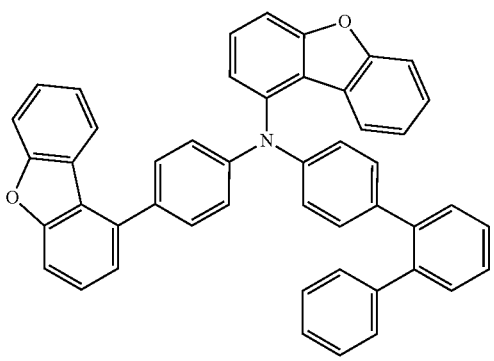
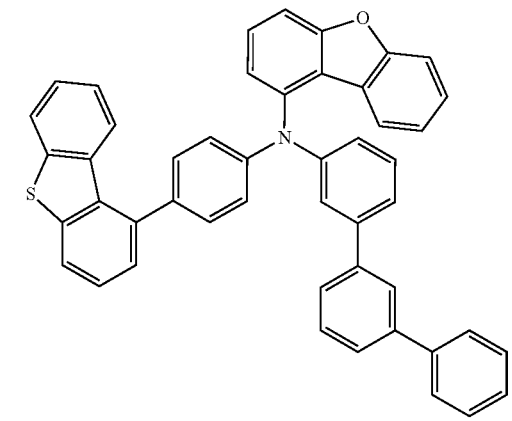
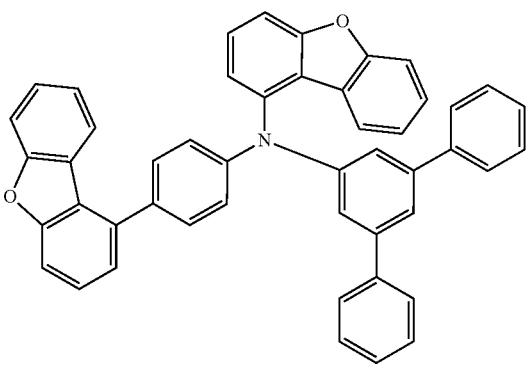
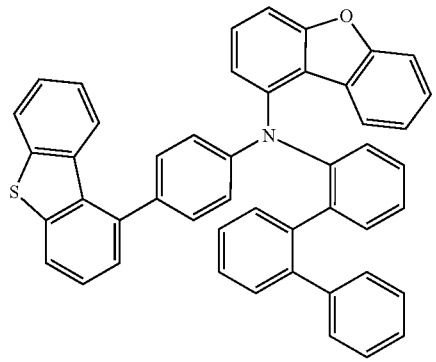
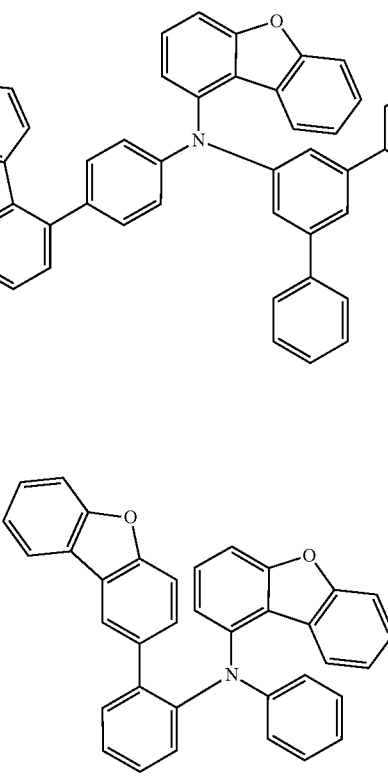

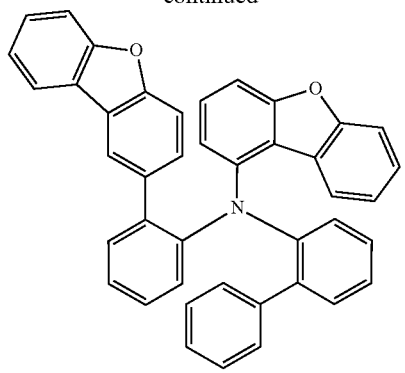
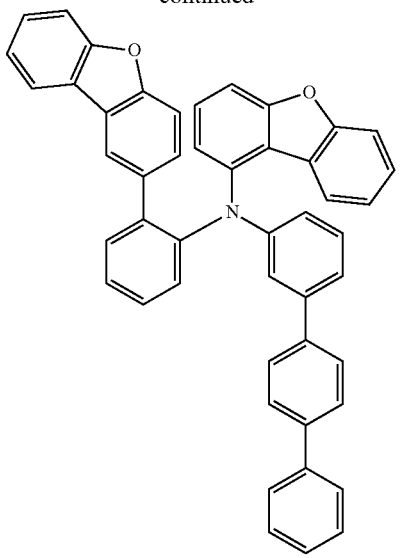
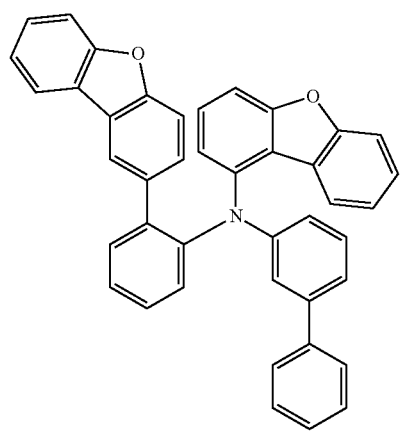
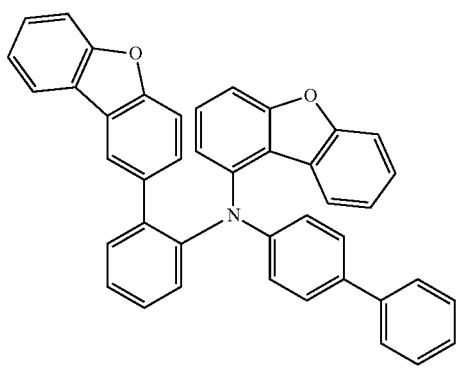
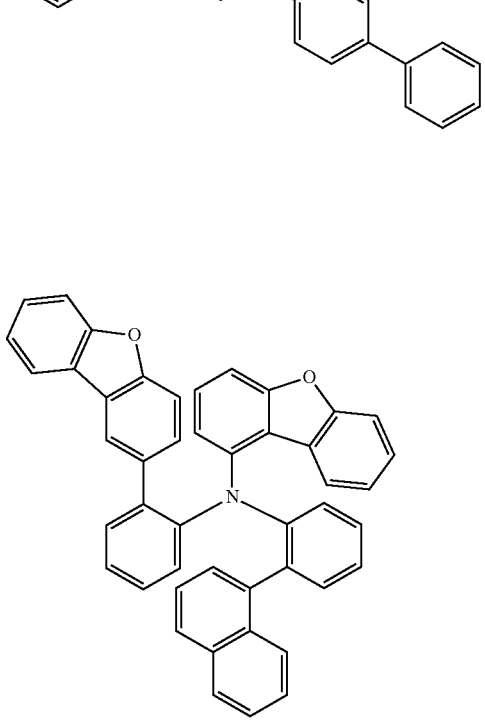
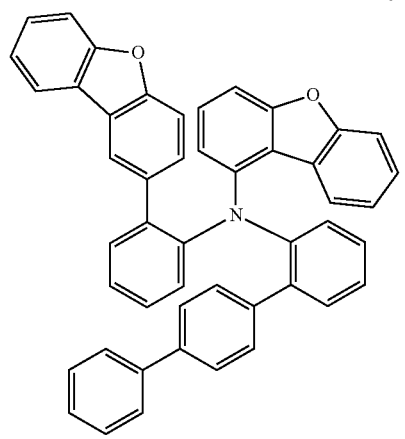

-continued
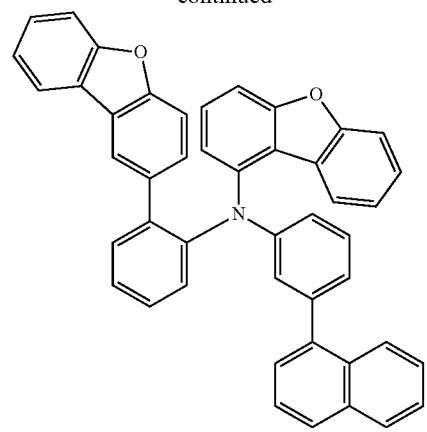
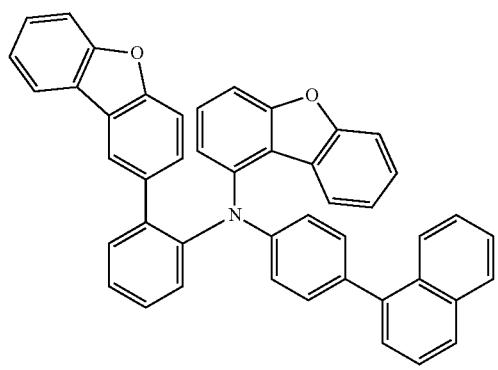
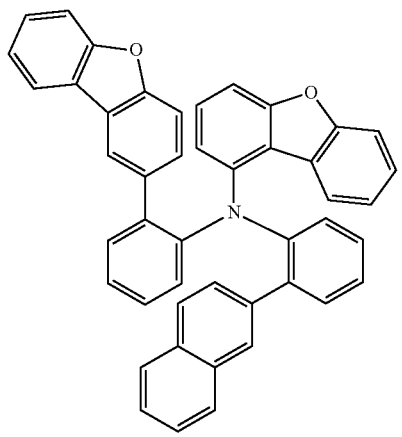
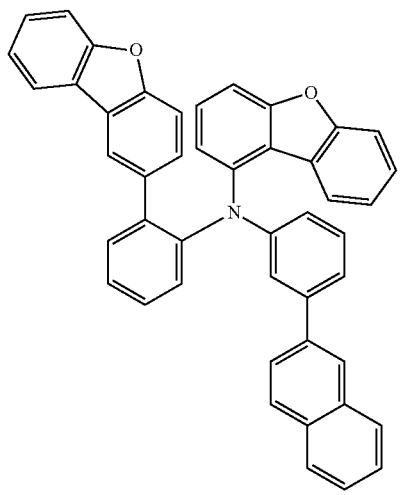
-continued
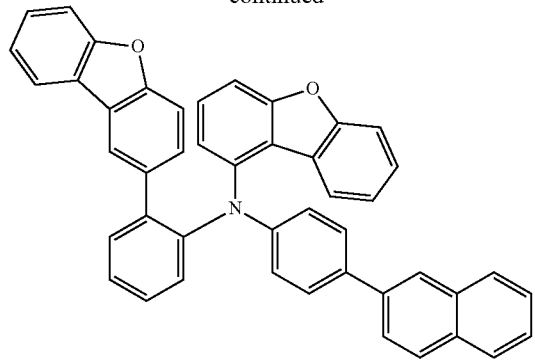
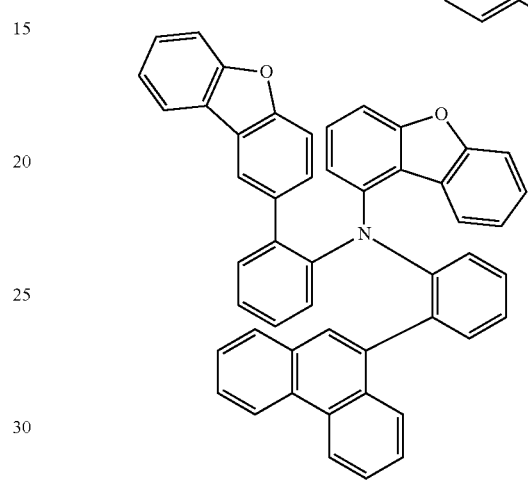
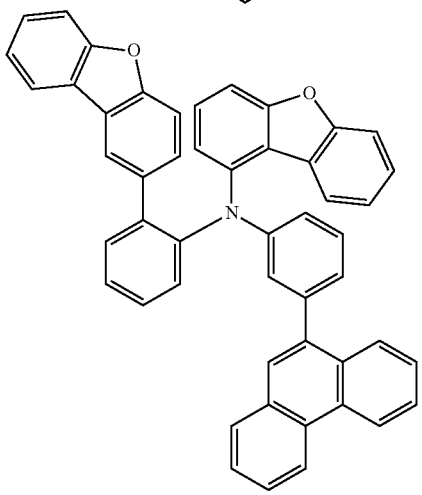
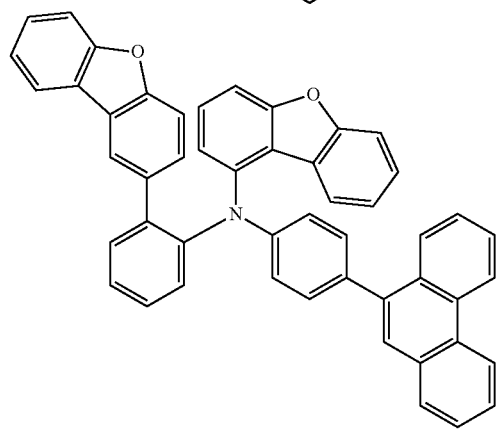

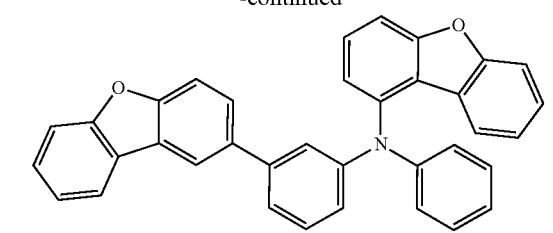
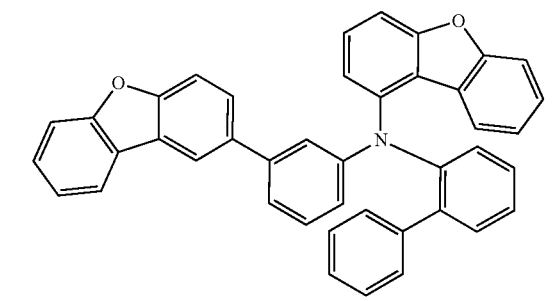
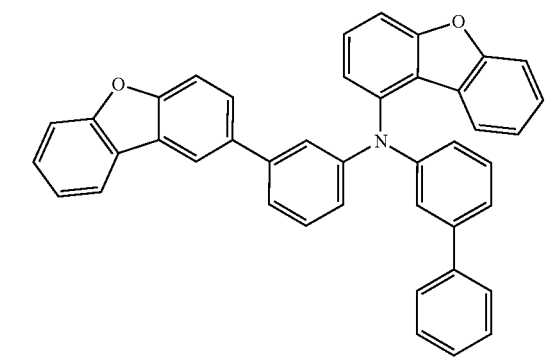
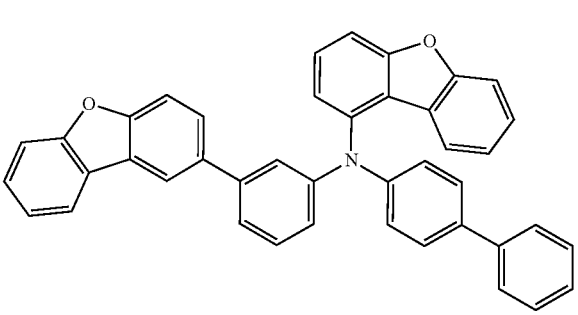
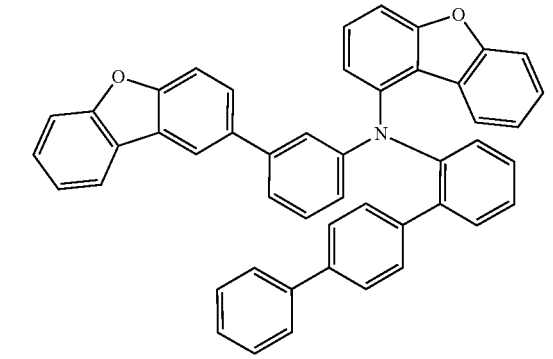
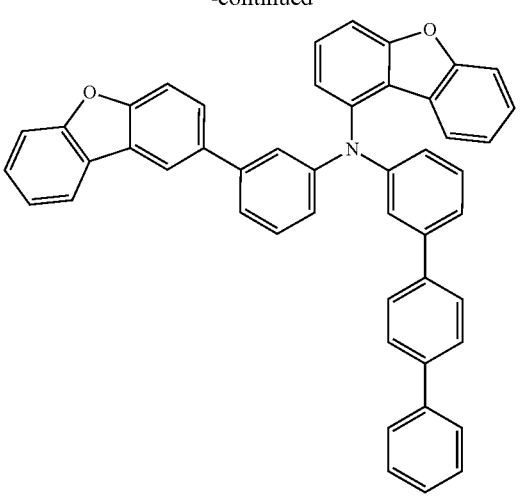
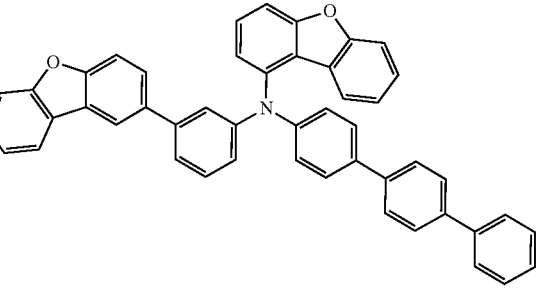
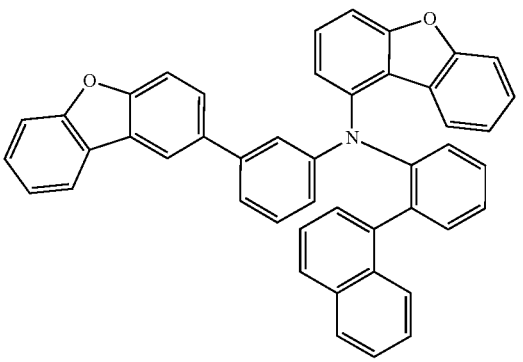
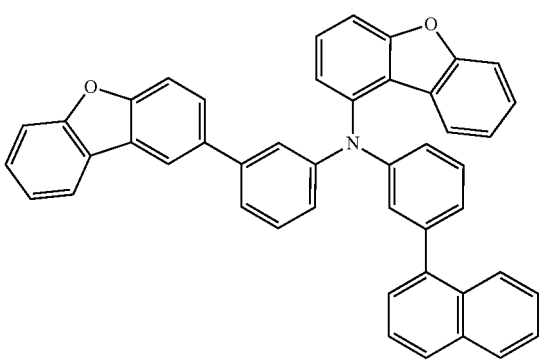

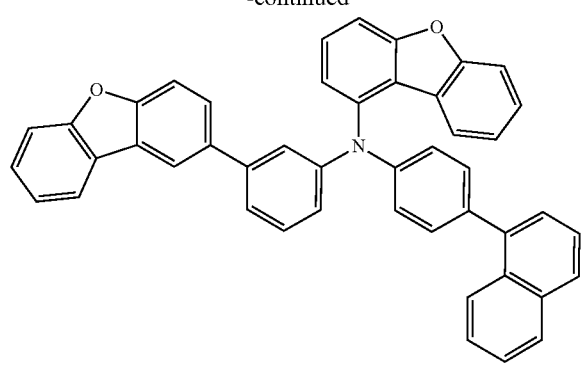
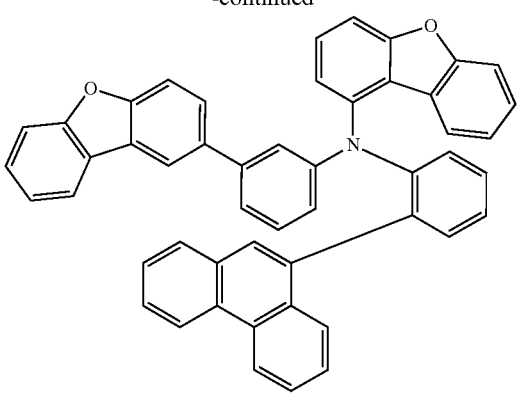
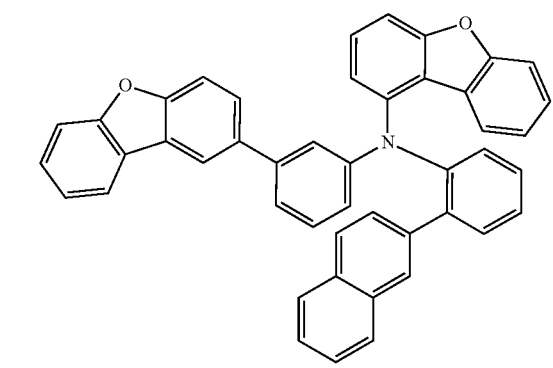
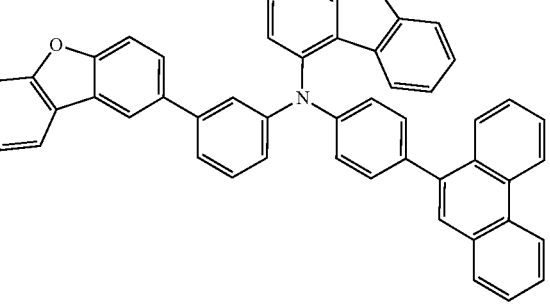
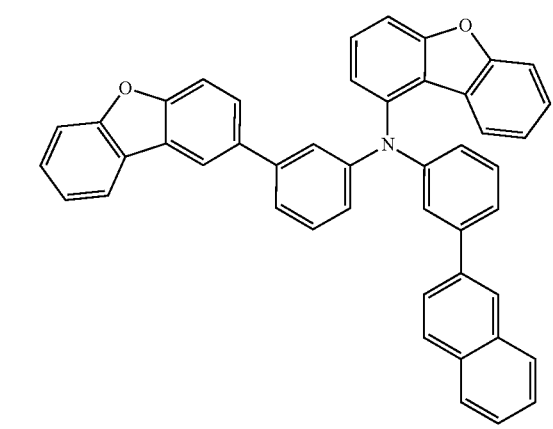
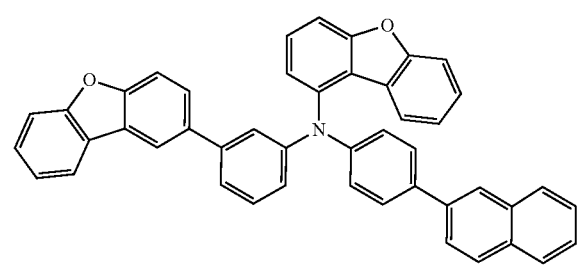
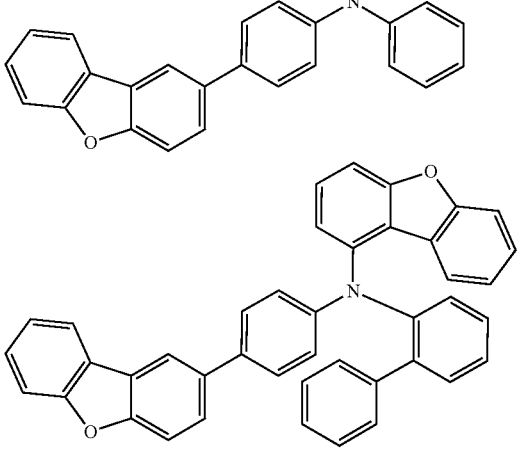

-continued
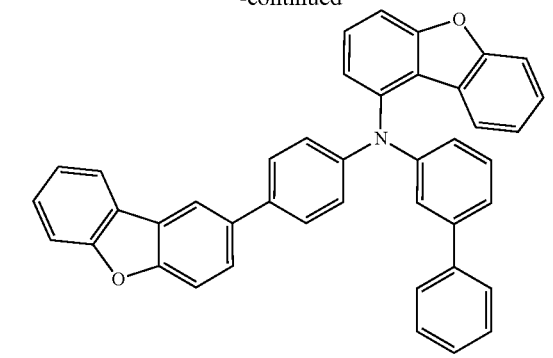
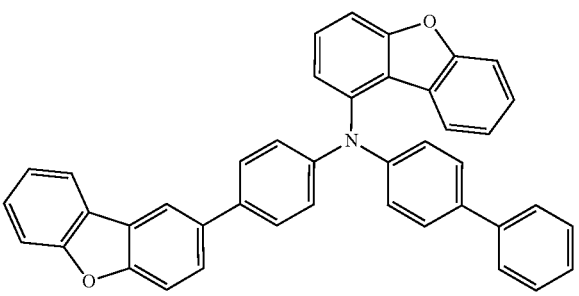
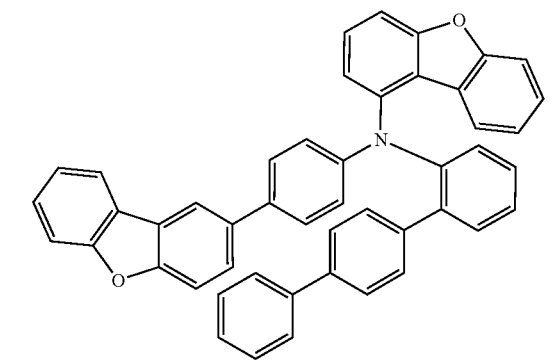
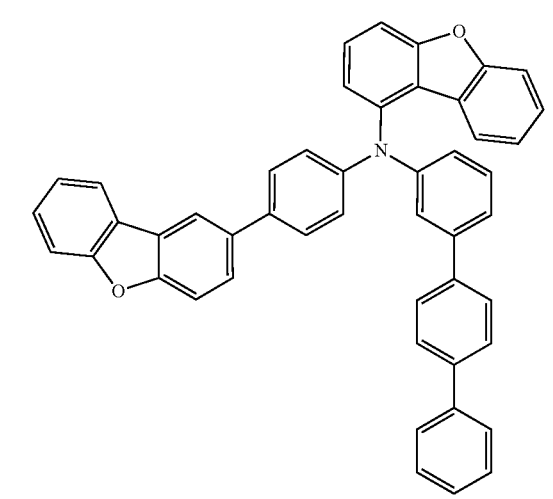
-continued
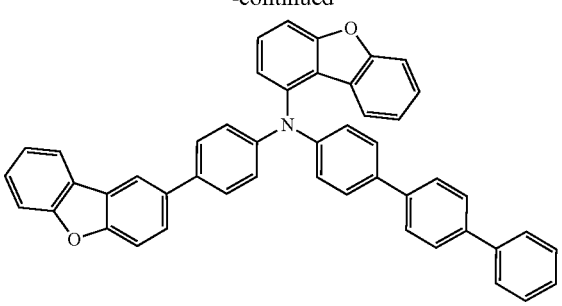
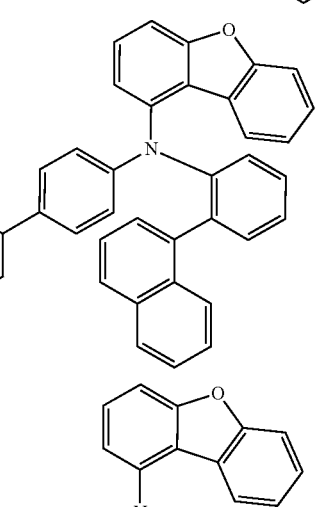
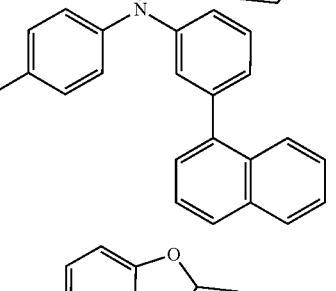
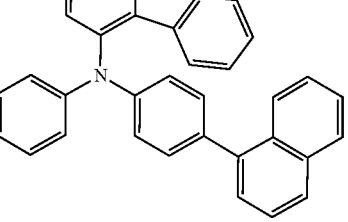
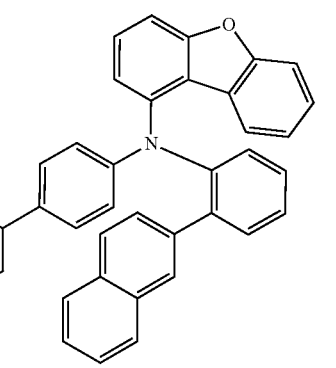

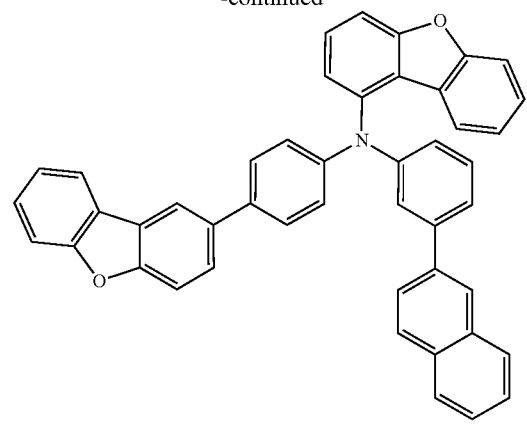
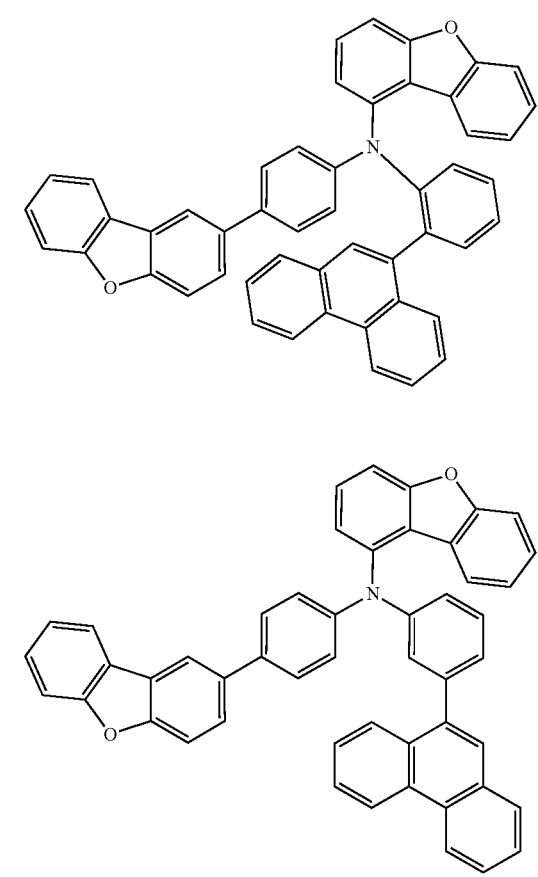
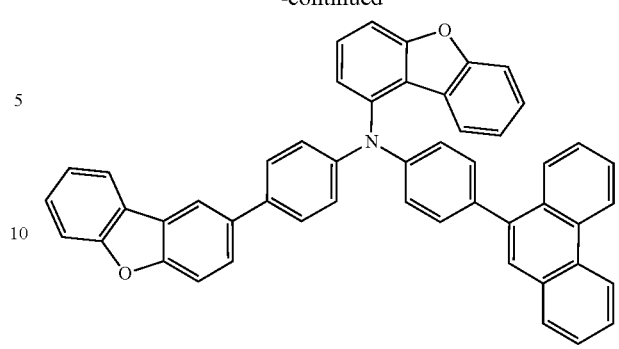
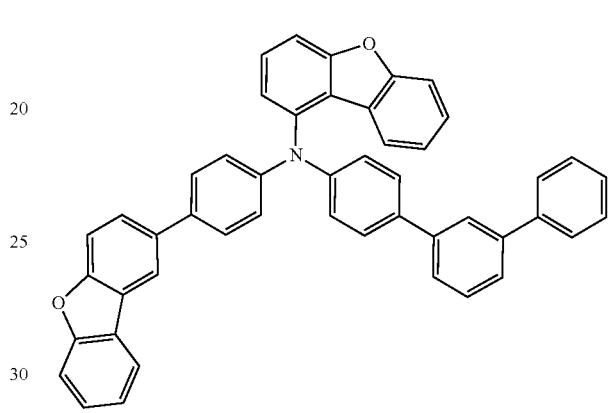
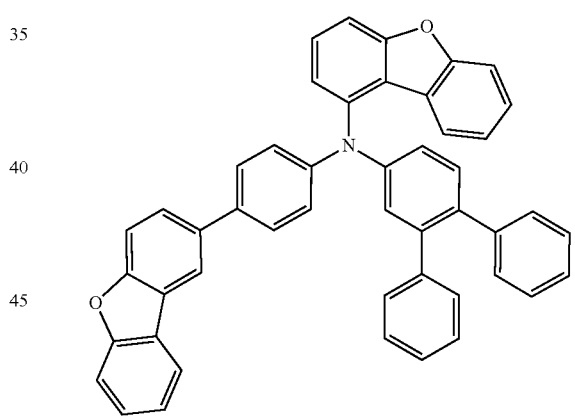
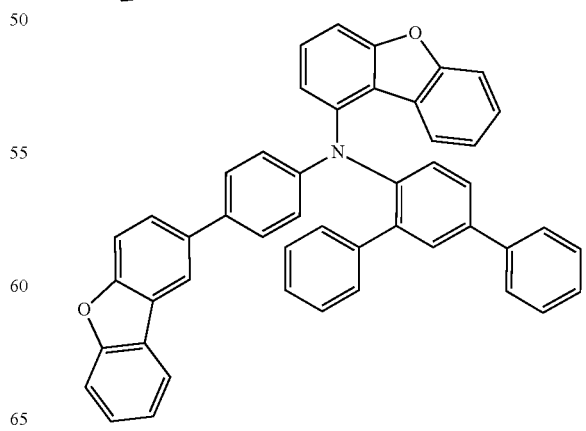

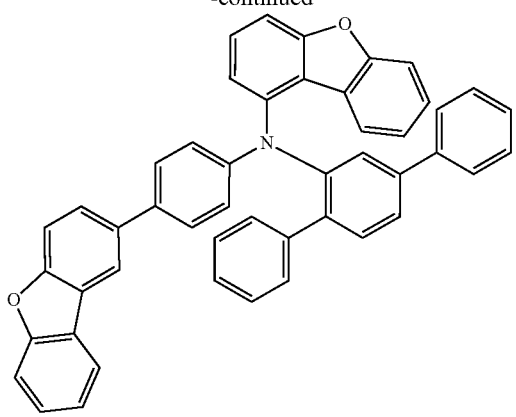
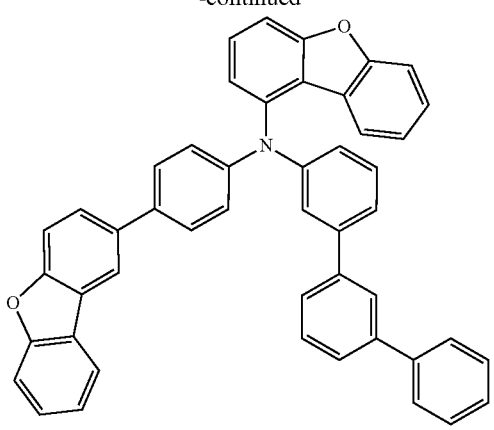
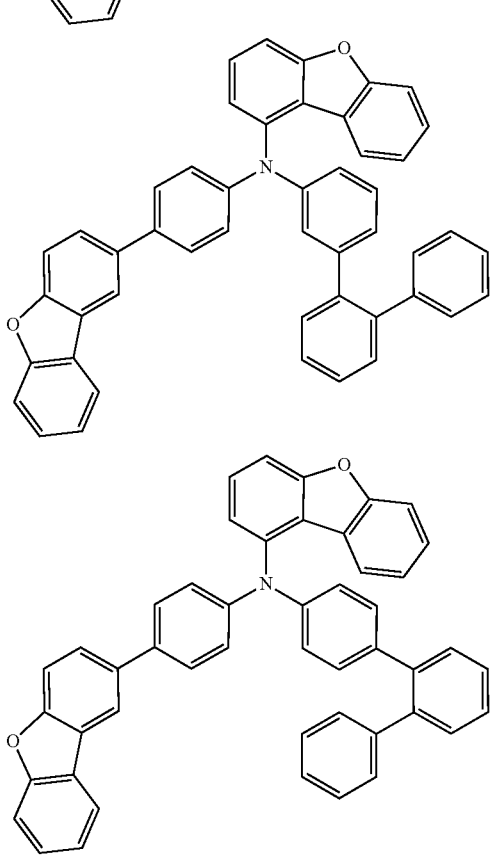

57
-continued
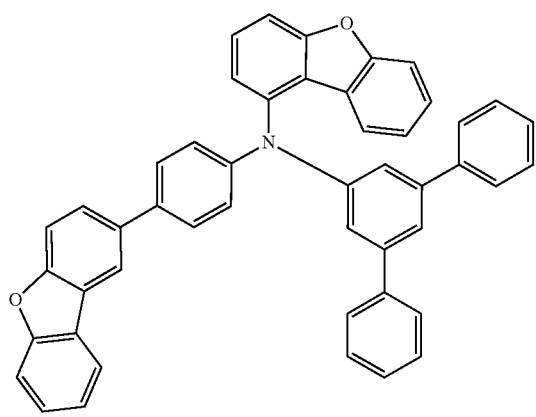
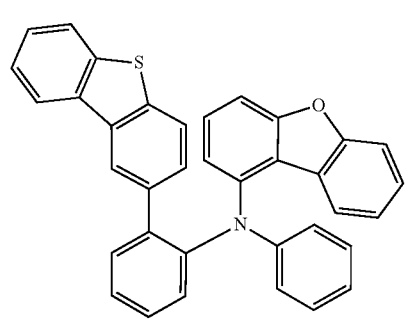
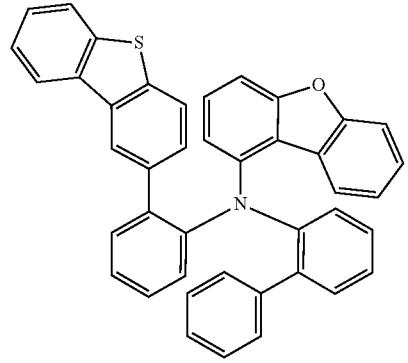
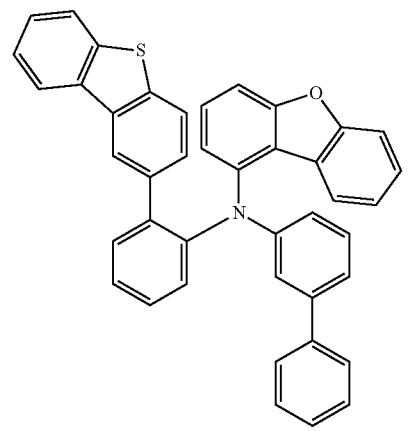
58
-continued
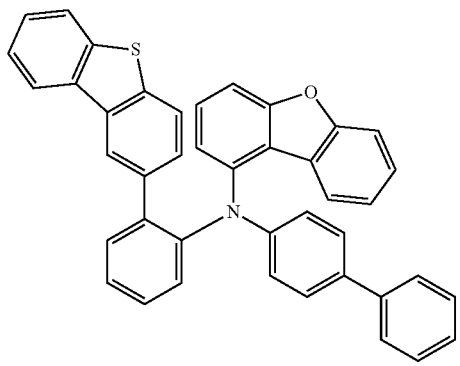
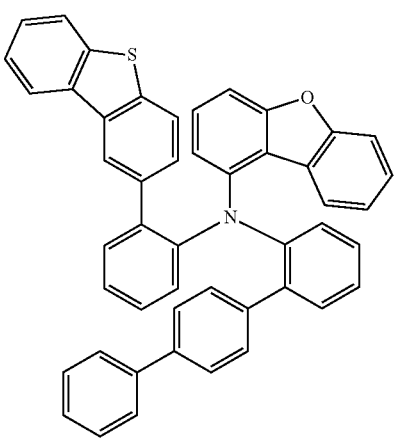
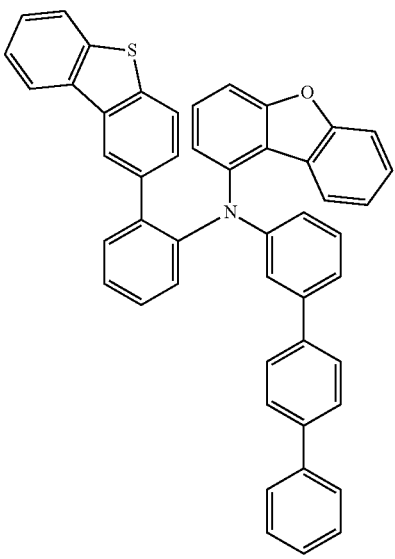

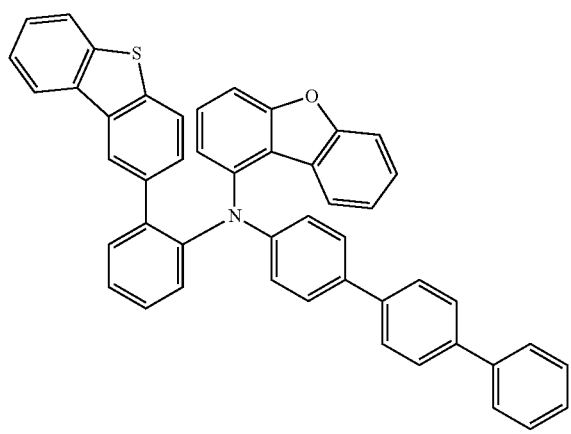
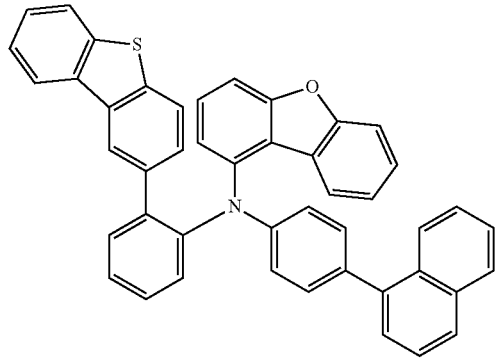
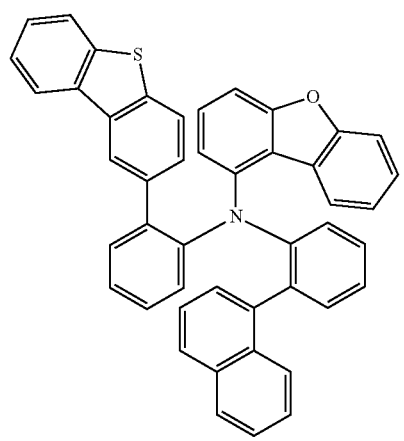
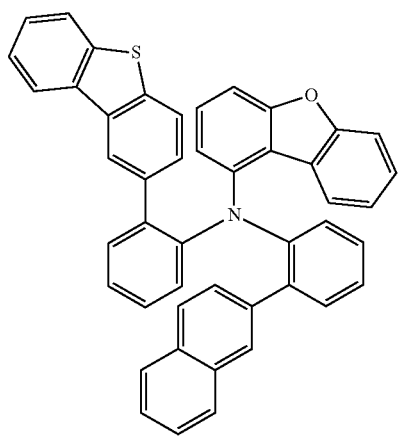
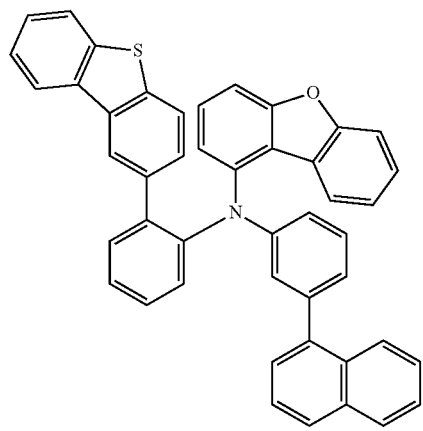
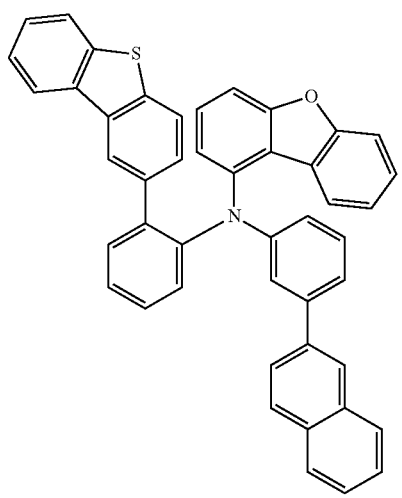

61
-continued
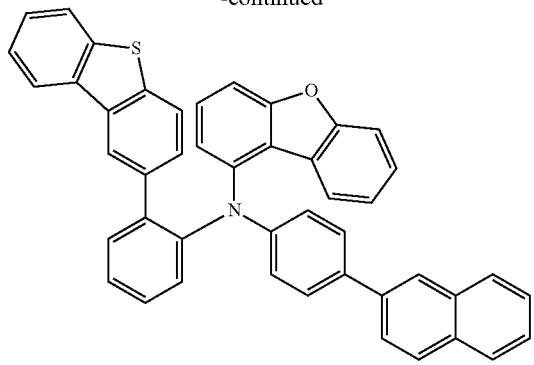
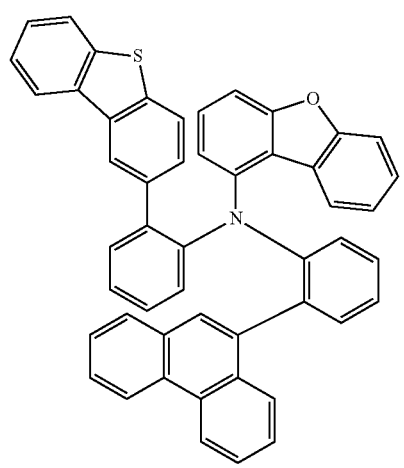
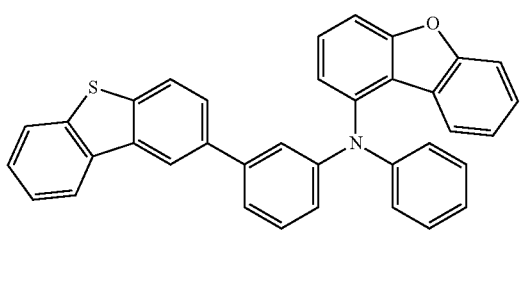
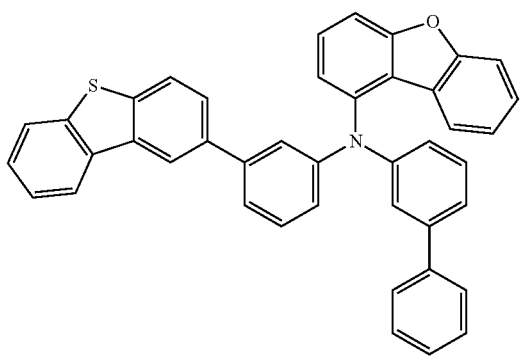
62
-continued
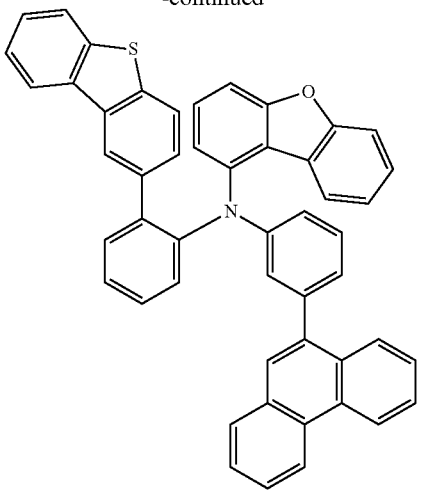
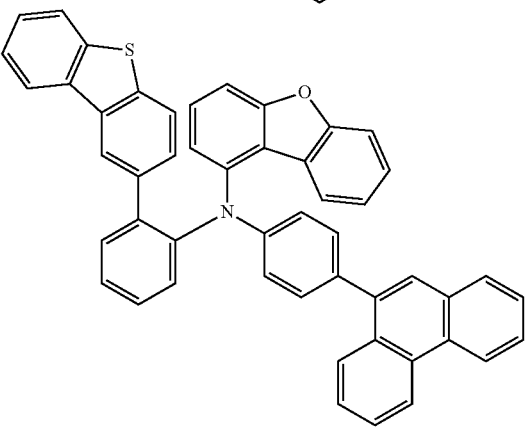
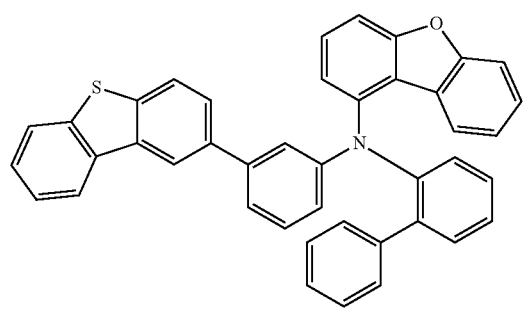
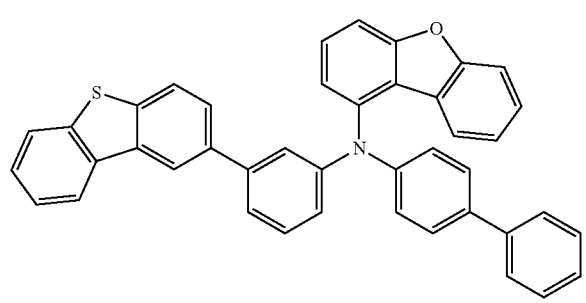

-continued
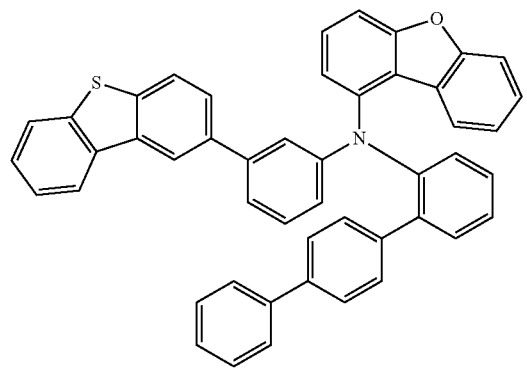
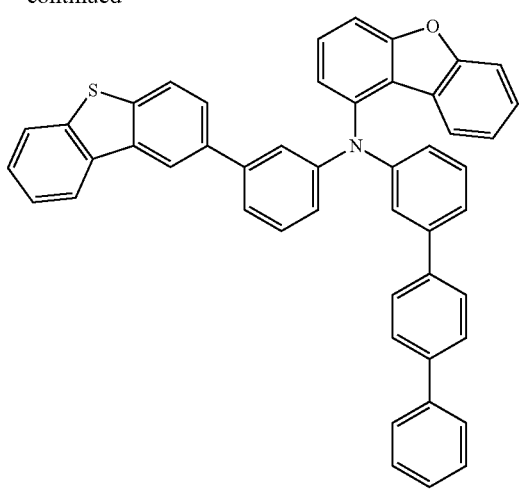
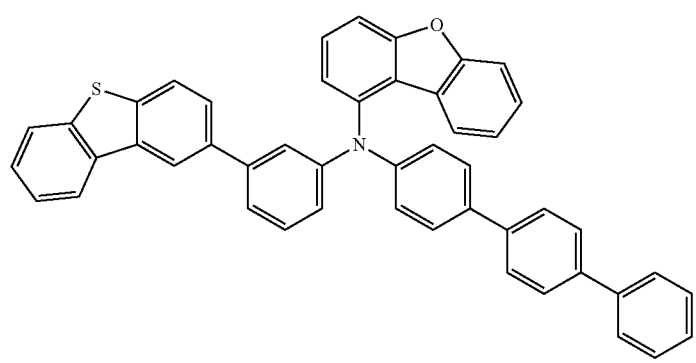
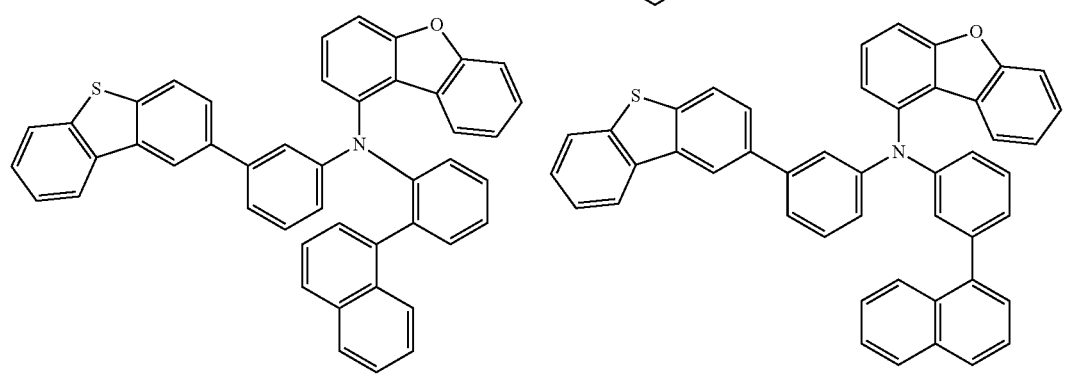
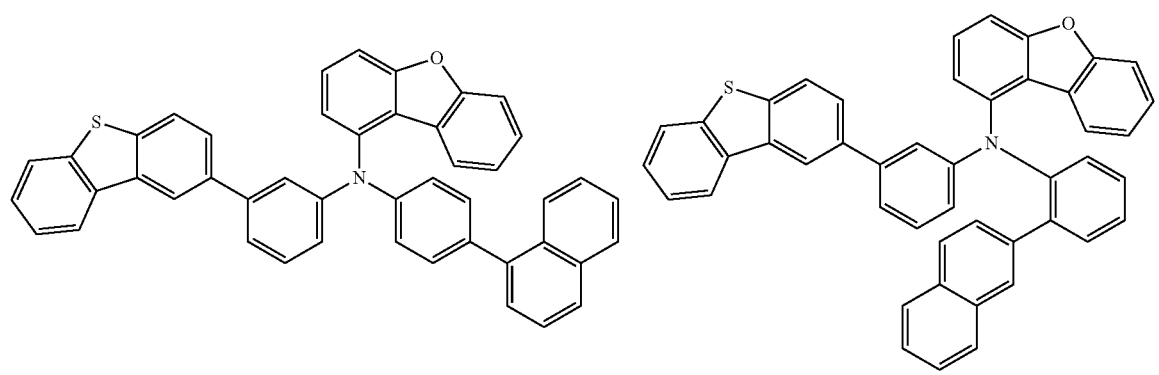

-continued
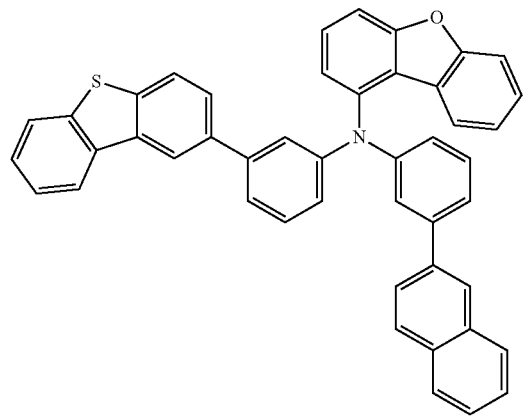
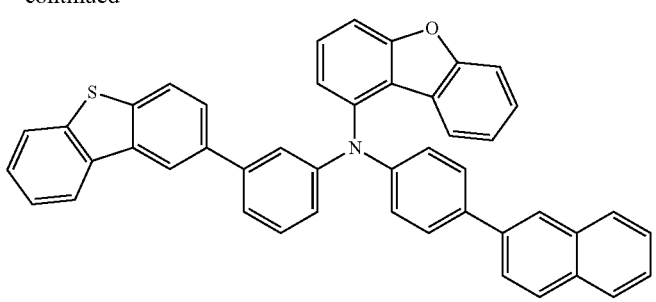
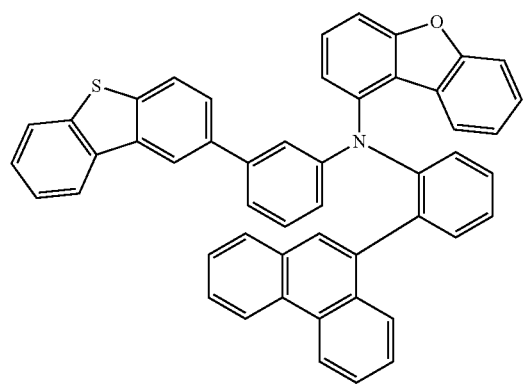
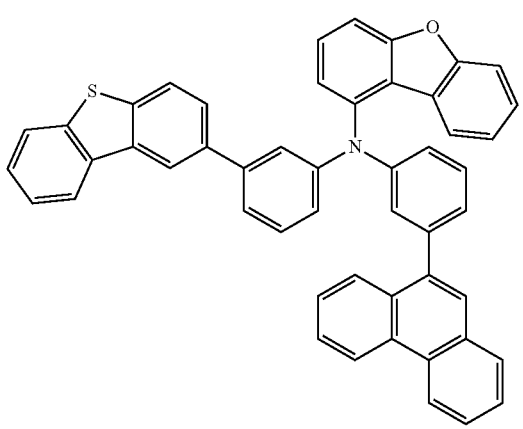
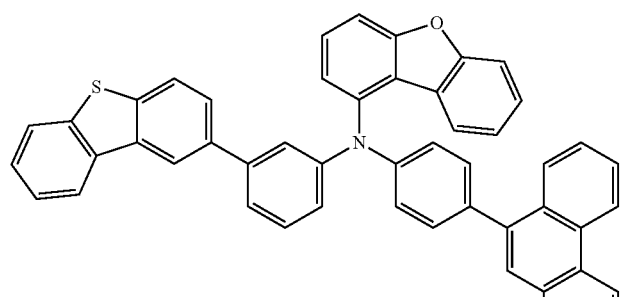
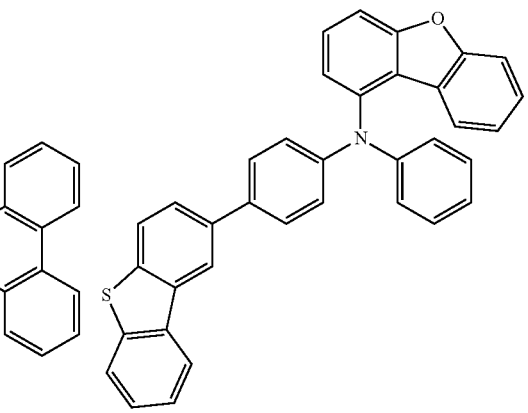
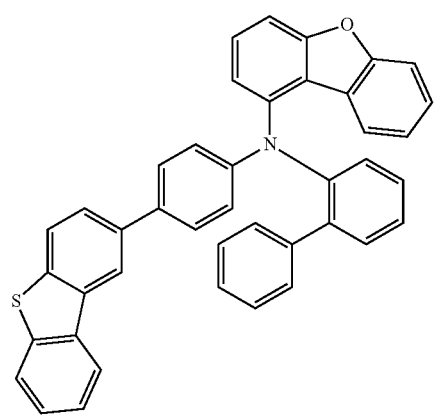
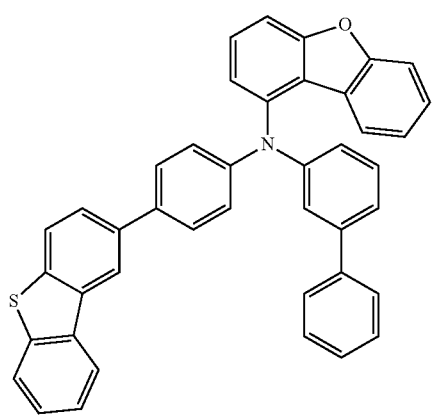

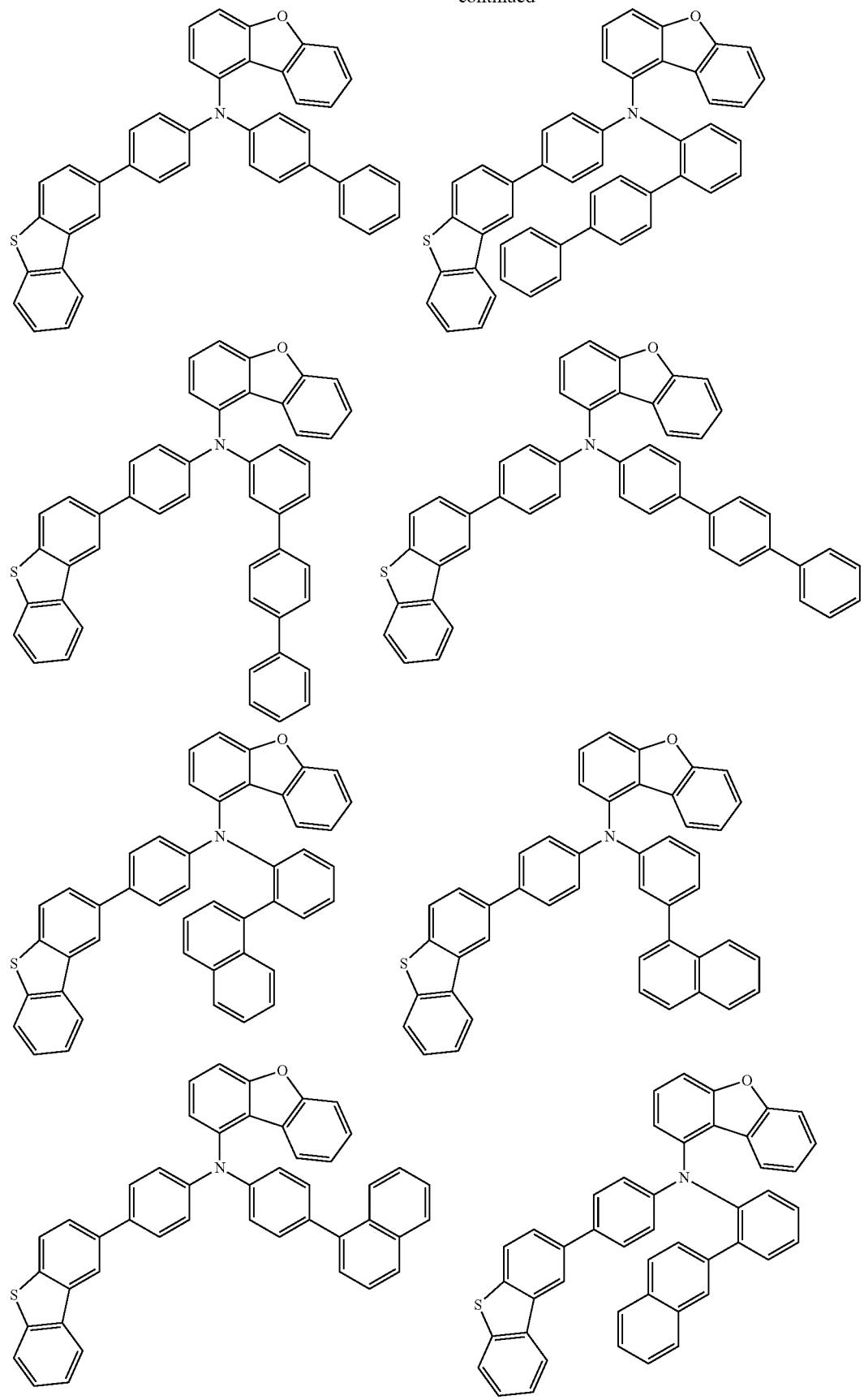

-continued
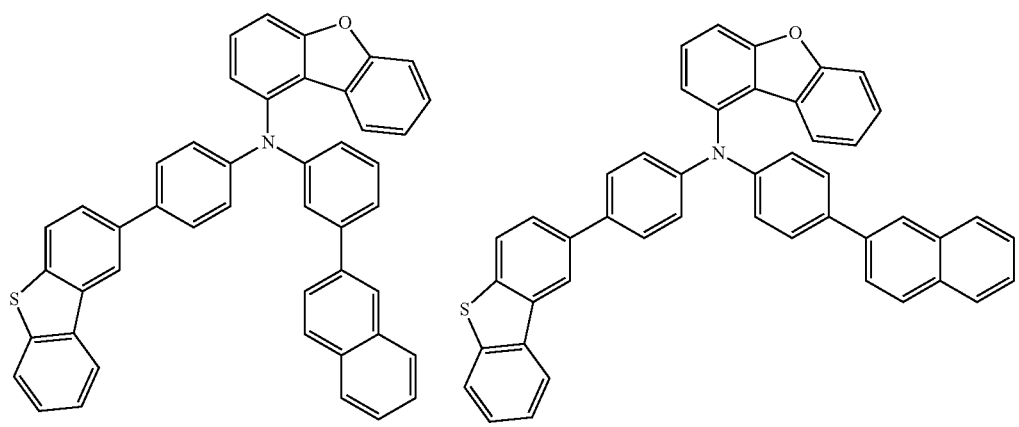
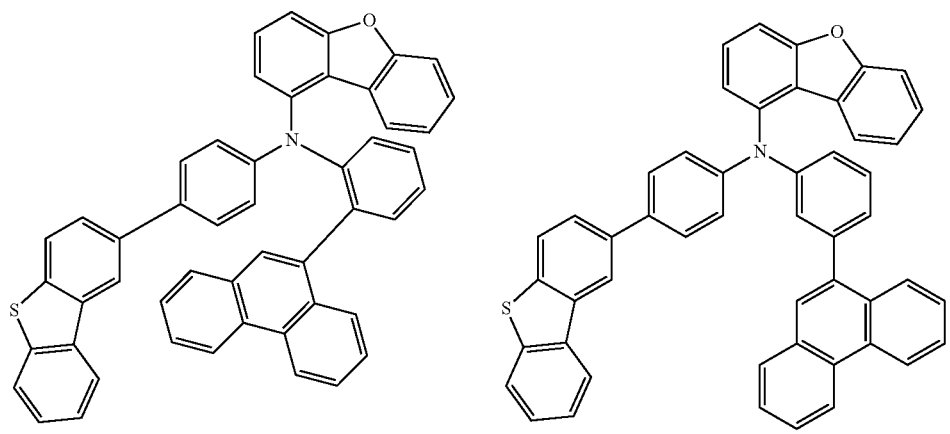
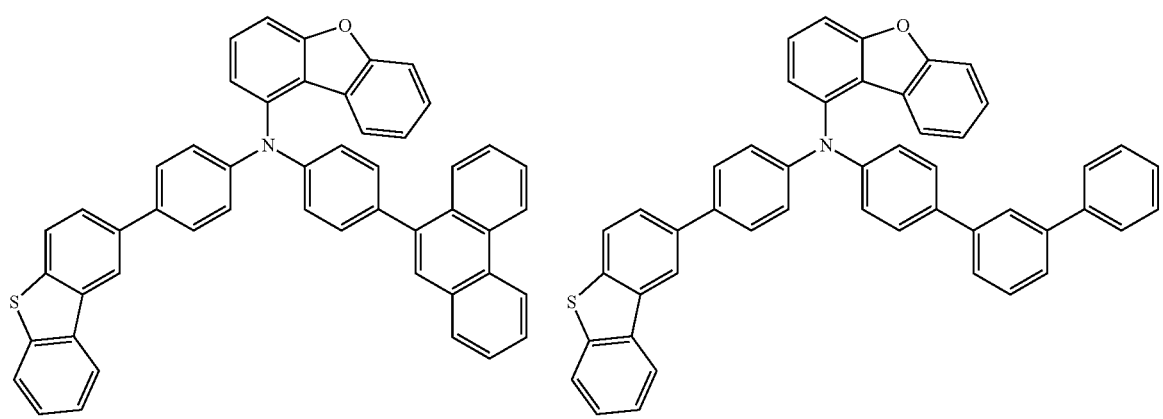
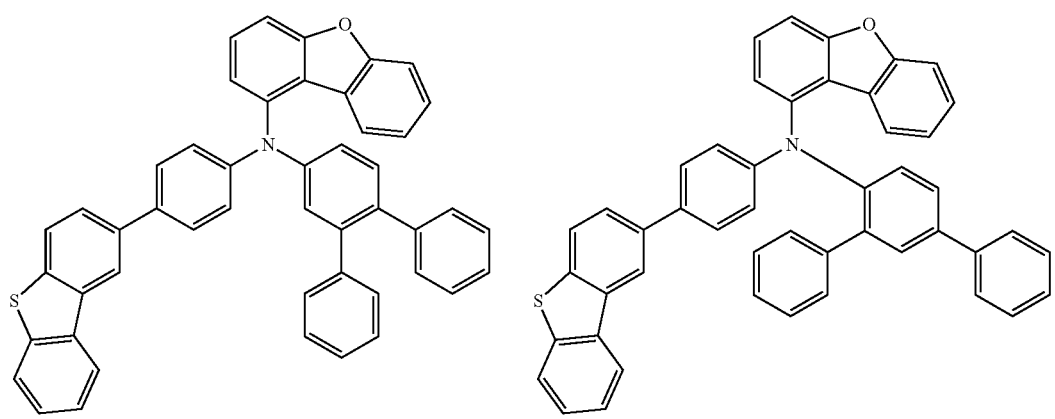

71
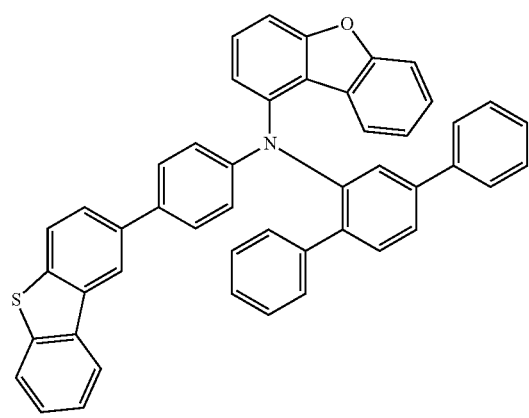
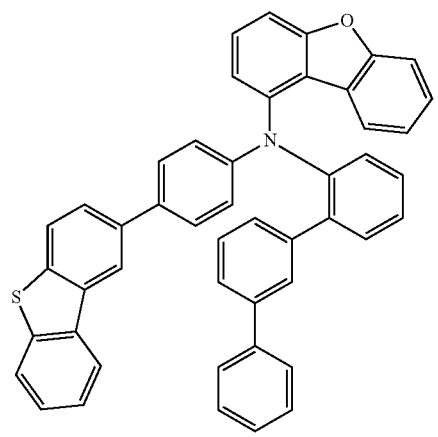
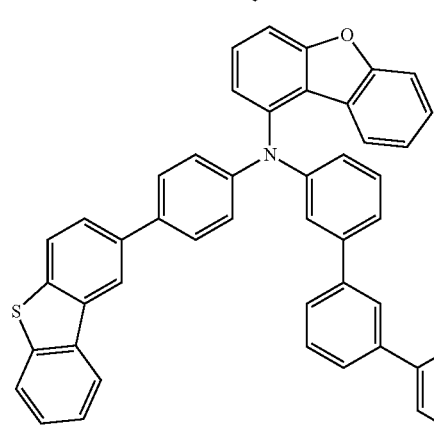
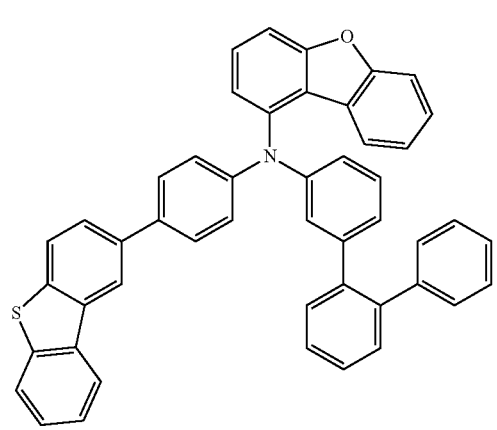
-continued
72
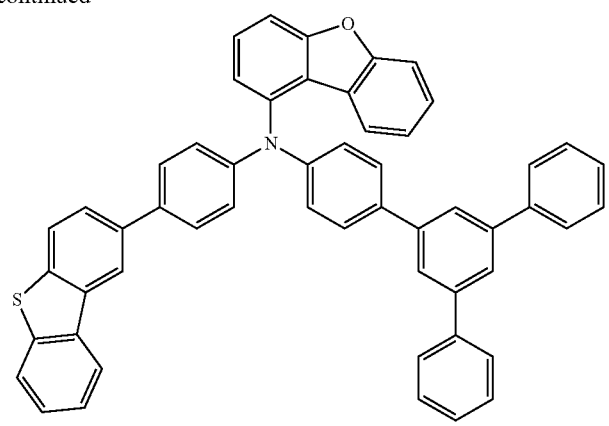
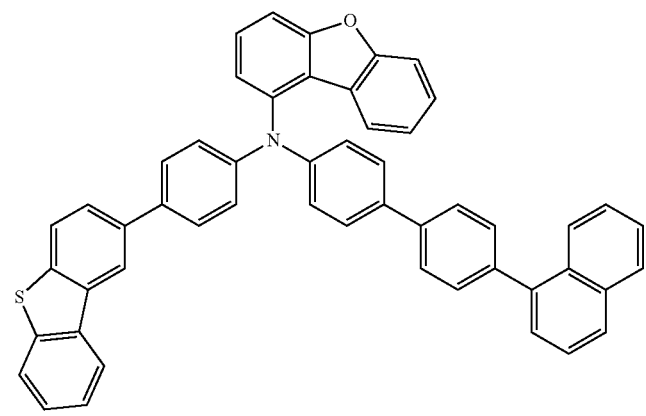
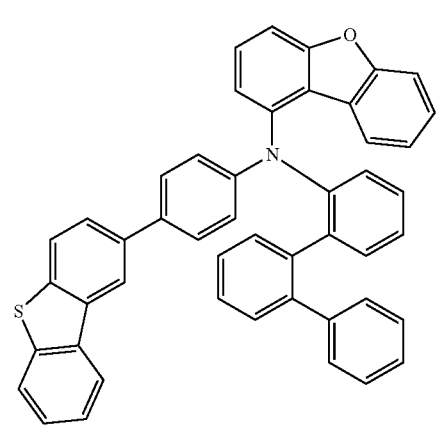
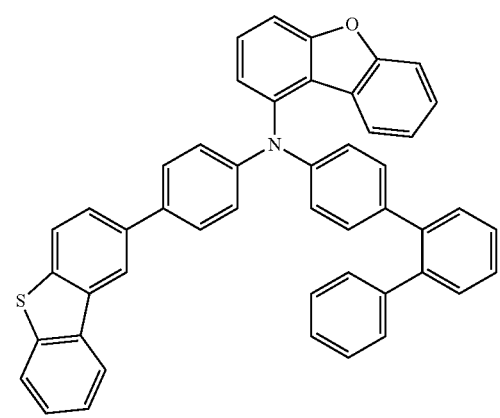

-continued
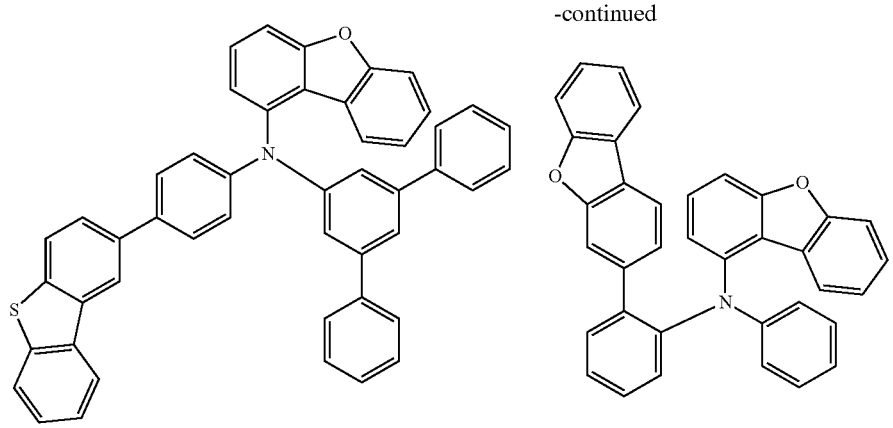
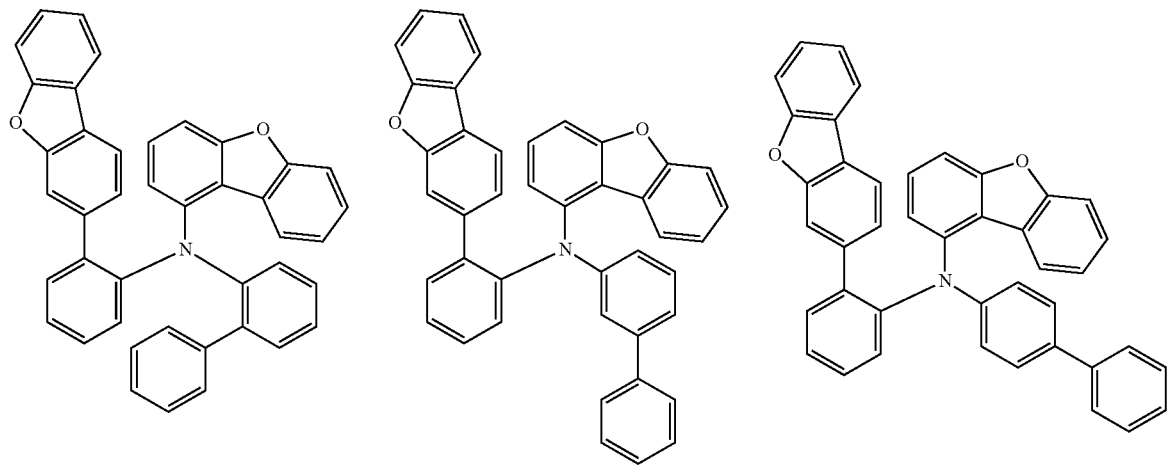
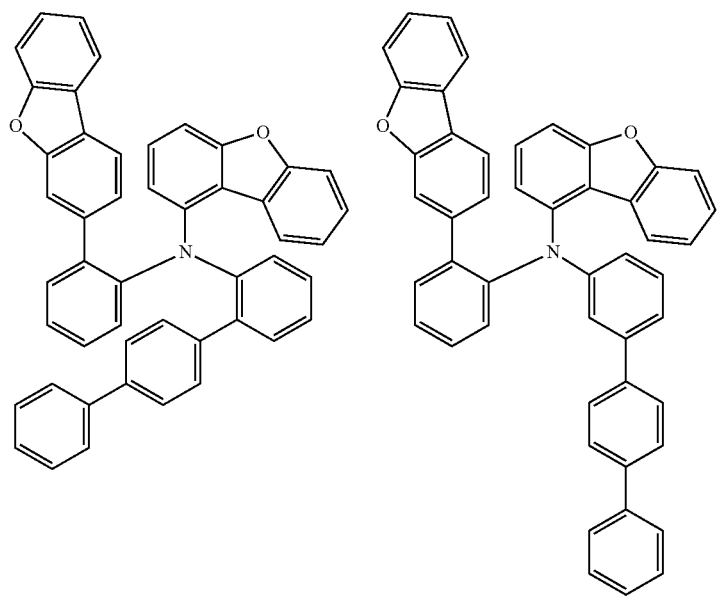

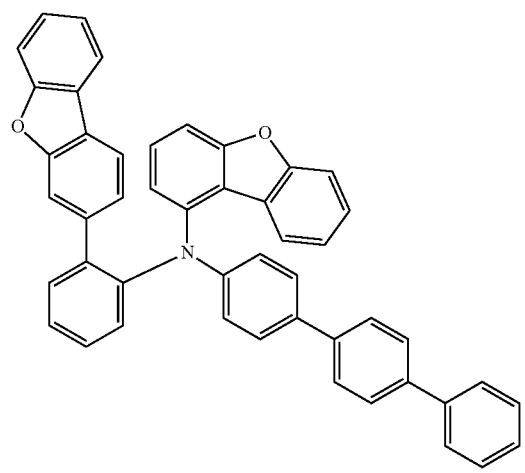
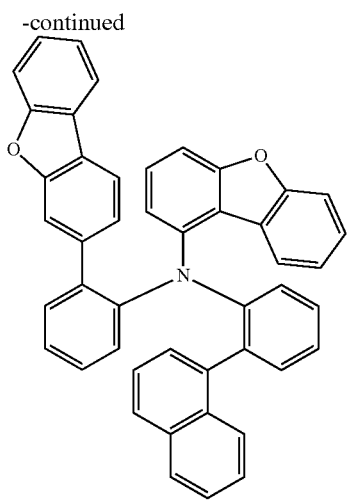
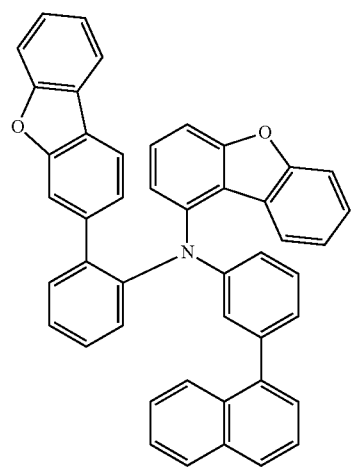
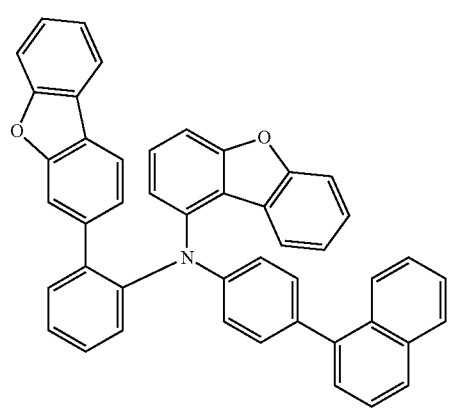
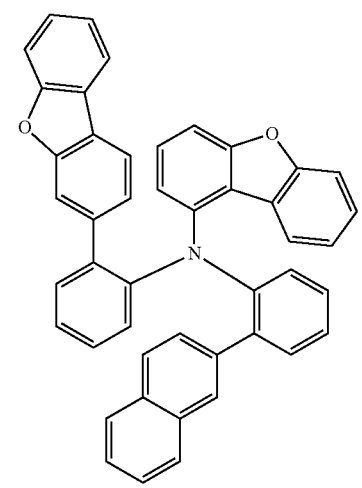
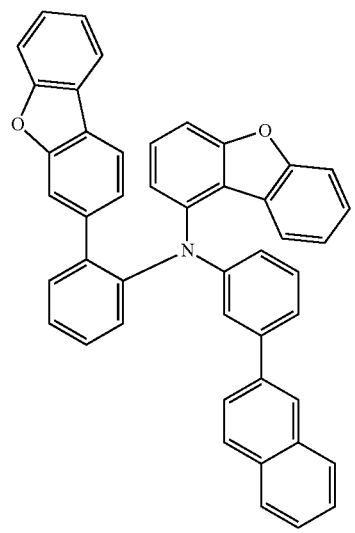
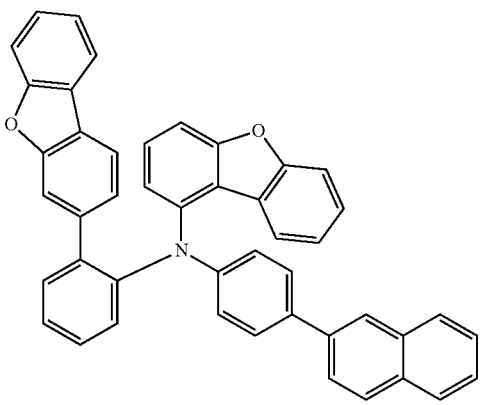
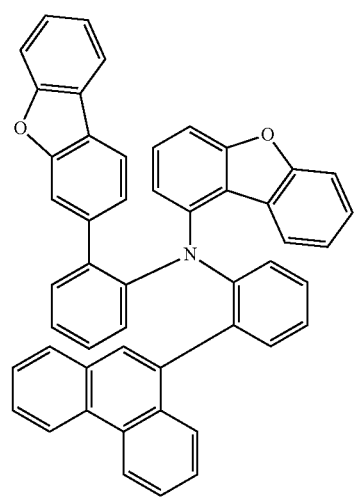

-continued
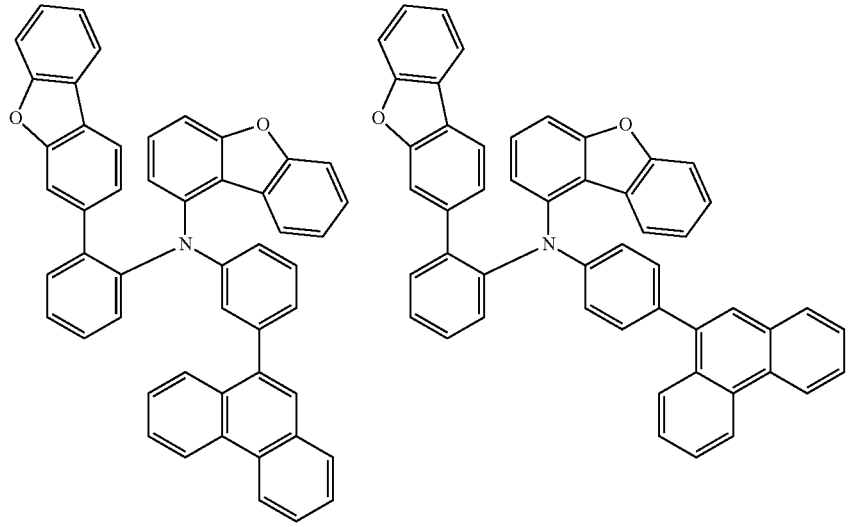
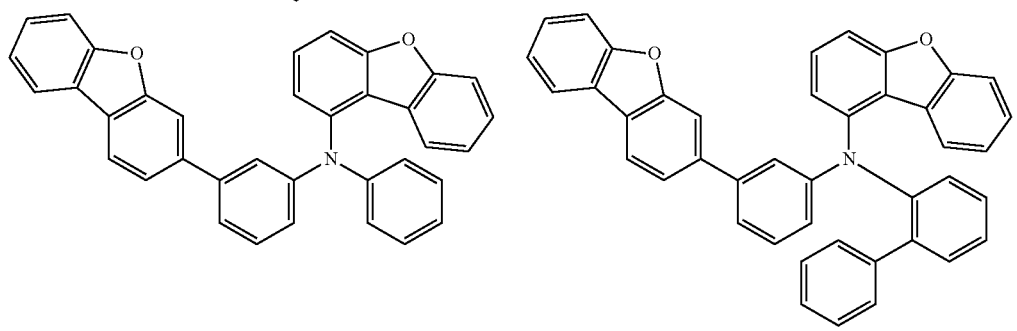
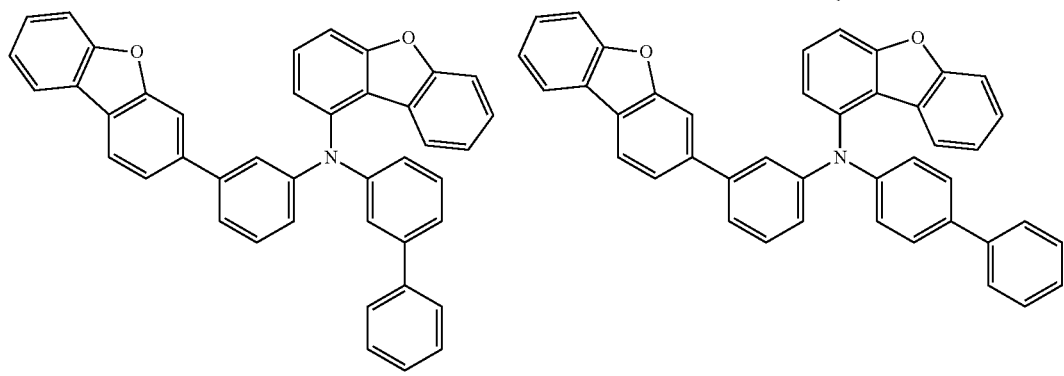
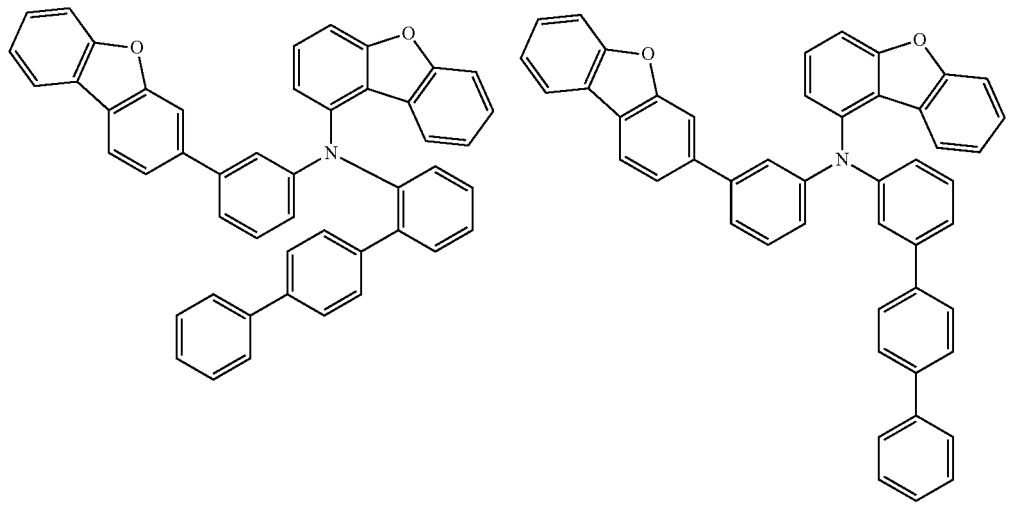

-continued
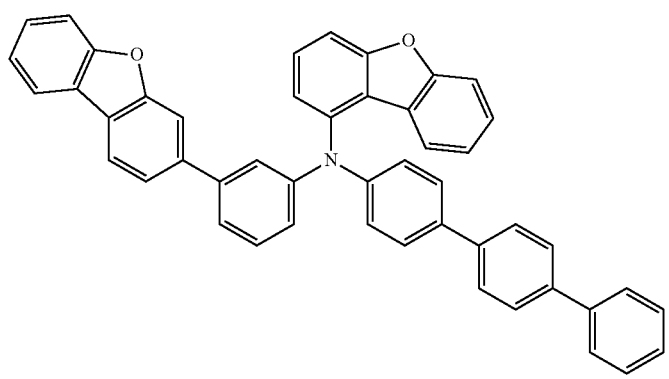
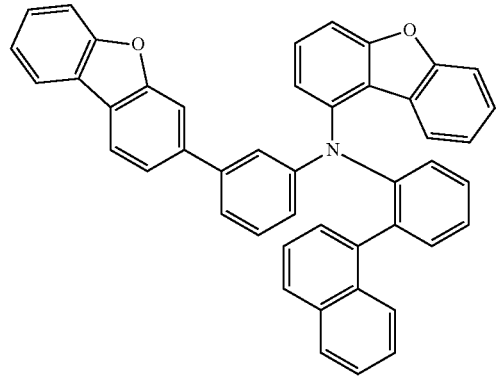
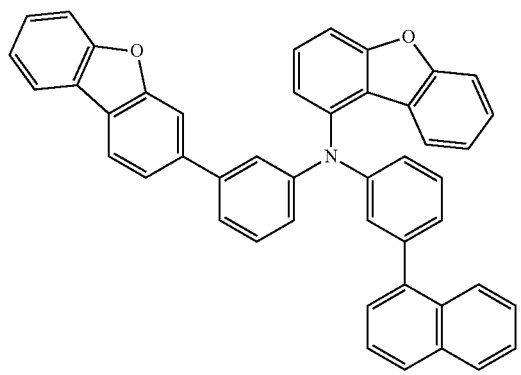
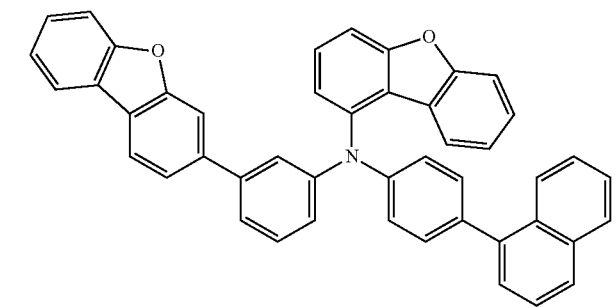
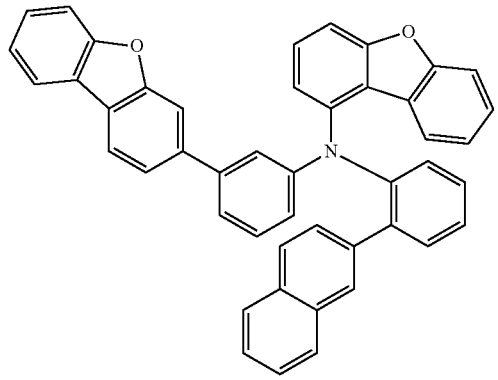
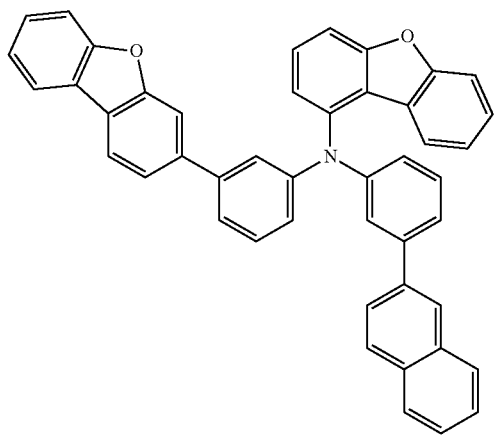
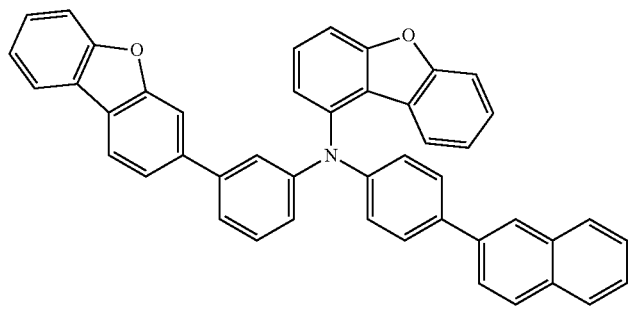
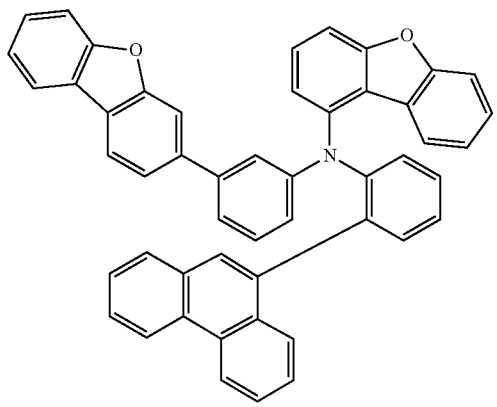

-continued
81
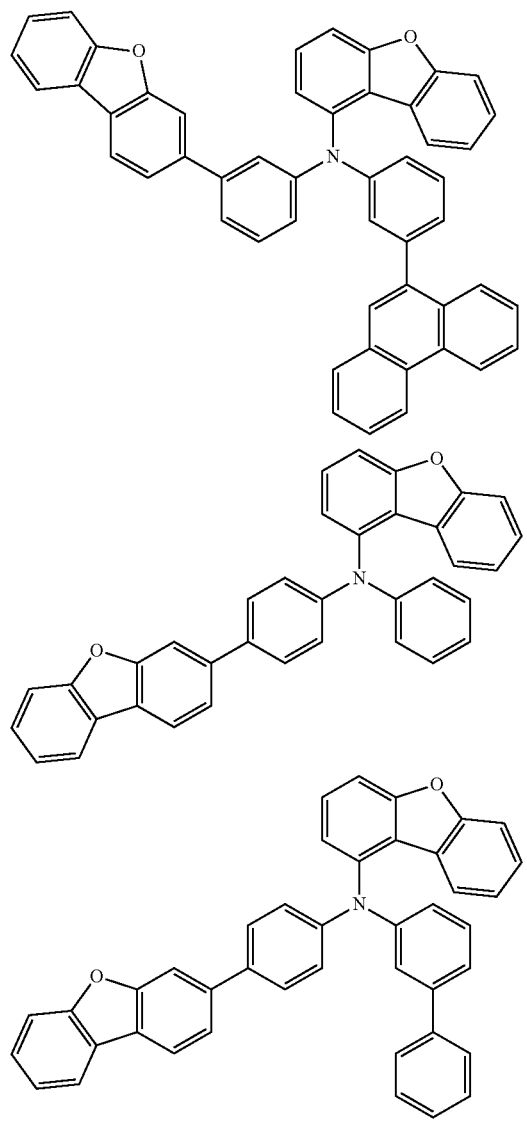
82
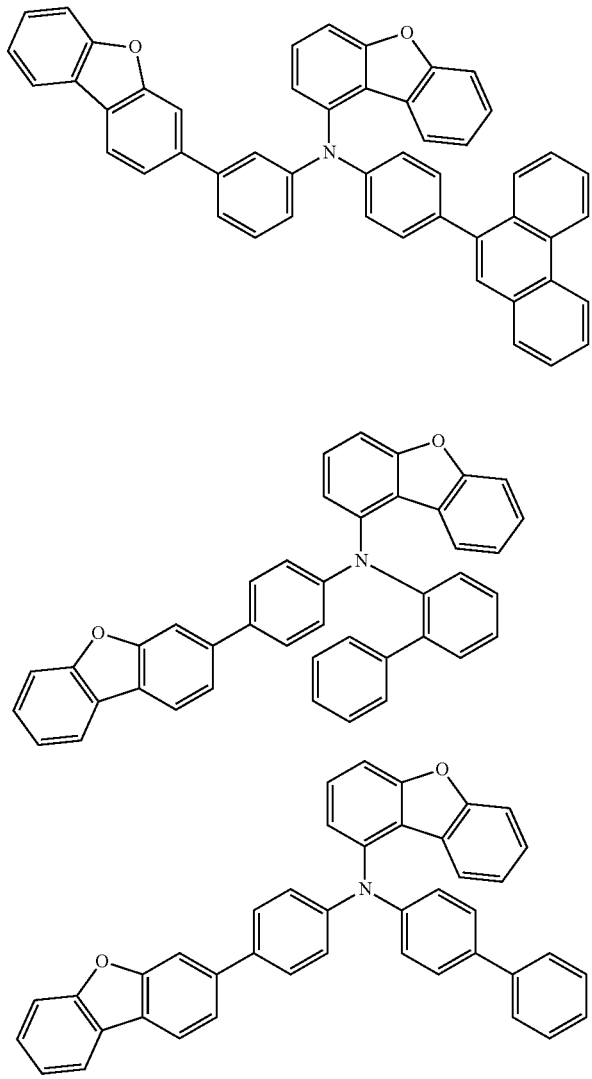
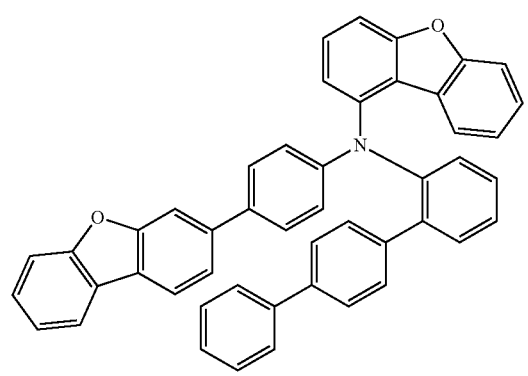
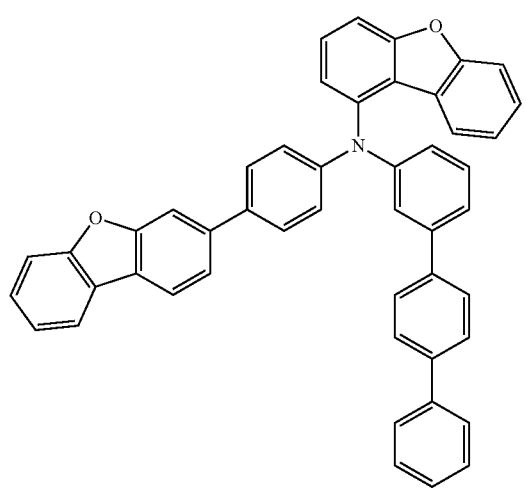

-continued
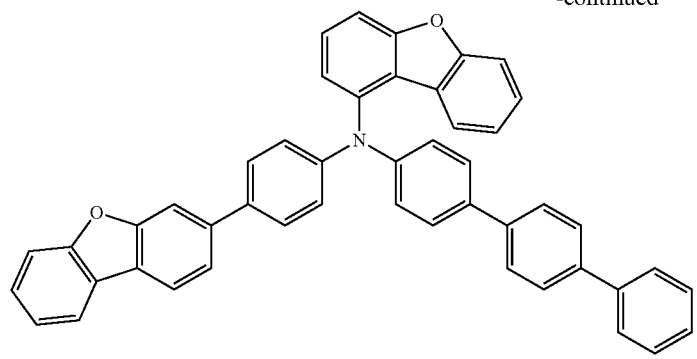
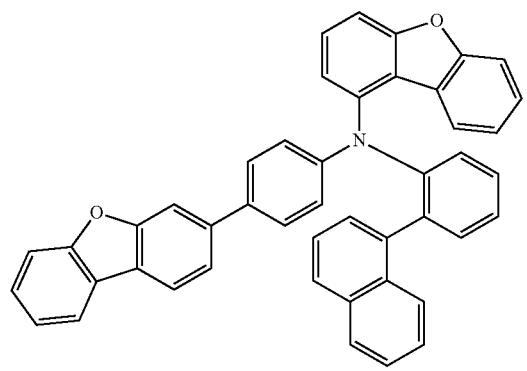
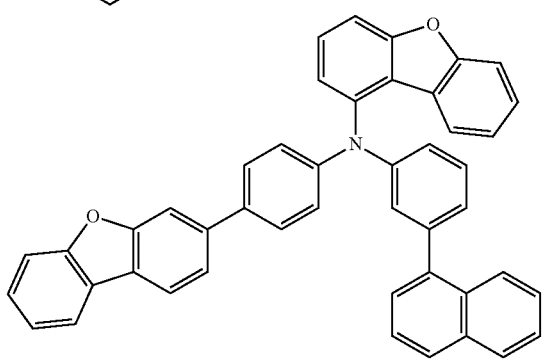
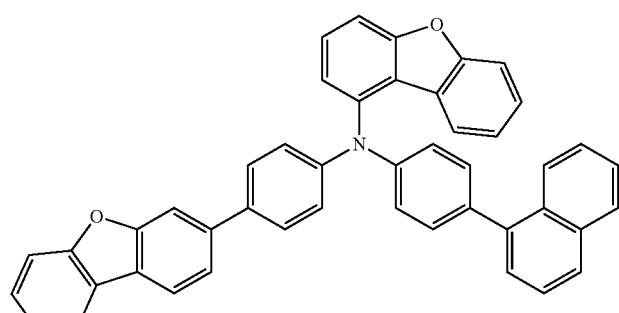
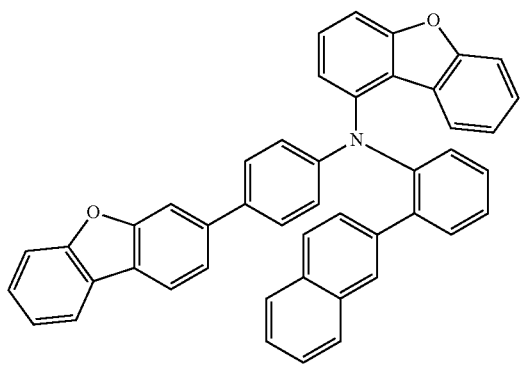
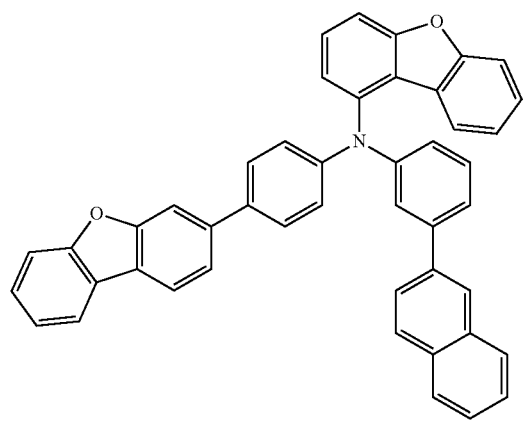
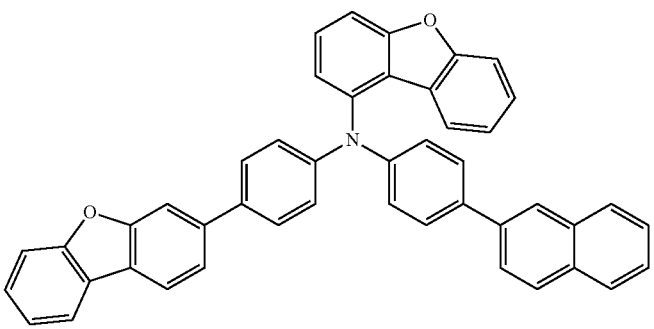

85 86
-continued
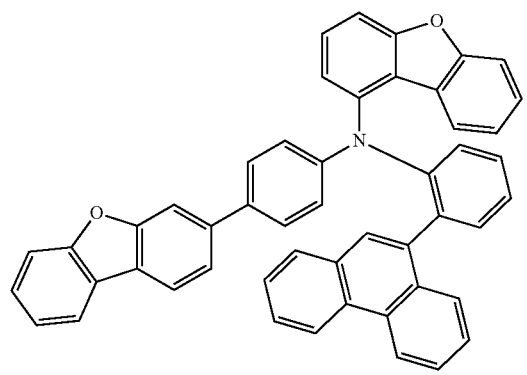
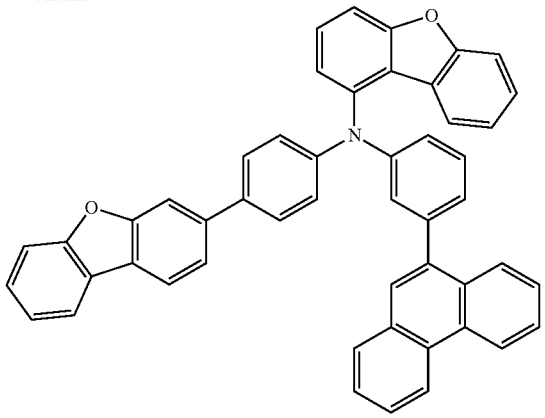
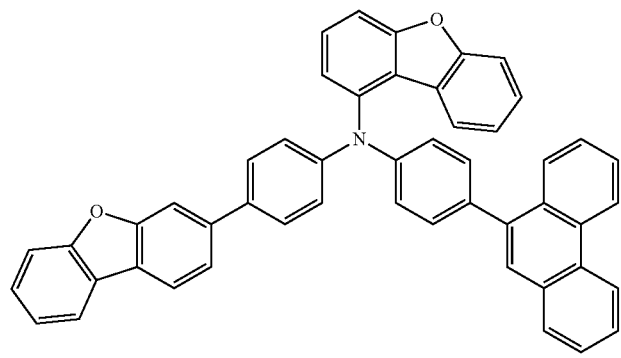
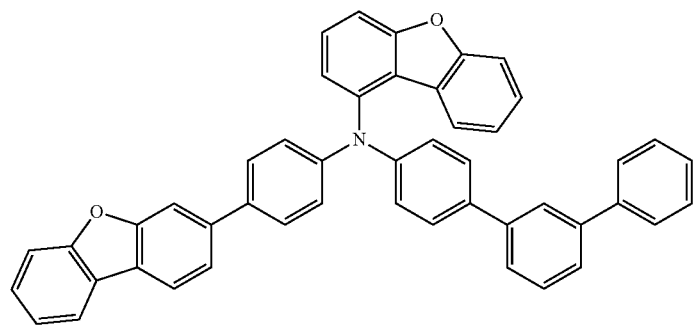
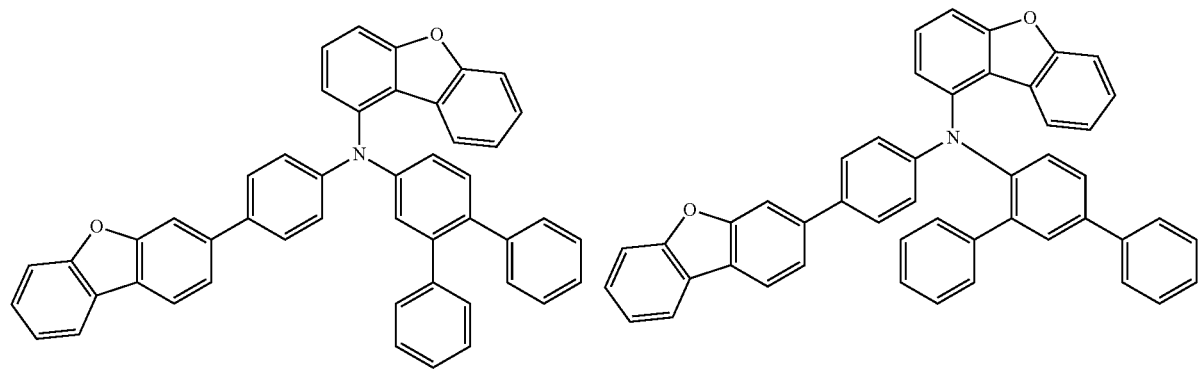

-continued
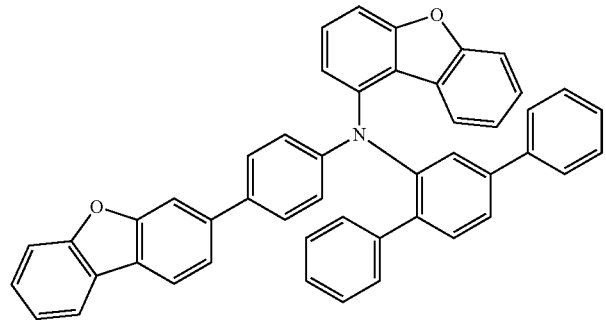
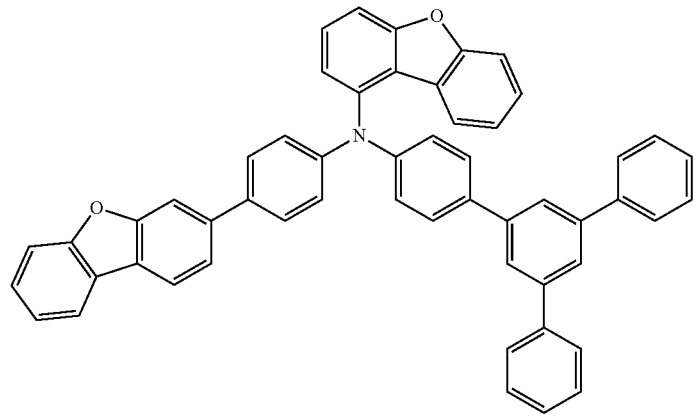
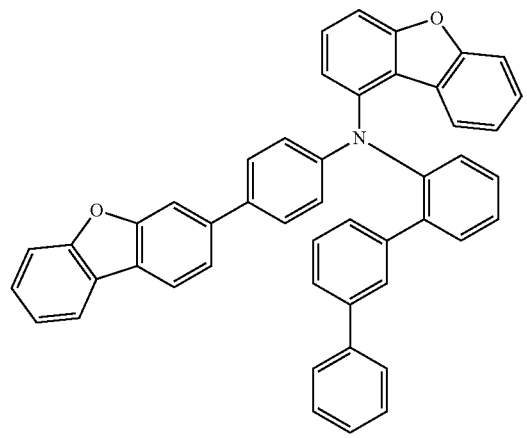
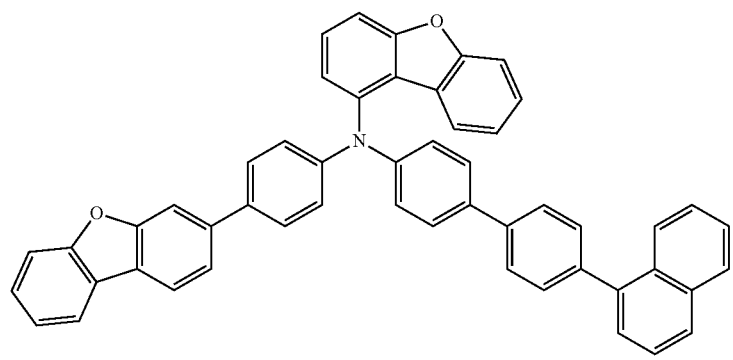

-continued
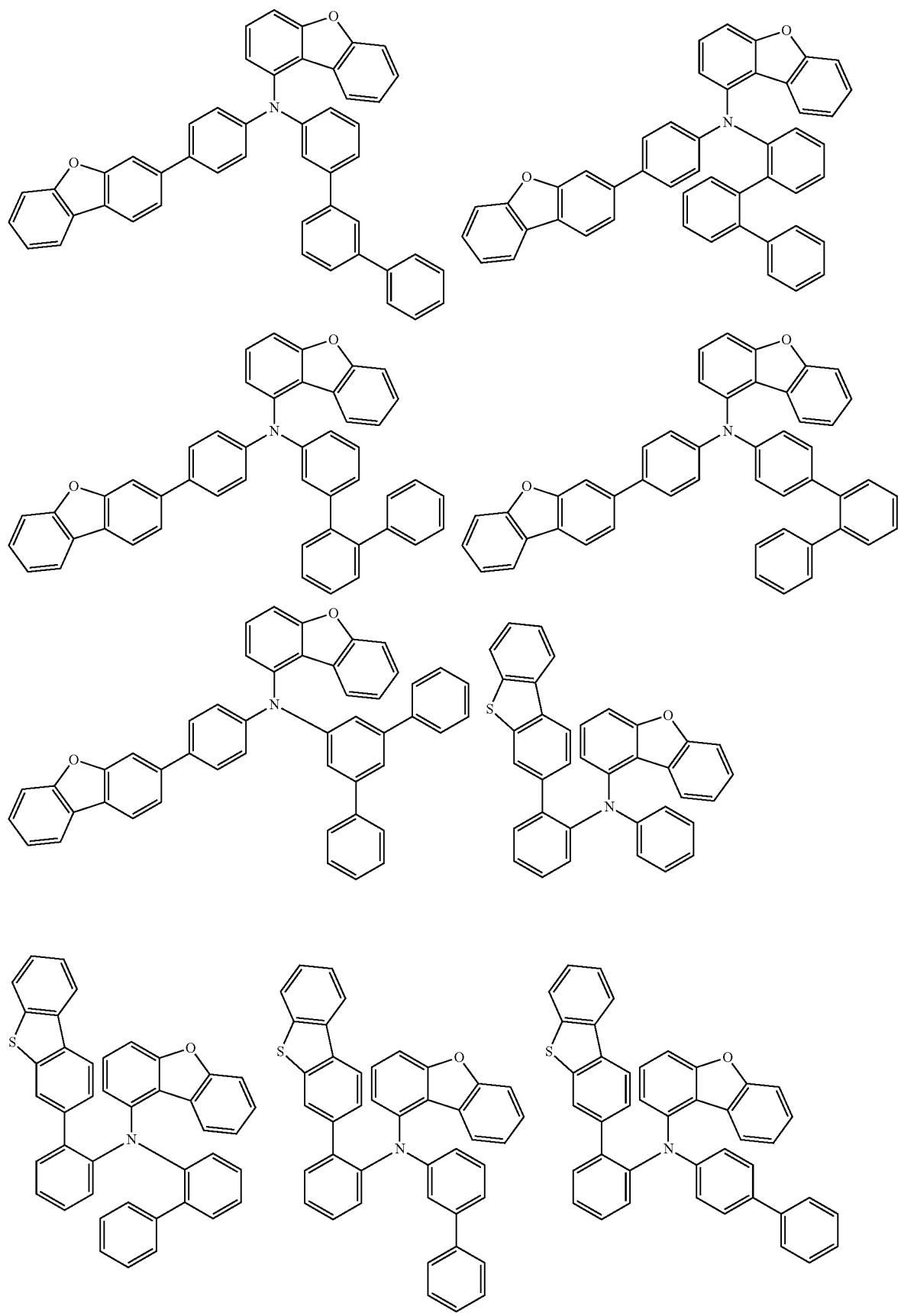

-continued
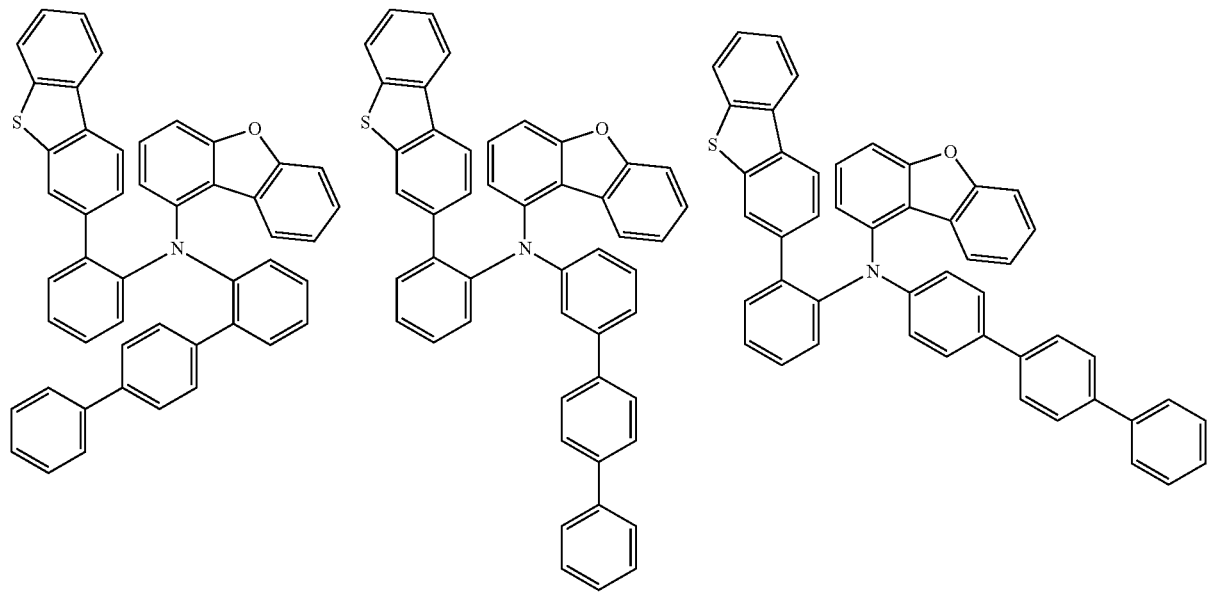
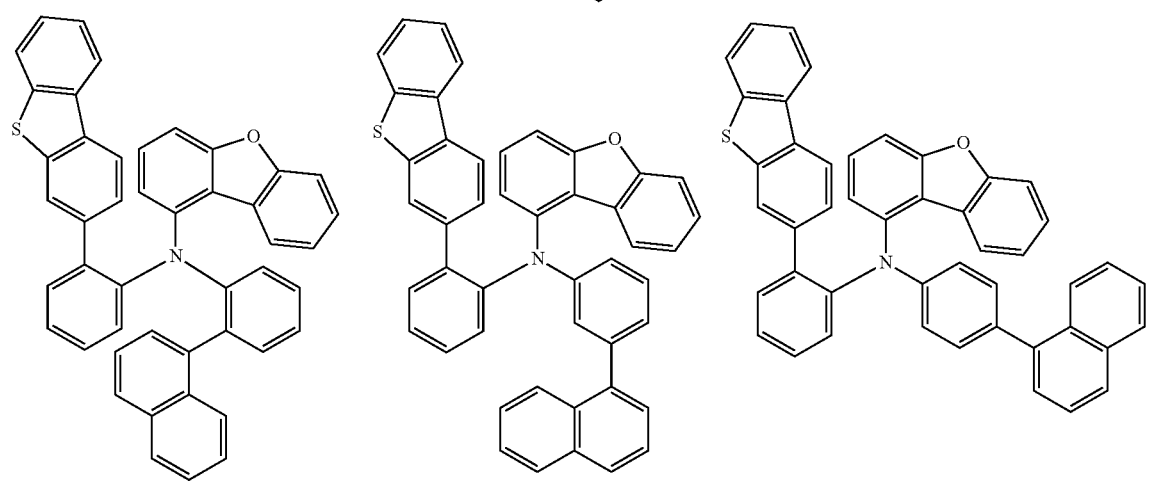
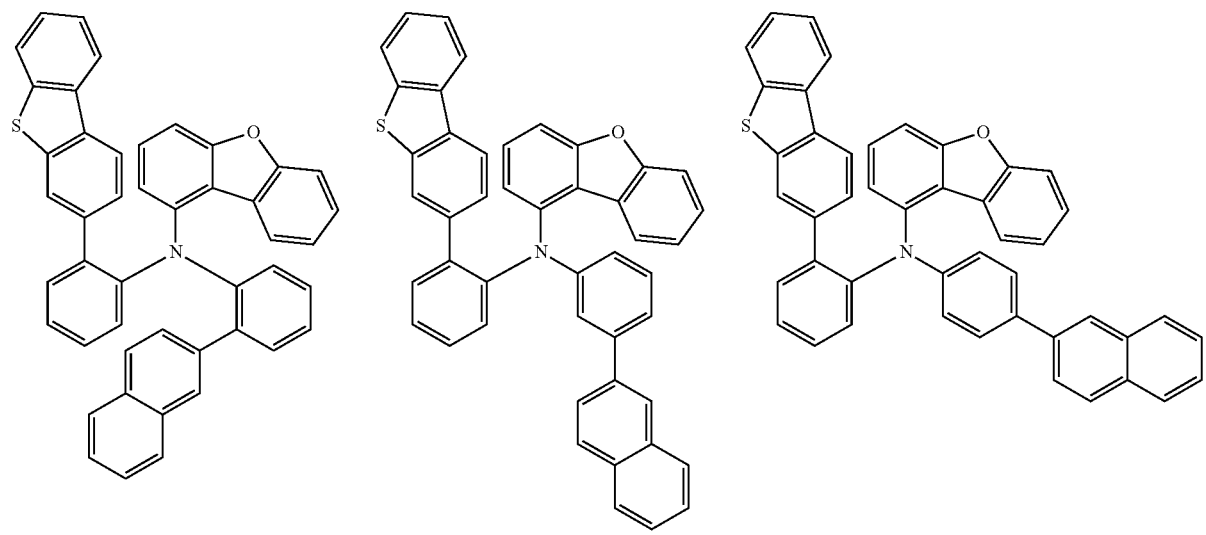

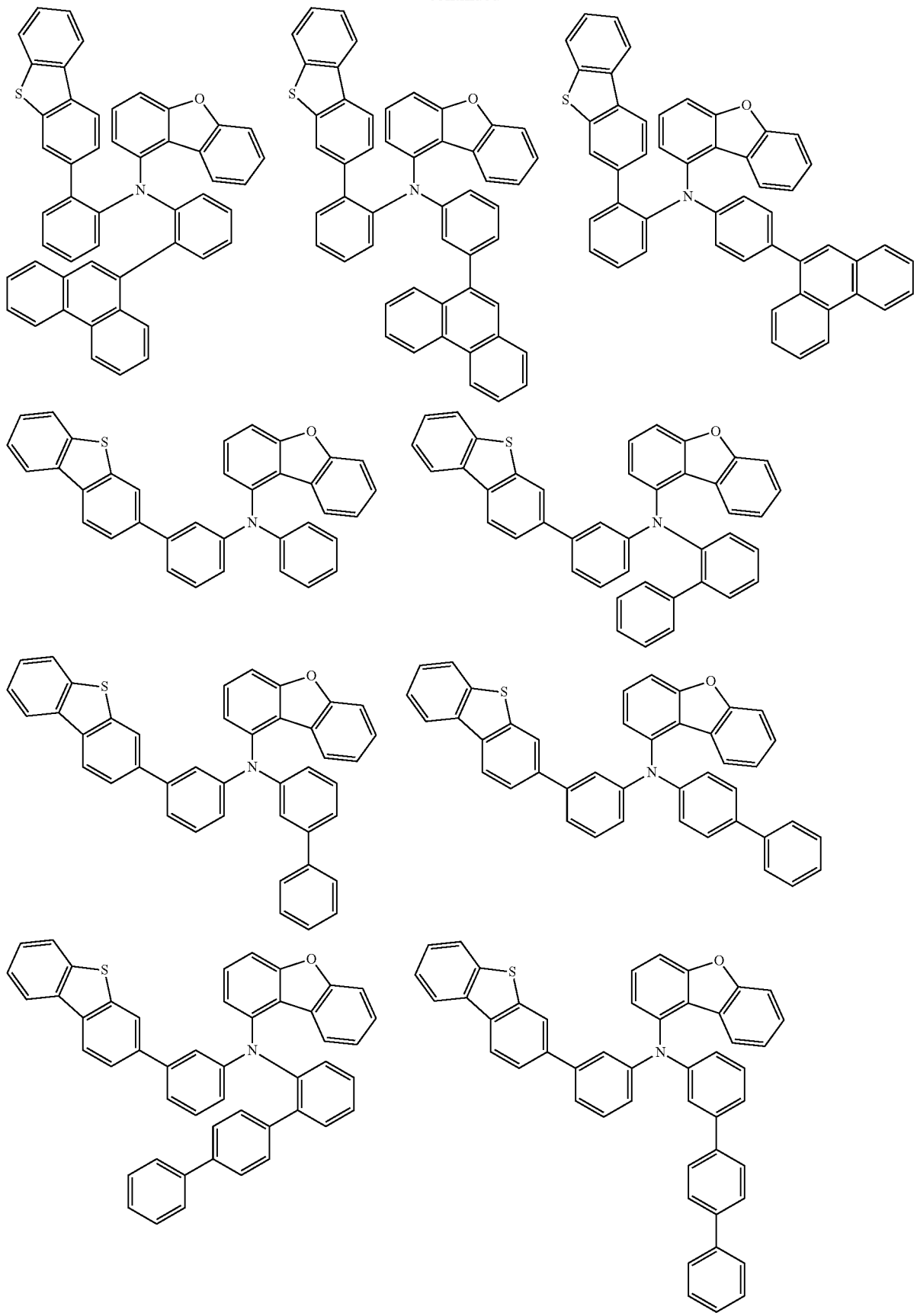

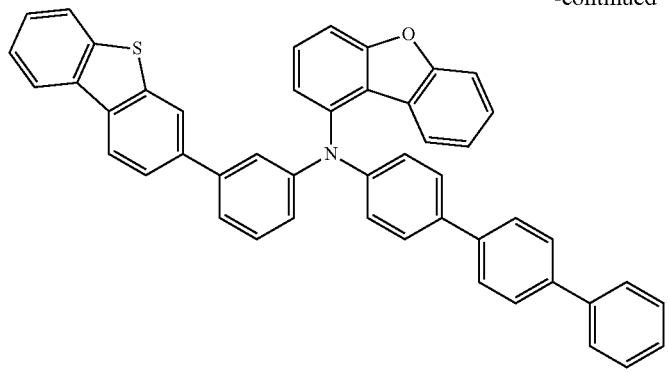
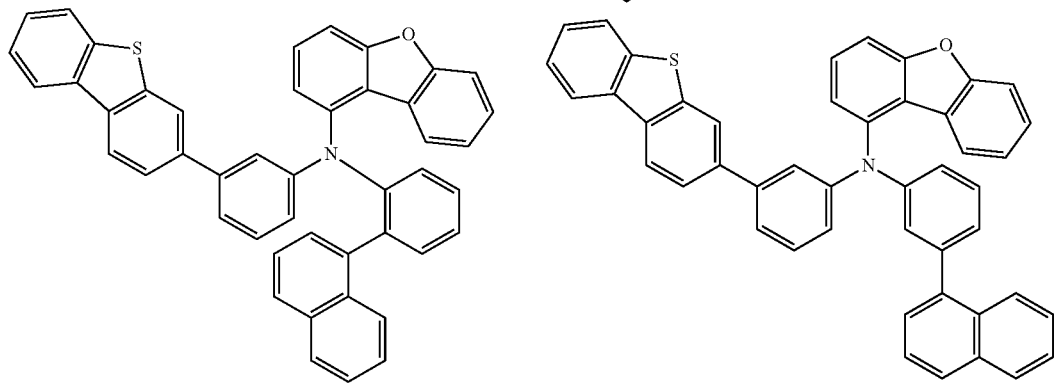
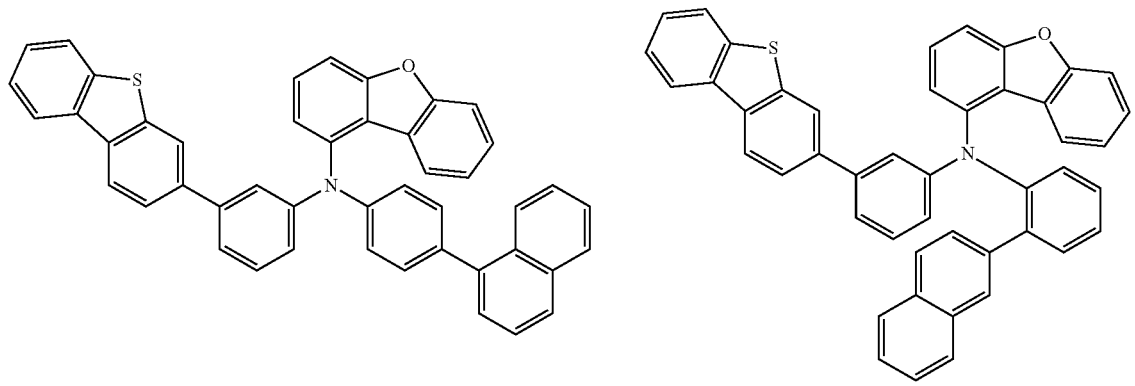
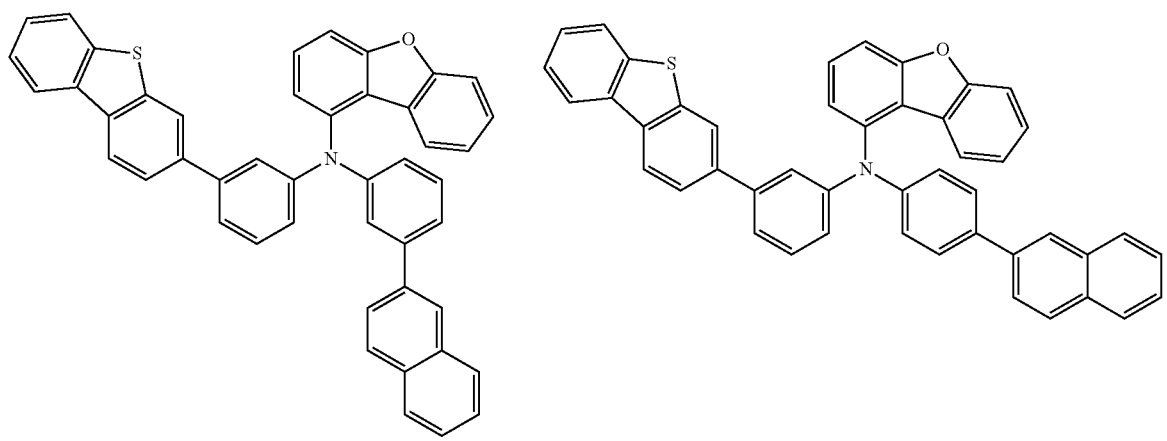

-continued
97
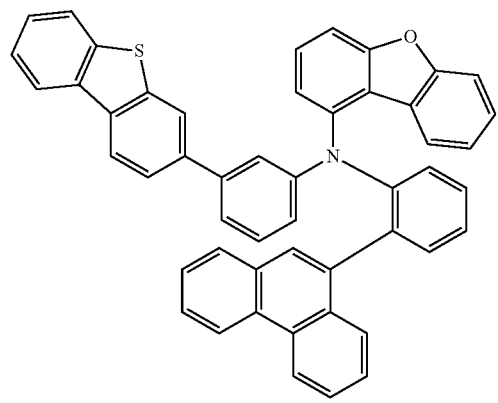
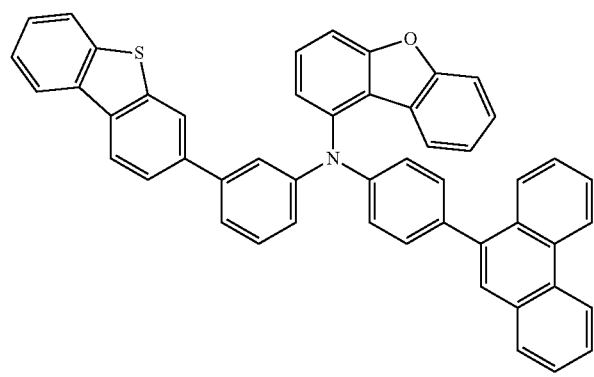
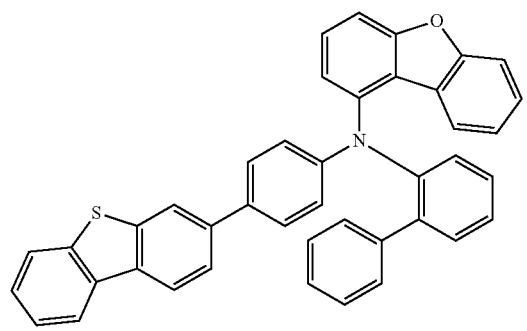
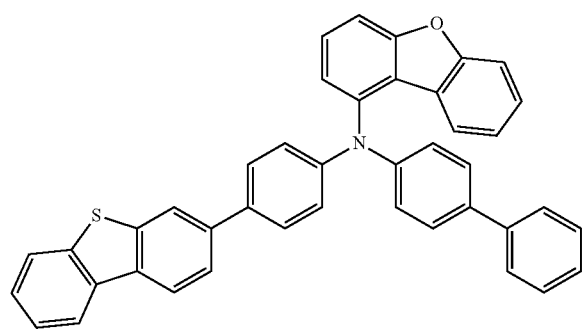
98
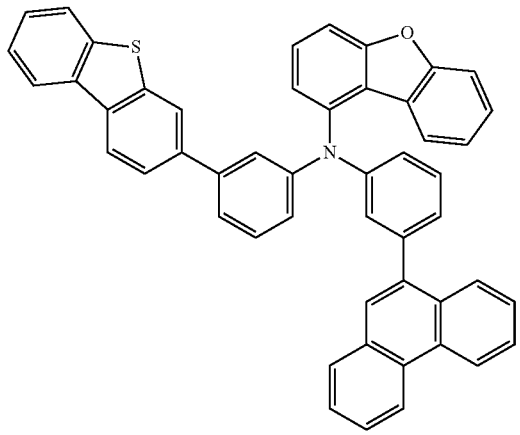
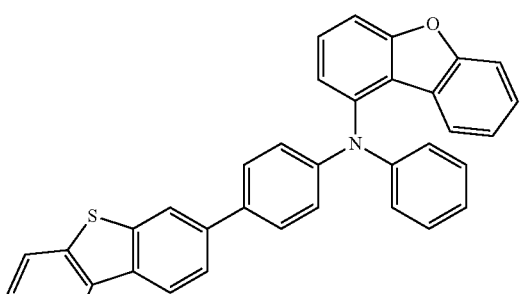
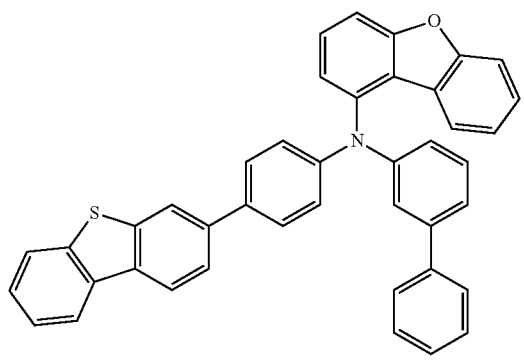
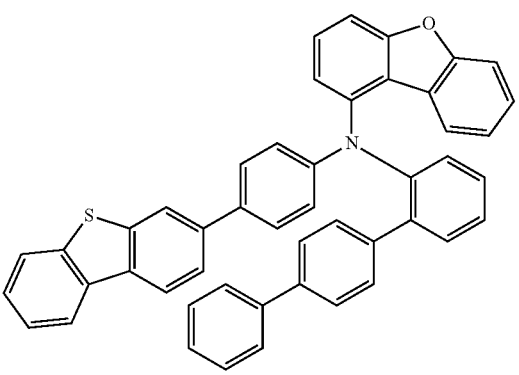

-continued
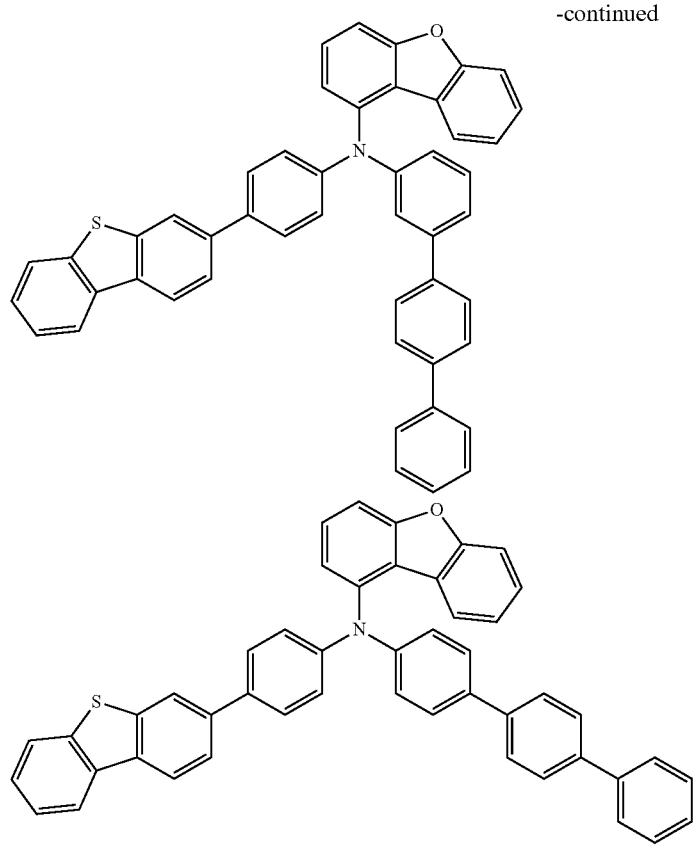
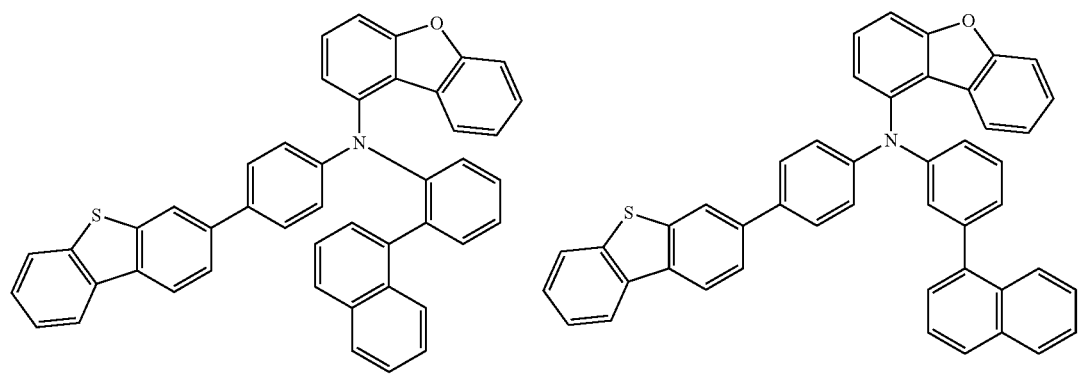
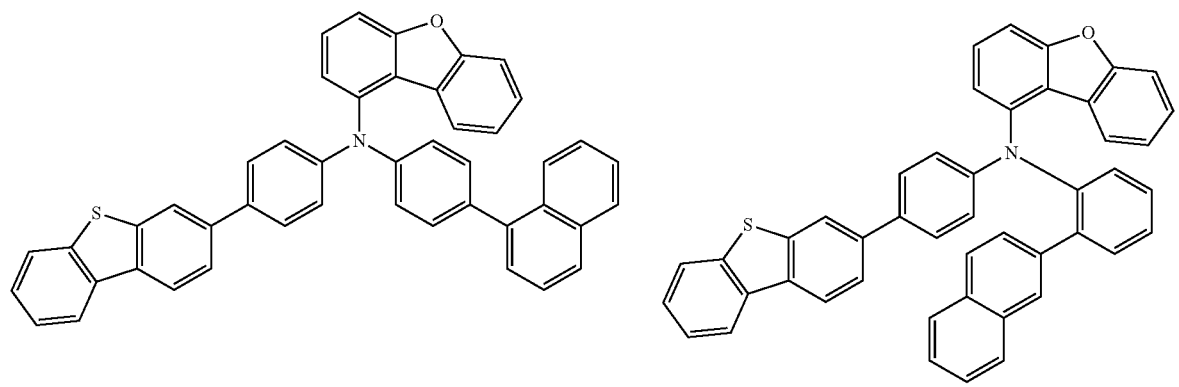

101
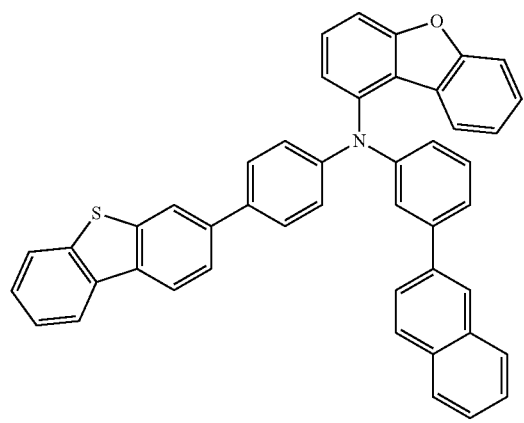
102
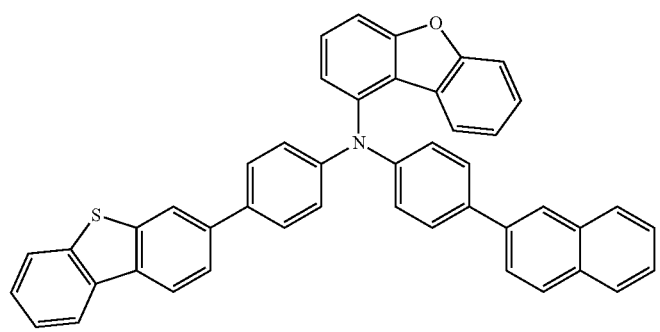
-continued
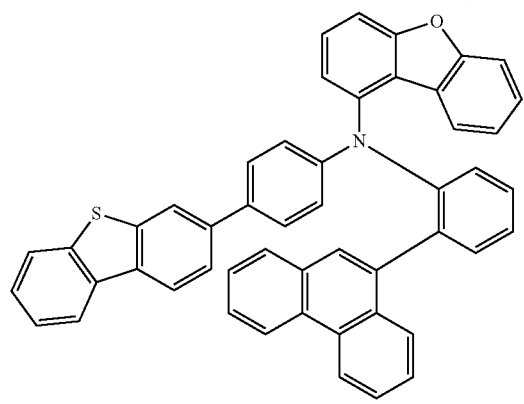
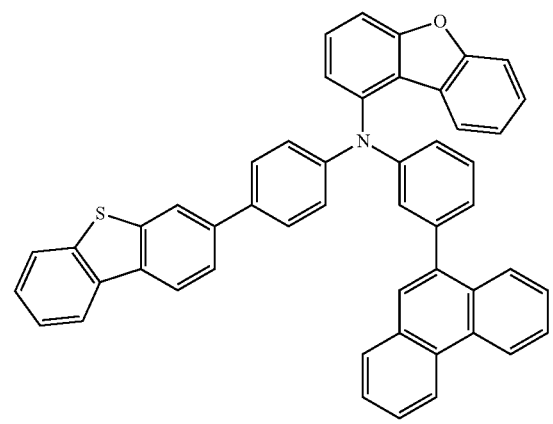
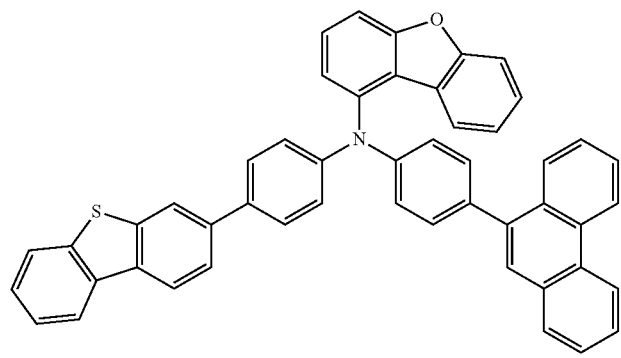
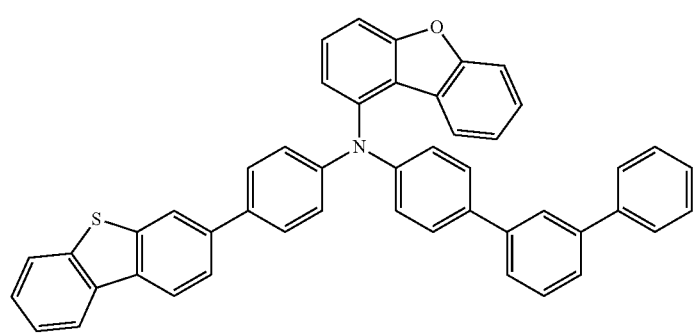

-continued
103
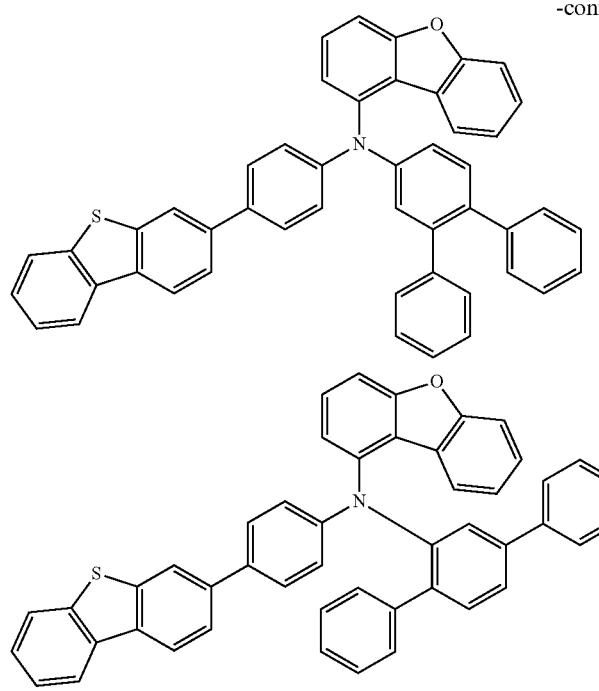
104
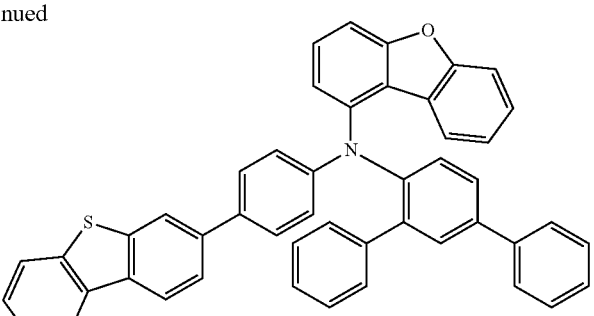
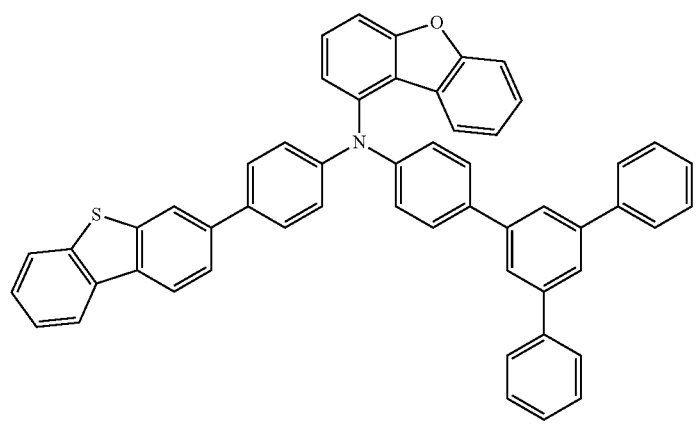
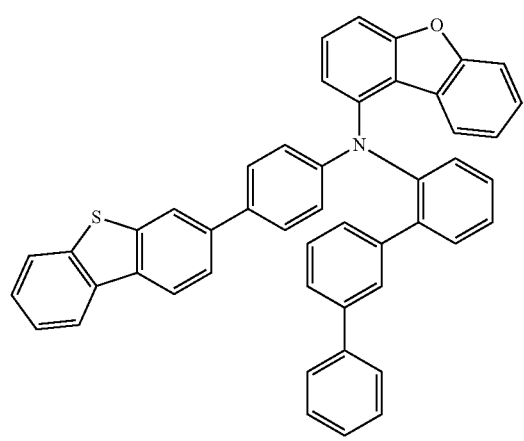

-continued
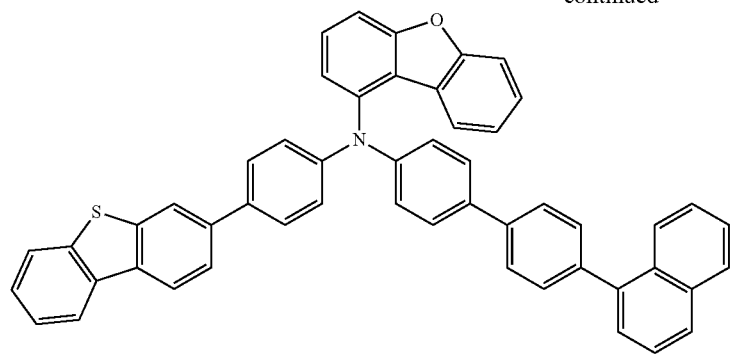
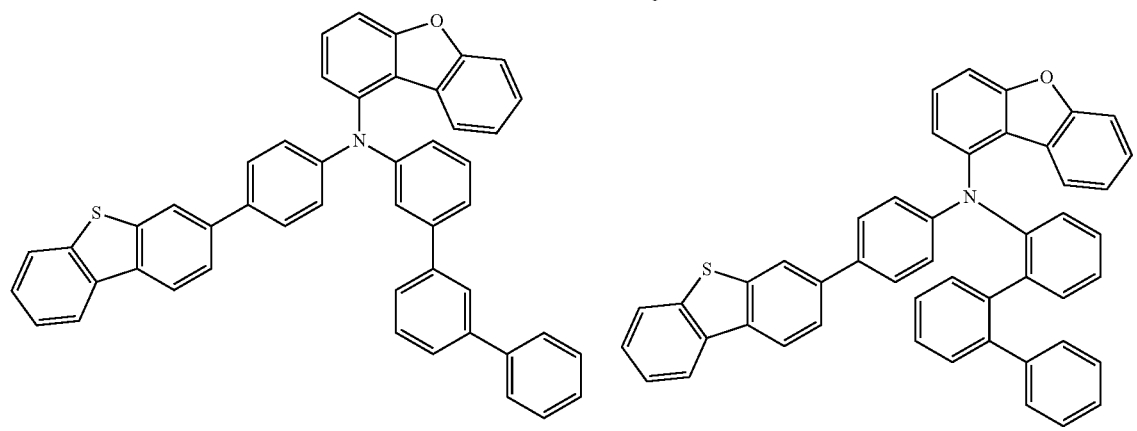
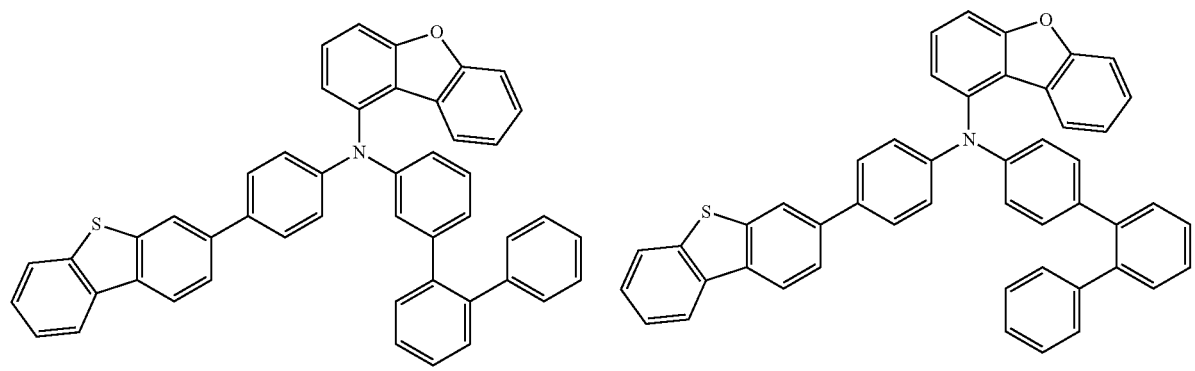
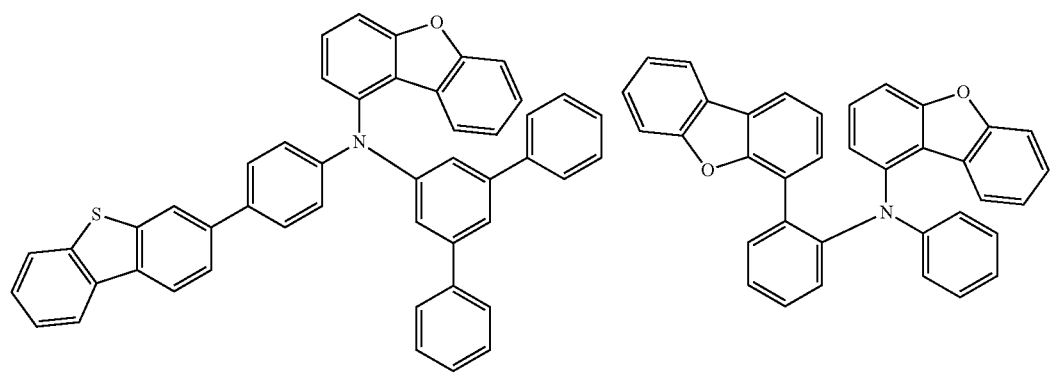

-continued
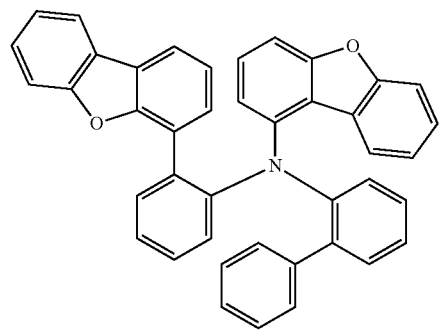
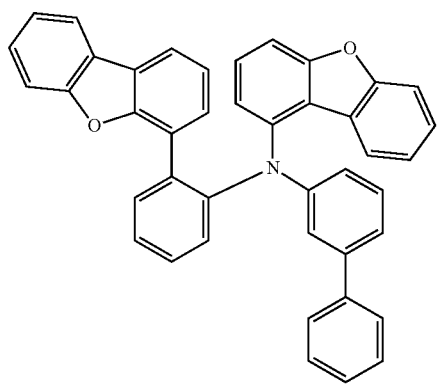
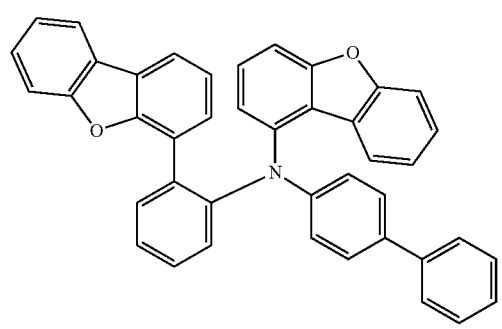
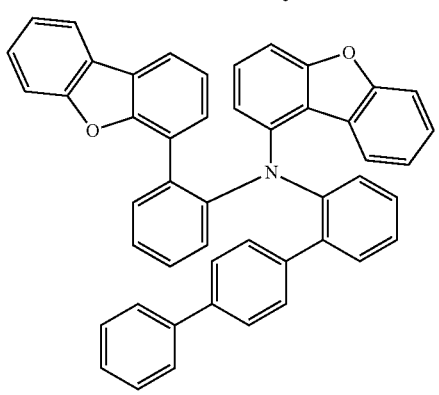
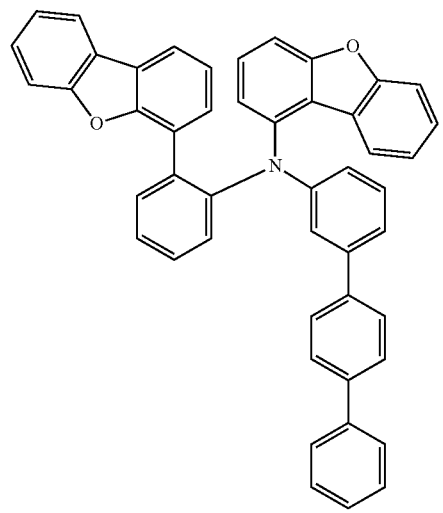
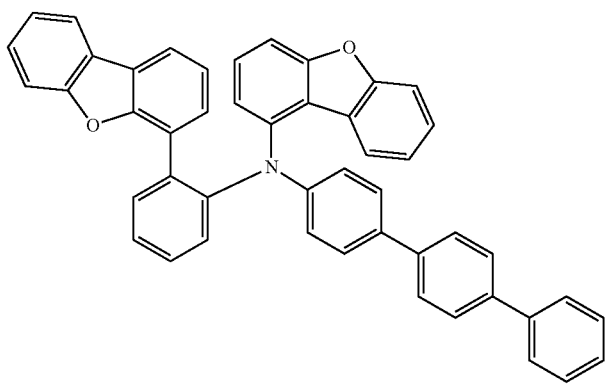
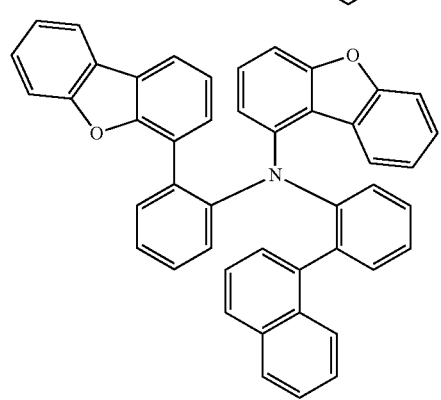
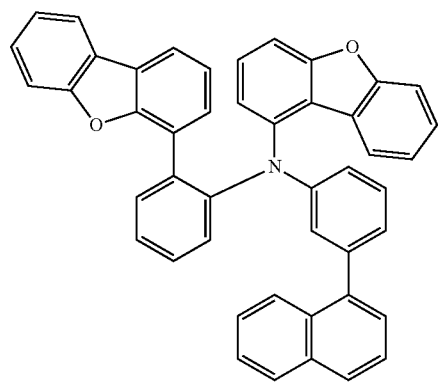

-continued
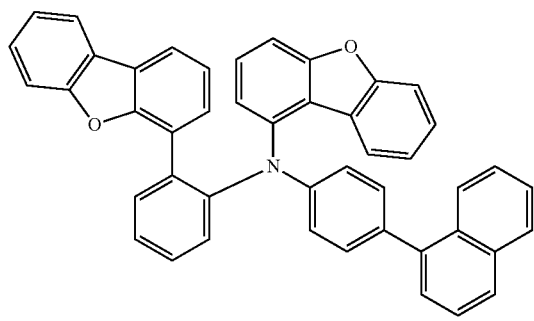
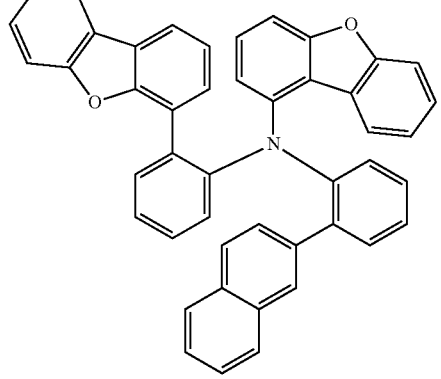
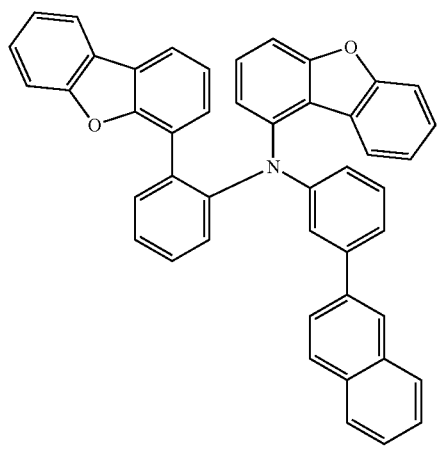
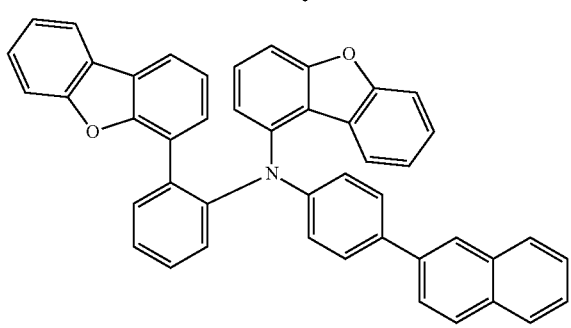
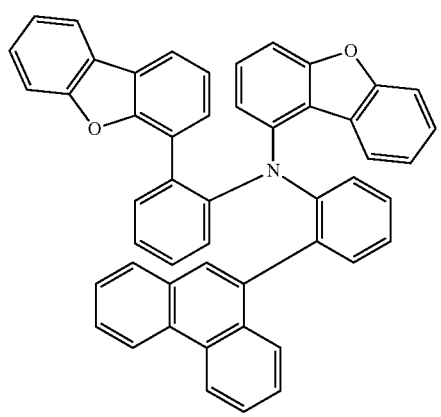
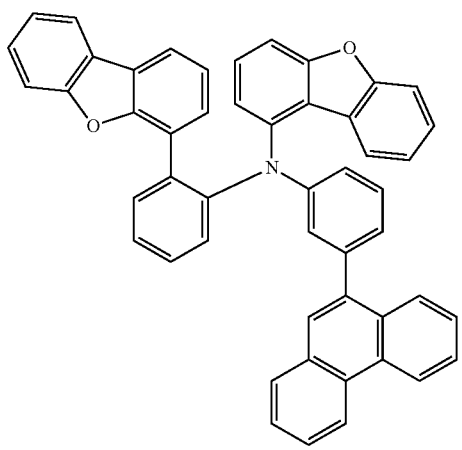
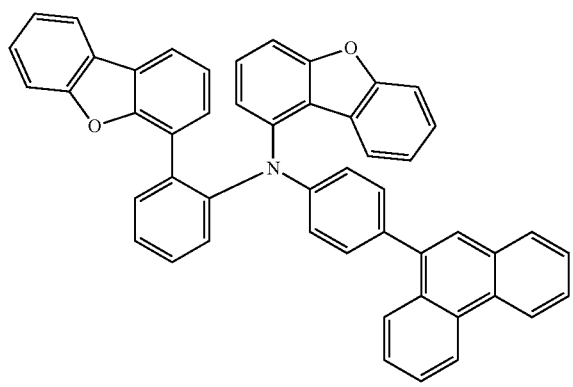
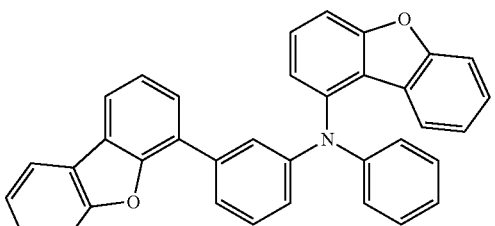

-continued
111
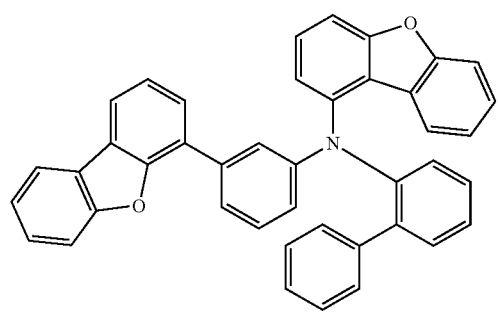
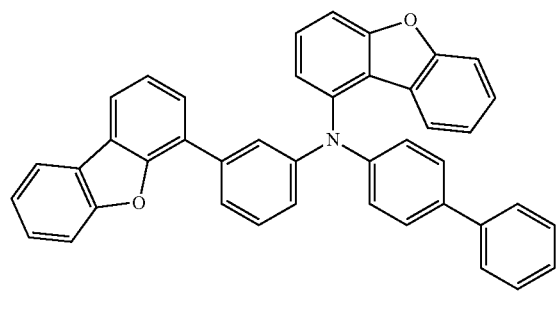
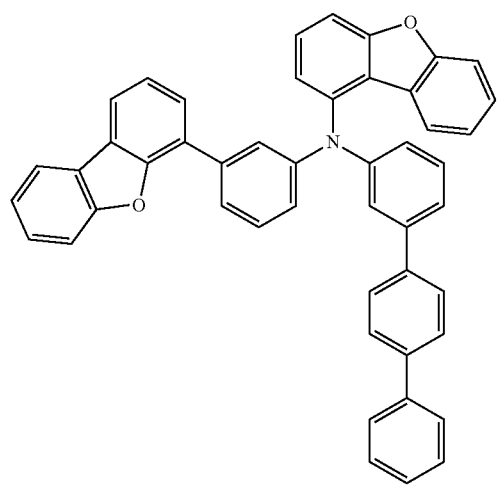
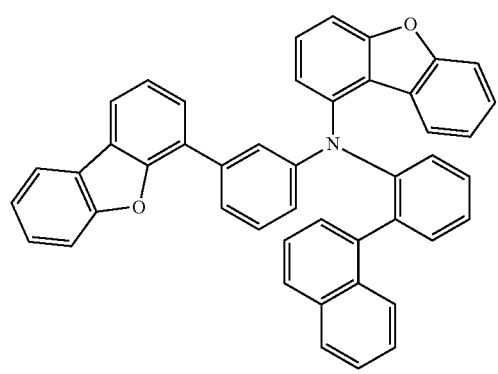
112
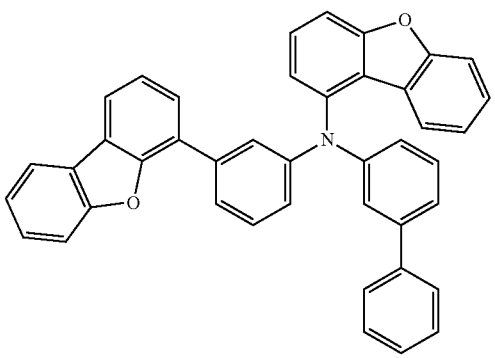
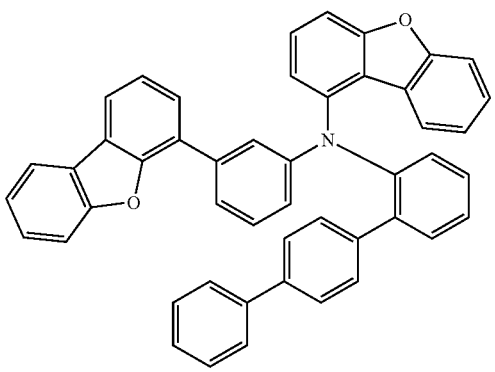
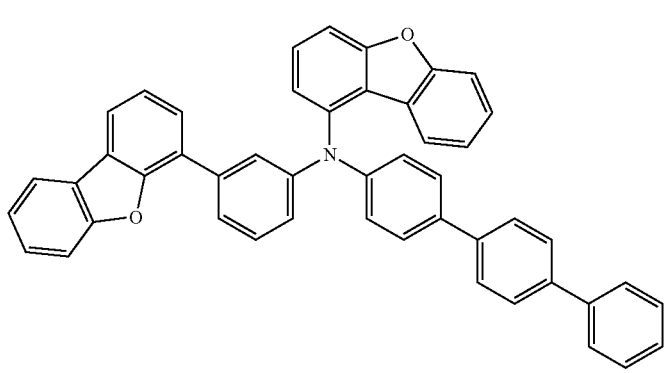
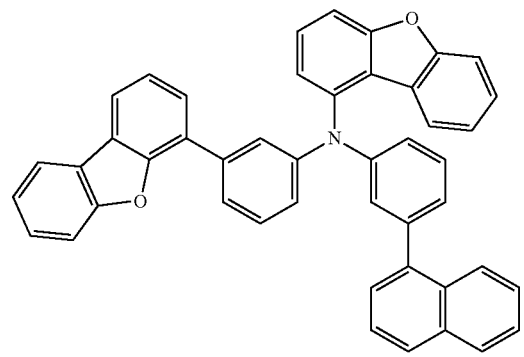

113 114
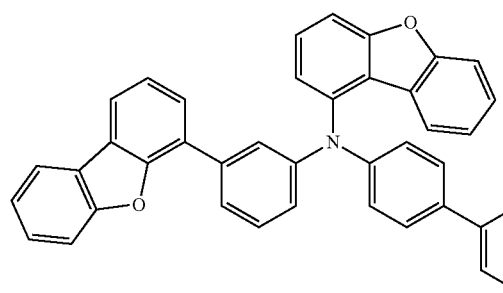 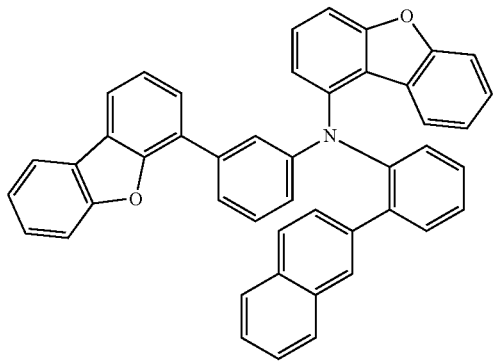
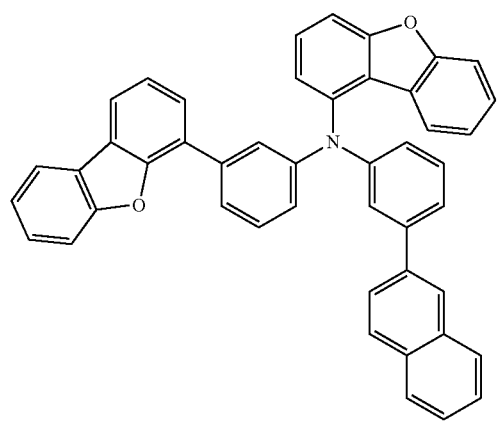 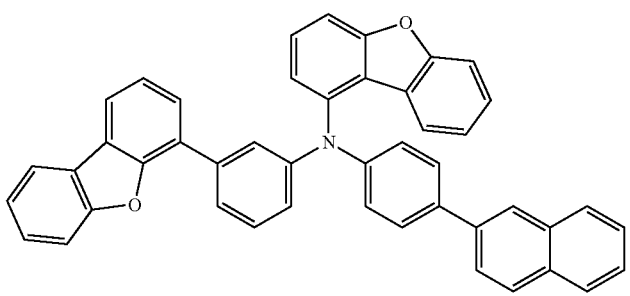
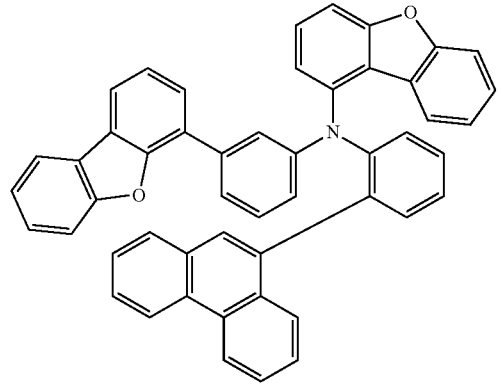 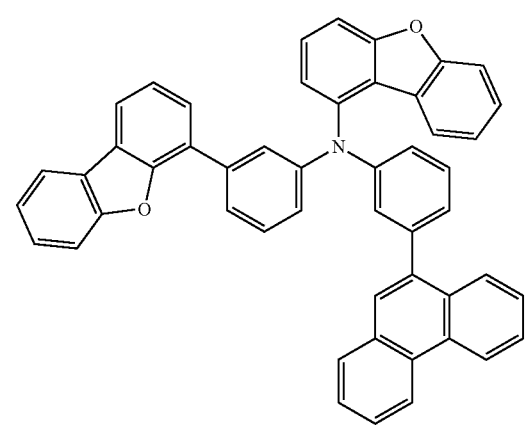
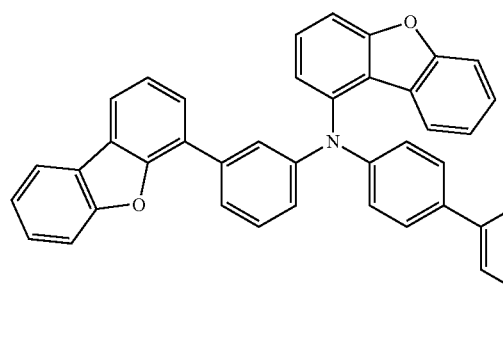 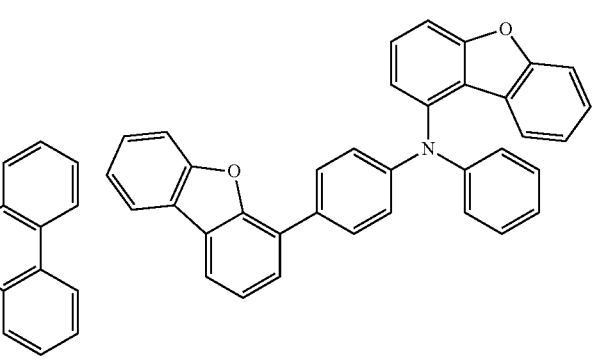

115
116
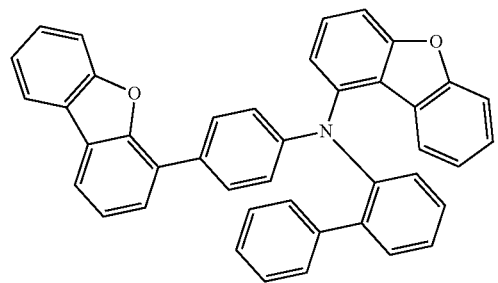
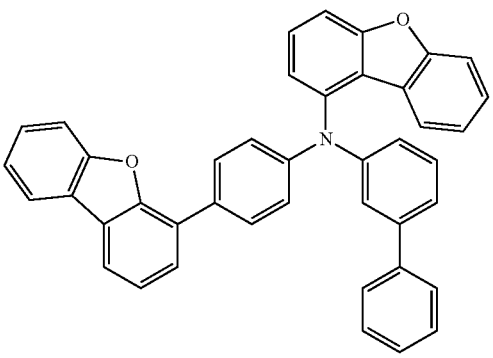
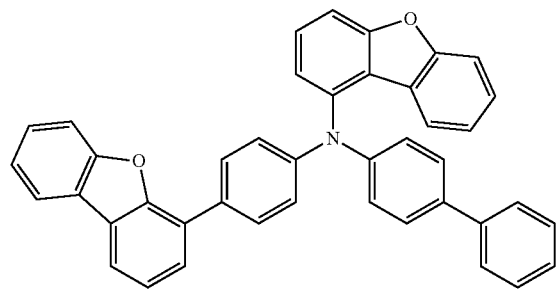
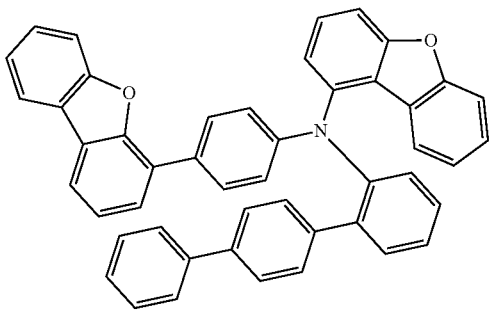
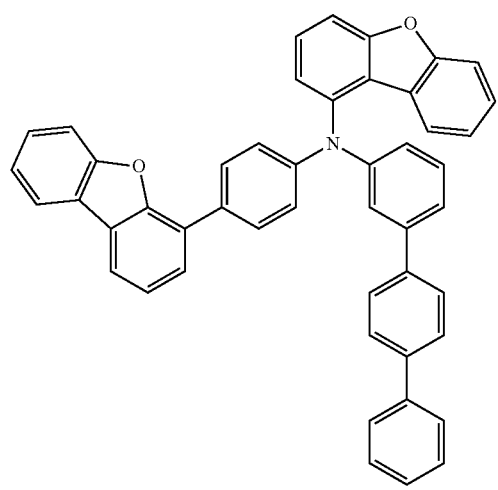
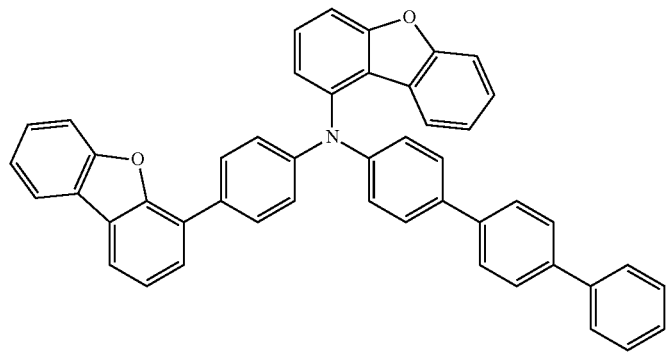
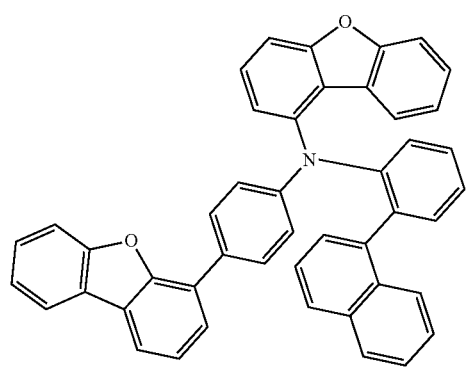
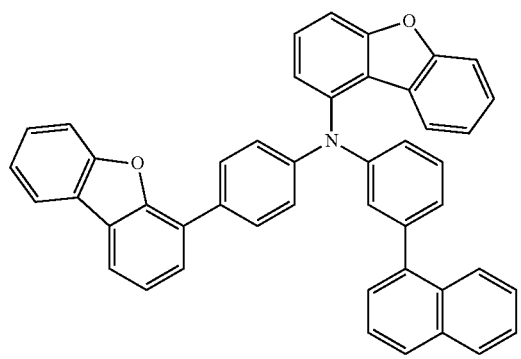

117 118
-continued
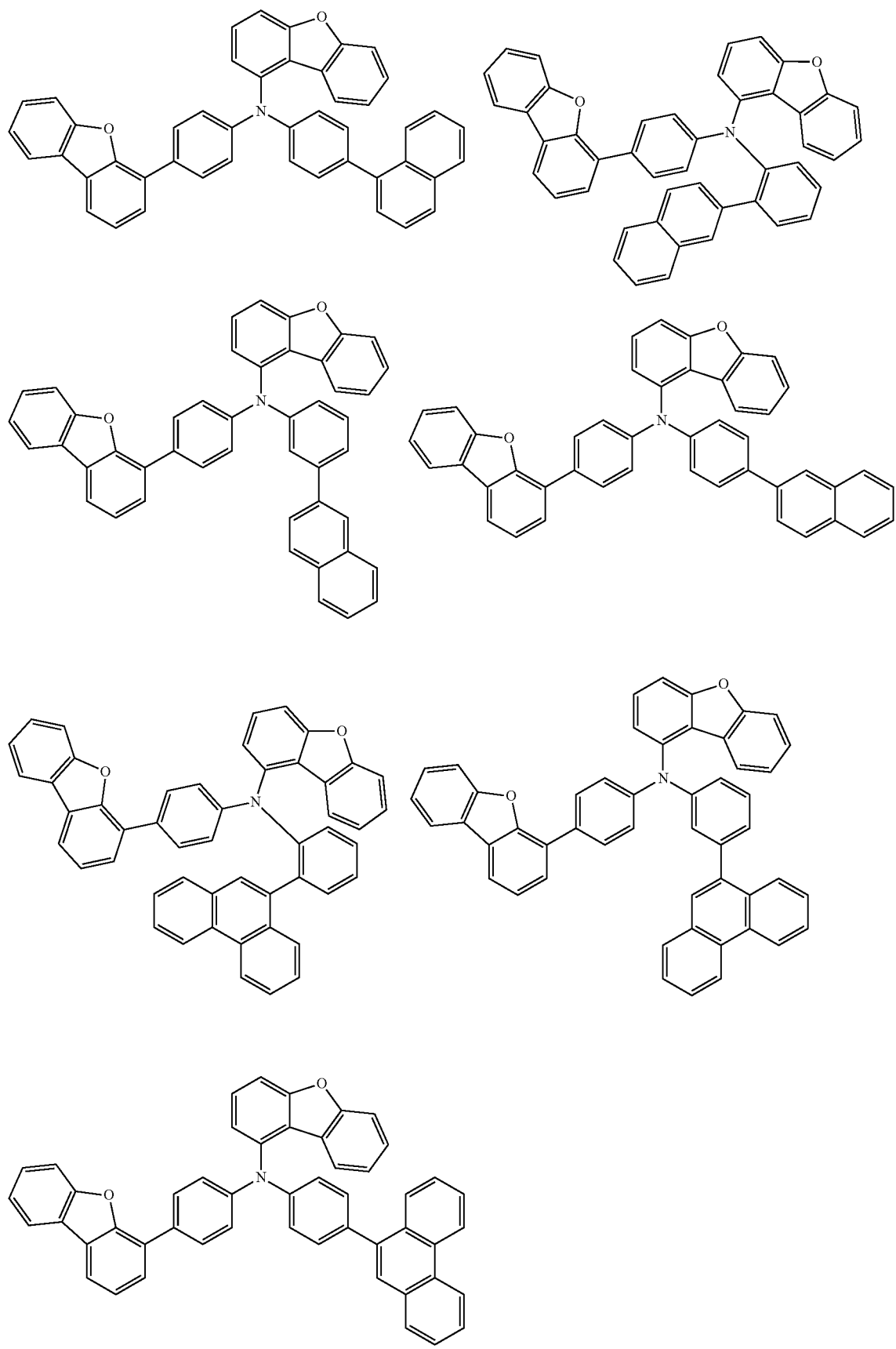

-continued
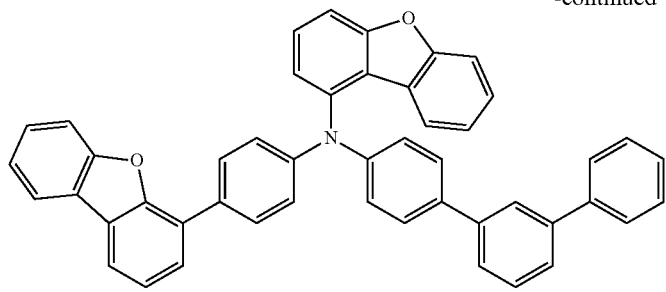
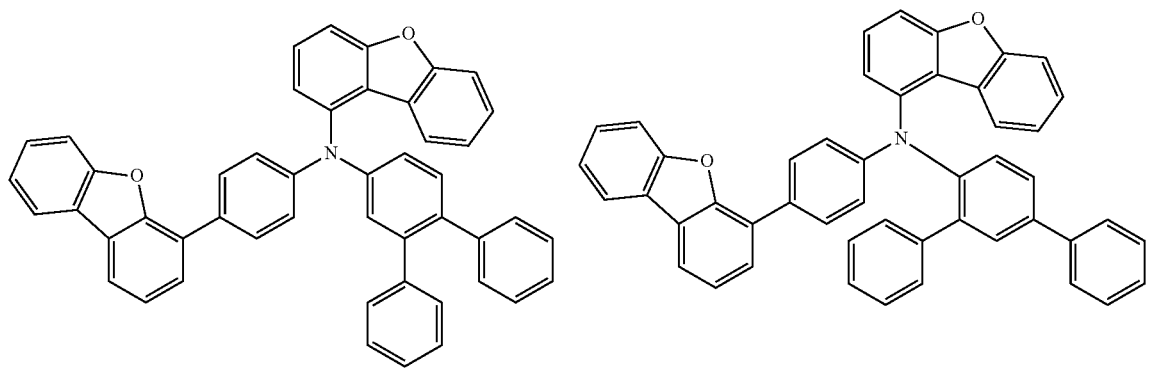
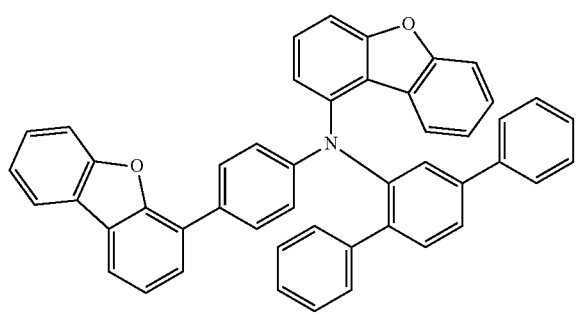
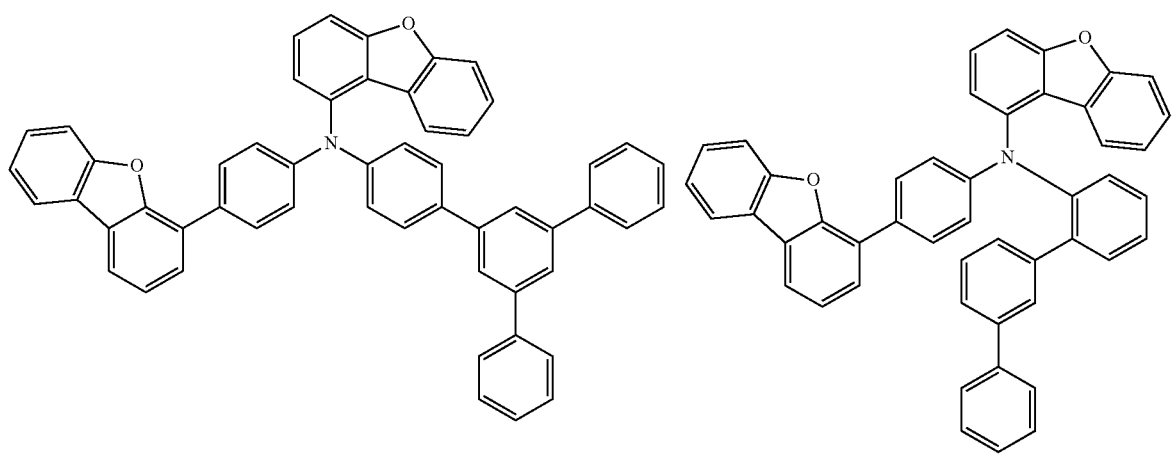

121
122
-continued
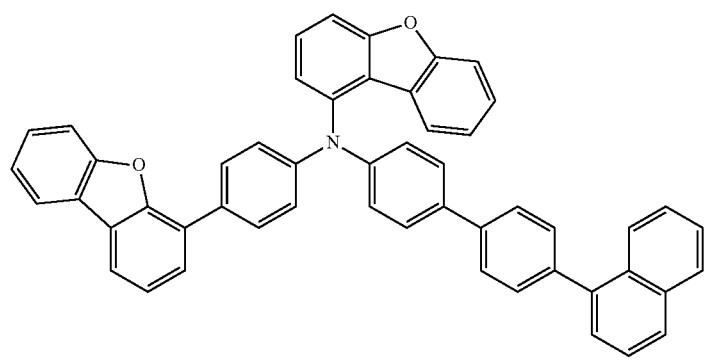
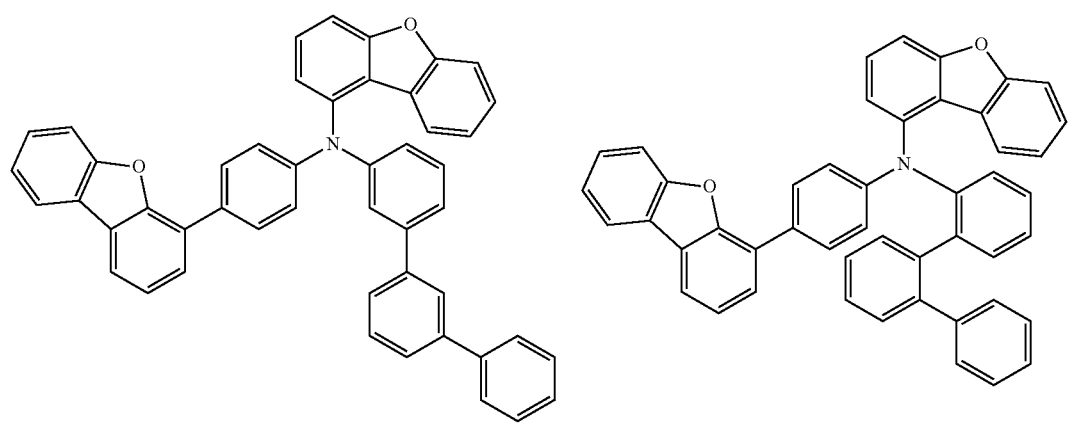
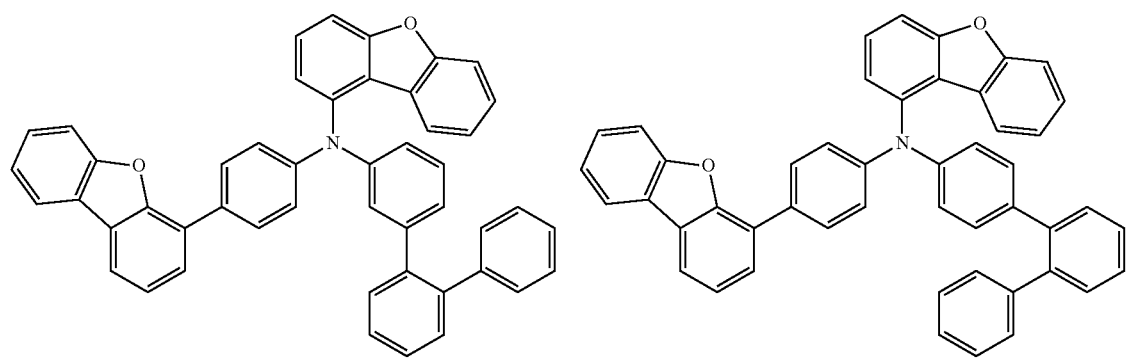
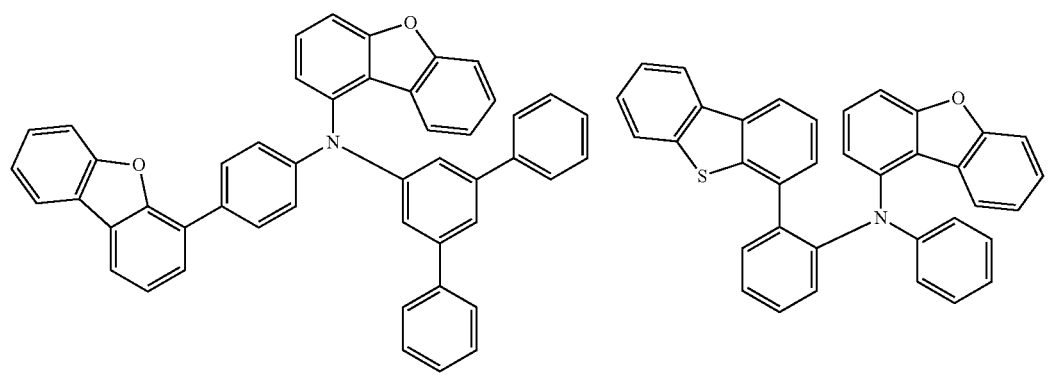

-continued
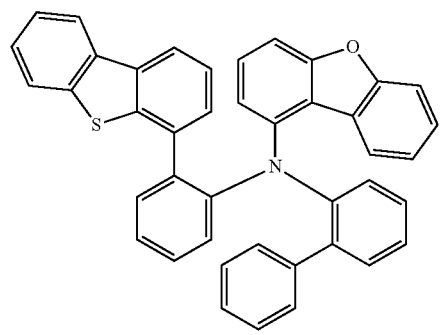
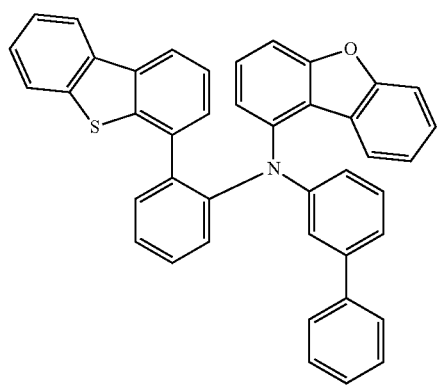
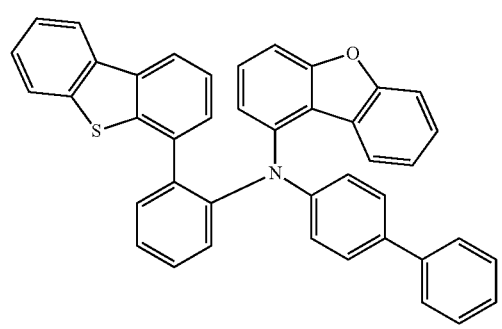
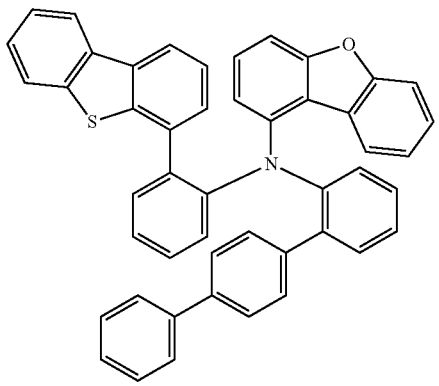
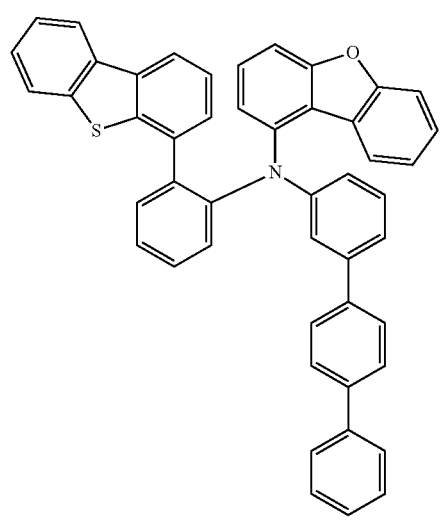
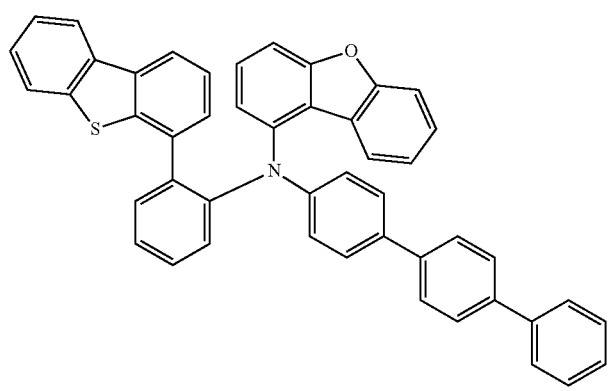
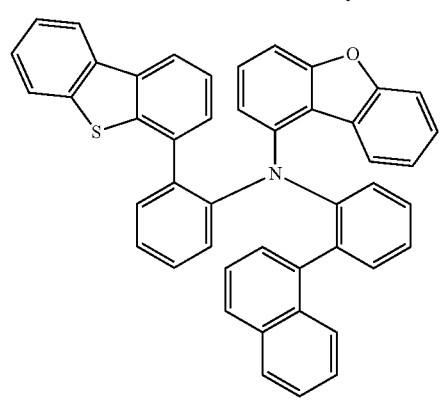
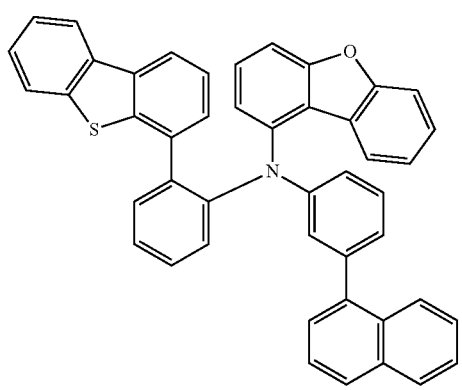

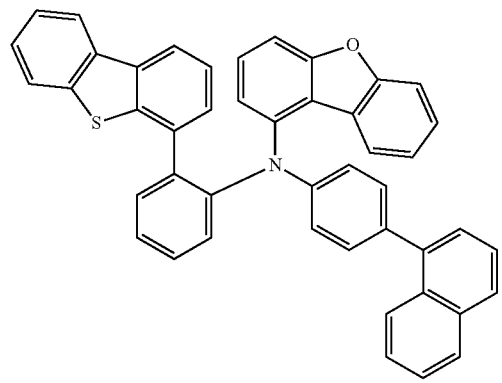
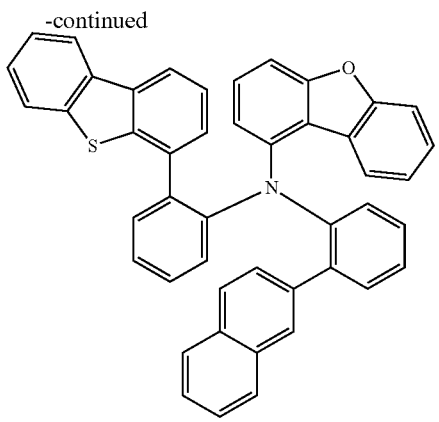
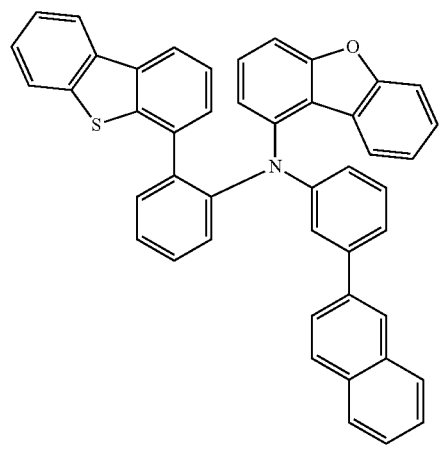
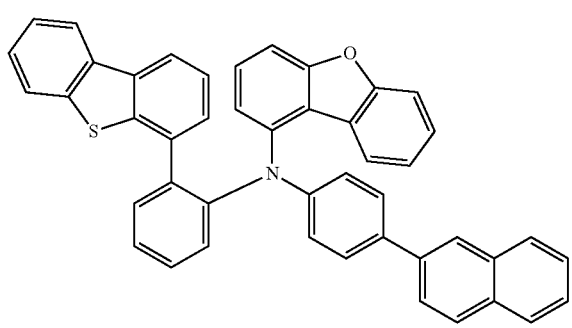
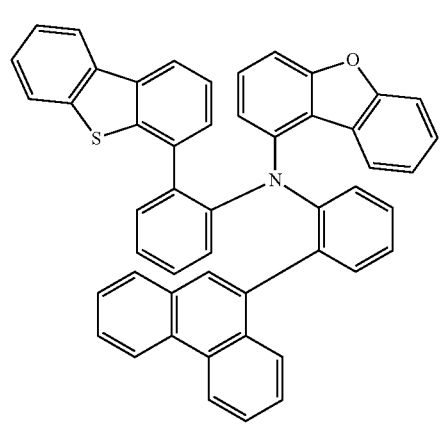
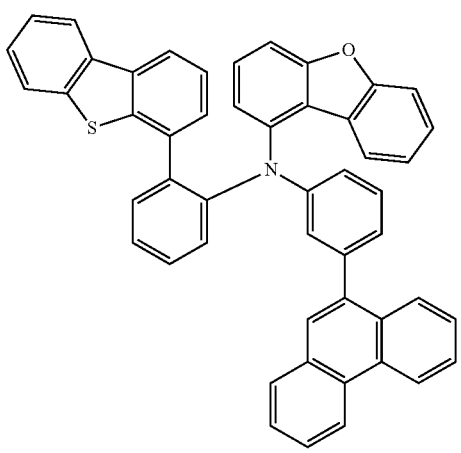
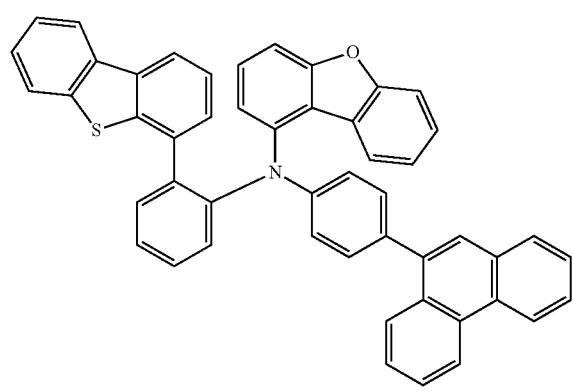
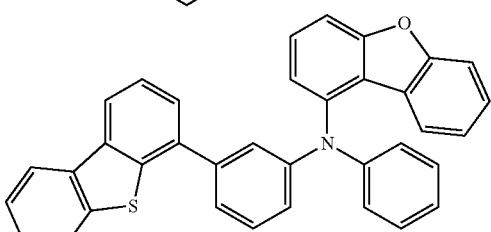

-continued
127
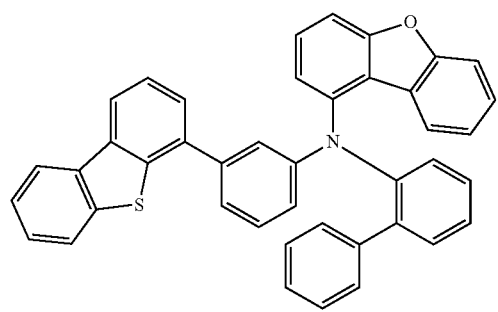
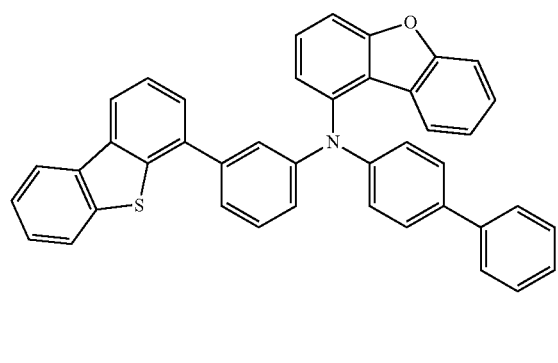
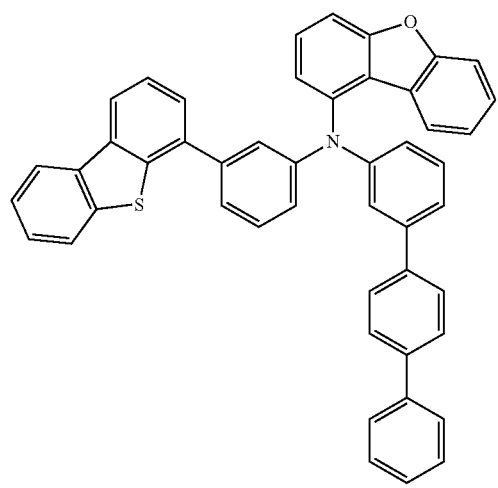
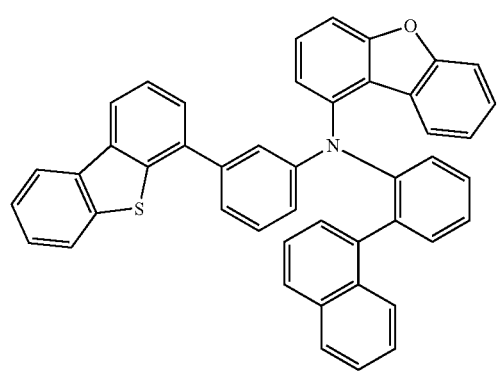
128
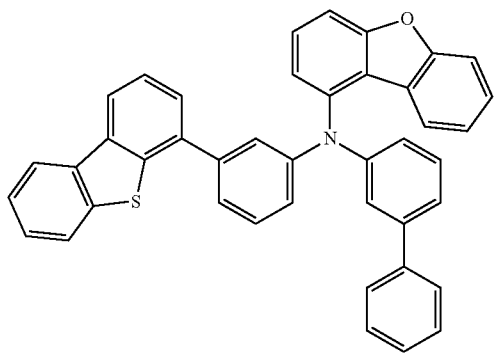
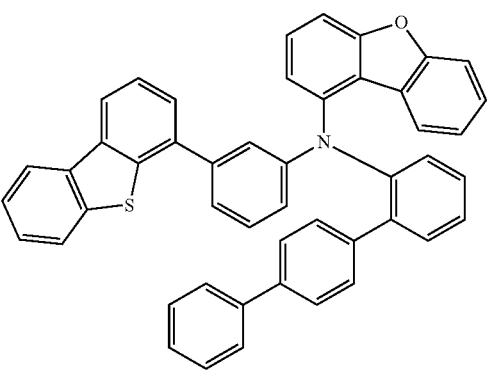
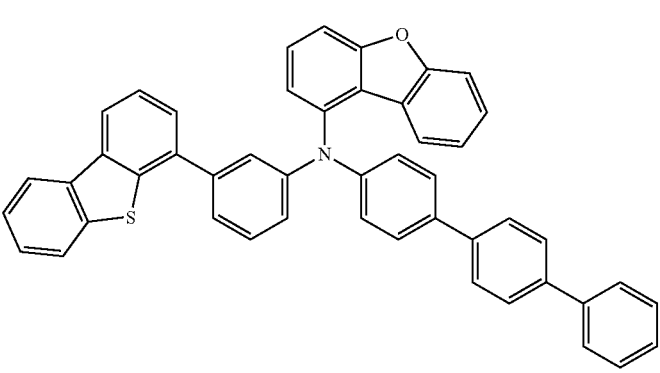
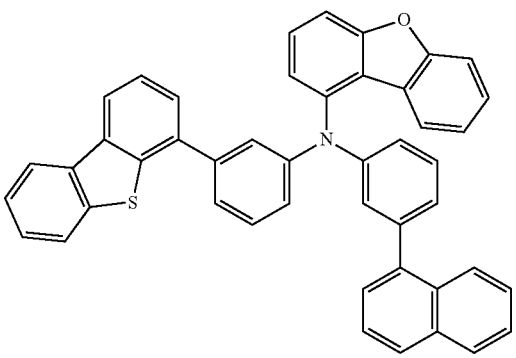

-continued
| 129 | 130 |
|---|---|
| 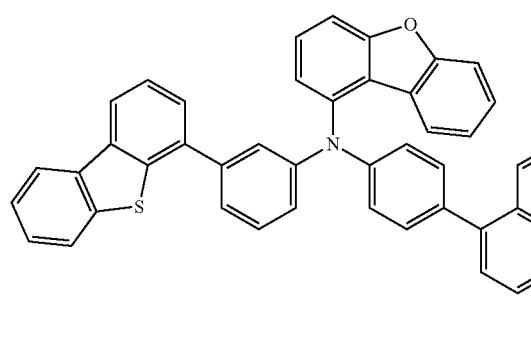 | 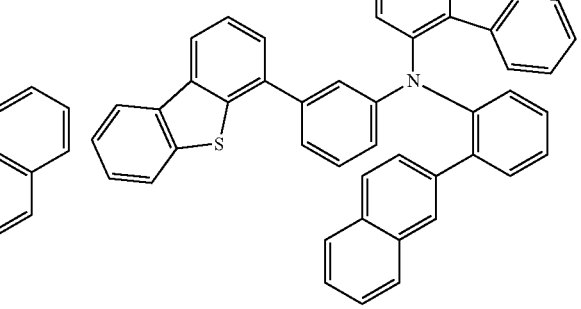 |
| 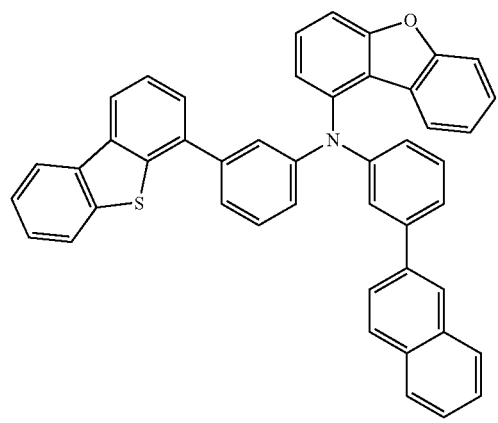 | 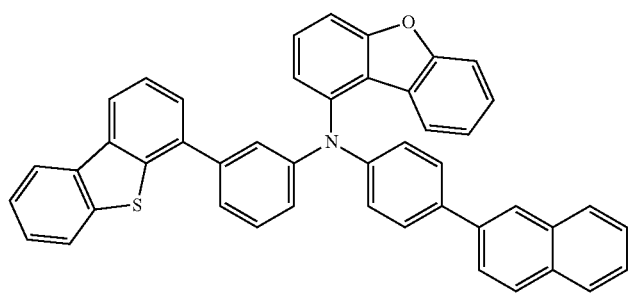 |
| 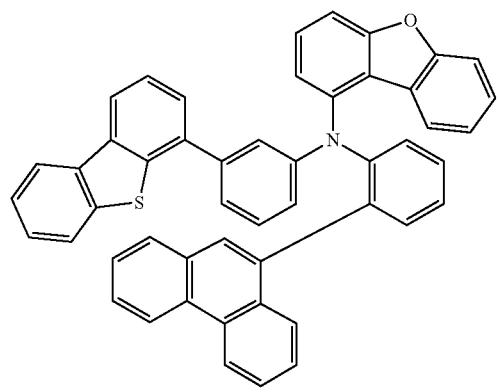 | 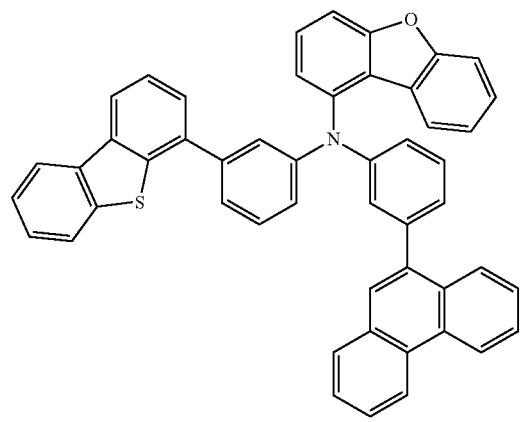 |
| 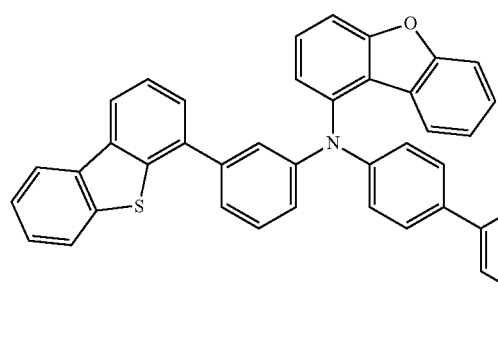 | 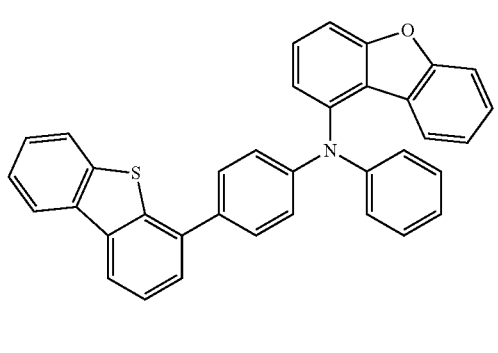 |

131
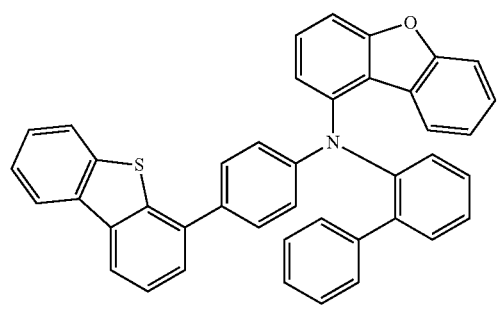
132
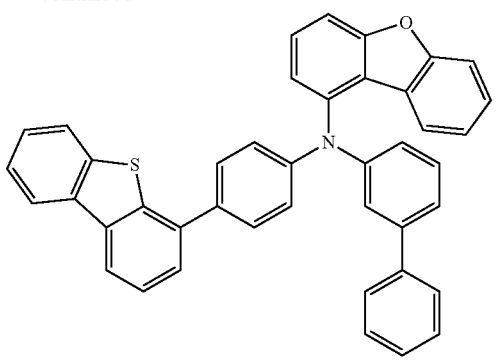
-continued
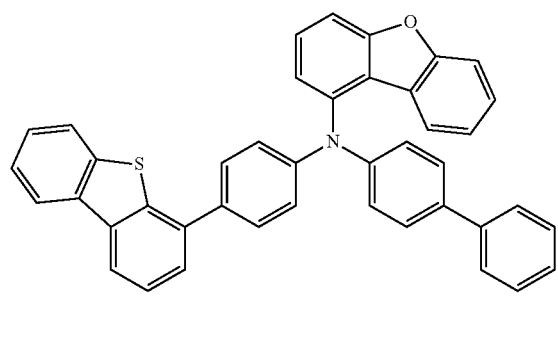
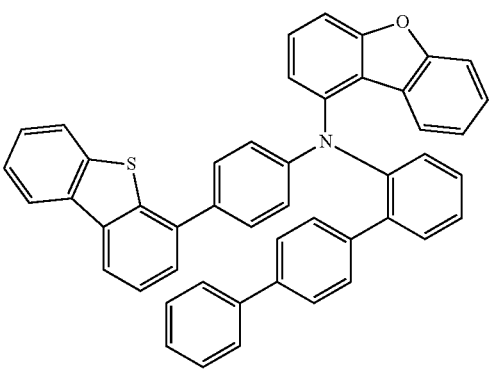
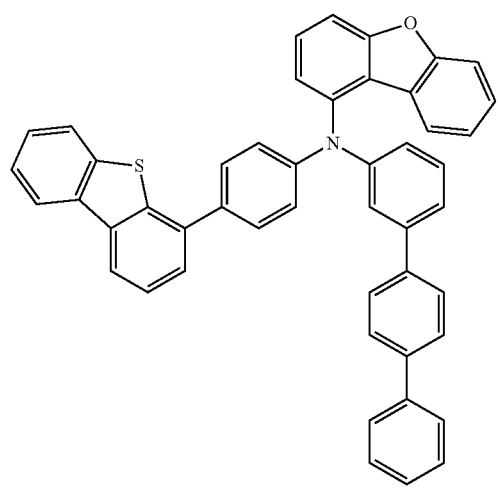
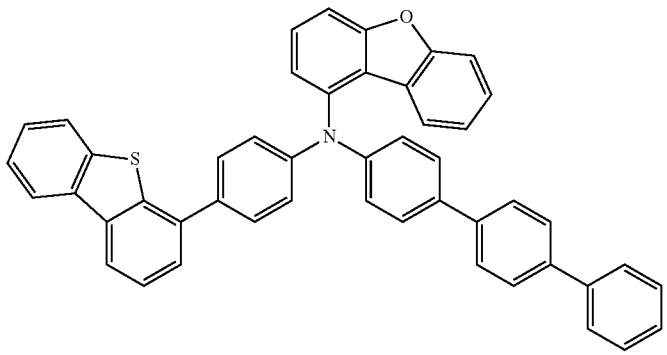
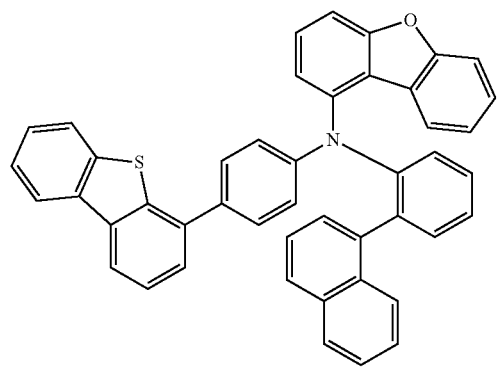
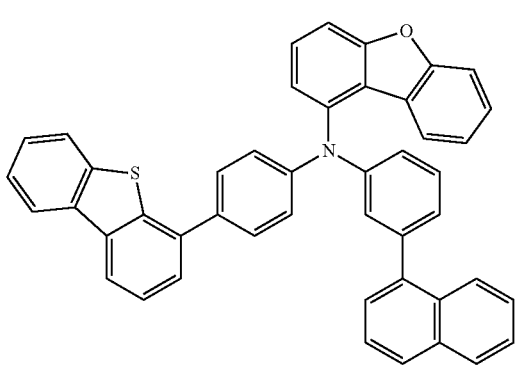

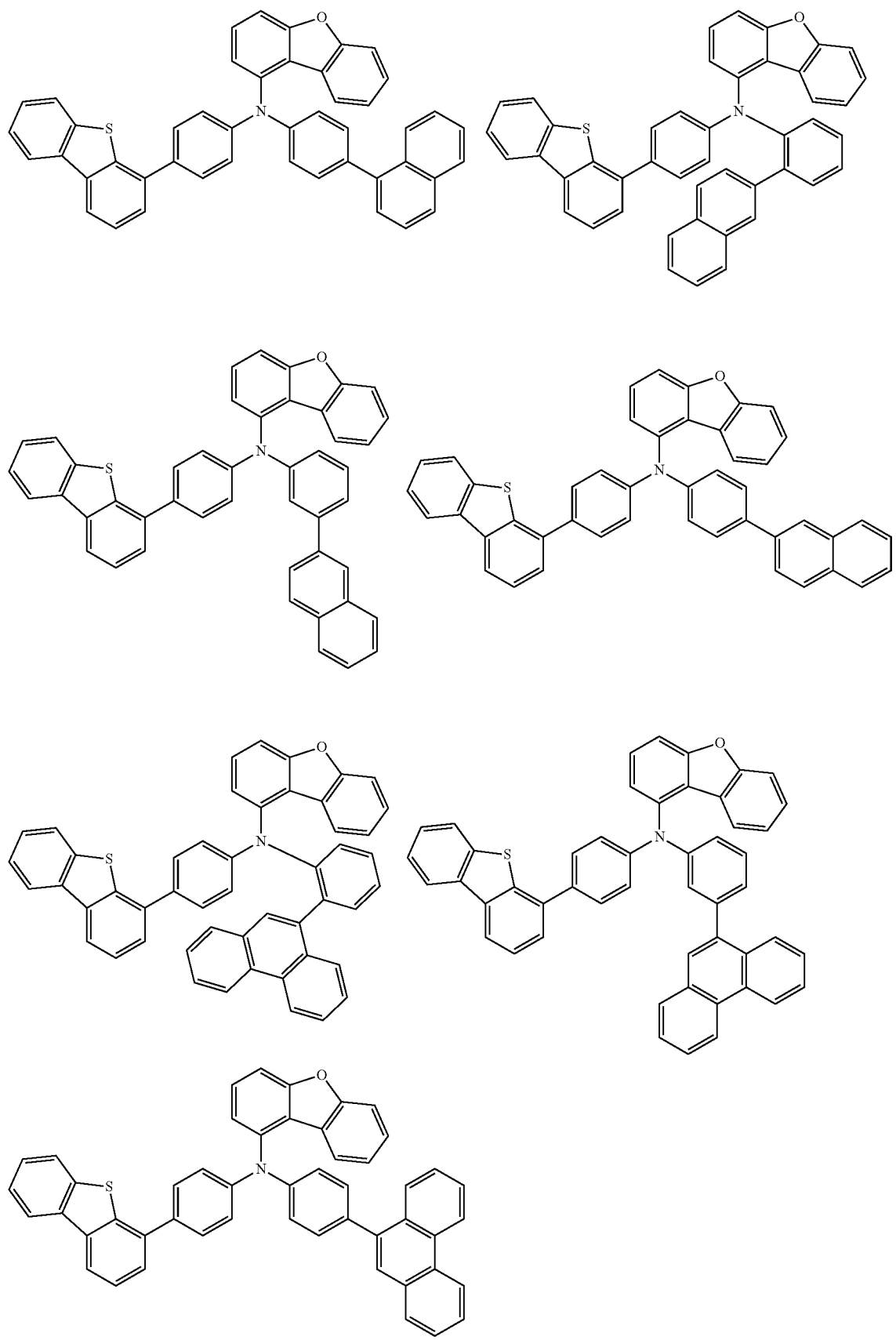

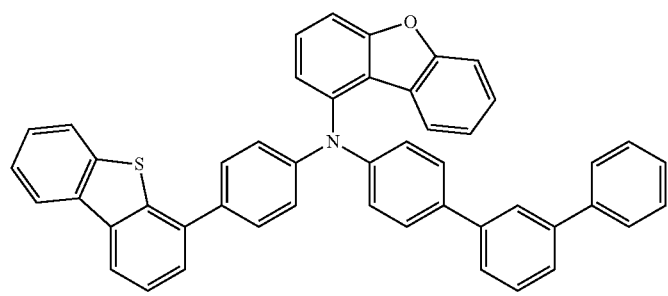
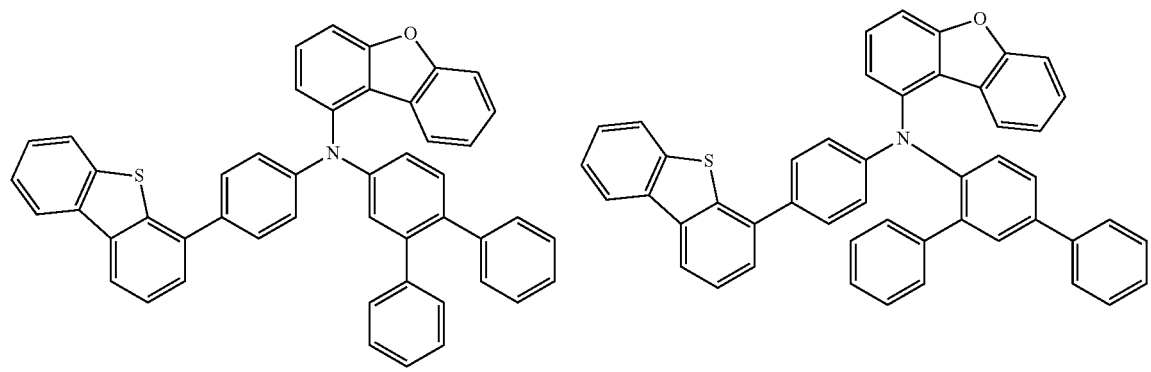
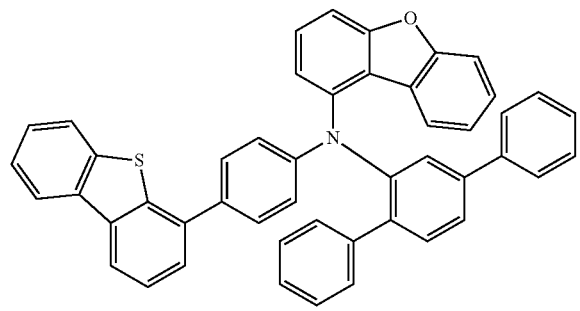
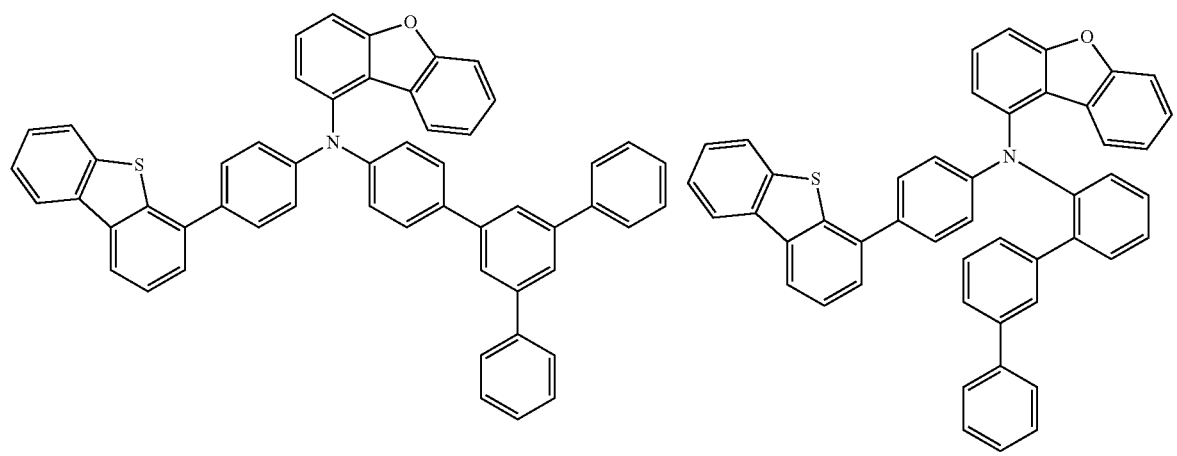

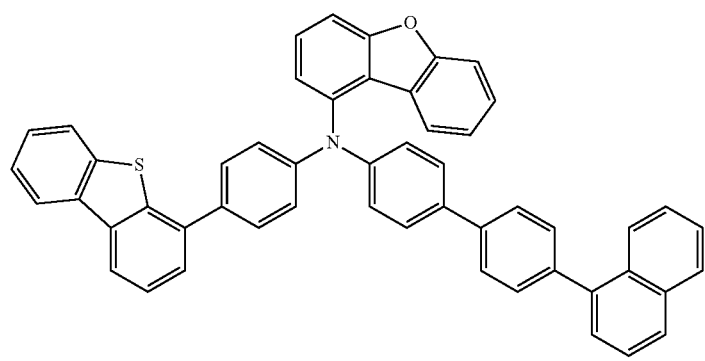
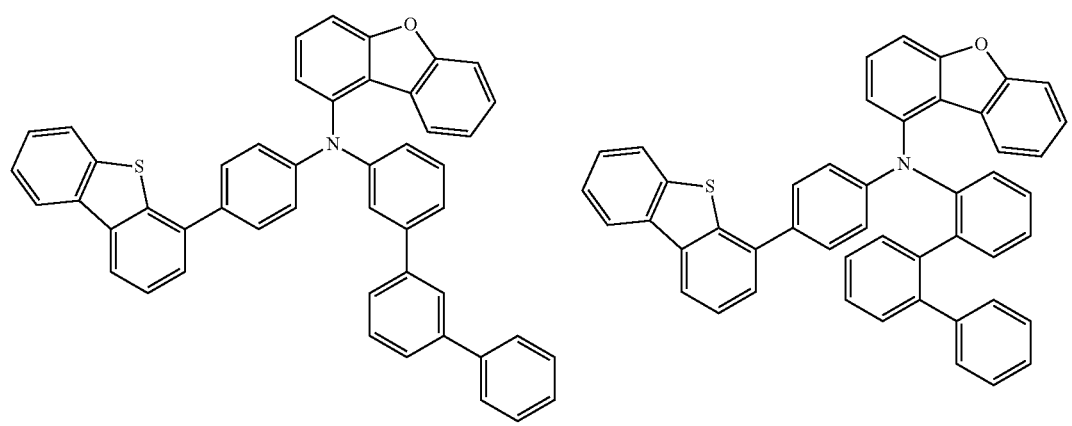
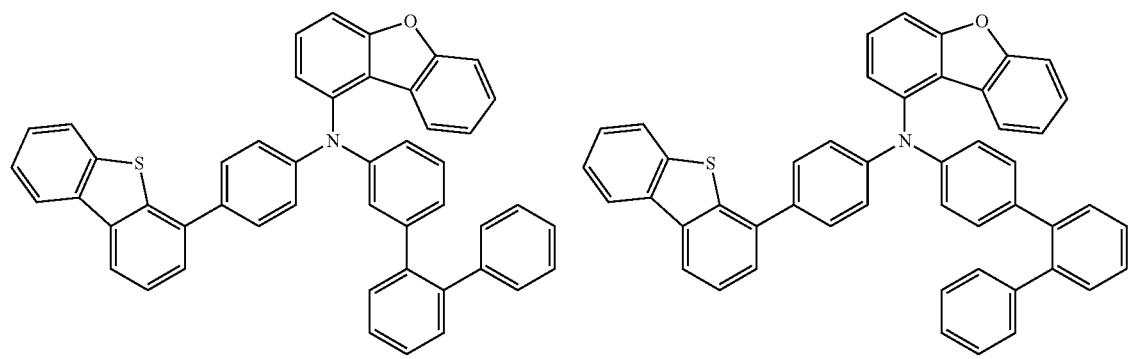
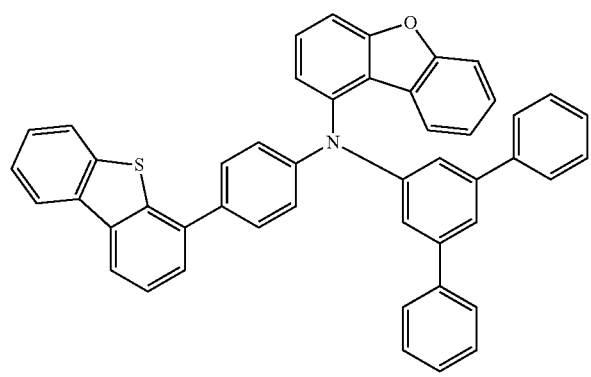

-continued
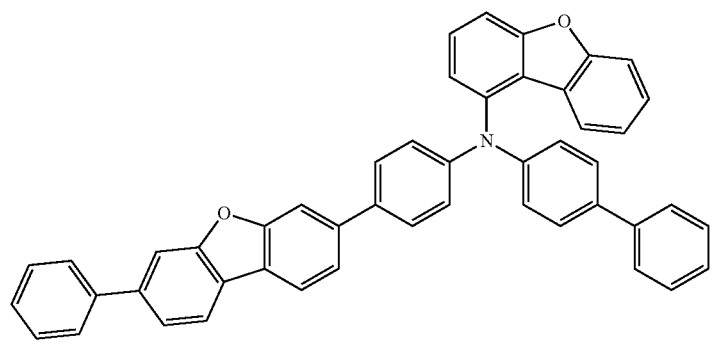
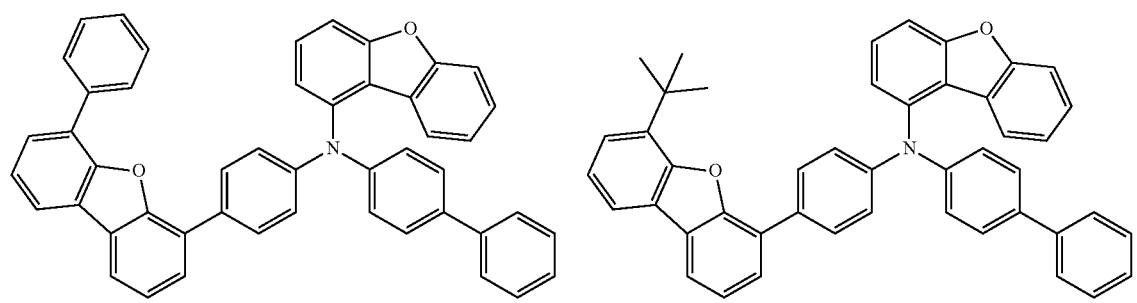
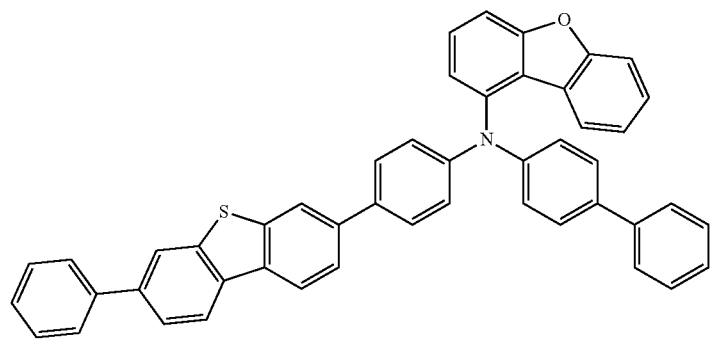
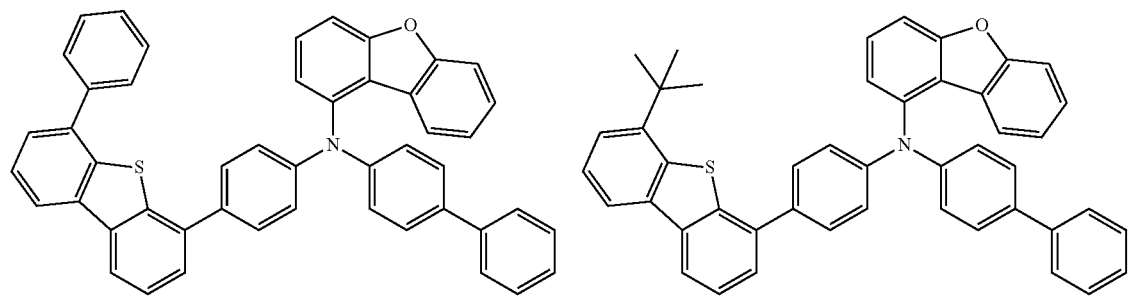
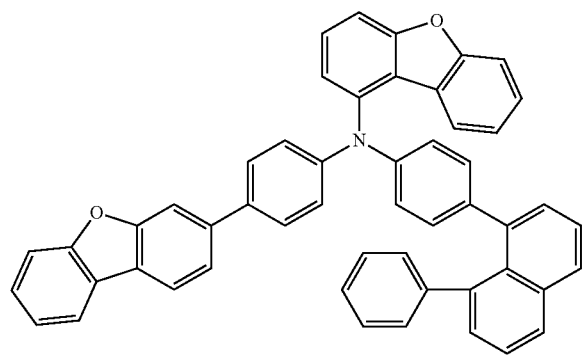

-continued
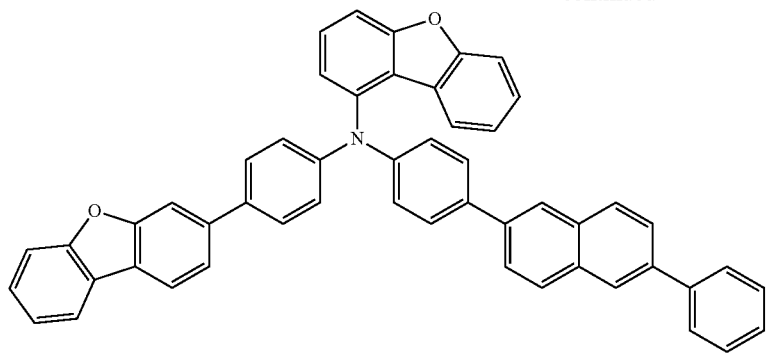
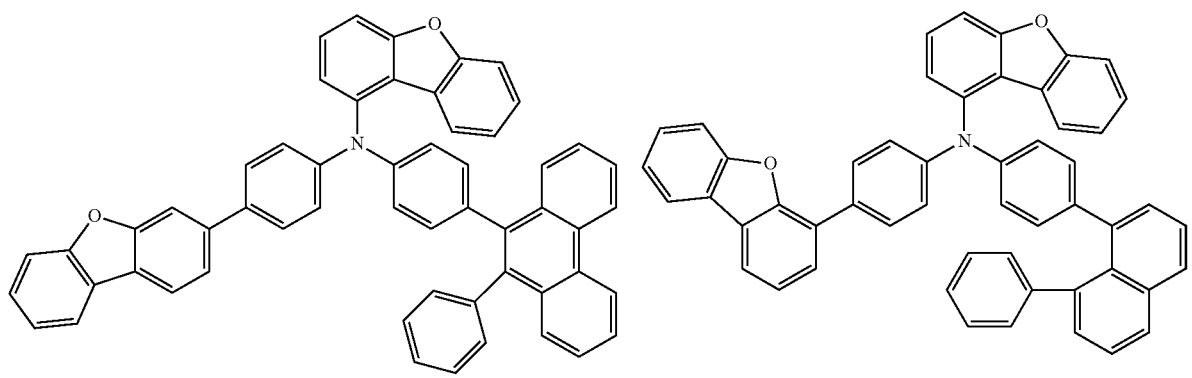
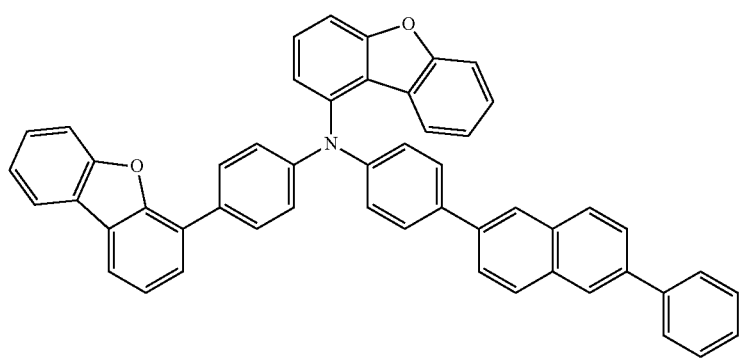
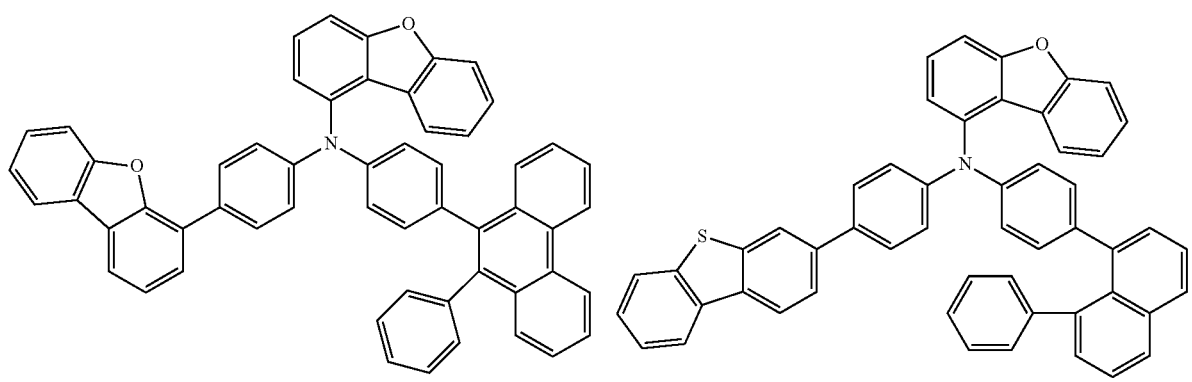

-continued
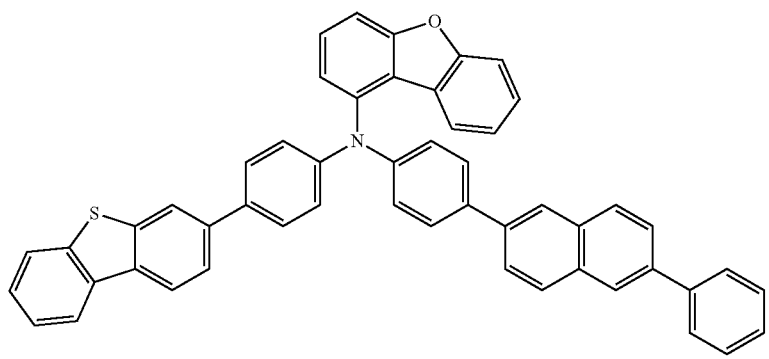
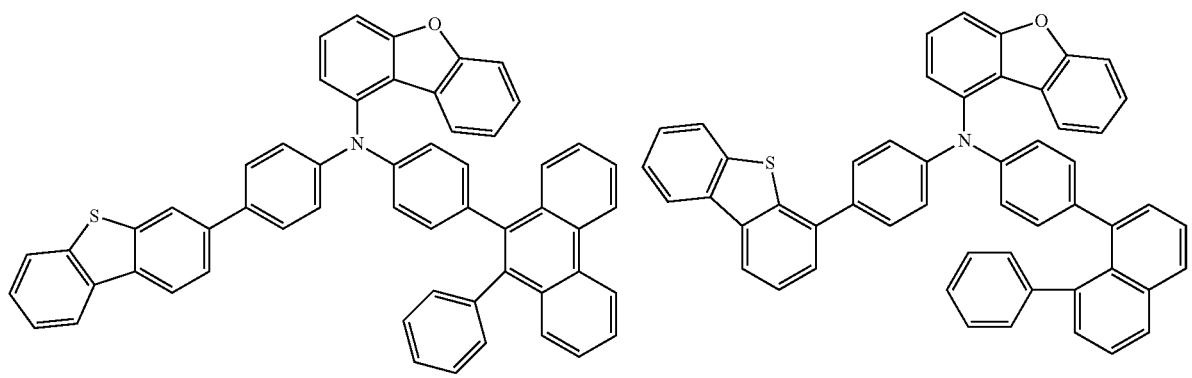
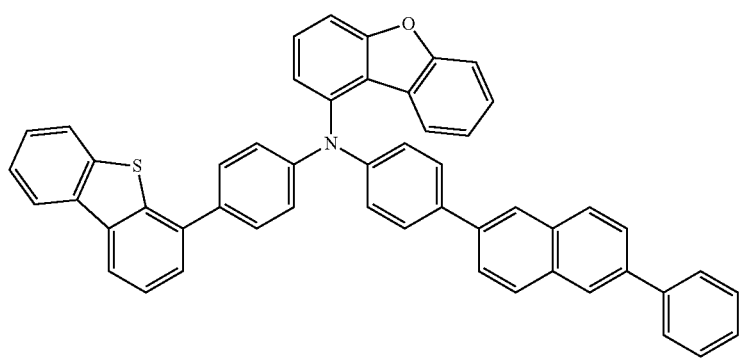
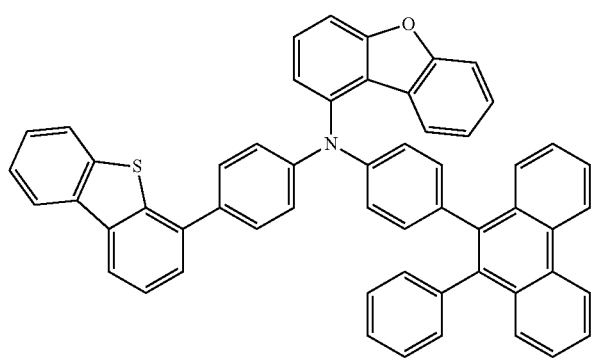

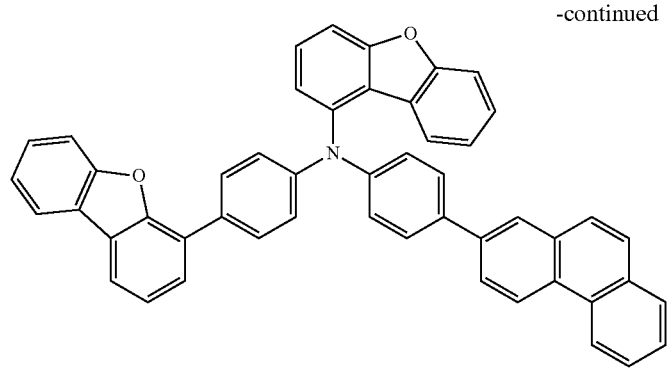
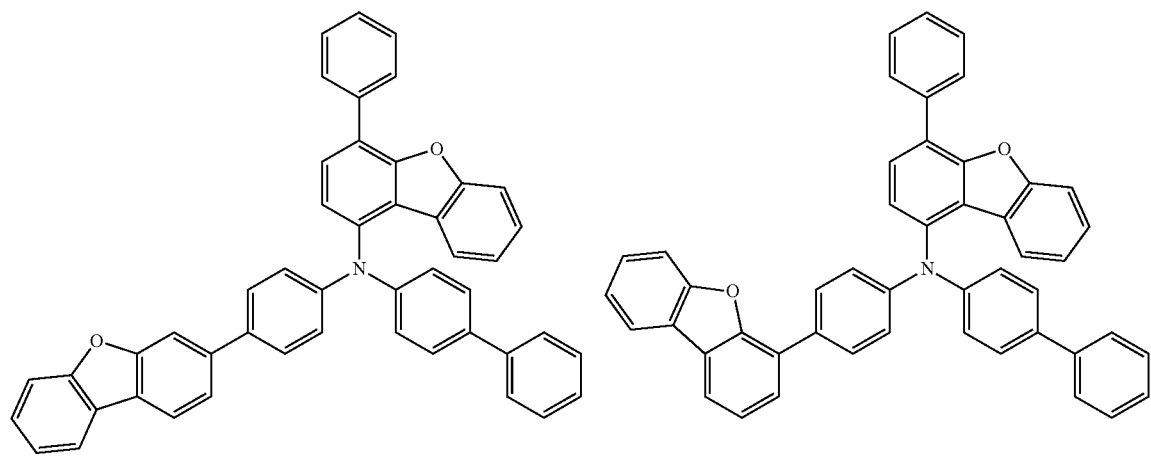
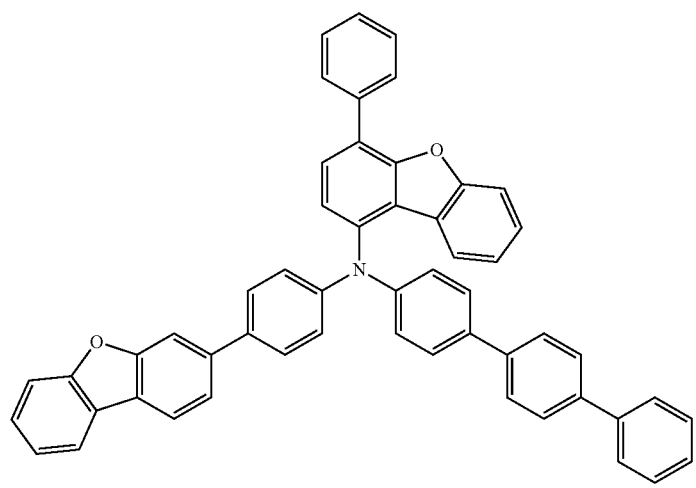

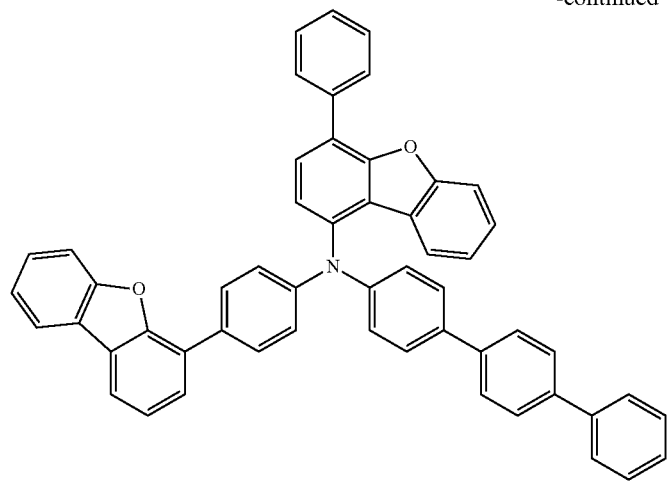
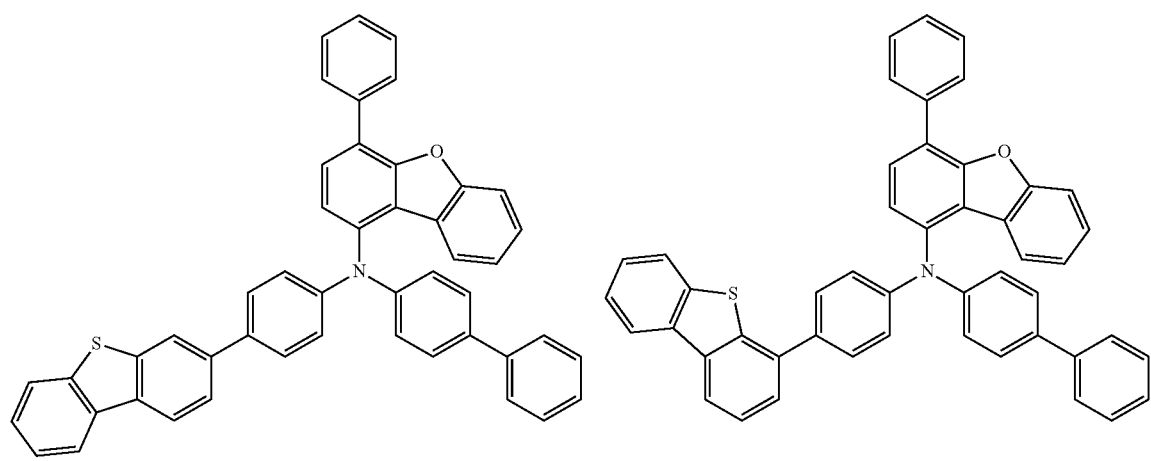
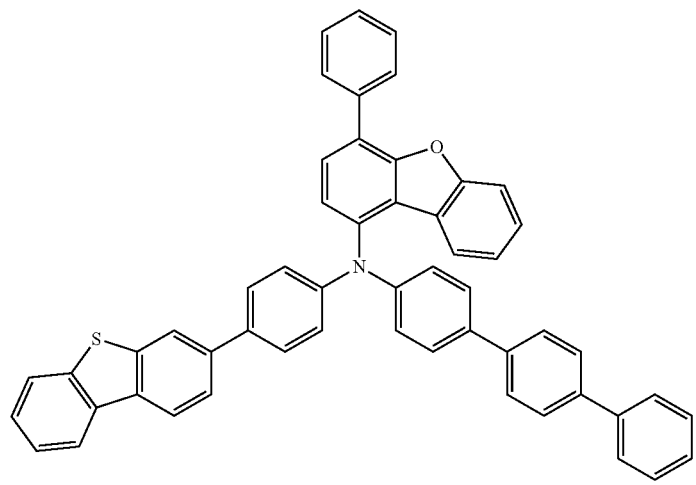

-continued
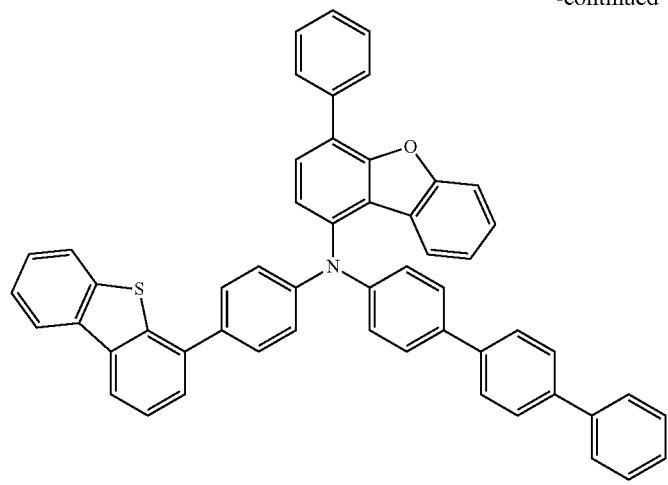
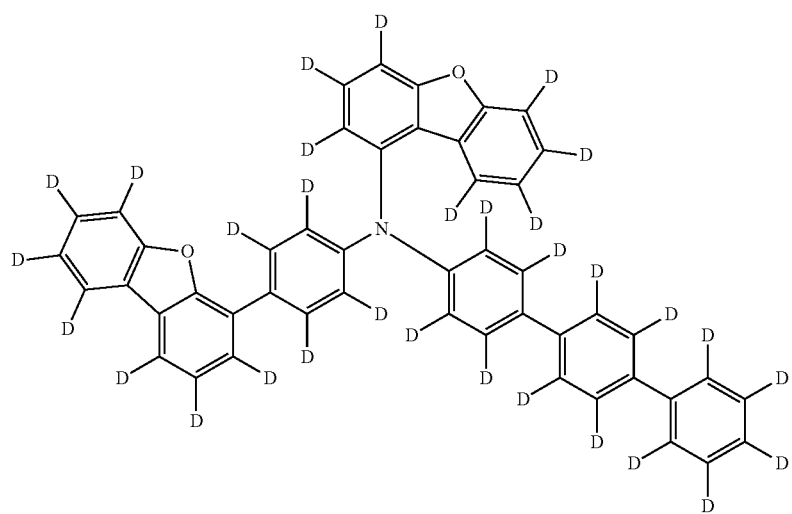
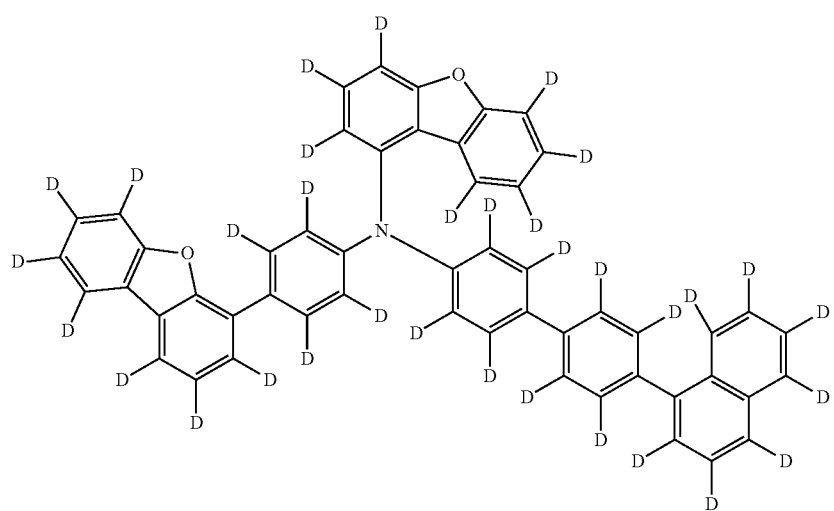

-continued
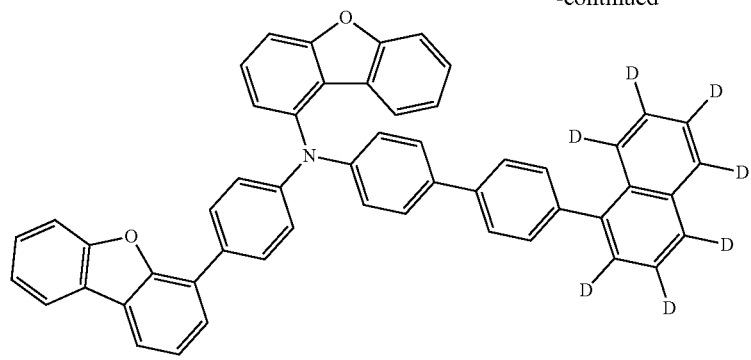
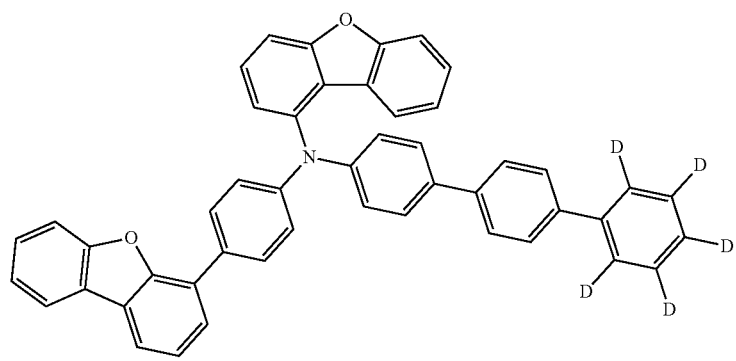
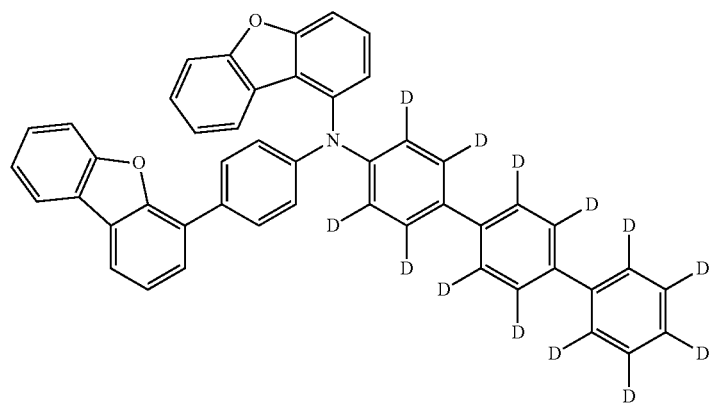
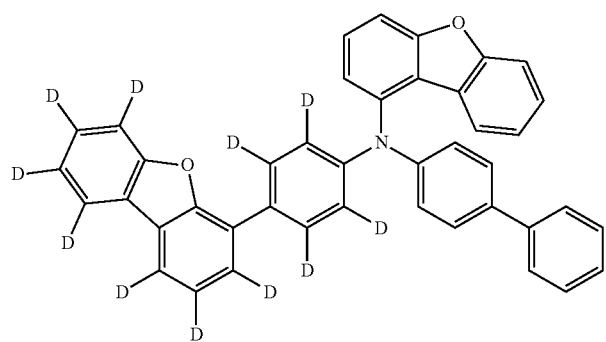

-continued
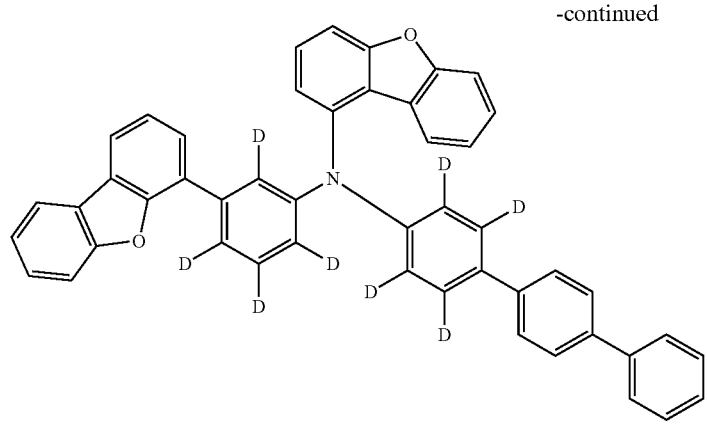
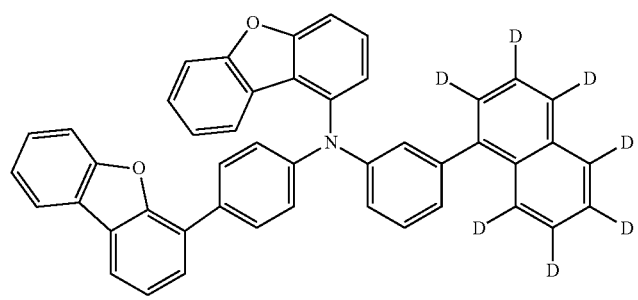
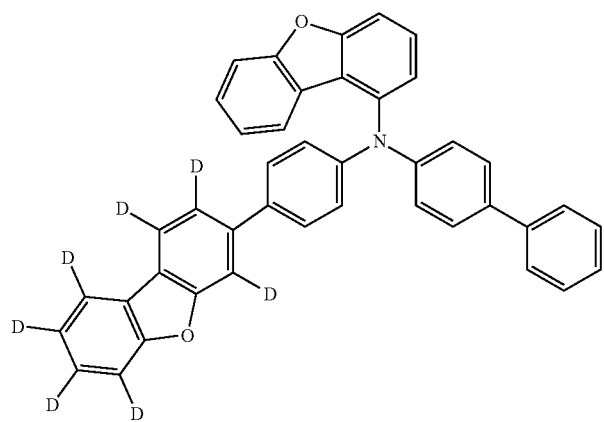
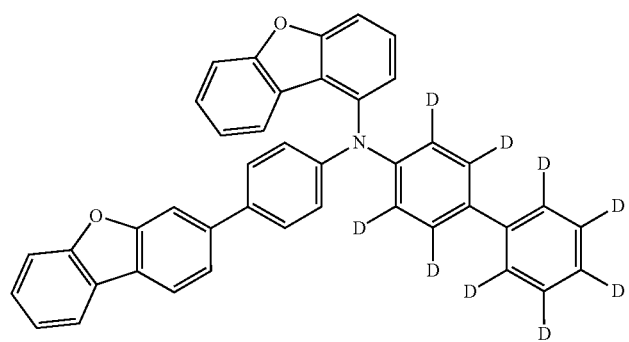

-continued

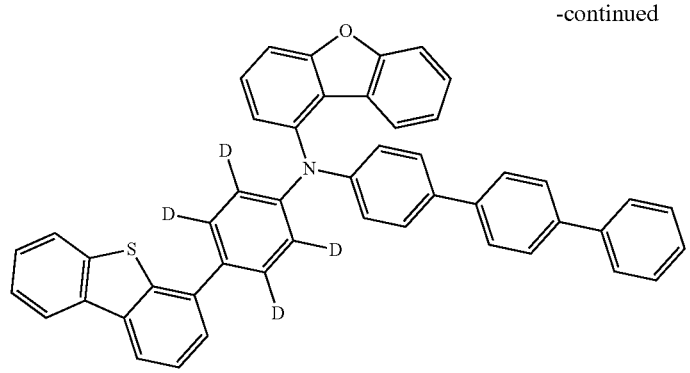

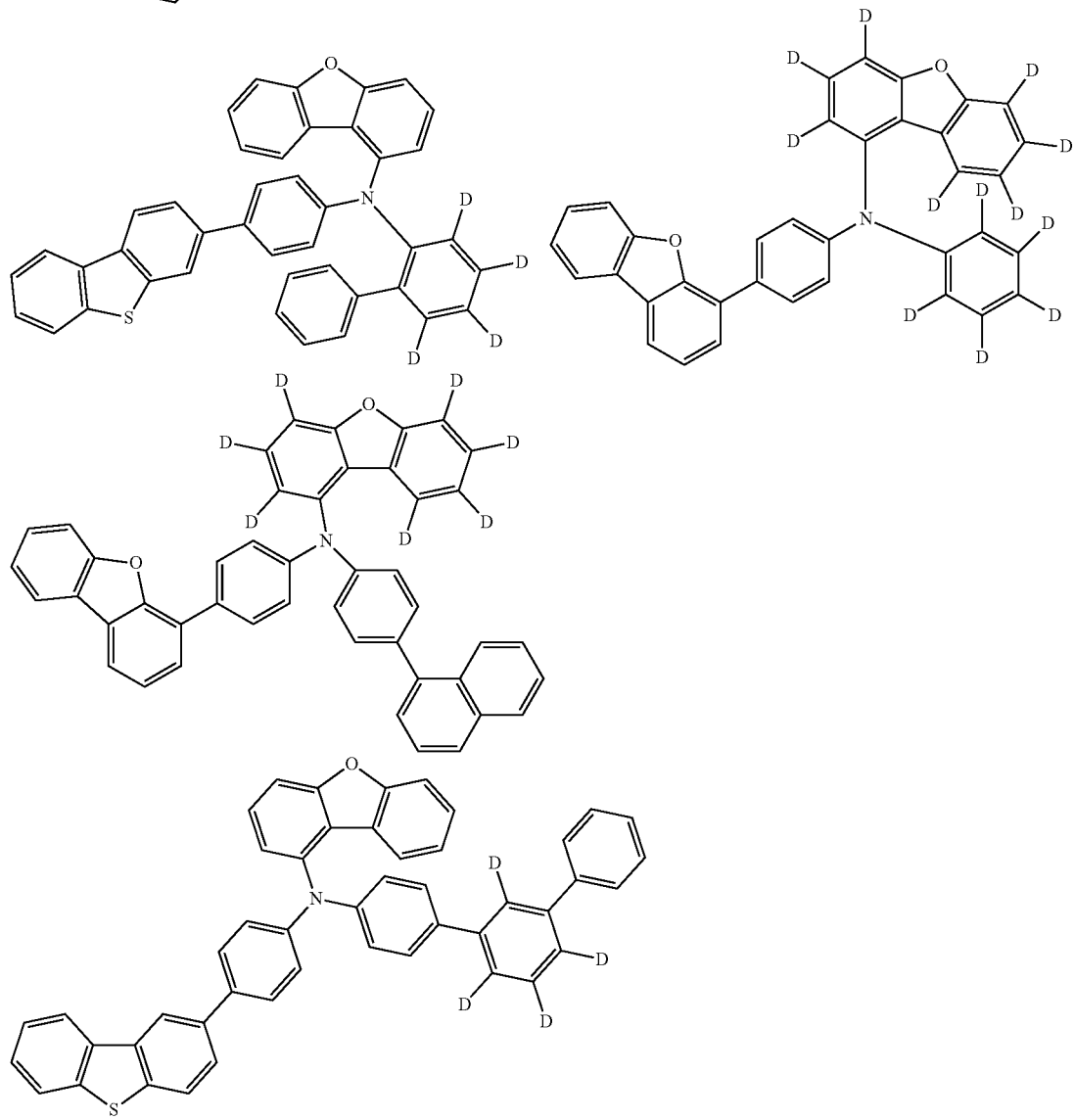

A method of producing the compound (1) is not particularly limited, and those skilled in the art may easily produce the compound (1) by the method described in Examples below, or by a method obtained by modifying the method with reference to a known synthesis method.

Material for Organic EL Device

The material for the organic EL device of the present invention contains the compound (1). The content of the compound (1) in the material for the organic EL device of the present invention is not particularly limited, and is, for example, 1% by mass or more (including 100%), preferably 10% by mass or more (including 100%), more preferably 50% by mass or more (including 100%), further preferably 80% by mass or more (including 100%), and particularly preferably 90% by mass or more (including 100%) based on the total mass of a layer containing the compound (1). The material for the organic EL device of the present invention is useful in producing the organic EL device.

Organic EL Device

Next, the organic EL device of the present invention will be described.

The organic EL device includes a cathode, an anode, and organic layers between the cathode and the anode. The organic layers include a light emitting layer, and at least one layer among the organic layers contains the compound (1).

Examples of the organic layer containing the compound (1) may include a hole transport zone (a hole injection layer, a hole transport layer, an electron blocking layer, and an exciton blocking layer) provided between the anode and the light emitting layer, the light emitting layer, a space layer, and an electron transport zone (an electron injection layer, an electron transport layer, and a hole blocking layer) provided between the cathode and the light emitting layer, but are not limited thereto. The compound (1) is preferably used as a material for the hole transport zone or the light emitting layer in a fluorescent or phosphorescent EL device, more preferably as a material for the hole transport zone, further preferably as a material for the hole transport layer or the electron blocking layer, and particularly preferably as a material for the hole transport layer.

The organic EL device of the present invention may be a fluorescent or phosphorescent light emission-type monochromatic light emitting device, or a fluorescent/phosphorescent hybrid-type white light emitting device, and may be a simple type having a single light emitting unit or a tandem type having a plurality of light emitting units. Among these, the fluorescent light emission-type device is preferable. Here, the "light emitting unit" refers to a minimum unit that includes organic layers among which at least one layer is a light emitting layer, and emits light through recombination between injected holes and electrons.

For example, as a typical device configuration of the simple-type organic EL device, the following device configurations may be exemplified.

(1) Anode/Light Emitting Unit/Cathode

Also, the above light emitting unit may be a stacked-type having a plurality of phosphorescent light emitting layers or fluorescent light emitting layers. In this case, a space layer may be provided between the light emitting layers for the purpose of preventing excitons generated in the phosphorescent light emitting layer from diffusing into the fluorescent light emitting layer. Typical layer configurations of the simple-type light emitting unit are described below. Layers in parentheses are optional.

(a) (hole injection layer/)hole transport layer/fluorescent light emitting layer(/electron transport layer/electron injection layer)

(b) (hole injection layer/)hole transport layer/phosphorescent light emitting layer(/electron transport layer/electron injection layer)

(c) (hole injection layer/)hole transport layer/first fluorescent light emitting layer/second fluorescent light emitting layer(/electron transport layer/electron injection layer)

(d) (hole injection layer/)hole transport layer/first phosphorescent light emitting layer/second phosphorescent light emitting layer(/electron transport layer/electron injection layer)

(e) (hole injection layer/)hole transport layer/phosphorescent light emitting layer/space layer/fluorescent light emitting layer(/electron transport layer/electron injection layer)

(f) (hole injection layer/)hole transport layer/first phosphorescent light emitting layer/second phosphorescent light emitting layer/space layer/fluorescent light emitting layer(/electron transport layer/electron injection layer)

(g) (hole injection layer/)hole transport layer/first phosphorescent light emitting layer/space layer/second phosphorescent light emitting layer/space layer/fluorescent light emitting layer(/electron transport layer/electron injection layer)

(h) (hole injection layer/)hole transport layer/phosphorescent light emitting layer/space layer/first fluorescent light emitting layer/second fluorescent light emitting layer(/electron transport layer/electron injection layer)

(i) (hole injection layer/)hole transport layer/electron blocking layer/fluorescent light emitting layer(/electron transport layer/electron injection layer)

(j) (hole injection layer/)hole transport layer/electron blocking layer/phosphorescent light emitting layer(/electron transport layer/electron injection layer)

(k) (hole injection layer/)hole transport layer/exciton blocking layer/fluorescent light emitting layer(/electron transport layer/electron injection layer)

(l) (hole injection layer/)hole transport layer/exciton blocking layer/phosphorescent light emitting layer(/electron transport layer/electron injection layer)

(m) (hole injection layer/)first hole transport layer/second hole transport layer/fluorescent light emitting layer(/electron transport layer/electron injection layer)

(n) (hole injection layer/)first hole transport layer/second hole transport layer/phosphorescent light emitting layer(/electron transport layer/electron injection layer)

(o) (hole injection layer/)first hole transport layer/second hole transport layer/fluorescent light emitting layer/first electron transport layer/second electron transport layer(/electron injection layer)

(p) (hole injection layer/)first hole transport layer/second hole transport layer/phosphorescent light emitting layer/first electron transport layer/second electron transport layer(/electron injection layer)

(q) (hole injection layer/)hole transport layer/fluorescent light emitting layer/hole blocking layer(/electron transport layer/electron injection layer)

(r) (hole injection layer/)hole transport layer/phosphorescent light emitting layer/hole blocking layer(/electron transport layer/electron injection layer)

(s) (hole injection layer/)hole transport layer/fluorescent light emitting layer/exciton blocking layer(/electron transport layer/electron injection layer)

(t) (hole injection layer/)hole transport layer/phosphorescent light emitting layer/exciton blocking layer(/electron transport layer/electron injection layer)

The above phosphorescent or fluorescent light emitting layers may emit different emission colors, respectively. Specifically, in the above stacked light emitting unit (f), a layer configuration such as (hole injection layer/)hole transport layer/first phosphorescent light emitting layer (red light emission)/second phosphorescent light emitting layer (green light emission)/space layer/fluorescent light emitting layer (blue light emission)/electron transport layer may be exemplified.

An electron blocking layer may be properly provided between each light emitting layer and the hole transport layer or the space layer. Also, a hole blocking layer may be properly provided between each light emitting layer and the electron transport layer. The employment of the electron blocking layer or the hole blocking layer allows to increase the probability of charge recombination in the light emitting layer and improve the light emission efficiency by confining electrons or holes within the light emitting layer.

As a typical device configuration of the tandem-type organic EL device, the following device configuration may be exemplified.

(2) Anode/First Light Emitting Unit/Intermediate Layer/Second Light Emitting Unit/Cathode Here, for example, each of the above first light emitting unit and second light emitting unit may be independently selected from the above described light emitting units.

The above intermediate layer is also generally referred to as an intermediate electrode, an intermediate conductive layer, a charge generating layer, an electron drawing layer, a connection layer, or an intermediate insulating layer, and a known material configuration which supplies electrons to the first light emitting unit, and holes to the second light emitting unit may be used.

FIG. 1 is a schematic view illustrating an example of a layer configuration of the organic EL device according to the embodiment of the present invention. An organic EL device 1 in this example includes a substrate 2, an anode 3, a cathode 4, and a light emitting unit 10 disposed between the anode 3 and the cathode 4. The light emitting unit 10 includes a light emitting layer 5. A hole transport zone 6 (a hole injection layer, a hole transport layer and the like) is provided between the light emitting layer 5 and the anode 3, and an electron transport zone 7 (an electron injection layer, an electron transport layer and the like) is provided between the light emitting layer 5 and the cathode 4. Also, an electron blocking layer (not illustrated) may be provided on the anode 3 side of the light emitting layer 5, and a hole blocking layer (not illustrated) may be provided on the cathode 4 side of the light emitting layer 5, respectively. These confine electrons or holes in the light emitting layer 5 and increase the generation efficiency of excitons in the light emitting layer 5 further.

FIG. 2 is a schematic view illustrating another example of a layer configuration of the organic EL device according to the embodiment of the present invention. An organic EL device 11 in this example includes the substrate 2, the anode 3, the cathode 4, and a light emitting unit 20 disposed between the anode 3 and the cathode 4. The light emitting unit 20 includes the light emitting layer 5. A hole transport zone disposed between the anode 3 and the light emitting layer 5 is formed of a first hole transport layer 6a and a second hole transport layer 6b. Also, an electron transport zone disposed between the light emitting layer 5 and the cathode 4 is formed of a first electron transport layer 7a and a second electron transport layer 7b. In the organic EL device 11, an electron transport layer as a single layer and hole transport layers composed of a plurality of layers may be combined, or a hole transport layer as a single layer and electron transport layers composed of a plurality of layers may be combined. Also, a hole blocking layer or an electron blocking layer may be provided in the organic EL device 11.

In the specification of this application, a host combined with a fluorescent dopant (a fluorescent light emitting material) is called a fluorescent host, and a host combined with a phosphorescent dopant is called a phosphorescent host. The fluorescent host and the phosphorescent host are not distinguished only by molecular structures. That is, the phosphorescent host means a material that forms a phosphorescent light emitting layer containing a phosphorescent dopant, but does not mean unavailability as a material that forms a fluorescent light emitting layer. The same also applies to the fluorescent host.

Hereinafter, descriptions will be made on each layer and each member constituting the organic EL device.

Substrate

The substrate is used as a support of the organic EL device. Examples of the substrate include a plate of glass, quartz, or plastic may be used. Also, a flexible substrate may be used. Examples of the flexible substrate include a plastic substrate made of polycarbonate, polyarylate, polyether sulfone, polypropylene, polyester, polyvinyl fluoride, or polyvinyl chloride. Also, an inorganic vapor deposition film may be used.

Anode

It is preferable that a metal, an alloy, an electrically conductive compound, or a mixture thereof which has a high work function (specifically, 4.0 eV or more) is used for the anode formed on the substrate. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene may be exemplified. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the above metals (for example, titanium nitride) may be exemplified.

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide, and 0.1 to 1 wt % of zinc oxide with respect to indium oxide. For the preparation, a vacuum vapor-deposition method, a coating method, an inkjet method, a spin coating method or the like may be also used.

The hole injection layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table).

It is also possible to use elements belonging to Group 1 or 2 of the periodic table, which are materials having low work functions, that is, alkali metals such as lithium (Li) and cesium (Cs), alkaline earth metals such as magnesium (Mg), calcium (Ca), and strontium (Sr), and alloys containing at least one of them (for example, MgAg, and AlLi), or rare earth metals such as europium (Eu), and ytterbium (Yb), and alloys containing at least one of them. When the anode is formed by using the alkali metals, the alkaline earth metals, and the alloys containing at least one of them, a vacuum vapor-deposition method or a sputtering method may be used. Also, when a silver paste is used, a coating method or an inkjet method may be used.

Hole Injection Layer

The hole injection layer is a layer containing a material having a high hole injection property (a hole injecting material). The hole injecting materials may be used alone or in combination in the hole injection layer.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Examples of the hole injection layer material also include aromatic amine compounds as low molecular organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)bi phenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High molecular compounds (oligomers, dendrimers, and polymers) may also be used. Examples of the high molecular compounds include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)met hacrylamide] (abbreviation: PTPDMA), and poly[N,N'-bis(4-butylphenyl)-N,N'-bis(phenyl)benzidine] (abbreviation: Poly-TPD). In addition, high molecular compounds to which an acid is added, such as poly(3,4-ethylenedioxythiophene)/poly(styrene sulfonic acid) (PEDOT/PSS), and polyaniline/poly(styrene sulfonic acid) (PAni/PSS), may also be used.

Also, it is also preferable to use an acceptor material such as a hexaazatriphenylene (HAT) compound represented by the following formula (K), in combination with another compound.

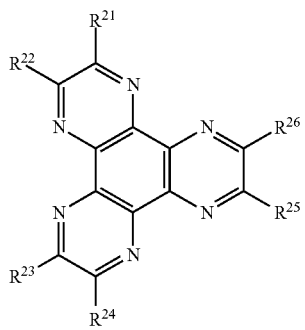

(K)

(In the formula (K), each of $R^{21}$ to $R^{26}$ independently represents a cyano group, $-CONH_2$, a carboxy group, or $-COOR^{27}$ ($R^{27}$ represents an alkyl group having 1 to 20 carbon atoms or a cycloalkyl group having 3 to 20 carbon atoms). Also, adjacent two selected from $R^{21}$ and $R^{22}$, $R^{23}$ and $R^{24}$, and $R^{25}$ and $R^{26}$ may be bonded to each other to form a group represented by $-CO-O-CO-$.)

Examples of $R^{27}$ include a methyl group, an ethyl group, an n-propyl group, an isopropyl group, an n-butyl group, an isobutyl group, a t-butyl group, a cyclopentyl group, and a cyclohexyl group.

The hole transport layer may also contain the above compound (1) which may be used in combination with, for example, the above acceptor material.

Hole Transport Layer

The hole transport layer is a layer containing a material having a high hole transporting property (a hole transporting material). The hole transport layer is provided between the anode and the light emitting layer, or is provided between the hole injection layer and the light emitting layer in the case where the hole injection layer is present. The hole transporting materials may be used alone or in combination in the hole transport layer. Examples of the hole transporting material include an aromatic amine compound, a carbazole derivative, and an anthracene derivative.

Examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). These aromatic amine compounds have a hole mobility of $10^{-6}$ $cm^2/Vs$ or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High molecular compounds such as poly(N-vinylcarbazole) (abbreviation: PVK) or poly(4-vinyltriphenylamine) (abbreviation: PVTPA) may also be used.

Meanwhile, compounds other than the above may also be used as long as they are compounds high in the hole transporting property rather than in the electron transporting property.

The hole transport layer may have a single-layer structure, or a multi-layer structure including two or more layers. For example, the hole transport layer may have a two-layer structure including a first hole transport layer (anode side) and a second hole transport layer (cathode side).

In the hole transport layer with the two-layer structure, the compound (1) may be contained in either the first hole transport layer or the second hole transport layer, or may be contained in both.

In one embodiment of the present invention, it is preferable that the compound (1) is contained in the second hole transport layer, in another embodiment, the compound (1) is contained in the first hole transport layer, and in a further embodiment, the compound (1) is contained in the first hole transport layer and the second hole transport layer.

In one embodiment of the present invention, the compound (1) included in the above hole transport zone or the compound (1) contained in either the above first hole transport layer or the above second hole transport layer is preferably a protium compound (1) in view of a production cost.

The above protium compound (1) refers to the compound (1) in which all hydrogen atoms in the formula (1) are protium atoms.

Accordingly, the present invention includes the compound (1) included in the above hole transport zone, or the organic EL device in which either the above first hole transport layer or the above second hole transport layer contains the compound (1) which substantially contains only the protium compound (1). "The compound (1) substantially containing only the protium compound (1)" indicates that the content ratio of the protium compound (1) based on the total amount of the compound represented by the formula (1) is 90 mol % or more, preferably 95 mol % or more, and more preferably 99 mol % or more (each including 100%).

Dopant Material of Light Emitting Layer

The light emitting layer is a layer containing a material having a high light emitting property (a dopant material), and various materials may be used. For example, a fluorescent light emitting material or a phosphorescent light emitting material may be used as the dopant material. The fluorescent light emitting material is a compound that emits light from a singlet excited state, and the phosphorescent light emitting material is a compound that emits light from a triplet excited state.

As for a blue-based fluorescent light emitting material that may be used for the light emitting layer, a pyrene derivative, a styrylamine derivative, a chrysene derivative, a fluoranthene derivative, a fluorene derivative, a diamine derivative, and a triarylamine derivative may be used. Specifically, N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA) may be exemplified.

As for a green-based fluorescent light emitting material that may be used for the light emitting layer, an aromatic amine derivative may be used. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

As for a red-based fluorescent light emitting material that may be used for the light emitting layer, a tetracene derivative, and a diamine derivative may be used. Specific examples thereof include N,N,N',N'-tetrakis(4-methylphenyl)tetracene-5,11-diamine (abbreviation: p-mPhTD), and 7,14-diphenyl-N,N,N',N'-tetrakis(4-methylphenyl)acenaphtho[1,2-a]fluoranthene-3,10-diamine (abbreviation: p-mPhAFD).

As for a blue-based phosphorescent light emitting material that may be used for the light emitting layer, a metal complex such as an iridium complex, an osmium complex, or a platinum complex is used. Specific examples thereof include bis[2-(4',6'-difluorophenyl)pyridinato-N,C2'] iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl) pyridinato-N,C2']iridium(III)acetylacetonate (abbreviation: FIracac).

As for a green-based phosphorescent light emitting material that may be used for the light emitting layer, an iridium complex is used. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolate)iridium(III)acetylacetonate (abbreviation: Ir(pbi)2(acac)), and bis(benzo[h]quinolinato)iridium(III) acetylacetonate (abbreviation: Ir(bzq)2(acac)).

As for a red-based phosphorescent light emitting material that may be used for the light emitting layer, a metal complex such as an iridium complex, a platinum complex, a terbium complex, or a europium complex is used. Specific examples thereof include organometallic complexes such as bis[2-(2'-benzo[4,5-α]thienyl)pyridinato-N,C3']iridium(III) acetylacetonate (abbreviation: Ir(btp)2(acac)), bis(1-phenylisoquinolinato-N,C2')iridium(III) acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrin platinum(II) (abbreviation: PtOEP).

In addition, rare earth metal complexes such as tris (acetylacetonate)(monophenanthroline)terbium(III) (abbreviation: Tb(acac)3(Phen)), tris(1,3-diphenyl-1,3-propandionato)(monophenanthroline)europium(III) (abbreviation: Eu(DBM)3(Phen)), and tris[1-(2-thenoyl)-3,3,3-trifluoroacetonato](monophenanthroline)europium(III) (abbreviation: Eu(TTA)3(Phen)) emit light from rare earth metal ions (electron transition between different multiplicities), and thus may be used as the phosphorescent light emitting material.

Host Material of Light Emitting Layer

The light emitting layer may have a configuration in which the above described dopant material is dispersed in another material (a host material). As for the host material, a material that has a higher lowest unoccupied orbital level (LUMO level) and a lower highest occupied orbital level (HOMO level) than the dopant material is preferably used.

As for the host material, for example
(1) a metal complex such as an aluminum complex, a beryllium complex, or a zinc complex,
(2) a heterocyclic compound such as an oxadiazole derivative, a benzimidazole derivative, or a phenanthroline derivative,
(3) a condensed aromatic compound such as a carbazole derivative, an anthracene derivative, a phenanthrene derivative, a pyrene derivative, or a chrysene derivative, or
(4) an aromatic amine compound such as a triarylamine derivative or a condensed polycyclic aromatic amine derivative is used.

Examples thereof include metal complexes such as tris (8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis (8-quinolinolato)zinc(II) (abbreviation: Znq), bis[2-(2-benzooxazolyl)phenolato]zinc(II) (abbreviation: ZnPBO), and bis[2-(2-benzothiazolyl)phenolato]zinc(II) (abbreviation: ZnBTZ);

heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2', 2''-(1,3,5-benzenetriyl)tris(1-phenyl-1H-benzimidazole) (abbreviation: TPBI), and bathophenanthroline (abbreviation: BPhen), bathocuproine (abbreviation: BCP);

condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluorene-2-yl)-N-phenylamino]biphenyl (abbreviation: DFLDPBi), and 4,4'-bis[N-(spiro-9,9'-bifluorene-2-yl)-N-phenylamino]biphenyl (abbreviation: BSPB). A plurality of types of host materials may also be used.

In particular, in the case of a blue fluorescent device, it is preferable to use the following anthracene compounds as the host material.

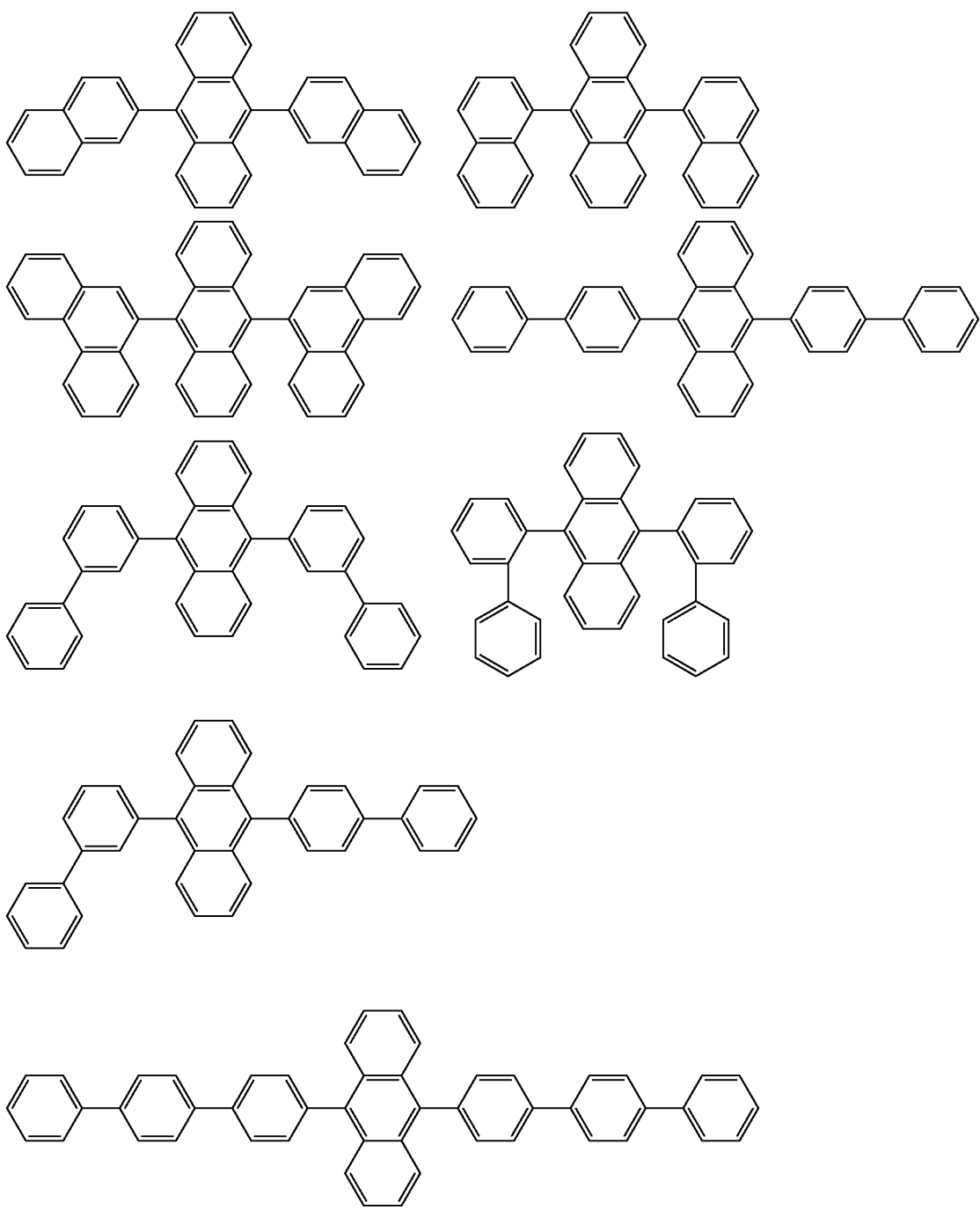

-continued
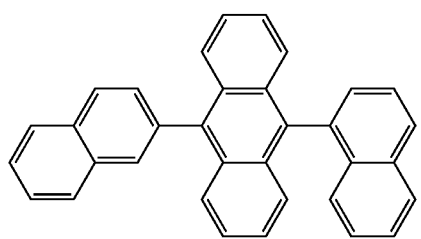 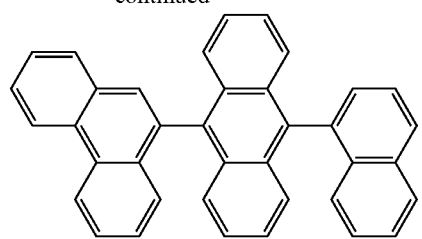
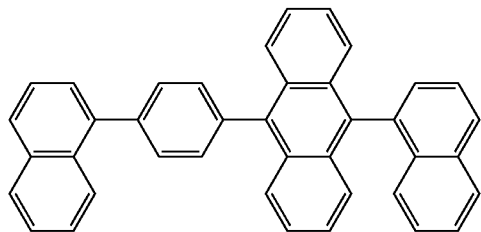 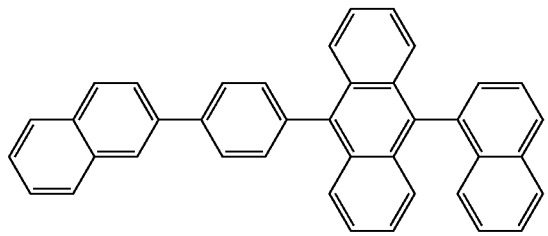
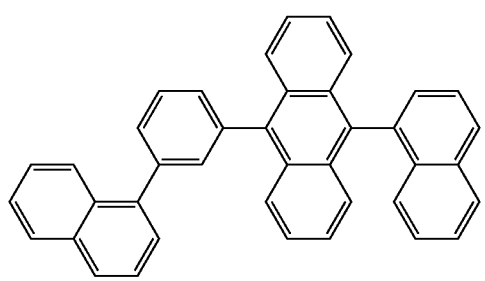 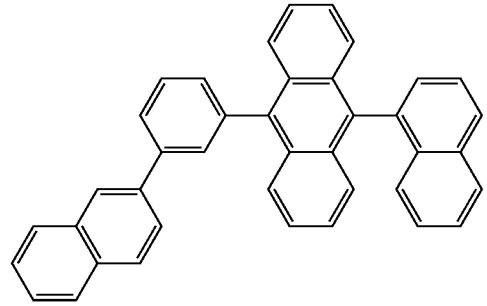
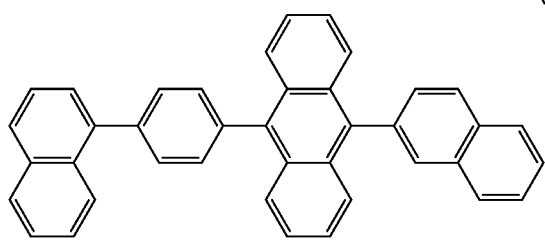 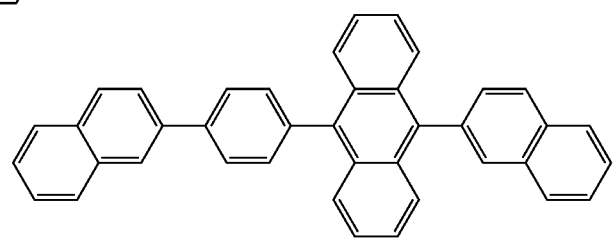
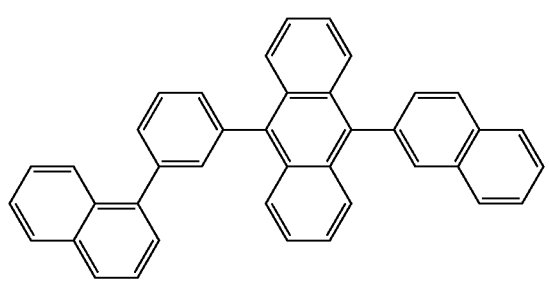 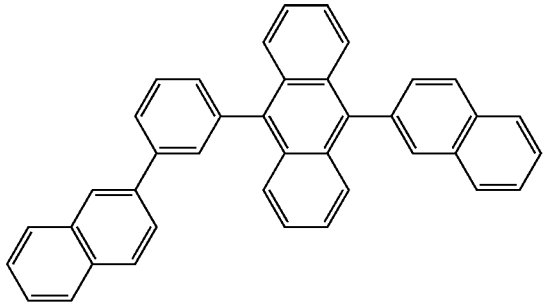
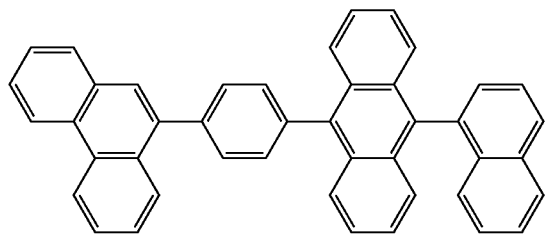 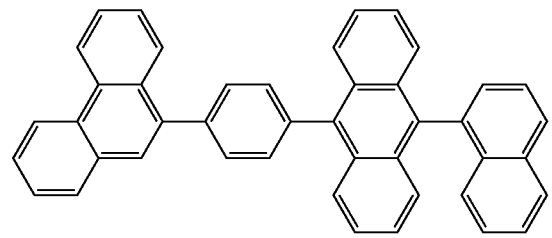

-continued
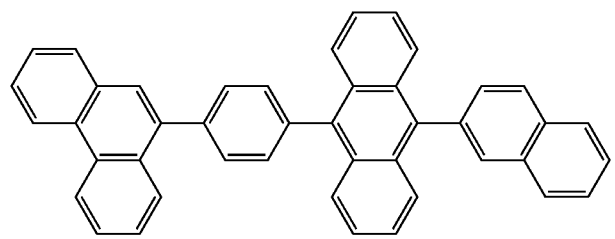
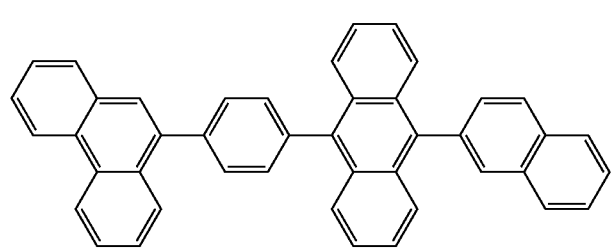
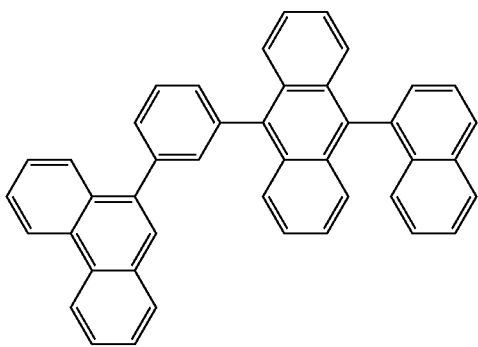
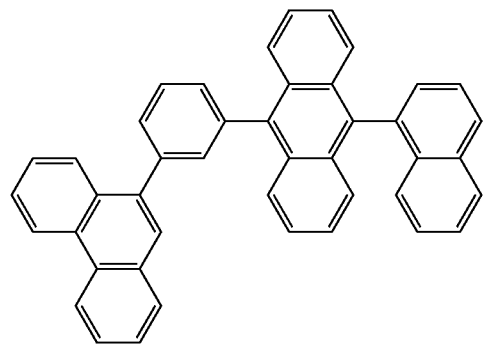
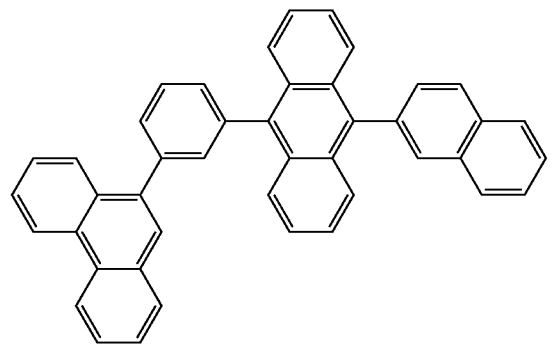
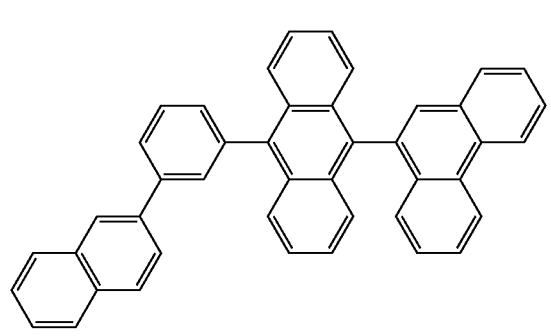
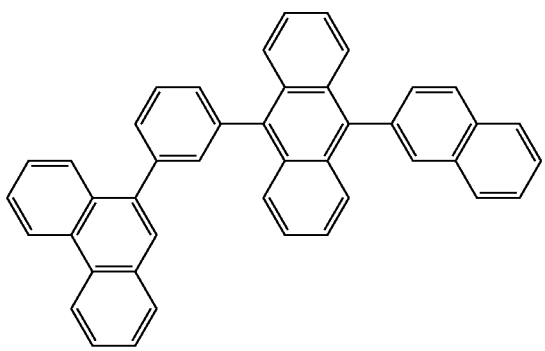
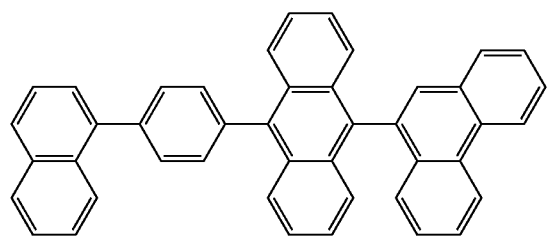
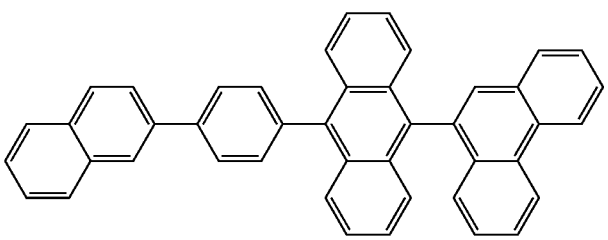

-continued
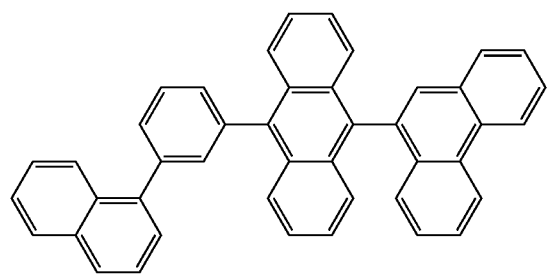
171
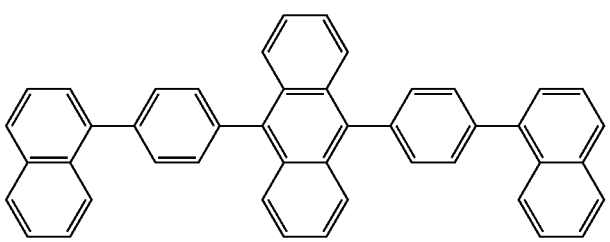
172
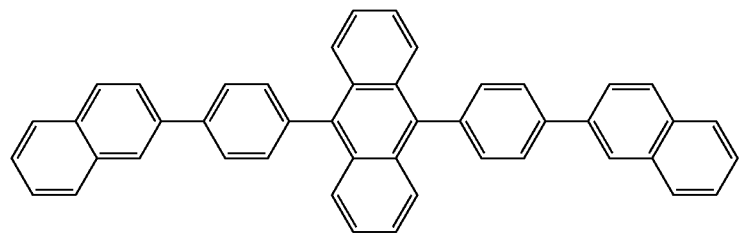
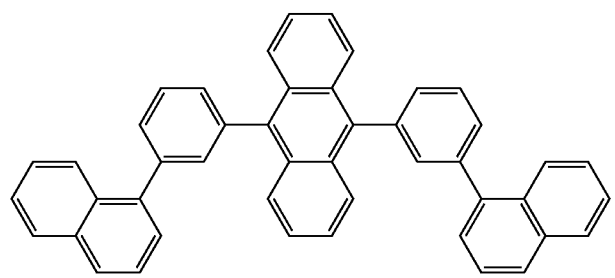
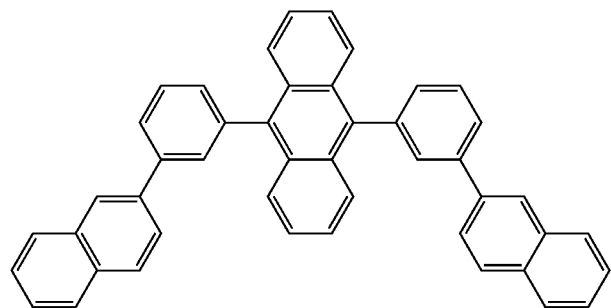
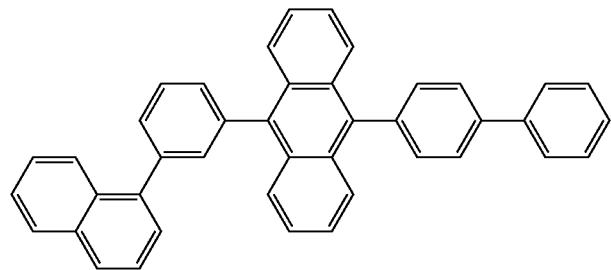
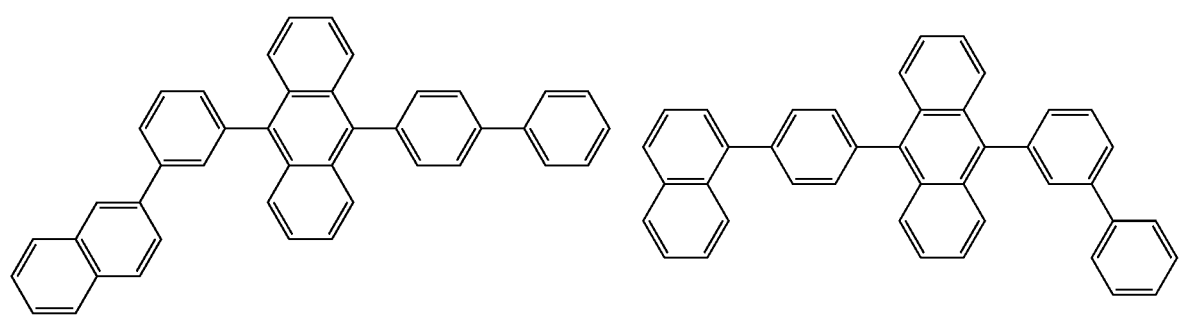

173 174
-continued
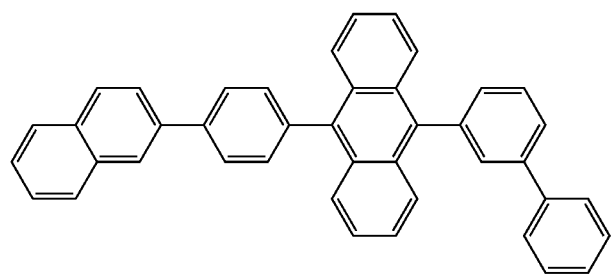
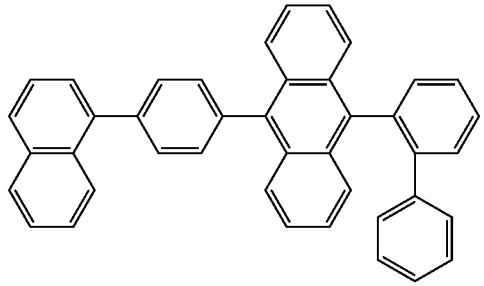
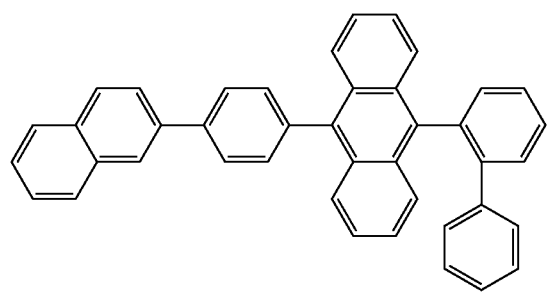
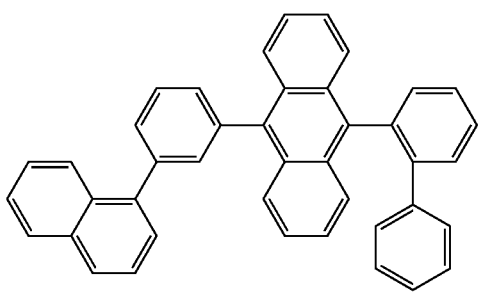
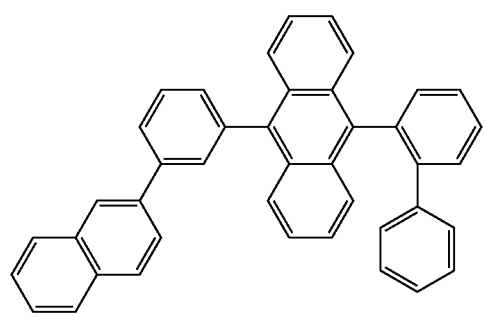
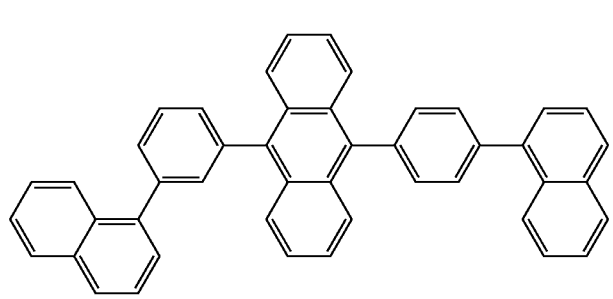
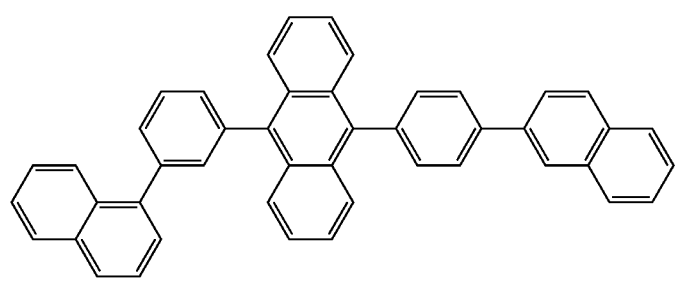
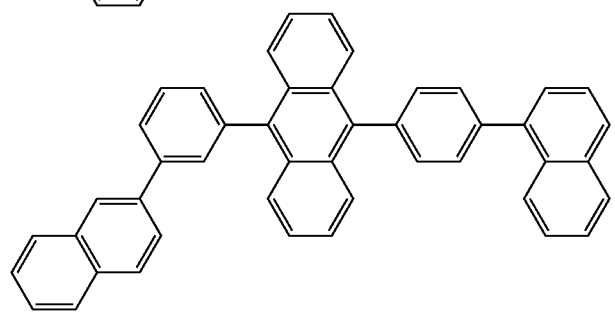

175 176
-continued
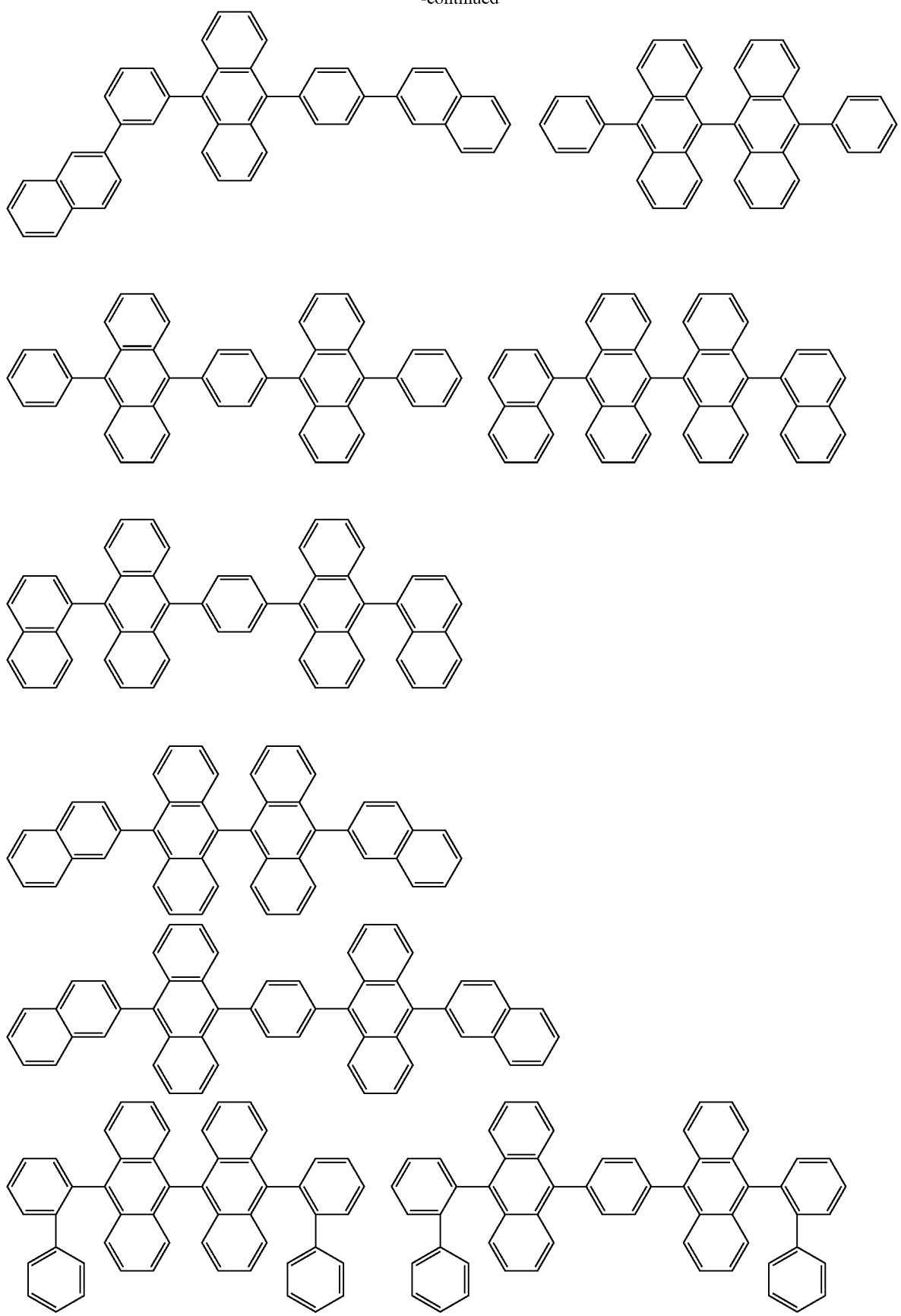

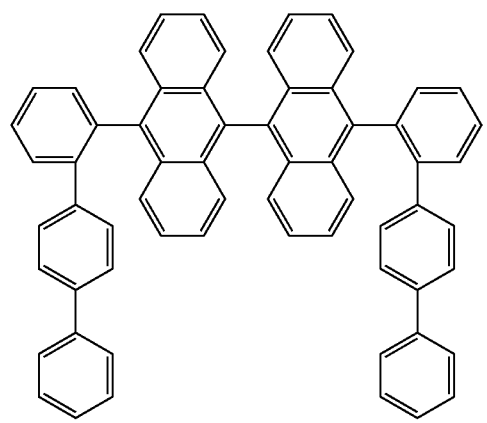
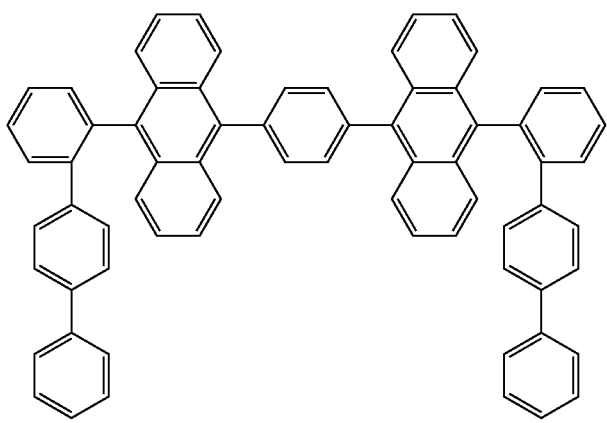
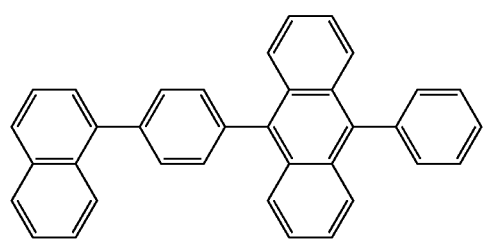
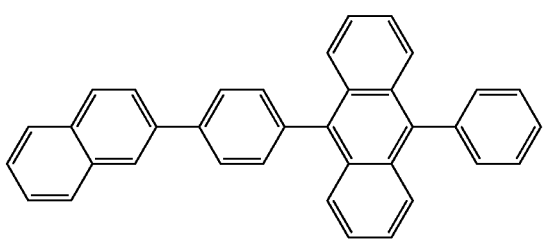
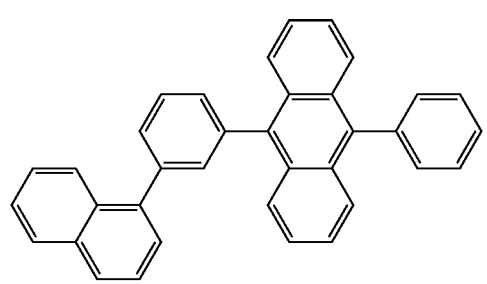
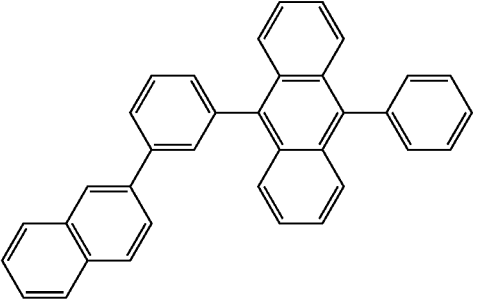
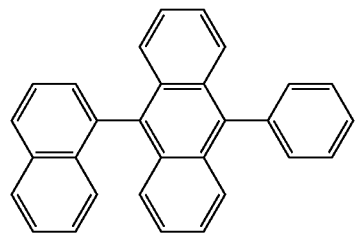
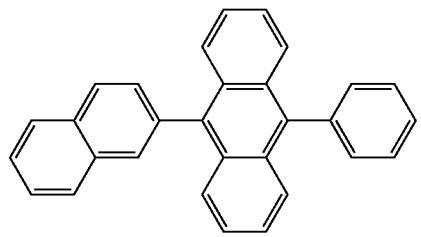
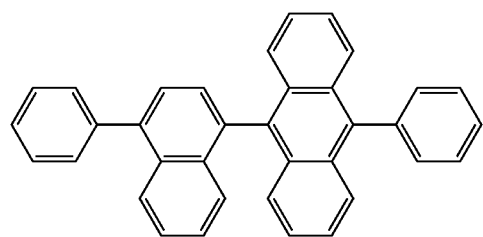
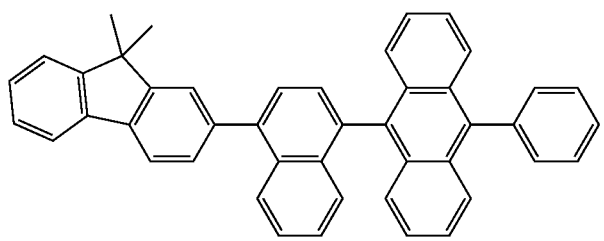
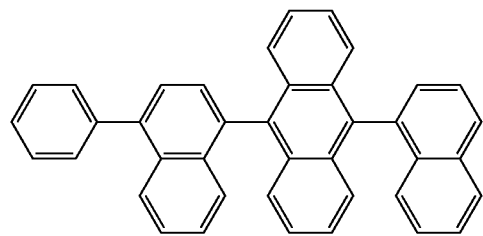
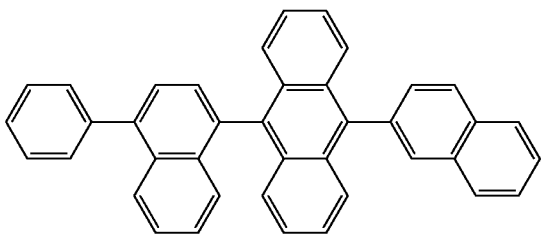

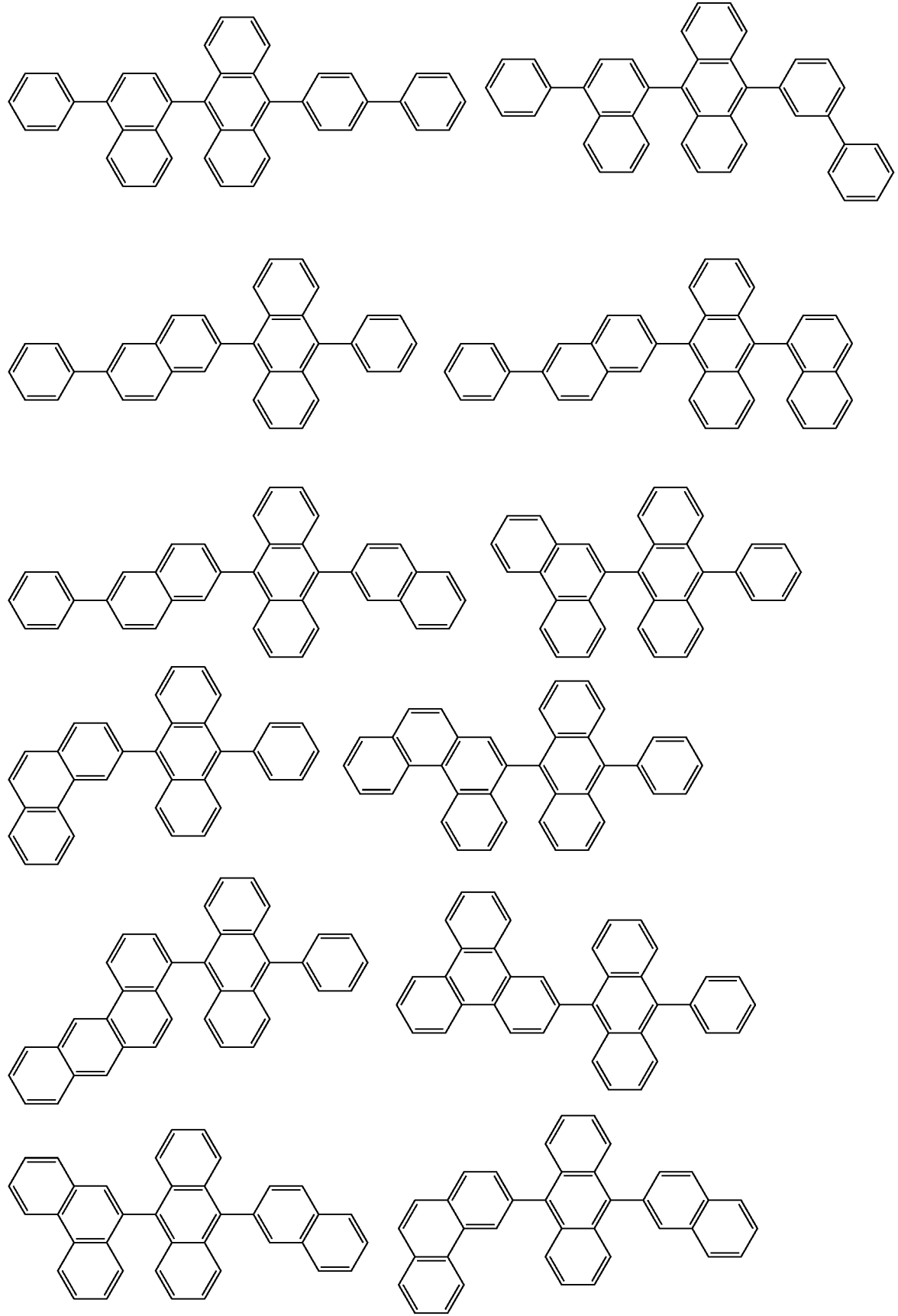

181 182
-continued
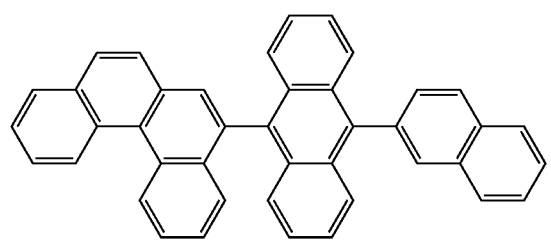
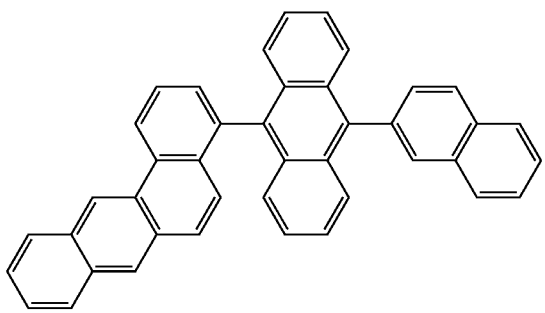
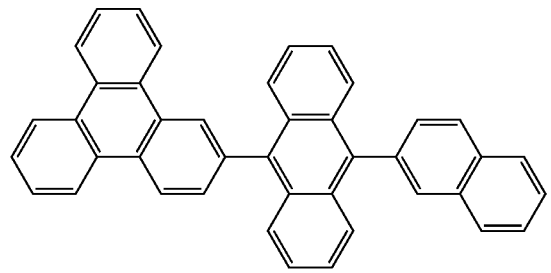
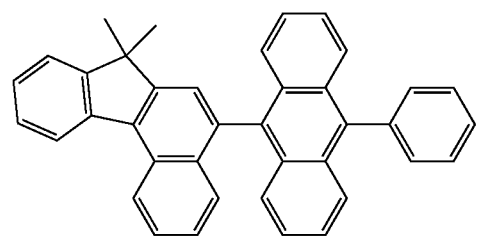
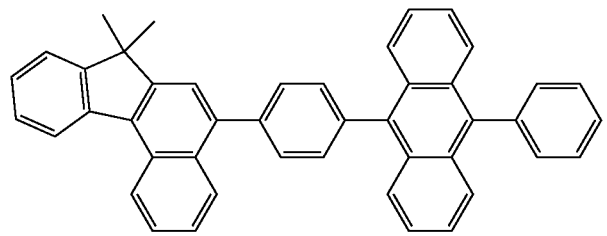
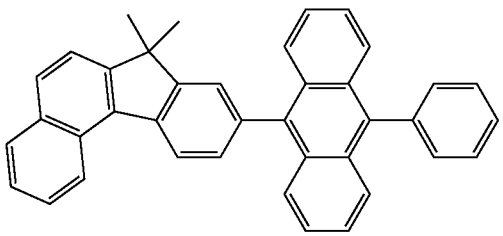
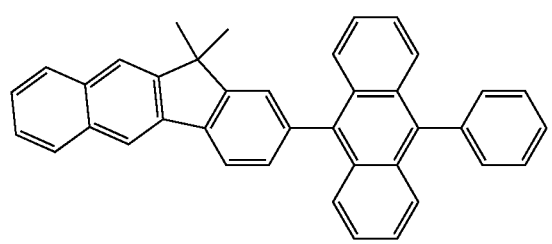
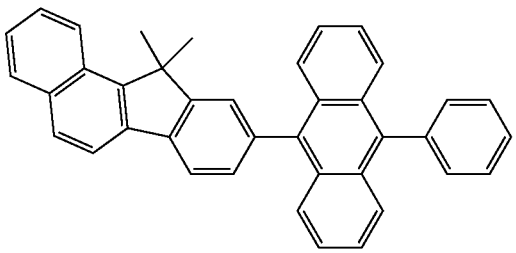
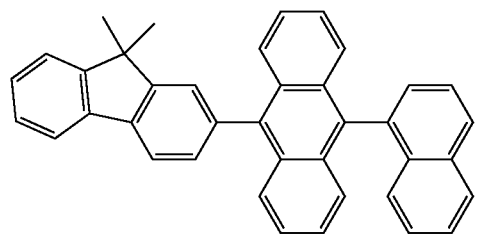
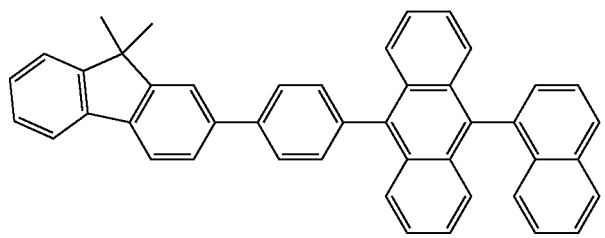
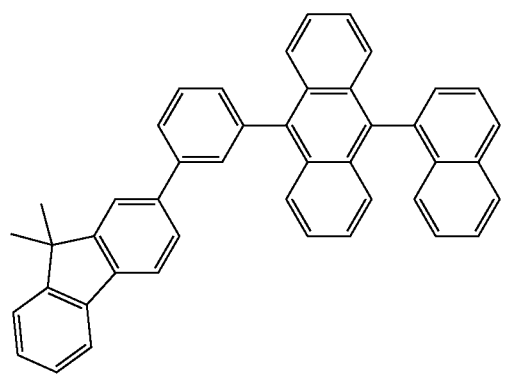
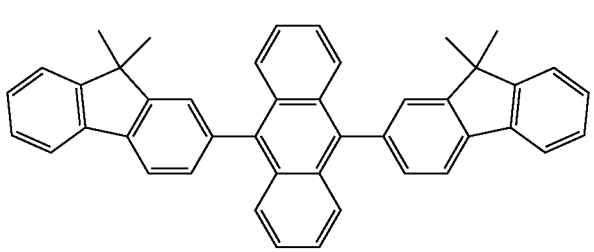

-continued
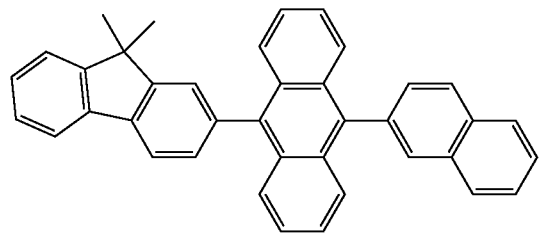
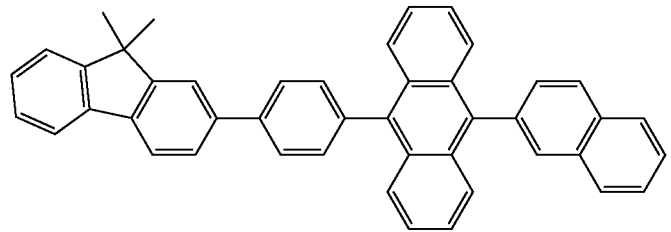
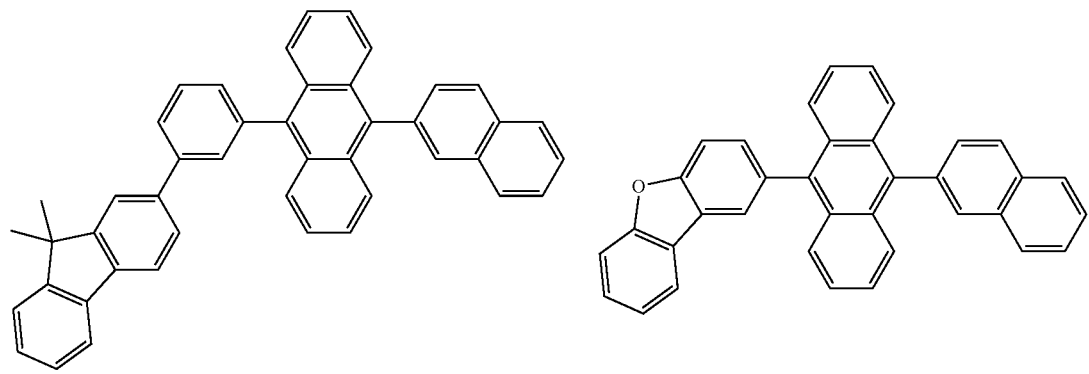
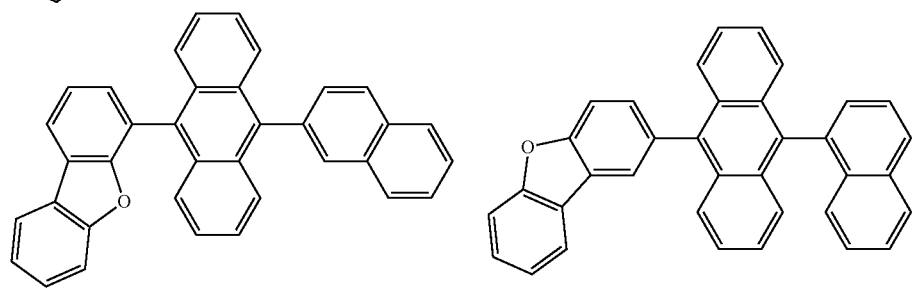
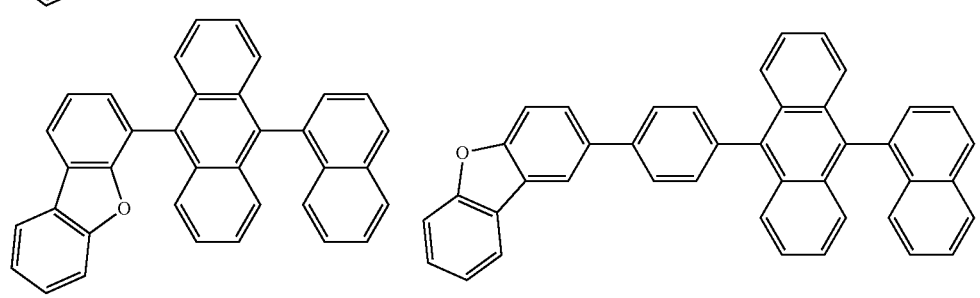
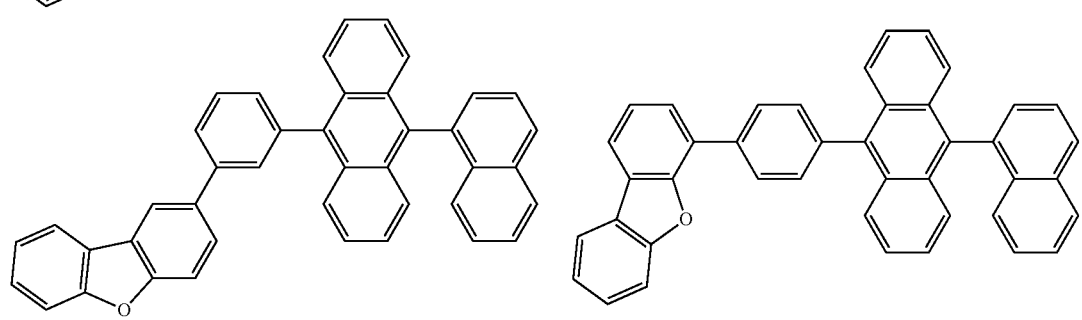

-continued
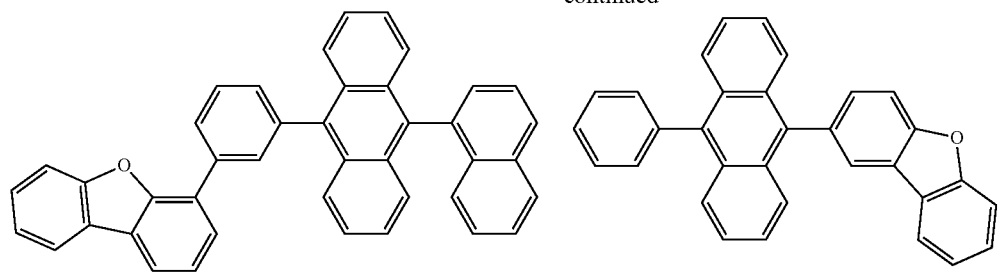
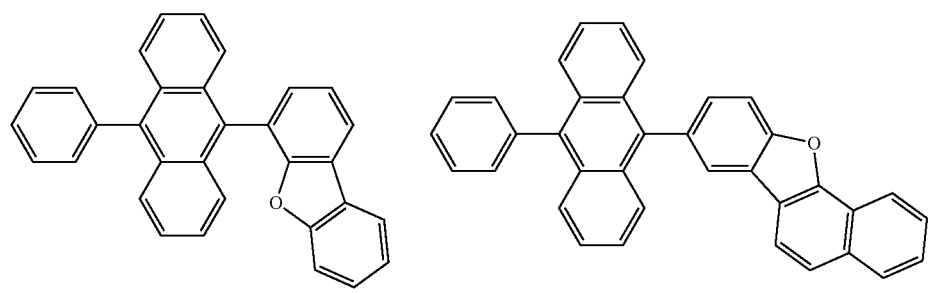
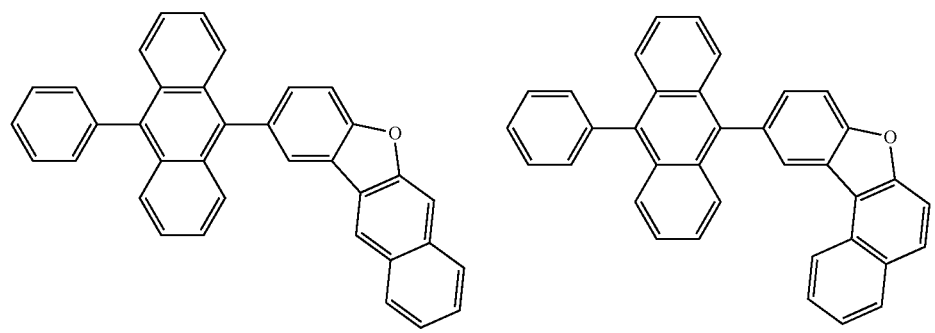
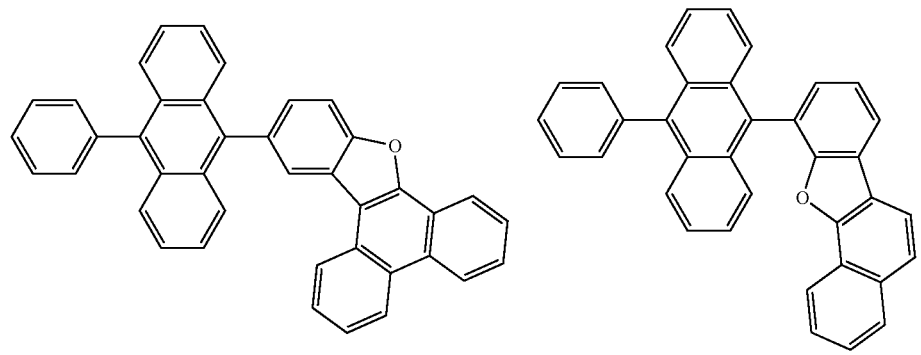
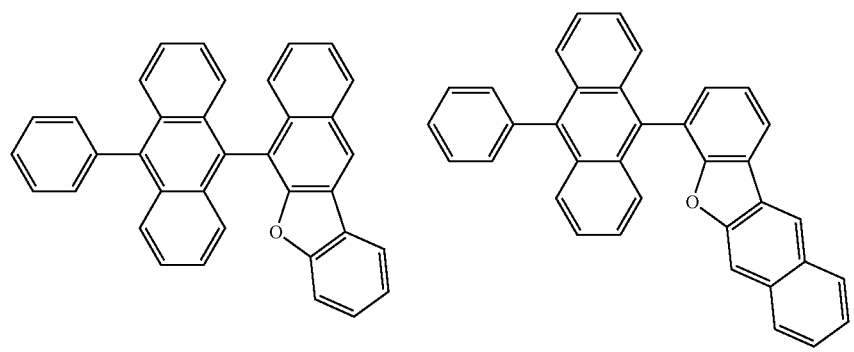

-continued
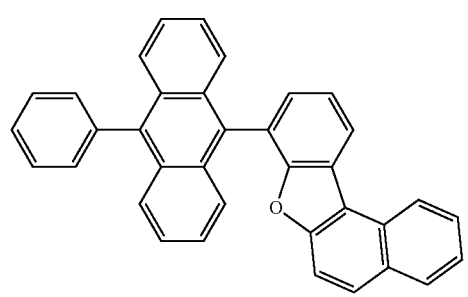
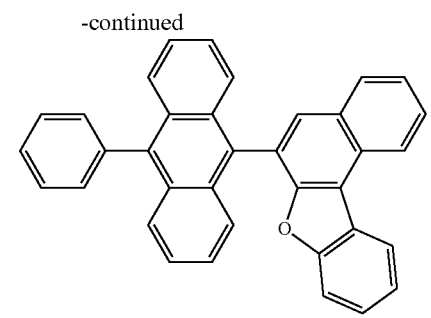
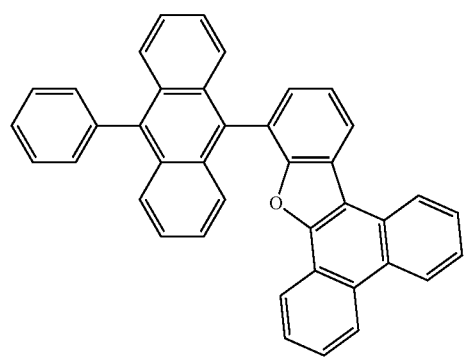
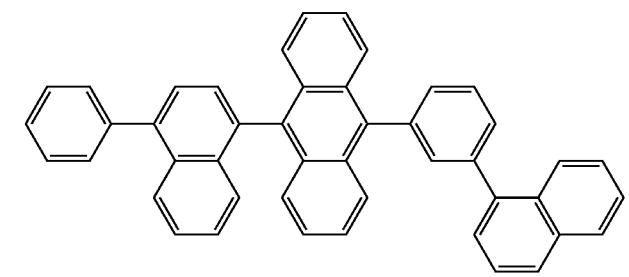
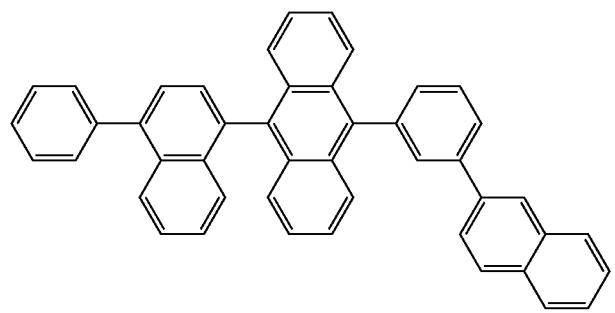
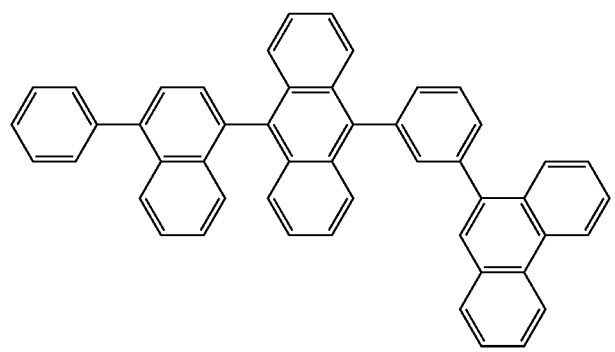
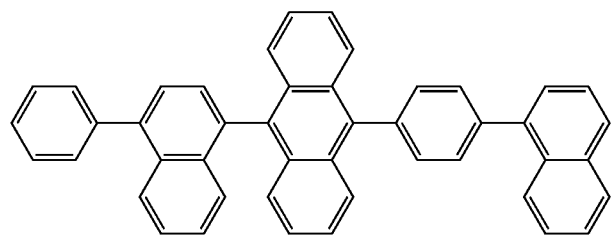

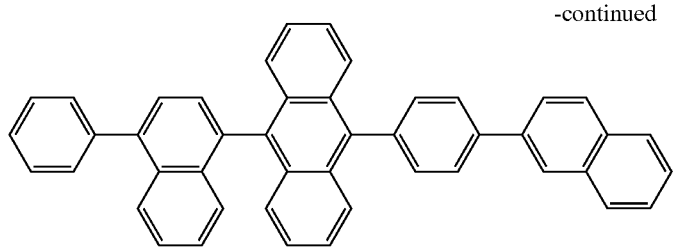
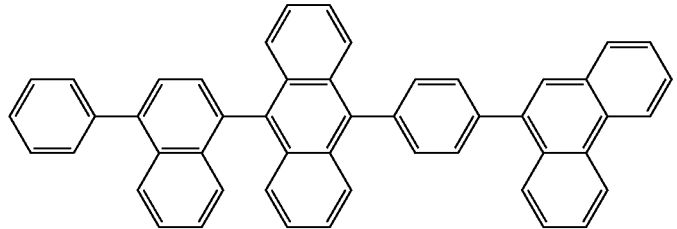
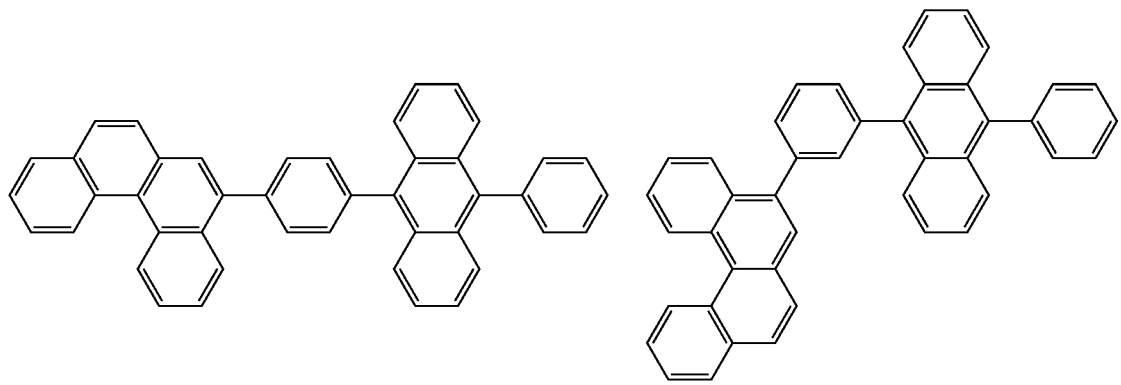
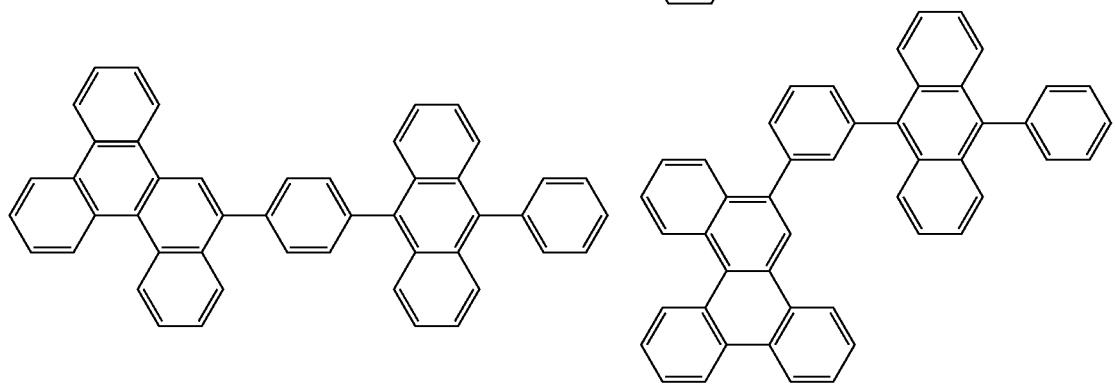
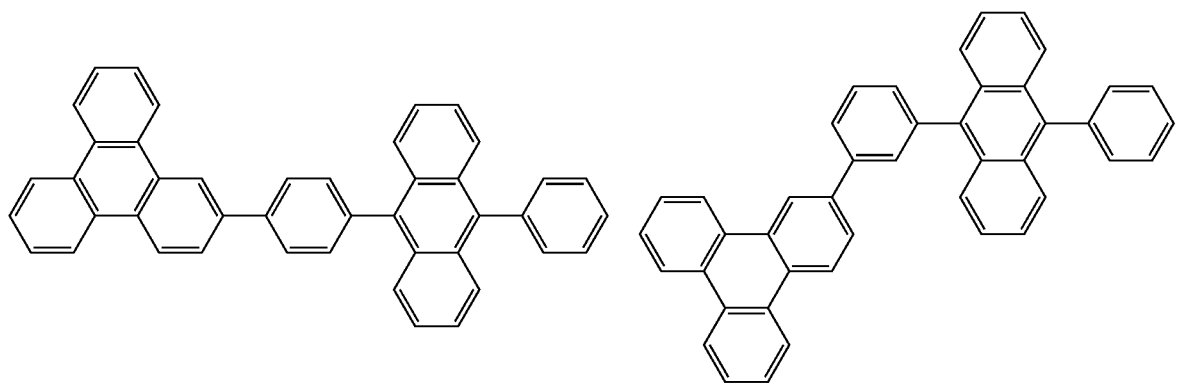

The electron transport zone is constituted by the electron injection layer, the electron transport layer, and the hole blocking layer. Also, one of the layers in the electron transport zone, particularly the electron transport layer preferably contains one or more selected from the group including an alkali metal, an alkaline earth metal, a rare earth metal, oxide of an alkali metal, halide of an alkali metal, oxide of an alkaline earth metal, halide of an alkaline earth metal, oxide of a rare earth metal, halide of a rare earth metal, an organic complex containing an alkali metal, an organic complex containing an alkaline earth metal, and an organic complex containing a rare earth metal.

Electron Transport Layer

The electron transport layer is a layer containing a material having a high electron transporting property (an electron transporting material). The electron transport layer is provided between the cathode and the light emitting layer, or is provided between the electron injection layer and the light emitting layer in the case where the electron injection layer is present. In the electron transport layer, for example, (1) a metal complex such as an aluminum complex, a beryllium complex, or a zinc complex,
(2) a heteroaromatic compound such as an imidazole derivative, a benzimidazole derivative, an azine derivative, a carbazole derivative, or a phenanthroline derivative, or
(3) a high molecular compound may be used.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzooxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs).

Examples of the high molecular compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The above materials have an electron mobility of $10^{-6}$ cm$^2$/Vs or more. Materials other than the above may also be used for the electron transport layer as long as they are materials high in the electron transporting property rather than in the hole transporting property.

The electron transport layer may be a single-layer, or a multi-layer including two or more layers. For example, the electron transport layer may be a layer including a first electron transport layer (anode side) and a second electron transport layer (cathode side). Each of the two or more electron transport layers is formed by the above electron transporting material.

Electron Injection Layer

The electron injection layer is a layer containing a material having a high electron injection property. In the electron injection layer, alkali metals, alkaline earth metals, or compounds thereof such as lithium (Li), cesium (Cs), calcium (Ca), lithium fluoride (LiF), cesium fluoride (CsF), calcium fluoride (CaF$_2$), or lithium oxide (LiO$_x$) may be used. Besides, a material having an electron transporting property, in which an alkali metal, an alkaline earth metal, or a compound thereof is contained, specifically Alq containing magnesium (Mg) may be used. In this case, electron injection from the cathode is efficiently promoted.

Otherwise, in the electron injection layer, a composite material obtained by mixing an organic compound with an electron donor (donor) may be used. Such a composite material is excellent in the electron injection property and the electron transporting property because the organic compound receives electrons from the electron donor. In this case, as for the organic compound, a material excellent in transporting received electrons is preferable, and specifically, for example, the material constituting the electron transport layer (a metal complex or a heteroaromatic compound) as described above may be used. The electron donor only has to be a material having an electron donation property to the organic compound. Specifically, alkali metals, alkaline earth metals and rare earth metals are preferable, and lithium, cesium, magnesium, calcium, erbium, and ytterbium may be exemplified. Also, alkali metal oxide or alkaline earth metal oxide is preferable, and lithium oxide, calcium oxide, and barium oxide may be exemplified. Also, a Lewis base such as magnesium oxide may also be used. Also, an organic compound such as tetrathiafulvalene (abbreviation: TTF) may be also used.

Cathode

It is preferable that a metal, an alloy, an electrically conductive compound, or a mixture thereof which has a low work function (specifically 3.8 eV or less) is used for the cathode. As a specific example of such a cathode material, elements belonging to Group 1 or 2 of the periodic table, that is, alkali metals such as lithium (Li) and cesium (Cs), alkaline earth metals such as magnesium (Mg), calcium (Ca), and strontium (Sr), and alloys containing any of them (for example, MgAg, and AlLi), and rare earth metals such as europium (Eu) and ytterbium (Yb) and alloys containing any of them may be exemplified.

When the cathode is formed by using the alkali metals, the alkaline earth metals, or the alloys containing any of them, a vacuum vapor-deposition method or a sputtering method may be used. Also, when a silver paste is used, a coating method or an inkjet method may be used.

By providing the electron injection layer, the cathode may be formed using various conductive materials such as Al, Ag, ITO, graphene, and indium oxide-tin oxide containing silicon or silicon oxide regardless of the magnitude of a work function. Such a conductive material may be deposited by using a sputtering method, an inkjet method, or a spin coating method.

Insulating Layer

The organic EL device applies an electric field to an ultrathin film and thus pixel defects are likely to occur due to leaks or short-circuit. In order to prevent them, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate thereof may also be used.

Space Layer

The above space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. In addition, the space layer may also be provided between the plurality of phosphorescent light emitting layers. The "carrier" mentioned herein means a charge carrier in a substance.

Since the space layer is provided between the light emitting layers, a material having both an electron transporting property and a hole transporting property is preferable. Also, one having a triplet energy of 2.6 eV or more is preferable in order to prevent triplet energy diffusion in the adjacent phosphorescent light emitting layer. As for the material used for the space layer, the same as those used for the hole transport layer as described above may be exemplified.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transport layer. When there are hole transport layers with a multi-layer structure, a hole transport layer closest to the light emitting layer may function as the electron blocking layer. The hole blocking layer is a layer that prevents holes from leaking from the light emitting layer to the electron transport layer. When there are electron transport layers with a multi-layer structure, an electron transport layer closest to the light emitting layer may function as the hole blocking layer. The exciton blocking layer has a function of preventing excitons generated in the light emitting layer from diffusing into the surrounding layers, and confining the excitons within the light emitting layer.

Each layer of the above organic EL device may be formed by a conventionally known vapor deposition method, or a coating method. For example, the formation may be performed by a known method using a vapor deposition method such as a vacuum vapor-deposition method, or a molecular beam vapor deposition method (MBE method), or a coating method using a solution of a compound forming a layer, such as a dipping method, a spin-coating method, a casting method, a bar-coating method, or a roll-coating method.

The film thickness of each layer is not particularly limited but is usually 5 nm to 10 μm, more preferably 10 nm to 0.2 μm because in general, when the film thickness is too small, defects such as pinholes are likely to occur, and conversely, when the film thickness is too large, a high driving voltage is required and the efficiency becomes poor.

The above organic EL device may be used for a display component such as an organic EL panel module, a display device such as a TV, a mobile phone, and a personal computer, and an electronic device such as a light emitting device of a vehicular lamp, and a lighting.

EXAMPLES

Hereinafter, the present invention will be described in more detail by using Examples, but the present invention is not limited to the following Examples.

Compounds represented by the formula (1) and the formula (1-1), which were used in producing organic EL devices in Examples 1 to 12 to be described below, are illustrated below.

Compound 1

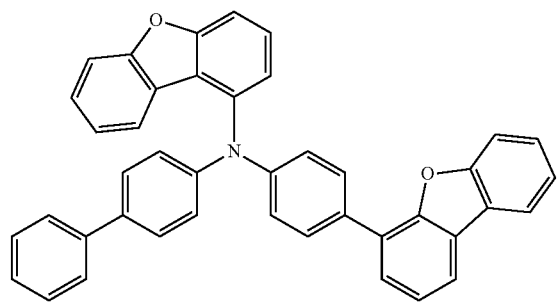

Compound 2

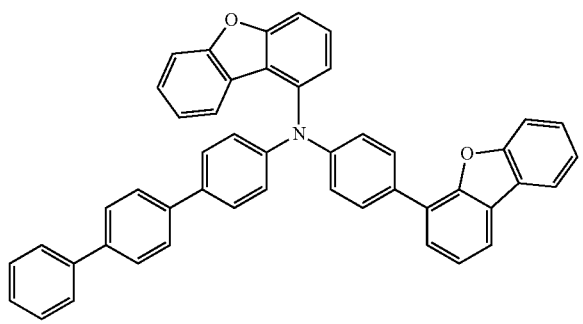

Compound 3

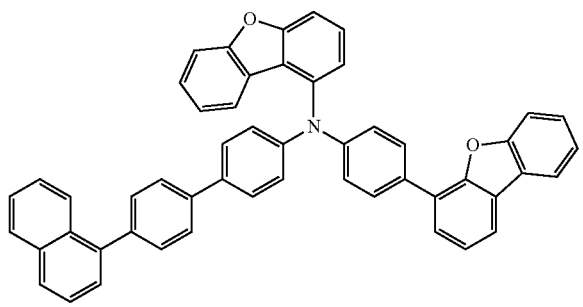

Compound 4

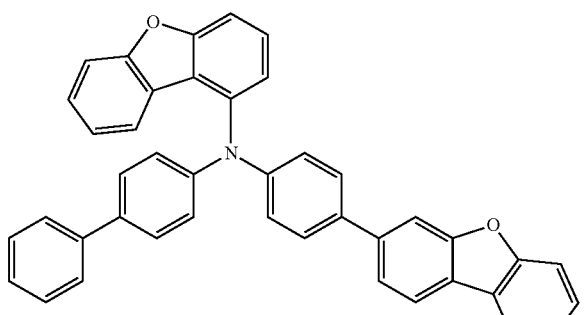

Compound 5

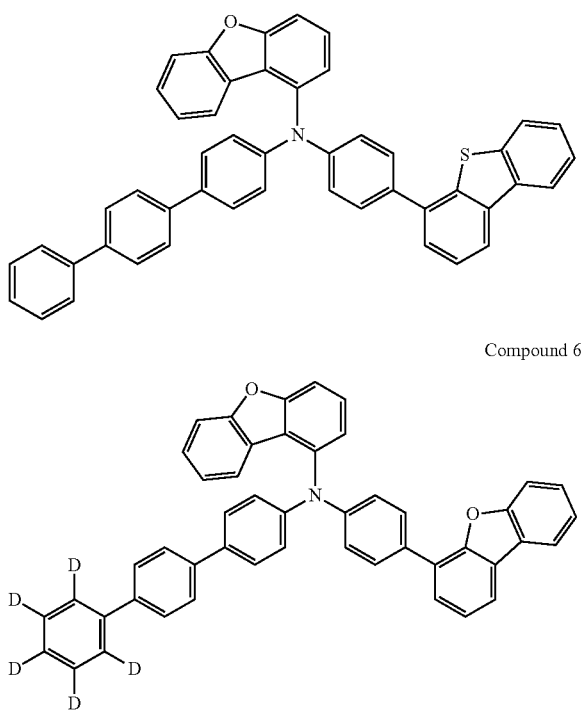

Compound 6

Compound 3

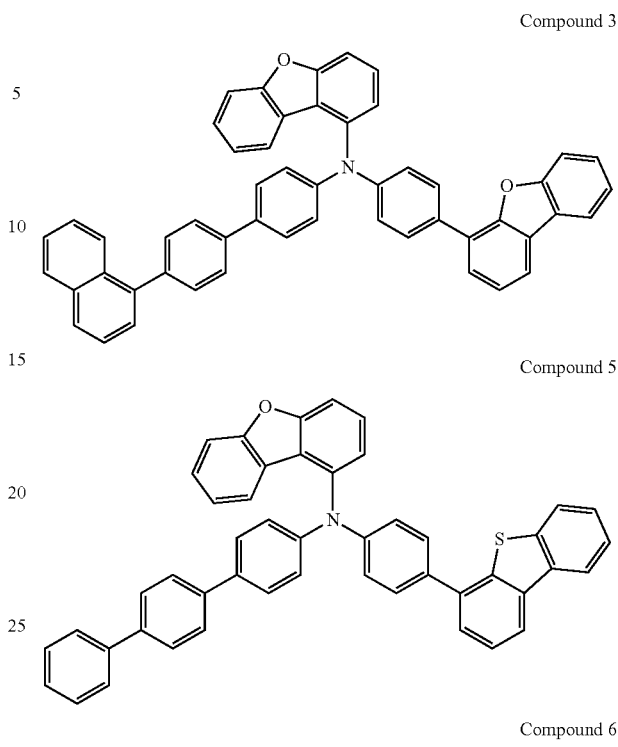

Compound 5

Compound 6

Compounds represented by the formula (1-2a), which were used in producing organic EL devices in Examples 1 to 12, are illustrated below.

Compound 1

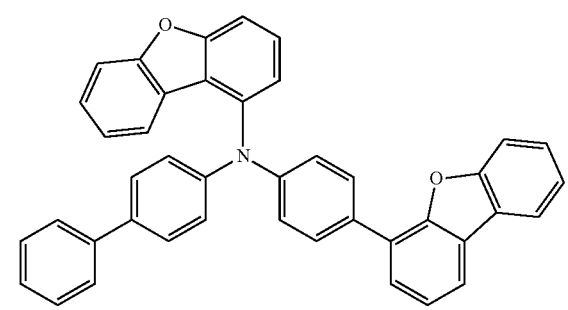

Compound 2

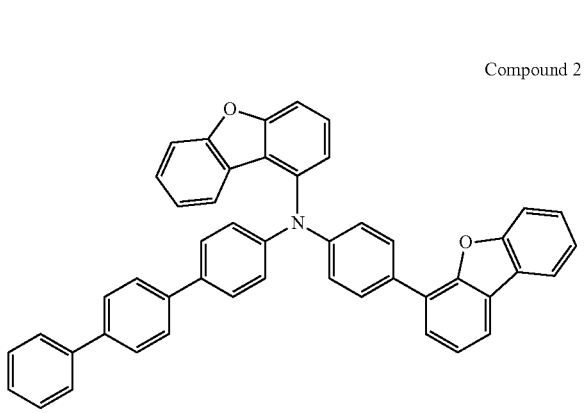

A compound represented by the formula (1-2b), which was used in producing organic EL devices in Examples 1 to 12, is illustrated below.

Compound 4

Compounds used in producing organic EL devices in Comparative Examples 1 to 12 are illustrated below.

Comparative compound 1
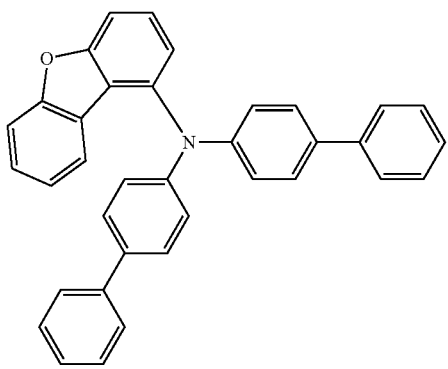
Comparative compound 2
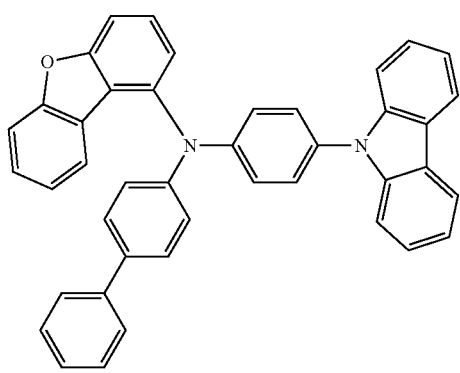
Comparative compound 3
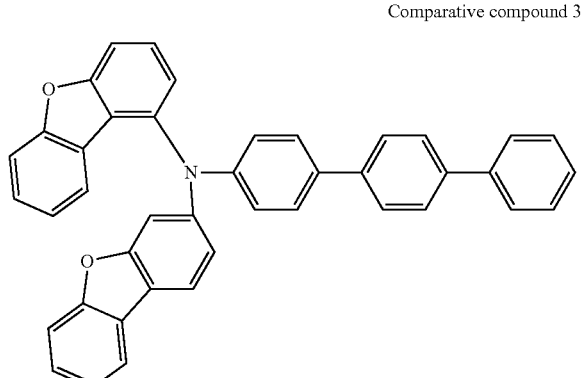
Comparative compound 4
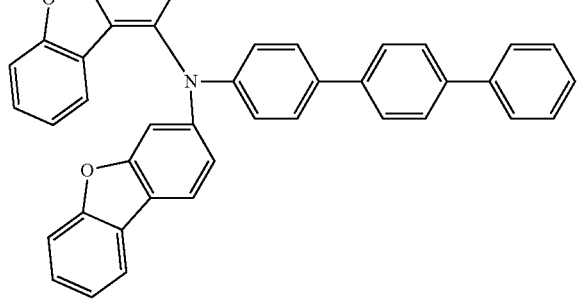
Comparative compound 5
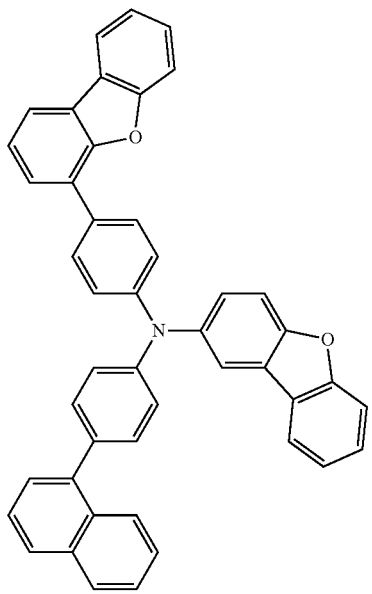
Comparative compound 6
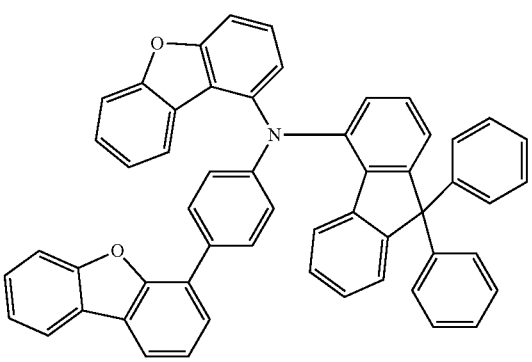
Other compounds used in producing organic EL devices in Examples 1 to 6 and Comparative Examples 1 to 6 are illustrated below.
HI-1

HT-1
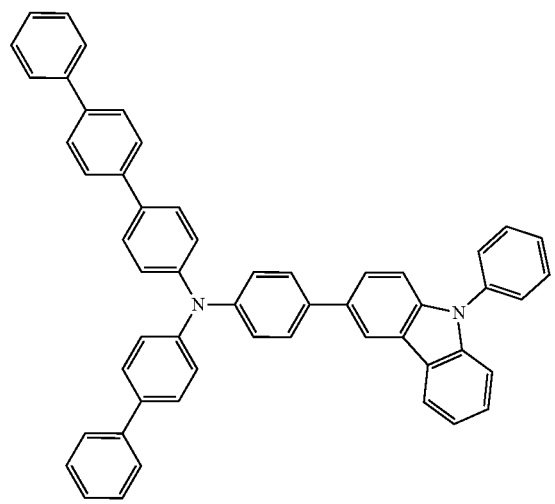
ET-2
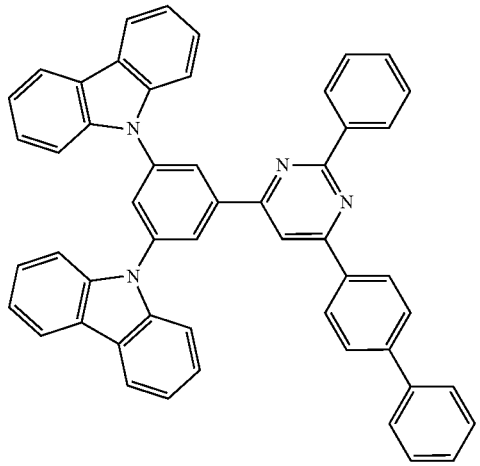
BH-1
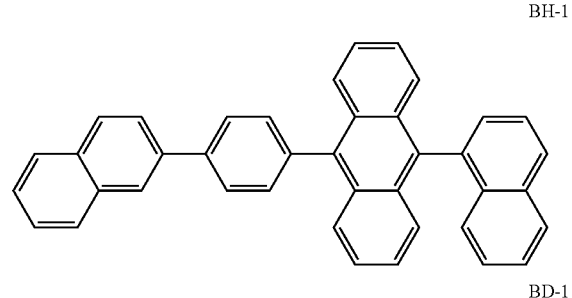
ET-3
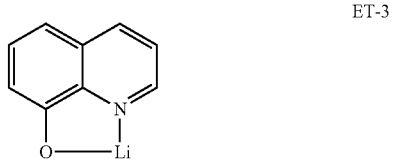
BD-1
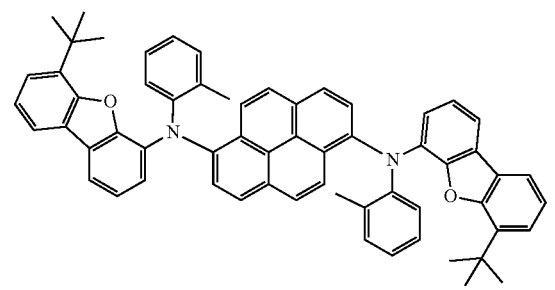
Other compounds used in producing organic EL devices in Examples 7 to 12 and Comparative Examples 7 to 12 are illustrated below.
ET-1
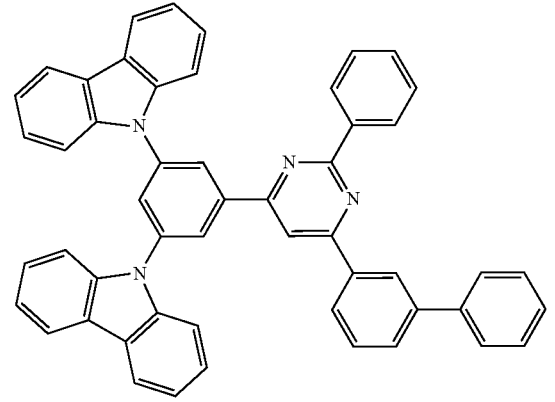
HI-1
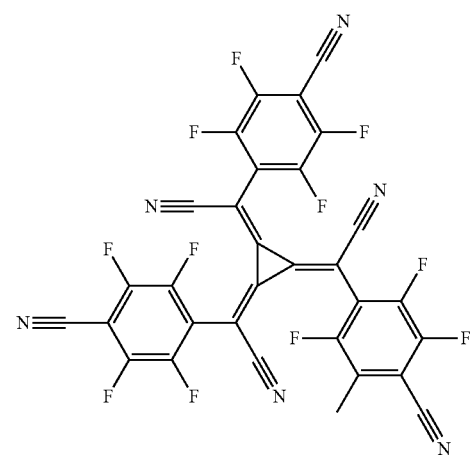

HT-2

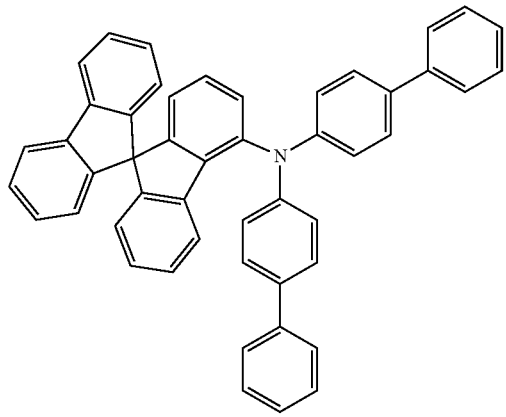

BH-1

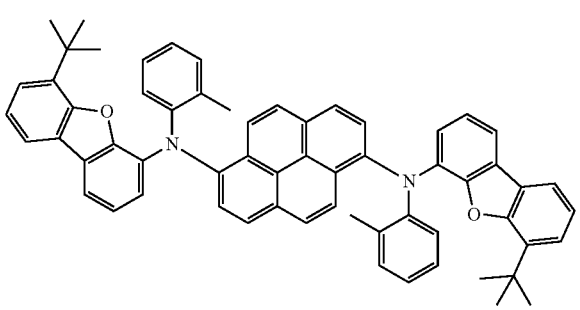

BD-1

ET-4

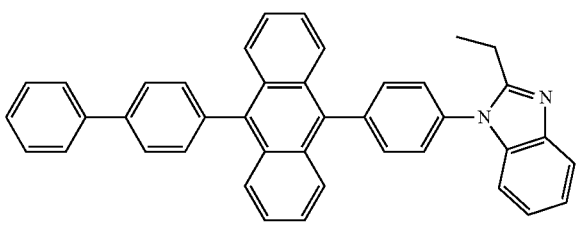

ET-5

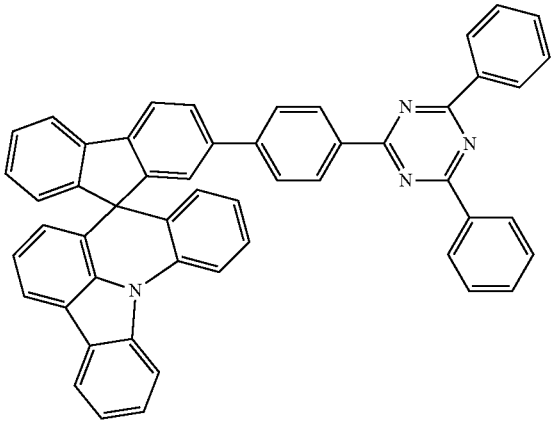

<Preparation of Organic EL Device>

An organic EL device was prepared as follows.

Example 1

A 25 mm×75 mm×1.1 mm thick glass substrate provided with an ITO transparent electrode (manufactured by GEO-MATEC Co., Ltd.) was subjected to ultrasonic cleaning in isopropyl alcohol for 5 min, and then subjected to UV ozone cleaning for 30 min. The thickness of the ITO transparent electrode was 130 nm.

After washed, the glass substrate provided with the ITO transparent electrode line was mounted on a substrate holder of a vacuum vapor deposition apparatus. First, on the surface on the side where the ITO transparent electrode line was formed, the above compound HT-1 and the above compound HI-1 were co-deposited so as to cover the above transparent electrode. Then, a co-deposited film with a film thickness of 10 nm was deposited so as to form a hole injection layer. The concentration of HI-1 in the hole injection layer was 3% by mass.

Next, on the hole injection layer, the above compound HT-1 as a first hole transport layer material was vapor-deposited so as to form a first hole transport layer with a film thickness of 75 nm.

Next, on the first hole transport layer, Compound 1 synthesized in Synthesis Example 1 below, as a second hole transport layer material, was vapor-deposited so as to form a second hole transport layer with a film thickness of 15 nm.

Next, on the second hole transport layer, the above compound BH-1 (a host material) and the above compound BD-1 (a dopant material) were co-deposited so as to form a co-deposited film with a film thickness of 25 nm. In the co-deposited film, the concentration of the compound BD-1 was 4% by mass. This co-deposited film functions as a light emitting layer.

Next, on the light emitting layer, the above compound ET-1 was vapor-deposited to deposit a film with a film thickness of 5 nm, and then a first electron transport layer was formed.

Next, on the first electron transport layer, the above compound ET-2 and the above compound ET-3 were co-deposited to deposit a co-deposited film with a film thickness of 25 nm, and then a second electron transport layer was formed. The concentration of the compound ET-3 in the second electron transport layer was 33% by mass.

Next, on the second electron transport layer, LiF was vapor-deposited to deposit a LiF film with a film thickness of 1 nm, and then an electron injecting electrode (cathode) was formed.

Then, on the LiF film, metal Al was vapor-deposited to deposit a metal Al film with a film thickness of 50 nm, and then, a metal Al cathode was formed and an organic EL device in Example 1 was obtained.

A device configuration of Example 1 is schematically illustrated as follows.

ITO (130)/HT-1:HI-1 (10:3%)/HT-1 (75)/compound 1 (15)/BH-1:BD-1 (25:4%)/ET-1 (5)/ET-2:ET-3 (25:33%)/LiF (1)/Al (50)

The numbers in parentheses indicate a film thickness (unit: nm). Also, similarly, in parentheses, numbers expressed as a percentage indicate the ratio (% by mass) of a compound described on the right, in the layer. The same also applies to the corresponding descriptions in the following Examples and Comparative Examples.

Examples 2 to 6

Organic EL devices were prepared as organic EL devices in Examples 2 to 6 in the same manner as in Example 1 except that instead of Compound 1 used for the second hole transport layer in Example 1, Compounds 2 to 6 synthesized in Synthesis Examples 2 to 6 below were used as hole transporting materials of second hole transport layers, respectively.

Comparative Examples 1 to 6

Organic EL devices were prepared as organic EL devices in Comparative Examples 1 to 6 in the same manner as in Example 1 except that instead of Compound 1 used for the second hole transport layer in Example 1, the above Comparative Compounds 1 to 6 were used as hole transporting materials of second hole transport layers, respectively.

Example 7

A 25 mm×75 mm×1.1 mm thick glass substrate provided with an ITO transparent electrode (manufactured by GEO-MATEC Co., Ltd.) was subjected to ultrasonic cleaning in isopropyl alcohol for 5 min, and then subjected to UV ozone cleaning for 30 min. The thickness of the ITO transparent electrode was 130 nm.

After washed, the glass substrate provided with the ITO transparent electrode line was mounted on a substrate holder of a vacuum vapor deposition apparatus. First, on the surface on the side where the ITO transparent electrode line was formed, Compound 1 synthesized in Synthesis Example 1 and the above compound HI-1 were co-deposited so as to cover the above transparent electrode. Then, a co-deposited film with a film thickness of 10 nm was deposited so as to form a hole injection layer. The concentration of HI-1 in the hole injection layer was 15% by mass.

Next, on the hole injection layer, Compound 1 synthesized in Synthesis Example 1, as a first hole transport layer material, was vapor-deposited so as to form a first hole transport layer with a film thickness of 80 nm.

Next, on the first hole transport layer, the above compound HT-2 as a second hole transport layer material was vapor-deposited so as to form a second hole transport layer with a film thickness of 10 nm.

Next, on the second hole transport layer, the above compound BH-1 (a host material) and the above compound BD-1 (a dopant material) were co-deposited so as to form a co-deposited film with a film thickness of 25 nm. In the co-deposited film, the concentration of the compound BD-1 was 4% by mass. This co-deposited film functions as a light emitting layer.

Next, on the light emitting layer, the above compound ET-4 and the above compound ET-5 were co-deposited to deposit a co-deposited film with a film thickness of 20 nm, and thus an electron transport layer was formed. The concentration of the compound ET-5 in the electron transport layer was 50% by mass.

Next, on the electron transport layer, LiF was vapor-deposited to deposit a LiF film with a film thickness of 1 nm, and then an electron injecting electrode (cathode) was formed.

Then, on the LiF film, metal Al was vapor-deposited to deposit a metal Al film with a film thickness of 50 nm, and then, a metal Al cathode was formed and an organic EL device in Example 7 was obtained.

A device configuration of Example 7 is schematically illustrated as follows.

ITO (130)/compound 1:HI-1 (10:15%)/compound 1 (80)/HT-2 (10)/BH-1:BD-1 (25:4%)/ET-4:ET-5 (20:50%)/LiF (1)/Al (50)

Examples 8 to 12

Organic EL devices were prepared as organic EL devices in Examples 8 to 12 in the same manner as in Example 7 except that instead of Compound 1 used for the hole injection layer and the first hole transport layer in Example 7, Compounds 2 to 6 synthesized in the above Synthesis Examples 2 to 6 were used as hole transporting materials of hole injection layers and first hole transport layers, respectively.

Comparative Examples 7 to 12

Organic EL devices were prepared as organic EL devices in Comparative Examples 7 to 12 in the same manner as in Example 7 except that instead of Compound 1 used for the hole injection layer and the first hole transport layer in Example 7, the above Comparative Compounds 1 to 6 were used as hole transporting materials of hole injection layers and first hole transport layers, respectively.

<Evaluation 1 of Organic EL Device>

For the organic EL devices prepared in Examples 1 to 12 and Comparative Examples 1 to 12, a voltage was applied to the organic EL device such that the current density became 10 mA/cm$^2$, and thus the external quantum efficiency was evaluated.

<Evaluation 2 of Organic EL Device>

For the organic EL devices in Examples 1 to 12 and Comparative Examples 1 to 12, a voltage was applied to the organic EL device such that the current density became 50 mA/cm$^2$, and then 95% life (LT95) was evaluated. Here, LT95 refers to time (hr) until the luminance is reduced to 95% of the initial luminance during constant current driving.

Results of the above evaluations 1 and 2 are noted in Tables 1 and 2.

TABLE 1

|  | Second Hole Transport Layer | External Quantum Efficiency (%) | LT95 [h] |
|---|---|---|---|
| Example 1 | Compound 1 | 9.8 | 120 |
| Example 2 | Compound 2 | 9.7 | 140 |
| Example 3 | Compound 3 | 10.1 | 113 |
| Example 4 | Compound 4 | 9.7 | 109 |
| Example 5 | Compound 5 | 9.7 | 122 |
| Example 6 | Compound 6 | 9.7 | 137 |
| Comparative Example 1 | Comparative Compound 1 | 9.4 | 50 |
| Comparative Example 2 | Comparative Compound 2 | 9.5 | 40 |
| Comparative Example 3 | Comparative Compound 3 | 9.2 | 80 |
| Comparative Example 4 | Comparative Compound 4 | 8.8 | 100 |
| Comparative Example 5 | Comparative Compound 5 | 9.3 | 60 |
| Comparative Example 6 | Comparative Compound 6 | 9.6 | 50 |

TABLE 2

|  | First Hole Transport Layer | External Quantum Efficiency (%) | LT95 [h] |
|---|---|---|---|
| Example 7 | Compound 1 | 8.0 | 190 |
| Example 8 | Compound 2 | 8.9 | 248 |
| Example 9 | Compound 3 | 9.1 | 203 |
| Example 10 | Compound 4 | 8.0 | 230 |
| Example 11 | Compound 5 | 8.8 | 217 |
| Example 12 | Compound 6 | 8.8 | 232 |
| Comparative Example 7 | Comparative Compound 1 | 5.9 | 129 |
| Comparative Example 8 | Comparative Compound 2 | 6.4 | 133 |
| Comparative Example 9 | Comparative Compound 3 | 6.6 | 141 |
| Comparative Example 10 | Comparative Compound 4 | 5.7 | 122 |
| Comparative Example 11 | Comparative Compound 5 | 6.7 | 105 |
| Comparative Example 12 | Comparative Compound 6 | 6.1 | 94 |

As is clear from Tables 1 and 2, it can be found that when Compounds 1 to 6 included in the formula (1) having a specific structure are used as hole transporting materials of organic EL devices, it is possible to obtain organic EL devices capable of achieving both a prolonged life and a high efficiency which cannot be realized in organic EL devices using Comparative Compounds 1 to 6.

It is presumed that the reason the organic EL devices using Compounds 1 to 6 have a high performance in both life and external quantum efficiency than the organic EL devices using Comparative Compounds 1 to 6 is that the compound specified by this application becomes very stable to electrons or excitons and has a high barrier ability in confining the excitons in the light emitting layer, but is not limited thereto.

Meanwhile, the organic EL devices of Comparative Examples 1 to 12 have a lower performance in either or both of the external quantum efficiency and the life than those of Examples 1 to 12. It may be thought that this is because the molecular structures of Comparative Compounds 1 to 6 deviate from the structure specified by the compound (1), by which at least one of the barrier ability and the stability is impaired.

Synthesis Example of Intermediate (1) Intermediate Synthesis Example A Synthesis of Intermediate A

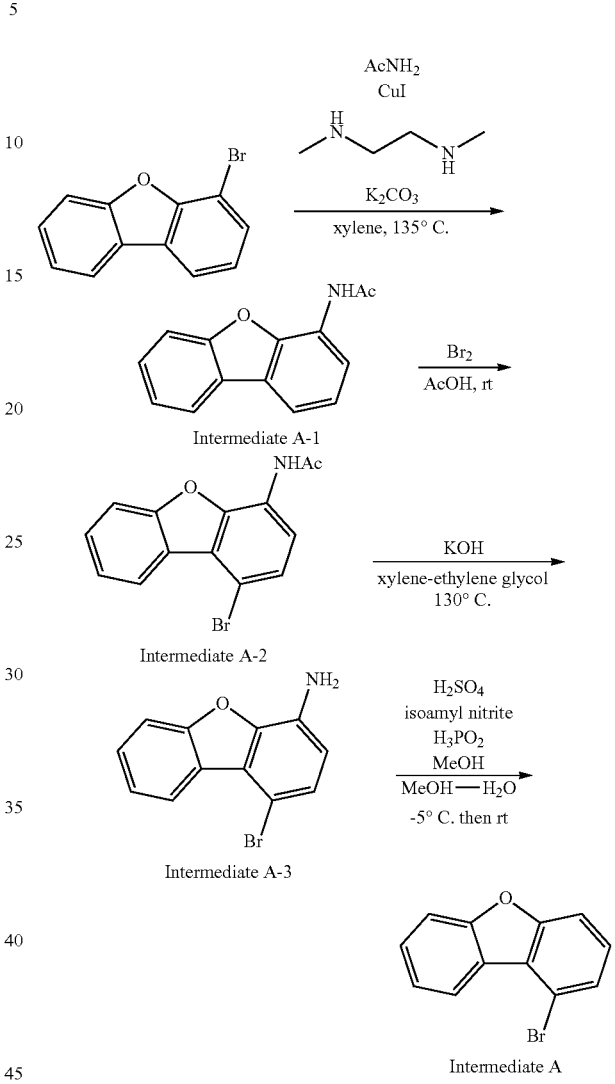

(1-1) Synthesis of Intermediate A-1

Under an argon atmosphere, a mixture of 1,200 g (4.86 mol) of 4-bromodibenzofuran, 573 g (9.71 mol) of acetamide, 184.98 g (971 mmol) of copper (I) iodide, 85.62 g (971 mmol) of N,N'-dimethylethylenediamine, 1,342 g (97.1 mol) of potassium carbonate, and 6 L of xylene was reacted at 135° C. for 5 h. After the reaction solution was cooled to room temperature, 4 L of water was added thereto, followed by stirring for 1 h to precipitate crystals. And then the precipitated crystals were collected by filtration and washed with water and n-heptane to obtain 950 g of an intermediate A-1. The yield was 75%.

(1-2) Synthesis of Intermediate A-2

Under an argon atmosphere, 809 g (5.06 mol) of bromine was added to a solution of 950 g (4.22 mol) of the intermediate A-1 synthesized in (1-1) in 7.1 L of acetic acid, followed by stirring at room temperature for 6 h. To the obtained solution, 7 L of water was dropped, and 63 g of sodium thiosulfate was added, followed by stirring at room temperature overnight to precipitate crystals. Then, the precipitated crystals were collected by filtration and sequentially washed with water, methanol, toluene, and n-heptane in turn to obtain 1,044 g of an intermediate A-2. The yield was 78%.

(1-3) Synthesis of Intermediate A-3

1,925 g (34.3 mmol) of potassium hydroxide was added to a solution of 1,044 g (3.43 mmol) of the intermediate A-2 synthesized in (1-2) in a mixture including 5 L of xylene and 700 mL of ethylene glycol, followed by stirring at 130° C. for 24 h. To the obtained solution, 500 mL of ethylene glycol was added, followed by further stirring at 130° C. for 3 days while reaction was performed. The reaction solution was cooled, and 3 L of water was added thereto. Then, through liquid separation, an organic layer was concentrated. The obtained residue was purified with silica gel column chromatography, and 721 g of an intermediate A-3 was obtained. The yield was 80%.

(1-4) Synthesis of Intermediate A

Under an argon atmosphere, 2,698 g (27.5 mmol) of concentrated sulfuric acid was dropped at −5 to 15° C. to a solution of 721 g (2.75 mol) of the intermediate A-3 synthesized in (1-3) in 3.6 L of acetonitrile and 3.6 L of water, followed by stirring at −5° C. for 30 min. Then, while the temperature was maintained at −3° C. or less, 483 g (4.13 mol) of isoamyl nitrite was dropped to the obtained solution, followed by stirring at −5° C. for 1 h. Then, to the solution, 908 g (13.8 mol) of hypophosphorous acid was dropped while kept at −2° C. or less. Next, to the solution, 3 L of methanol was added, followed by stirring at room temperature overnight while reaction was performed. To the reaction solution, toluene was added, and through liquid separation, a toluene layer was washed with saturated saline. The obtained residue was purified with silica gel column chromatography to obtain 418 g of an intermediate A. The yield was 61.4%.

(2) Intermediate Synthesis Example B Synthesis of Intermediate B (2-1) Synthesis of Intermediate B-1

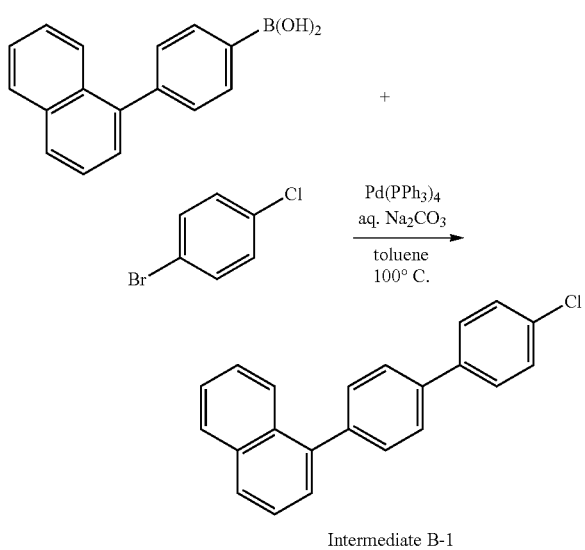

Intermediate B-1

Under an argon atmosphere, a mixture of 3.72 g (15 mmol) of 4-(1-naphthalenyl)phenylboronic acid (synthesized on the basis of the method described in WO 2019/146781), 2.87 g (15 mmol) of 4-bromochlorobenzene, 347 mmol (0.30 mmol) of tetrakis(triphenylphosphine)palladium(0), 22.5 mL of 2M aqueous sodium carbonate solution, and 45 mL of toluene was stirred at 100° C. for 7 h. After the temperature was returned to room temperature, water was added thereto and extraction was performed with toluene. The obtained toluene layer was dried over anhydrous sodium sulfate and concentrated under reduced pressure. The obtained residue was purified with silica gel column chromatography to obtain 3.07 g of a white solid. The yield was 65%.

(2-2) Synthesis of Intermediate B

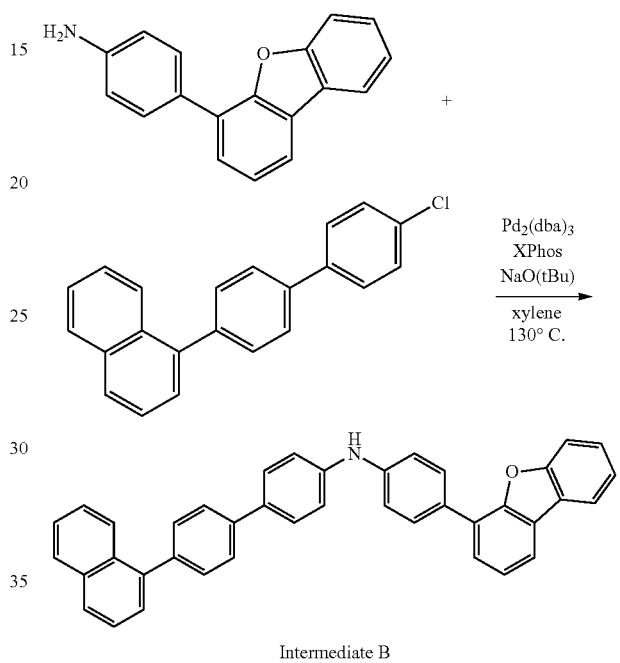

Intermediate B

Under an argon atmosphere, a xylene 1.2 L-solution with 67 g (258 mmol) of 4-(dibenzo[b,d]furan-4-yl)benzeneamine (synthesized on the basis of the method described in WO 2016/006711), and 54 g (172 mmol) of the intermediate B-1 synthesized in (2-1) was heated to 100° C., and 3.14 g (3.43 mmol) of tris(dibenzylideneacetone)dipalladium(0), 3.27 g (6.86 mmol) of XPhos, and 19.78 g (206 mmol) of sodium-t-butoxide were added thereto, followed by stirring at 130° C. for 3 h while reaction was performed. The reaction solution was cooled to room temperature and filtered with addition of methanol. The obtained residue was dissolved in toluene, and silica gel was added thereto, followed by stirring for 30 min. Then, filtering was performed, and the obtained filtrate was filtered with addition of methanol to obtain 70 g of a white solid. The yield was 76%.

(3) Intermediate Synthesis Example C Synthesis of Intermediate C

-continued

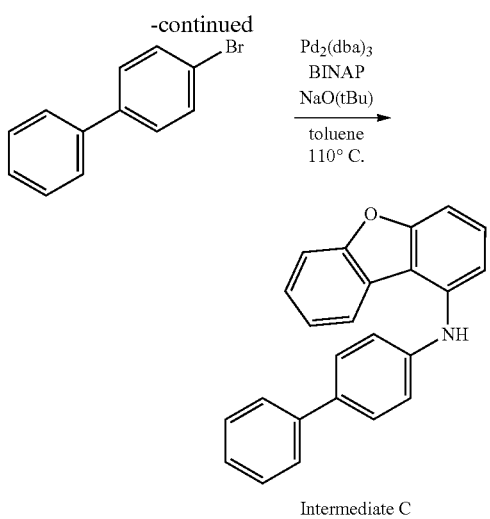

Intermediate C

Under a nitrogen atmosphere, a toluene 100 mL-solution with 3.66 g (20 mmol) of 1-aminodibenzofuran, 4.66 g (20 mmol) of 4-bromo-1,1'-biphenyl, 0.366 g (0.40 mmol) of tris(dibenzylideneacetone)dipalladium(0), 0.498 g (0.80 mmol) of BINAP, and 2.307 g (24 mmol) of sodium-t-butoxide was stirred at 110° C. for 7 h and reacted. The reaction solution was cooled to room temperature, and the filtrate was concentrated under reduced pressure. The obtained residue was purified by silica gel column chromatography and recrystallization to obtain 4.88 g of a white solid. The yield was 73%.

(4) Intermediate Synthesis Example D Synthesis of Intermediate D

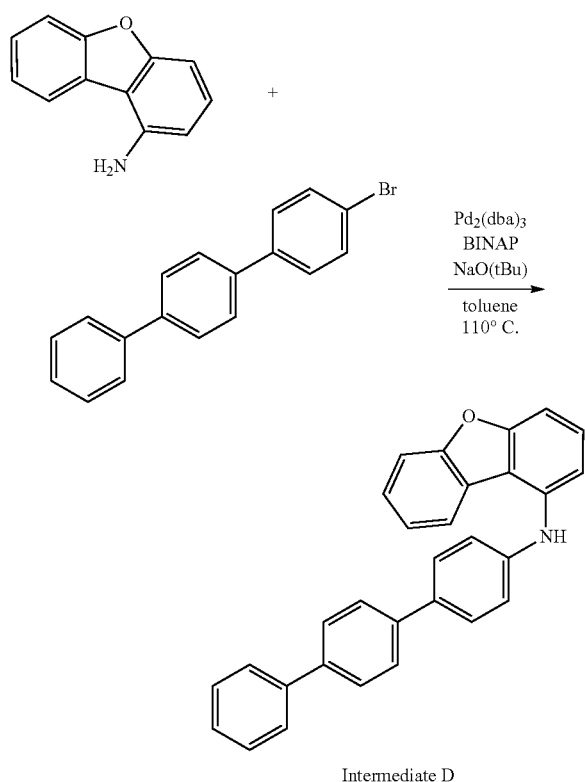

Intermediate D

Under a nitrogen atmosphere, a toluene 100 mL-solution with 3.66 g (20 mmol) of 1-aminodibenzofuran, 6.18 g (20 mmol) of 4-bromo-1,1':4',1''-terphenyl instead of 4-bromo-1,1'-biphenyl, 0.366 g (0.40 mmol) of tris(dibenzylideneacetone)dipalladium(0), 0.498 g (0.80 mmol) of BINAP, and 2.307 g (24 mmol) of sodium-t-butoxide was stirred at 110° C. for 7 h and reacted. The reaction solution was cooled to room temperature, and the filtrate was concentrated under reduced pressure. The obtained residue was purified by silica gel column chromatography and recrystallization to obtain 6.25 g of a white solid. The yield was 76%.

(5) Intermediate Synthesis Example E Synthesis of Intermediate E

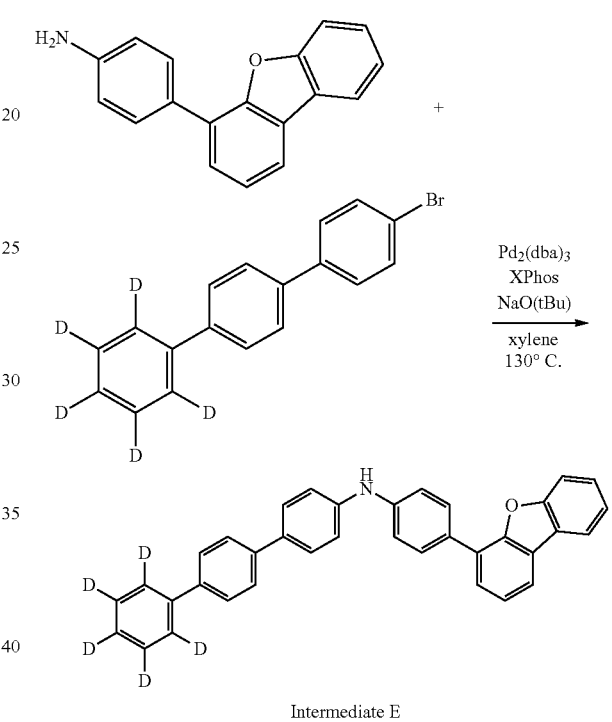

Intermediate E

Under an argon atmosphere, a xylene 75 mL-solution with 3.89 g (15 mmol) of 4-(dibenzo[b,d]furan-4-yl)benzeneamine (synthesized on the basis of the method described in WO 2016/006711), and 4.71 g (15 mmol) of 4''-bromo-1,1':4', 1''-terphenyl-2,3,4,5,6-d5 (synthesized on the basis of the method described in WO 2012/091471) was heated to 100° C., and 0.274 g (0.30 mmol) of tris(dibenzylideneacetone) dipalladium(0), 0.572 g (1.2 mmol) of XPhos, and 2.16 g (22.5 mmol) of sodium-t-butoxide were added thereto, followed by stirring at 130° C. for 3 h while reaction was performed. The reaction solution was cooled to room temperature and filtered with addition of methanol. The obtained residue was dissolved in toluene, and silica gel was added thereto, followed by stirring for 30 min. Then, filtering was performed, and the obtained filtrate was filtered with addition of methanol to obtain 5.25 g of a white solid. The yield was 71%.

Synthesis Example 1 (Synthesis of Compound 1)

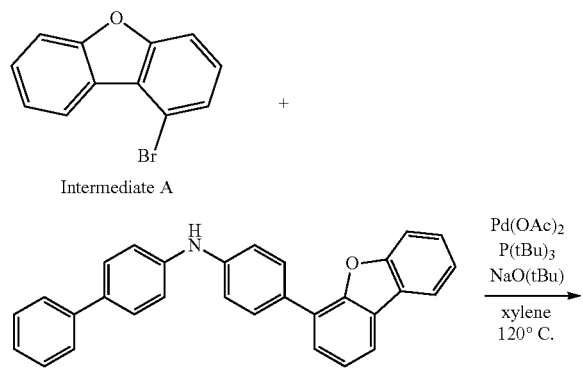

Under an argon atmosphere, a xylene 436 mL-solution with 14.9 g (60.3 mmol) of the intermediate A synthesized in Intermediate Synthesis Example A, 23.6 g (57.4 mmol) of N-(4-(dibenzo[b,d]furan-4-yl)phenyl)-[1,1'-biphenyl]-4-amine (synthesized on the basis of the method described in WO 2007/125714), 0.258 g (1.149 mmol) of acetic acidpalladium(II), and 0.465 g (2.298 mmol) of tri-t-butylphosphine was heated to 120° C., and 6.62 g (68.9 mmol) of sodium-t-butoxide was added thereto, followed by stirring for 1 h while reaction was performed. The reaction solution was cooled to room temperature and filtered through celite. The filtrate was concentrated under reduced pressure. The obtained residue was purified by silica gel column chromatography and recrystallization to obtain 20.6 g of a white solid.

As a result of mass spectrum analysis, the obtained substance was identified as Compound 1 represented by the above chemical structural formula, and m/e=577 for a molecular weight of 577.20. The yield was 62%.

Synthesis Example 2 (Synthesis of Compound 2)

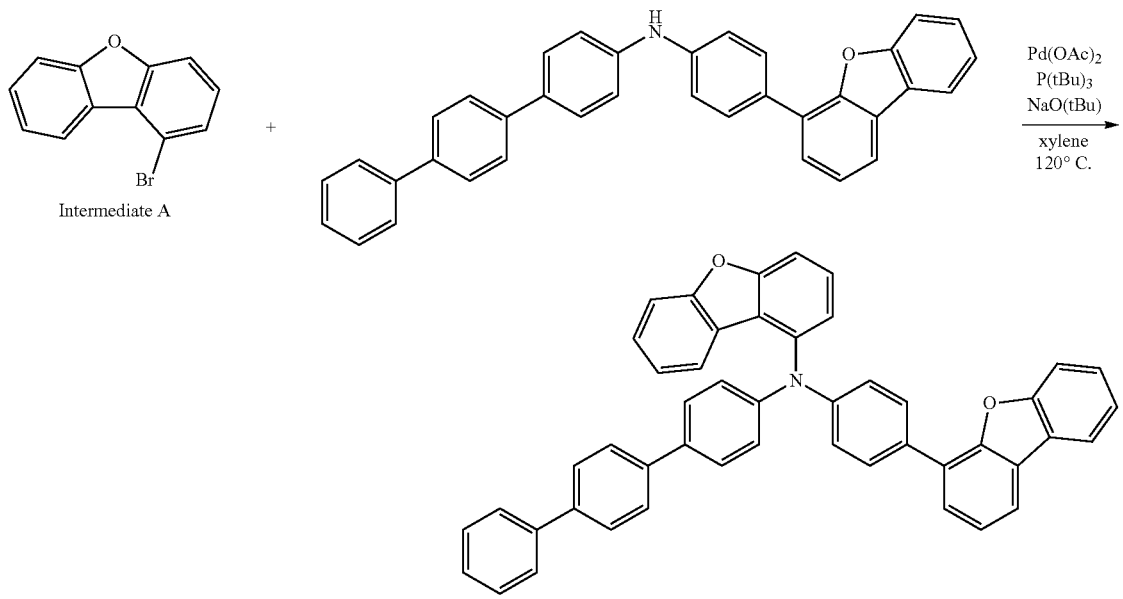

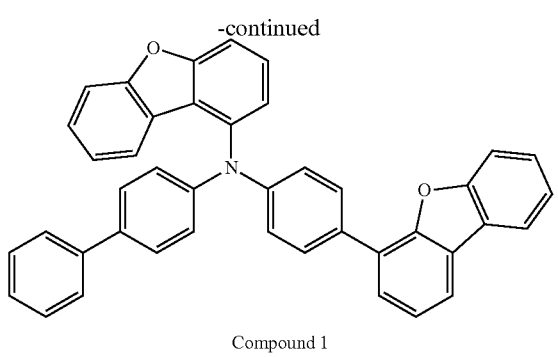

Compound 1

Under an argon atmosphere, a xylene 436 mL-solution with 14.9 g (60.3 mmol) of the intermediate A synthesized in Intermediate Synthesis Example A, 28.0 g (57.4 mmol) of N-(4-(dibenzo[b,d]furan-4-yl)phenyl)-[1,1':4',1''-terphenyl]-4-amine (synthesized on the basis of the method described in WO 2010/061824), 0.258 g (1.149 mmol) of acetic acidpalladium(II), and 0.465 g (2.298 mmol) of tri-t-butylphosphine was heated to 120° C., and 6.62 g (68.9 mmol) of sodium-t-butoxide was added thereto, followed by stirring for 1 h. The reaction solution was cooled to room temperature and filtered through celite. The filtrate was concentrated under reduced pressure. The obtained residue was purified by silica gel column chromatography and recrystallization to obtain 25.6 g of a white solid.

As a result of mass spectrum analysis, the obtained substance was identified as Compound 2 represented by the above chemical structural formula, and m/e=653 for a molecular weight of 653.24. The yield was 68%.

Synthesis Example 3 (Synthesis of Compound 3)

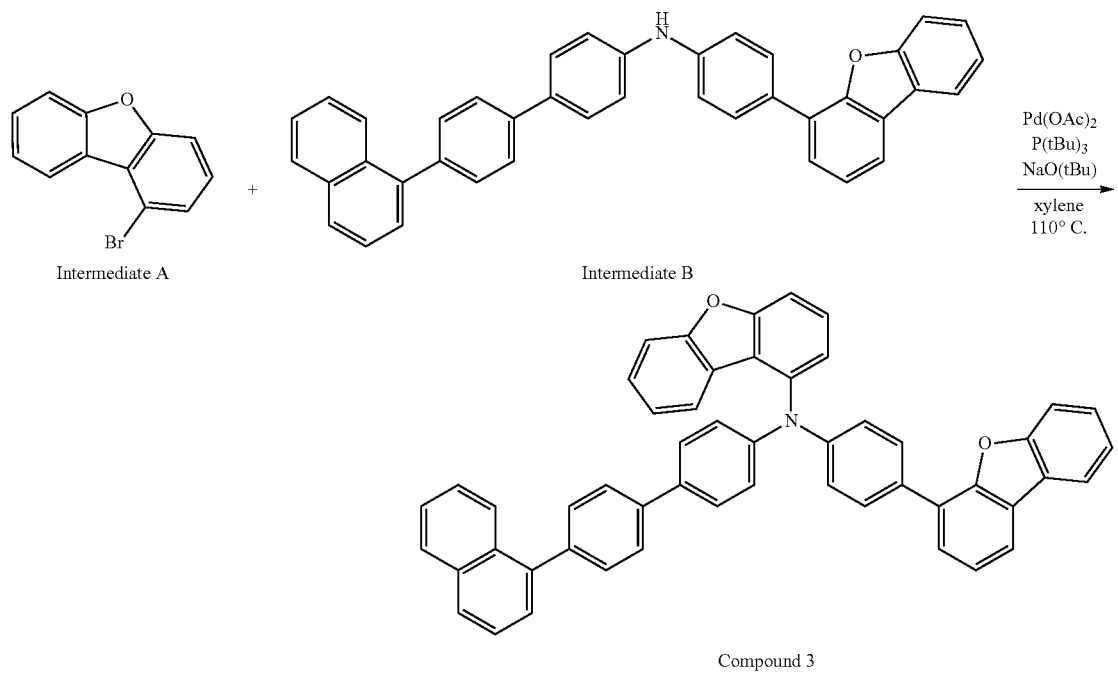

Compound 3

Under an argon atmosphere, a xylene 700 mL-solution with 47.87 g (89 mmol) of the intermediate A synthesized in Intermediate Synthesis Example A, 22 g (89 mmol) of the intermediate B synthesized in Intermediate Synthesis Example B, 0.4 g (1.781 mmol) of acetic acidpalladium(II), and 0.72 g (3.56 mmol) of tri-t-butylphosphine was heated to 90° C., and 10.27 g (107 mmol) of sodium-t-butoxide was added thereto, followed by stirring at 110° C. for 22 h while reaction was performed. The reaction solution was cooled to room temperature, and the filtrate was concentrated under reduced pressure. The obtained residue was purified by silica gel column chromatography and recrystallization to obtain 46 g of a white solid.

As a result of mass spectrum analysis, the obtained substance was Compound 3 represented by the above chemical structural formula, and m/e=704 for a molecular weight of 703.84. The yield was 73%.

Synthesis Example 4 (Synthesis of Compound 4)

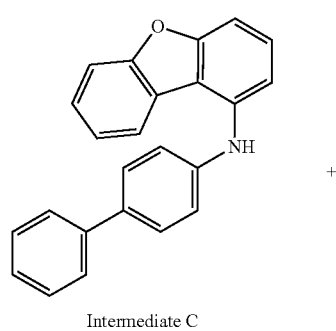

Intermediate C

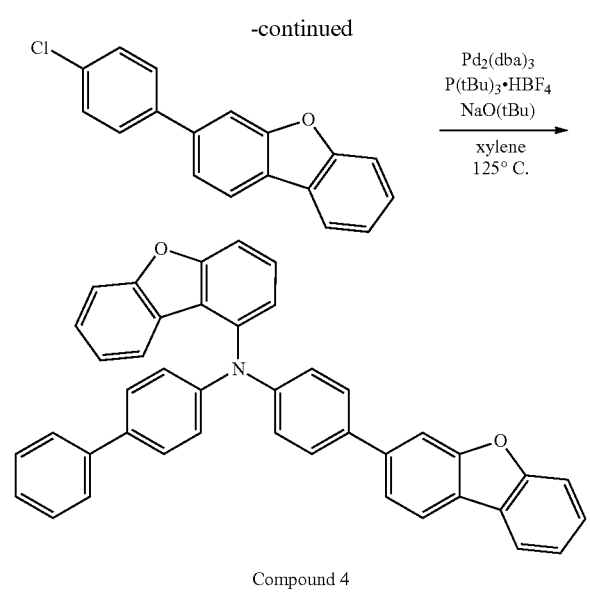

Compound 4

Under an argon atmosphere, a xylene 62.6 mL-solution with 4.2 g (12.52 mmol) of the intermediate C synthesized in Intermediate Synthesis Example C, 3.84 g (13.77 mmol) of 3-(4-chlorophenyl)dibenzo[b,d]furan (synthesized on the basis of the method described in WO 2018/164239), 0.229 g (0.250 mmol) of tris(dibenzylideneacetone)dipalladium (0), 0.291 g (1.00 mmol) of tri-t-butylphosphonium tetrafluoroborate, and 3.61 g (37.6 mmol) of sodium-t-butoxide was stirred at 125° C. for 7 h and reacted. The reaction solution was cooled to room temperature, and the filtrate was concentrated under reduced pressure. The obtained residue was purified by silica gel column chromatography and recrystallization to obtain 3.99 g of a white solid.

As a result of mass spectrum analysis, the obtained substance was Compound 4 represented by the above chemical structural formula, and m/e=578 for a molecular weight of 577.68. The yield was 53%.

Synthesis Example 5 (Synthesis of Compound 5)

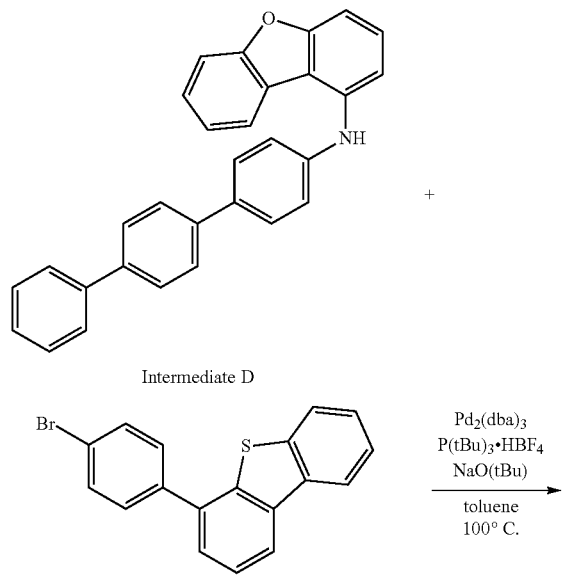

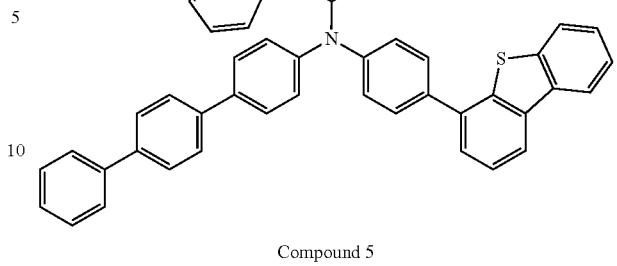

Compound 5

Under an argon atmosphere, a toluene 50 mL-solution with 4.12 g (10.0 mmol) of the intermediate D synthesized in Intermediate Synthesis Example D, 3.46 g (10.2 mmol) of 4-(4-bromophenyl)dibenzo[b,d]thiophene (synthesized on the basis of the method described in WO 2016/199784), 0.183 g (0.20 mmol) of tris(dibenzylideneacetone)dipalladium(0), 0.232 g (0.80 mmol) of tri-t-butylphosphonium tetrafluoroborate, and 1.44 g (15 mmol) of sodium-t-butoxide was stirred at 100° C. for 7 h and reacted. The reaction solution was cooled to room temperature, and the filtrate was concentrated under reduced pressure. The obtained residue was purified by silica gel column chromatography and recrystallization to obtain 1.66 g of a white solid.

As a result of mass spectrum analysis, the obtained substance was Compound 5 represented by the above chemical structural formula, and m/e=670 for a molecular weight of 669.84. The yield was 25%.

Synthesis Example 6 (Synthesis of Compound 6)

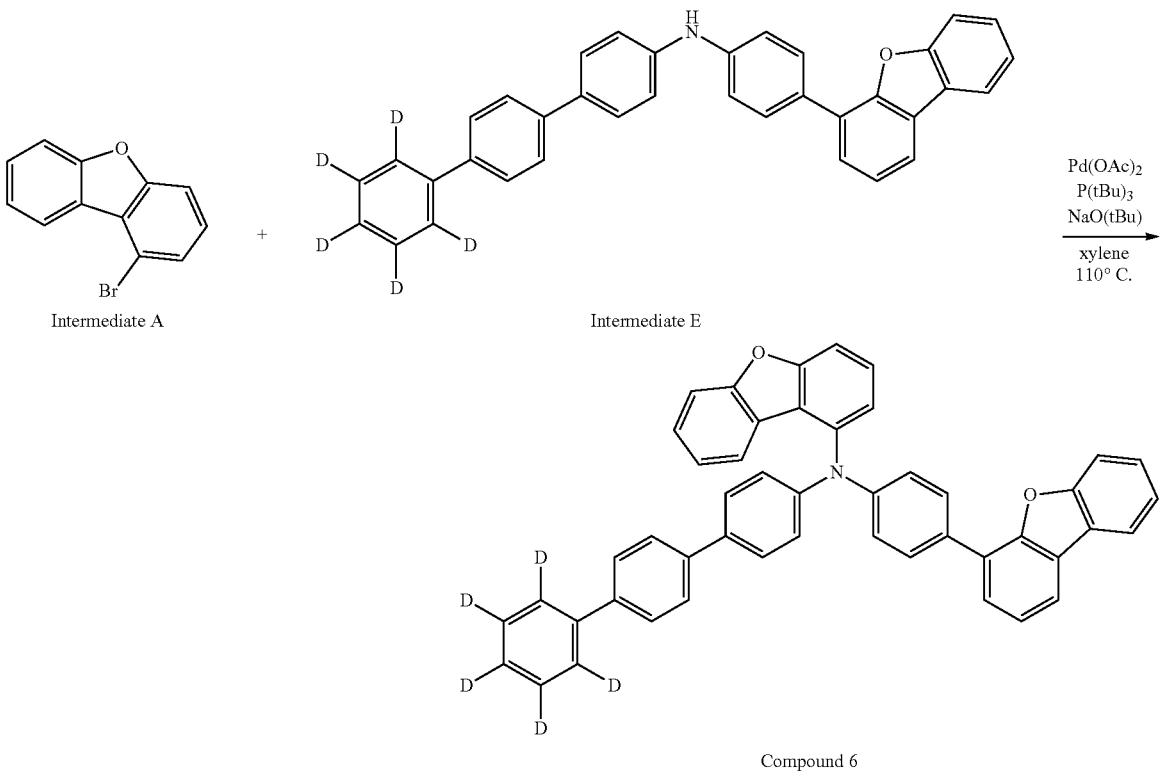

Compound 6

Under an argon atmosphere, a xylene 700 mL-solution with 2.47 g (10 mmol) of the intermediate A synthesized in Intermediate Synthesis Example A, 4.93 g (10 mmol) of the intermediate E synthesized in Intermediate Synthesis Example E, 0.045 g (0.2 mmol) of acetic acidpalladium(II), and 0.162 g (0.8 mmol) of tri-t-butylphosphine was heated to 90° C., and 1.44 g (15 mmol) of sodium-t-butoxide was added thereto, followed by stirring at 110° C. for 4 h while reaction was performed. The reaction solution was cooled to room temperature, and the filtrate was concentrated under reduced pressure. The obtained residue was purified by silica gel column chromatography and recrystallization to obtain 4.28 g of a white solid.

As a result of mass spectrum analysis, the obtained substance was Compound 6 represented by the above chemical structural formula, and m/e=659 for a molecular weight of 658.81. The yield was 65%.

REFERENCE SIGNS LIST 1, 11: organic EL device
2: substrate
3: anode
4: cathode
5: light emitting layer
6: hole transport zone (hole transport layer)
6a: first hole transport layer
6b: second hole transport layer
7: electron transport zone (electron transport layer)
7a: first electron transport layer
7b: second electron transport layer
10, 20: light emitting unit

The invention claimed is:

1. A compound of formula (1-2a-1) or formula (1-2c-1):

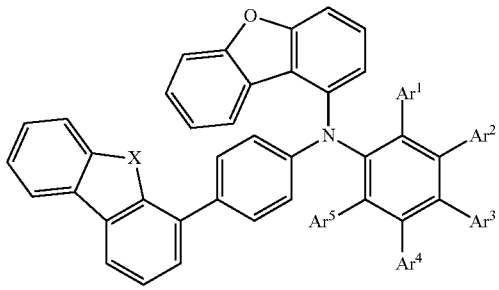

(1-2a-1)

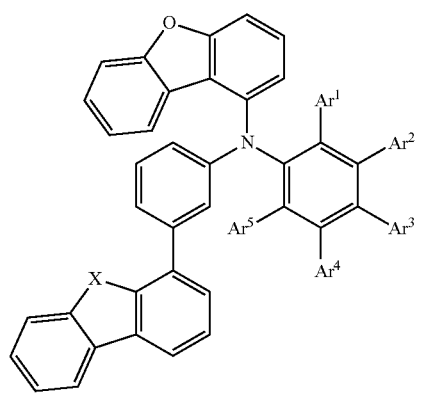

(1-2c-1)

wherein,

X represents an oxygen atom or a sulfur atom, $Ar^1$ and $Ar^5$ each represents a hydrogen atom, $Ar^2$ to $Ar^4$ each independently represents a hydrogen atom or an unsubstituted aryl group selected from the group consisting of a biphenylyl group, a naphthyl group, a phenylnaphthyl group, and a phenanthryl group, provided that at least one of $Ar^2$ to $Ar^4$ represents an unsubstituted aryl group selected from a biphenylyl group, a naphthyl group, a phenylnaphthyl group, and a phenanthryl group and that $Ar^2$ to $Ar^4$ are not bonded to each other to form a ring.

2. The compound according to claim 1, wherein one of $Ar^2$ to $Ar^4$ represents an unsubstituted aryl group selected from a biphenylyl group, a naphthyl group, a phenylnaphthyl group, and a phenanthryl group, and the others each represents a hydrogen atom.

3. The compound according to claim 1, wherein the compound represented by the formula (1-2a-1), or formula (1-2c-1) contains at least one deuterium atom.

4. A material for an organic electroluminescence device, comprising the compound according to claim 1.

5. An organic electroluminescence device comprising an anode, a cathode, and organic layers between the anode and the cathode,
wherein one of the organic layers is a light emitting layer, and
at least one layer of the organic layers contains the compound according to claim 1.

6. The organic electroluminescence device according to claim 5, wherein the organic layers include a hole transport zone provided between the anode and the light emitting layer, and the compound is included in the hole transport zone.

7. The organic electroluminescence device according to claim 6, wherein the compound represented by the formula (1-2a-1), or formula (1-2c-1) and included in the hole transport zone has at least one deuterium atom.

8. The organic electroluminescence device according to claim 6, wherein the hole transport zone includes a first hole transport layer on an anode side and a second hole transport layer on a cathode side, and at least one of the first hole transport layer and the second hole transport layer contains the compound.

9. The organic electroluminescence device according to claim 8, wherein the first hole transport layer contains the compound.

10. The organic electroluminescence device according to claim 8, wherein the second hole transport layer contains the compound.

11. The organic electroluminescence device according to claim 8, wherein the second hole transport layer is adjacent to the light emitting layer.

12. The organic electroluminescence device according to claim 5, wherein the light emitting layer contains a fluorescent dopant material.

13. The organic electroluminescence device according to claim 5, wherein the light emitting layer contains a phosphorescent dopant material.

14. An electronic device comprising the organic electroluminescence device according to claim 5.

15. The compound according to claim 1 wherein the compound of formula (1-2a-1) is selected from the group consisting of the formulas

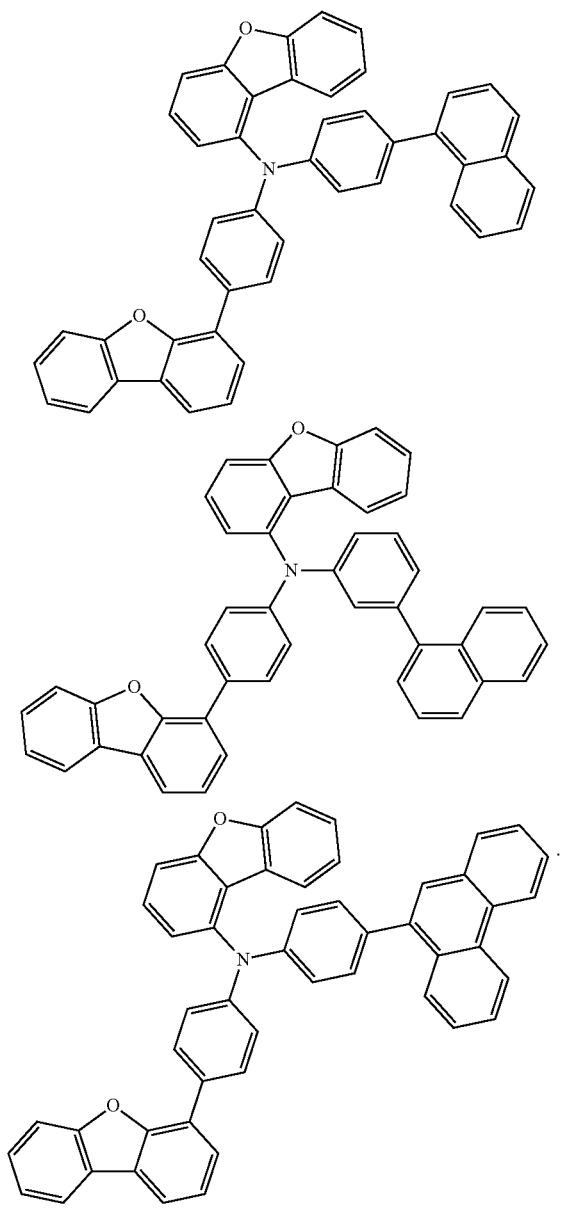

and the compound of formula (1-2c-1) is of the formula:

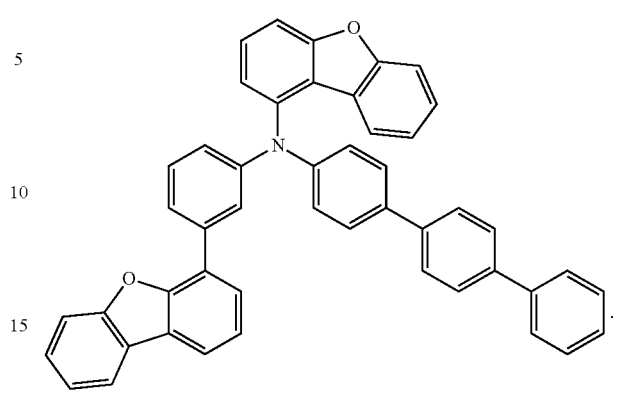

16. The compound according to claim 1 wherein X in formula (1-2a-1), or formula (1-2c-1) is an oxygen atom.

17. The compound according to claim 1, wherein in formula (1-2a-1), or formula (1-2c-1) $Ar^2$ represents a hydrogen atom, and $Ar^3$ represents an unsubstituted aryl group selected from a biphenylyl group, a naphthyl group, a phenylnaphthyl group, and a phenanthryl group.

18. The compound according to claim 1, wherein in formula (1-2a-1) and in formula (1-2c-1) $Ar^3$ represents an unsubstituted aryl group selected from the group consisting of a biphenylyl group, a naphthyl group, a phenylnaphthyl group, and a phenanthryl group, and $Ar^2$ and $Ar^4$ each represents a hydrogen atom.

19. The compound according to claim 1, wherein in formula (1-2a-1) and in formula (1-2c-1) two of $Ar^2$ to $Ar^4$ each independently represents an unsubstituted aryl group selected from the group consisting of a biphenylyl group, a naphthyl group, a phenylnaphthyl group, and a phenanthryl group, and the other represents a hydrogen atom.

20. The compound according to claim 1, wherein the compound is of the formula (1-2a-1) and $Ar^3$ represents an unsubstituted aryl group selected from the group consisting of a naphthyl group, a phenylnaphthyl group, and a phenanthryl group, and $Ar^2$ and $Ar^4$ each represents a hydrogen atom.

21. The compound according to claim 1, wherein the compound is of the formula (1-2c-1) and $Ar^3$ represents an unsubstituted biphenylyl group, and $Ar^2$ and $Ar^4$ each represents a hydrogen atom.

* * * * *